(12) United States Patent
Abreu

(10) Patent No.: US 9,848,815 B2
(45) Date of Patent: *Dec. 26, 2017

(54) APPARATUS AND METHOD FOR MEASURING BIOLOGIC PARAMETERS

(71) Applicant: GEELUX HOLDINGS, LTD., Tortola (VG)

(72) Inventor: Marcio Marc Abreu, Bridgeport, CT (US)

(73) Assignee: GEELUX HOLDINGS, LTD., Tortola (VG)

(*) Notice: Subject to any disclaimer, the term of this patent is extended or adjusted under 35 U.S.C. 154(b) by 555 days.

This patent is subject to a terminal disclaimer.

(21) Appl. No.: 14/500,362

(22) Filed: Sep. 29, 2014

(65) Prior Publication Data

US 2015/0148628 A1 May 28, 2015

Related U.S. Application Data

(63) Continuation of application No. 10/786,623, filed on Feb. 26, 2004, now Pat. No. 8,849,379, which is a
(Continued)

(51) Int. Cl.
*A61B 5/00* (2006.01)
*A61B 5/024* (2006.01)
(Continued)

(52) U.S. Cl.
CPC .......... *A61B 5/4064* (2013.01); *A61B 5/0008* (2013.01); *A61B 5/0075* (2013.01);
(Continued)

(58) Field of Classification Search
CPC ....... A61B 5/0008; A61B 5/0015; A61B 5/01; A61B 5/1455; A61B 5/0059; A61B 5/68;
(Continued)

(56) References Cited

U.S. PATENT DOCUMENTS 3,463,885 A  8/1969  Upton
3,531,642 A  9/1970  Barnes et al.
(Continued)

FOREIGN PATENT DOCUMENTS

CN  2398565 Y  9/2000
CN  2446955 Y  9/2001
(Continued)

OTHER PUBLICATIONS

An Examiner's First Report; issued by the Australian Government, IP Australia dated Apr. 21, 2009, which corresponds to Australian Patent Application No. 2006306422.
(Continued)

*Primary Examiner* — Eric Winakur
(74) *Attorney, Agent, or Firm* — Studebaker & Brackett PC

(57) ABSTRACT

Support structures for positioning sensors on a physiologic tunnel for measuring physical, chemical and biological parameters of the body and to produce an action according to the measured value of the parameters. The support structure includes a sensor fitted on the support structures using a special geometry for acquiring continuous and undisturbed data on the physiology of the body. Signals are transmitted to a remote station by wireless transmission such as by electromagnetic waves, radio waves, infrared, sound and the like or by being reported locally by audio or visual transmission. The physical and chemical parameters include brain function, metabolic function, hydrodynamic function, hydration status, levels of chemical compounds in the blood, and the like. The support structure includes patches, clips, eyeglasses, head mounted gear and the like, containing passive or active sensors positioned at the end of the tunnel with sensing systems positioned on and accessing a physiologic tunnel.

20 Claims, 95 Drawing Sheets

Related U.S. Application Data continuation-in-part of application No. 10/420,295, filed on Apr. 22, 2003, now Pat. No. 7,187,960.

(60) Provisional application No. 60/497,306, filed on Aug. 25, 2003, provisional application No. 60/475,470, filed on Jun. 4, 2003, provisional application No. 60/449,800, filed on Feb. 26, 2003, provisional application No. 60/374,133, filed on Apr. 22, 2002.

(51) Int. Cl.
 A61B 5/1455 (2006.01)
 A61B 5/021 (2006.01)
 A61B 5/01 (2006.01)
 A61B 5/145 (2006.01)

(52) U.S. Cl.
 CPC ............. *A61B 5/01* (2013.01); *A61B 5/021* (2013.01); *A61B 5/02416* (2013.01); *A61B 5/412* (2013.01); *A61B 5/6803* (2013.01); *A61B 5/6821* (2013.01); *A61B 5/7405* (2013.01); *A61B 5/746* (2013.01); *A61B 5/14532* (2013.01); *A61B 5/14546* (2013.01); *A61B 5/14553* (2013.01); *A61B 2562/02* (2013.01)

(58) Field of Classification Search
 CPC ... A61B 5/6813; A61B 5/6814; A61B 5/6821; A61B 5/683
 See application file for complete search history.

(56) References Cited

U.S. PATENT DOCUMENTS

| | | | |
|---|---|---|---|
| 3,545,260 A | 12/1970 | Lichtenstein et al. | |
| 3,585,849 A | 6/1971 | Grolman | |
| 3,626,757 A | 12/1971 | Benzinger | |
| 3,724,263 A | 4/1973 | Rose et al. | |
| 3,769,961 A | 11/1973 | Fatt et al. | |
| 3,897,272 A | 7/1975 | Medlar | |
| 3,897,790 A | 8/1975 | Magilton et al. | |
| 3,963,019 A | 6/1976 | Quandt | |
| 4,186,184 A | 1/1980 | Zaffaroni | |
| 4,231,052 A | 10/1980 | Day et al. | |
| 4,297,685 A | 10/1981 | Brainard, II | |
| 4,305,399 A | 12/1981 | Beale | |
| 4,312,358 A | 1/1982 | Barney | |
| 4,321,261 A | 3/1982 | Ellis et al. | |
| 4,330,299 A | 5/1982 | Cerami | |
| 4,331,161 A | 5/1982 | Patel | |
| 4,344,315 A | 8/1982 | Moxon et al. | |
| 4,344,438 A | 8/1982 | Schultz | |
| 4,386,831 A | 6/1983 | Grounauer | |
| 4,444,990 A | 4/1984 | Villar | |
| 4,485,820 A | 12/1984 | Flower | |
| 4,488,558 A | 12/1984 | Simbruner et al. | |
| 4,595,020 A | 6/1986 | Palti | |
| 4,597,392 A | 7/1986 | Opitz et al. | |
| 4,628,938 A | 12/1986 | Lee | |
| 4,629,424 A | 12/1986 | Lauks et al. | |
| 4,771,792 A | 9/1988 | Seale | |
| 4,784,149 A | 11/1988 | Berman et al. | |
| 4,830,014 A | 5/1989 | Goodman et al. | |
| 4,846,196 A | 7/1989 | Wiksell et al. | |
| 4,860,755 A | 8/1989 | Erath | |
| 4,922,913 A | 5/1990 | Waters, Jr. et al. | |
| 4,944,303 A | 7/1990 | Katsuragi | |
| 4,947,849 A | 8/1990 | Takahashi et al. | |
| 4,951,671 A | 8/1990 | Coan | |
| 4,979,831 A | 12/1990 | Schertz et al. | |
| 5,005,577 A | 4/1991 | Frenkel | |
| 5,046,482 A | 9/1991 | Everest | |
| 5,062,432 A | 11/1991 | James et al. | |
| 5,076,274 A | 12/1991 | Matsumoto | |
| 5,109,852 A | 5/1992 | Kaye et al. | |
| 5,115,815 A | 5/1992 | Hansen | |
| 5,148,807 A | 9/1992 | Hsu | |
| 5,165,409 A | 11/1992 | Coan | |
| 5,179,953 A | 1/1993 | Kursar | |
| 5,183,044 A | 2/1993 | Nishio et al. | |
| 5,190,039 A | 3/1993 | Takeuchi et al. | |
| 5,209,231 A | 5/1993 | Cote et al. | |
| 5,217,015 A | 6/1993 | Kaye et al. | |
| 5,222,495 A | 6/1993 | Clarke et al. | |
| 5,222,809 A | 6/1993 | Ehrenkranz | |
| 5,246,867 A | 9/1993 | Lakowicz et al. | |
| 5,251,627 A | 10/1993 | Morris | |
| 5,255,979 A | 10/1993 | Ferrari | |
| 5,295,495 A | 3/1994 | Maddess | |
| 5,297,554 A | 3/1994 | Glynn et al. | |
| 5,341,805 A | 8/1994 | Stavridi et al. | |
| 5,342,283 A | 8/1994 | Good | |
| 5,342,789 A | 8/1994 | Chick et al. | |
| 5,352,411 A | 10/1994 | Khuri | |
| 5,356,780 A | 10/1994 | Robinson et al. | |
| 5,375,595 A | 12/1994 | Sinha et al. | |
| 5,383,452 A | 1/1995 | Buchert | |
| 5,431,170 A * | 7/1995 | Mathews | A61B 5/0002 600/323 |
| 5,433,197 A | 7/1995 | Stark | |
| 5,435,307 A | 7/1995 | Friauf et al. | |
| 5,441,476 A | 8/1995 | Kitado et al. | |
| 5,503,770 A | 4/1996 | James et al. | |
| 5,507,288 A * | 4/1996 | Bocker | A61B 5/0002 600/322 |
| 5,522,662 A | 6/1996 | Shiokawa | |
| 5,636,635 A | 6/1997 | Massie et al. | |
| 5,653,239 A | 8/1997 | Pompei et al. | |
| 5,664,578 A | 9/1997 | Boczan | |
| 5,673,692 A | 10/1997 | Schulze et al. | |
| 5,711,915 A | 1/1998 | Siegmund et al. | |
| 5,796,341 A | 8/1998 | Stratiotis | |
| 5,813,982 A | 9/1998 | Baratta | |
| 5,817,008 A | 10/1998 | Rafert et al. | |
| 5,820,557 A | 10/1998 | Hattori et al. | |
| 5,830,139 A | 11/1998 | Abreu | |
| 5,833,633 A | 11/1998 | Sarvazyan | |
| 5,854,078 A | 12/1998 | Asher et al. | |
| 5,860,934 A | 1/1999 | Sarvazyan | |
| 5,862,803 A | 1/1999 | Besson et al. | |
| 5,898,004 A | 4/1999 | Asher et al. | |
| 5,984,880 A | 11/1999 | Lander et al. | |
| 5,994,701 A | 11/1999 | Tsuchimoto et al. | |
| 6,011,984 A | 1/2000 | Van Antwerp et al. | |
| 6,028,323 A | 2/2000 | Liu | |
| 6,040,194 A | 3/2000 | Chick et al. | |
| 6,042,266 A | 3/2000 | Cheslock et al. | |
| 6,047,203 A | 4/2000 | Sackner et al. | |
| 6,072,180 A | 6/2000 | Kramer et al. | |
| 6,120,460 A | 9/2000 | Abreu | |
| 6,123,668 A | 9/2000 | Abreu | |
| 6,126,595 A | 10/2000 | Amano et al. | |
| 6,135,968 A | 10/2000 | Brounstein | |
| 6,152,875 A | 11/2000 | Hakamata | |
| 6,178,346 B1 | 1/2001 | Amundson et al. | |
| 6,181,957 B1 | 1/2001 | Lambert et al. | |
| 6,187,599 B1 | 2/2001 | Asher et al. | |
| 6,196,714 B1 | 3/2001 | Bellifemine et al. | |
| 6,197,534 B1 | 3/2001 | Lakowicz et al. | |
| 6,197,928 B1 | 3/2001 | Tsien et al. | |
| 6,203,193 B1 | 3/2001 | Egawa | |
| 6,213,943 B1 | 4/2001 | Abreu | |
| 6,256,522 B1 | 7/2001 | Schultz | |
| 6,290,658 B1 | 9/2001 | Kolich | |
| 6,292,685 B1 | 9/2001 | Pompei | |
| 6,300,871 B1 | 10/2001 | Irwin et al. | |
| 6,312,393 B1 | 11/2001 | Abreu | |
| 6,319,540 B1 | 11/2001 | Van Antwerp et al. | |
| 6,385,473 B1 | 5/2002 | Haines et al. | |
| 6,385,474 B1 | 5/2002 | Rather et al. | |
| 6,423,001 B1 | 7/2002 | Abreu | |
| 6,432,050 B1 | 8/2002 | Porat et al. | |
| 6,470,893 B1 | 10/2002 | Boesen | |

(56) References Cited

U.S. PATENT DOCUMENTS

| | | |
|---|---|---|
| 6,529,617 B1 | 3/2003 | Prokoski |
| 6,536,945 B2 | 3/2003 | Rolston |
| 6,542,081 B2 | 4/2003 | Torch |
| 6,543,933 B2 | 4/2003 | Stergiopoulos et al. |
| 6,544,193 B2 | 4/2003 | Abreu |
| 6,681,127 B2 | 1/2004 | March |
| 6,731,976 B2 | 5/2004 | Penn et al. |
| 6,789,901 B1 | 9/2004 | Kormos |
| 6,791,087 B1 | 9/2004 | Okumura |
| 6,846,106 B1 | 1/2005 | Chen et al. |
| 7,187,960 B2 | 3/2007 | Abreu |
| 7,340,293 B2 | 3/2008 | McQuilkin |
| 7,346,386 B2 | 3/2008 | Pompei |
| 7,515,054 B2 | 4/2009 | Torch |
| 7,597,668 B2 | 10/2009 | Yarden |
| 7,621,877 B2 | 11/2009 | Schnall |
| 7,689,437 B1 | 3/2010 | Teller et al. |
| 7,756,559 B2 | 7/2010 | Abreu |
| 7,787,938 B2 | 8/2010 | Pompei |
| 7,837,623 B2 | 11/2010 | Aubry et al. |
| 8,103,071 B2 | 1/2012 | Schnell et al. |
| 8,172,459 B2 | 5/2012 | Abreu |
| 8,328,420 B2 | 12/2012 | Abreu |
| 8,500,271 B2 | 8/2013 | Howell et al. |
| 8,527,022 B1 | 9/2013 | Lash et al. |
| 8,721,562 B2 | 5/2014 | Abreu |
| 8,834,020 B2 | 9/2014 | Abreu |
| 8,849,379 B2 | 9/2014 | Abreu |
| 9,007,220 B2 | 4/2015 | Johns et al. |
| 2001/0028309 A1 | 10/2001 | Torch |
| 2002/0026119 A1 | 2/2002 | Pompei |
| 2002/0035340 A1 | 3/2002 | Fraden et al. |
| 2002/0049374 A1 | 4/2002 | Abreu |
| 2002/0049389 A1 | 4/2002 | Abreu |
| 2002/0068876 A1 | 6/2002 | Pompei et al. |
| 2002/0111657 A1 | 8/2002 | Dae et al. |
| 2002/0126731 A1 | 9/2002 | Stergiopoulos et al. |
| 2003/0055473 A1 | 3/2003 | Ramsden et al. |
| 2003/0060863 A1 | 3/2003 | Dobak, III |
| 2003/0067958 A1 | 4/2003 | Jang |
| 2003/0108223 A1 | 6/2003 | Prokoski |
| 2003/0111605 A1 | 6/2003 | Sato et al. |
| 2003/0179094 A1 | 9/2003 | Abreu |
| 2003/0210146 A1 | 11/2003 | Tseng |
| 2003/0212340 A1 | 11/2003 | Lussier et al. |
| 2004/0039298 A1 | 2/2004 | Abreu |
| 2004/0059212 A1 | 3/2004 | Abreu |
| 2004/0076316 A1 | 4/2004 | Fauci |
| 2004/0082862 A1 | 4/2004 | Chance |
| 2004/0125996 A1 | 7/2004 | Eddowes et al. |
| 2004/0152991 A1 | 8/2004 | Pompei |
| 2004/0154550 A1 | 8/2004 | McQuilkin |
| 2004/0170216 A1 | 9/2004 | Russak et al. |
| 2004/0210159 A1 | 10/2004 | Kibar |
| 2004/0246548 A1 | 12/2004 | Papuchon et al. |
| 2005/0250996 A1 | 11/2005 | Shirai et al. |
| 2006/0122473 A1 | 6/2006 | Kill et al. |
| 2006/0215728 A1 | 9/2006 | Jang |
| 2006/0264726 A1 | 11/2006 | Mannheimer et al. |
| 2007/0055171 A1 | 3/2007 | Fraden |
| 2007/0219434 A1 | 9/2007 | Abreu |
| 2008/0043809 A1 | 2/2008 | Herbert |
| 2008/0200830 A1 | 8/2008 | Pompei |
| 2008/0214949 A1 | 9/2008 | Stivoric et al. |
| 2009/0105605 A1 | 4/2009 | Abreu |
| 2009/0157056 A1 | 6/2009 | Ferren et al. |
| 2010/0022909 A1 | 1/2010 | Padiy |
| 2010/0113894 A1 | 5/2010 | Padiy |
| 2010/0204765 A1 | 8/2010 | Hall et al. |
| 2011/0024626 A1 | 2/2011 | O'Donnell et al. |
| 2011/0040161 A1 | 2/2011 | Abreu |
| 2011/0077546 A1 | 3/2011 | Fabian |
| 2011/0092822 A1 | 4/2011 | Pompei |
| 2012/0031405 A1 | 2/2012 | Geist et al. |
| 2012/0136285 A1 | 5/2012 | Korb et al. |
| 2013/0124039 A1 | 5/2013 | Abreu |
| 2013/0215928 A1 | 8/2013 | Bellifemine |
| 2013/0292571 A1 | 11/2013 | Mukherjee et al. |

FOREIGN PATENT DOCUMENTS

| | | |
|---|---|---|
| CN | 1328432 A | 12/2001 |
| DE | 4433104 C1 | 5/1996 |
| EP | 0236028 A2 | 9/1987 |
| EP | 0411121 A1 | 2/1991 |
| EP | 2 120 681 B1 | 7/2011 |
| EP | 1 951 110 B1 | 10/2012 |
| JP | S61-48369 A | 3/1986 |
| JP | H10-075934 A | 3/1998 |
| JP | H10-239158 A | 9/1998 |
| JP | H11-164826 A | 6/1999 |
| JP | 2001-500394 A | 1/2001 |
| JP | 2001/031151 A | 2/2001 |
| JP | 2002-525132 A | 8/2002 |
| JP | 3885024 B2 | 2/2007 |
| WO | 93/01745 A1 | 2/1993 |
| WO | 97/19188 A1 | 5/1997 |
| WO | 98/22820 A1 | 5/1998 |
| WO | 99/51142 A2 | 10/1999 |
| WO | 00/10007 A2 | 2/2000 |
| WO | 00/13580 A1 | 3/2000 |
| WO | 00/16051 A1 | 3/2000 |
| WO | 00/16099 A1 | 3/2000 |
| WO | 00/18237 A1 | 4/2000 |
| WO | 00/64492 A1 | 11/2000 |
| WO | 02/03855 A1 | 1/2002 |
| WO | 02/28271 A2 | 4/2002 |
| WO | 02/067688 A1 | 9/2002 |
| WO | 2005/015163 A2 | 2/2005 |
| WO | 2010-042738 A2 | 4/2010 |

OTHER PUBLICATIONS

An Examiner's Report No. 2; issued by the Australian Government, IP Australia dated Nov. 10, 2010, which corresponds to Australian Patent Application No. 2006306422.

English translation of an Office Action; issued by the Korean Intellectual Property Office dated Jun. 21, 2013, which corresponds to Korean Patent Application No. 10-2008-7012335.

English translation of an Office Action; issued by the Japanese Patent Office dated Nov. 17, 2011, which corresponds to Japanese Patent Application No. 2008-537828.

English translation of a Second Office Action; issued by the Japanese Patent Office dated Nov. 13, 2012, which corresponds to Japanese Patent Application No. 2008-537828.

English translation of a Third Office Action; issued by the Japanese Patent Office dated Nov. 26, 2013, which corresponds to Japanese Patent Application No. 2008-537828.

Overton, Staci. "Brain Temperature Tunnel Discovered." Medical Breakthroughs Reported by Ivanhoe, Jun. 2, 2003.

International Search Report; PCT/US2014/060199; dated Jan. 8, 2015.

International Search Report; PCT/US2014/060201; dated Mar. 3, 2015.

Dittmar, A. et al., A Non Invasive Wearable Sensor for the Measurement of Brain Temperature. Proceedings of the 28th IEEE EMBS Annual International Conference. Aug. 30-Sep. 3, 2006. pp. 900-902, New York City, USA.

An Office Action and Examination Search Report issued by the Canadian Intellectual Property Office dated Mar. 26, 2015, which corresponds to Canadian Patent Application No. 2,627,278.

International Search Report; PCTUS2015/010873; dated Apr. 10, 2015.

English translation of an Unfavorable Technical Opinion; issued by the National Institute of Industrial Property, which corresponds to Brazilian Patent Application BR122013001249-4.

RCA Technical Notes, Contact Lens Tonometer by Robert E. Morey, RCA TN No. 602, dated Dec. 1964, 2 pages.

Ophthal. Physiol. Opt., 1989, vol. 9, April, Research Note, Multiple Applications of the NCT: An Assessment of Instrument's Effect on

(56) References Cited

OTHER PUBLICATIONS

IOP by G.E. Russell and J.P.G. Bergmanson, pp. 212-214.
Arch Ophthalmol—vol. 97, Mar. 1979, The Pneumatonograph—A Laboratory Study, by Robert A. Moses, M.D. and Walter J. Grodzki Jr., D.D.S., pp. 547-552.
IEEE Transactions on bio-Medical Engineering, vol. BME-14, No. 2, Apr. 1967, Miniature Passive Pressure Transensor for Implanting in the Eye, by C.C. Collins, pp. 74-83.
Trans. Amer. Acad. of O. & O., Jan.-Feb. 1957, Tonometer Calibration, An Attempt to Remove Discrepancies Found in the 1954 Calibration Scale for Schiotz Tonometers by Jonas S. Friedenwald, M.D., pp. 108-123.
Investigative Ophthalmology, Feb. 1962, The Relationship Between Pressure and Volume Changes in Living and Dead Rabbit Eyes, by John E. Eisenlohr and Maurice E. Longhorn, pp. 63-77.
Investigative Ophthalmology, Sep. 1971, vol. 10, No. 9, Theory and Calibration of the Schiotz Tonometer VII. Experimental Results of Tonometric Measurements: Scale Reading Versus Indentation Volume, by Robert A. Moses and Walter J. Grodzki, pp. 716-723.
The British Journal of Ophthalmology, Jun. 1920, Communications-Tonometry, by HJ. Schiötz, pp. 249-261.
American Journal of Opthalmology, vol. 20, No. 10, Oct. 1937, Contribution to the Theory and Practice of Tonometry by Jonas S. Friedenwald, M.D., pp. 985-1024.
Ophthalmologica vol. 150, No. 5, (1965), Rheology of the Human Sclera, Unifying Formulation of Ocular Rigidity, by W.K. McEwen and Roger St. Helen, pp. 321-346.
A.M.A. Archives of Ophthalmology, vol. 57, Apr. 1957, Tonometer Calibration, by Earle H. McBain, M.D., pp. 520-531.
The Photonics Dictionary, 1996 Book 4, 42nd Edition, pp. D-24, D153.
Manual of Skin Diseases, Fifth Edition, Gordon C. Sauer, MD., 1985, pp. 204, 373.
FM-2 Fluarotron™ Master Ocular Fluorophotometer, 1994 OcuMetrics, Inc.
Textbook of Biochemistry With Clinical Correlations, Second Edition, Thomas M. Devlin, Ph.D., 1986, pp. 118, 139.
Physical Optics, Third Revised Edition, Robert W. Wood, 1961, pp. 650-651.
An Examiner's First Report; issued by the Australian Government, IP Australia dated Dec. 18, 2008, which corresponds to Australian Patent Application No. 2004263812.
An Examiner's First Report; issued by the Australian Government, IP Australia dated Mar. 10, 2010, which corresponds to Australian Patent Application No. 2009212808.
An Examiner's First Report; issued by the Australian Government, IP Australia dated Feb. 19, 2010, which corresponds to Australian Patent Application Na 2009212861.
An Examiner's First Report; issued by the Australian Government, IP Australia dated Nov. 4, 2013, which corresponds to Australian Patent Application Na 2012247045.
An Office Action issued by the Canadian Intellectual Property Office dated May 3, 2012, which corresponds to Canadian Patent Application No. 2,517,869.
English translation of a First Office Action and Search Report; issued by the State Intellectual Property Office of the People's Republic of China dated Jul. 21, 2014, which corresponds to Chinese Patent Application No. 201310097177.3.
English translation of a First Office Action and Search Report; issued by the State Intellectual Property Office of the People's Republic of China dated Jul. 22, 2014, which corresponds to Chinese Patent Application No. 201310097142.X.
A supplementary European Search Report; issued by the European Patent Office dated Oct. 17, 2008, which corresponds to European Patent Application No. 04785841.0-1265.
A "Communication pursuant to Article 94(3) EPC," issued by the European Patent Office dated Jan. 27, 2009, which corresponds to European Patent Application No. 04785841.0-1265.

A "Communication pursuant to Article 94(3) EPC," issued by the European Patent Office dated Sep. 12, 2013, which corresponds to European Patent Application No. 04785841.0-1657.
English Translation of Relevant Portion of Office Action; issued by the State of Israel Department of Justice, Patent Office dated Jul. 3, 2013, which corresponds to Israeli Patent Application No. 1704896.
English translation of Notification of Reasons for Refusal; issued by the Japanese Patent Office dated Jun. 11, 2009, which corresponds to Japanese Patent Application No. 2006-508817.
English translation of Notification of Reasons for Refusal; issued by the Japanese Patent Office dated Jan. 12, 2010, which corresponds to Japanese Patent Application No. 2006-508817.
A Summarized English Translation of Office Action; issued by the Instituto Mexicana de la Propiedad Industrial dated Jul. 4, 2008, which corresponds to Mexican National Phase Patent Application No. PA/a/2005/009159.
An Office Action; issued by the Instituto Mexicana de la Propiedad Industrial dated Sep. 25, 2009, which corresponds to Mexican National Phase Patent Application No. PA/a/2005/009159.
International Search Report & Written Opinion; PCT/US2004/005496; dated May 6, 2005.
English translation of an Office Action; issued by the Japanese Patent Office dated Jan. 22, 2009, which corresponds to Japanese Patent Application No. 2004-515642.
English translation of an Office Action; issued by the National Institute of Industrial Property dated Jul. 1, 2013, which corresponds to Brazilian Patent Application PI0309578-9.
English translation of an Office Action; issued by the National Institute of Industrial Property, which corresponds to Brazilian Patent Application PI0309578-9.
English translation of the "First Office Action," and "Search Report," issued by the State Intellectual Property Office of the People's Republic of China dated Jun. 4, 2014, which corresponds to Chinese Application No. 201210361917.5.
A "Communication pursuant to Article 94(3) EPC," issued by the European Patent Office dated Jan. 27, 2009, which corresponds to European Patent Application No. 03 754 363.4-1265.
A second "Communication pursuant to Article 94(3) EPC," issued by the European Patent Office dated Sep. 13, 2013, which corresponds to European Patent Application No. 03 754 363.4-1657.
A third "Communication pursuant to Article 94(3) EPC," issued by the European Patent Office dated Mar. 4, 2014, which corresponds to European Patent Application No. 03 754 363.4-1657.
A fourth "Communication pursuant to Article 94(3) EPC," issued by the European Patent Office dated Sep. 24, 2014, which corresponds to European Patent Application No. 03 754 363.4-1657.
English translation of an Office Action; issued by the State of Israel Department of Justice, Patent Office dated Nov. 26, 2008, which corresponds to Israeli Patent Application No. 164685.
English translation of an Office Action; issued by the Korean Intellectual Property Office dated Dec. 26, 2011, which corresponds to Korean Patent Application No. 10-2010-7018173.
International Search Report; PCT/US03/12382; dated May 13, 2005.
International Search Report; PCT/US2006/041238; dated Aug. 31, 2007.
An Office Action issued by the Canadian Intellectual Property Office dated Aug. 2, 2011, which corresponds to Canadian Patent Application No. 2,627,278.
A Second Office Action issued by the Canadian Intellectual Property Office dated Mar. 14, 2012, which corresponds to Canadian Patent Application No. 2,627,278.
A "Communication pursuant to Particle 94(3) EPC," issued by the European Patent Office dated May 13, 2011, which corresponds to European Patent Application No. 06 826 452.2-2319.
English translation of an Office Action; issued by the State of Israel Department of Justice, Patent Office dated Jun. 23, 2011, which corresponds to Israeli Patent Application No. 191039.
An Examiner's First Report; issued by the Australian Government, IP Australia dated Jan. 13, 2012, which corresponds to Australian Patent Application No. 2011202015.

(56) References Cited

OTHER PUBLICATIONS

Patent Examination Report No. 1; issued by the Australian Government, IP Australia dated Dec. 13, 2013, which corresponds to Australian Patent Application No. 2012203667.

* cited by examiner

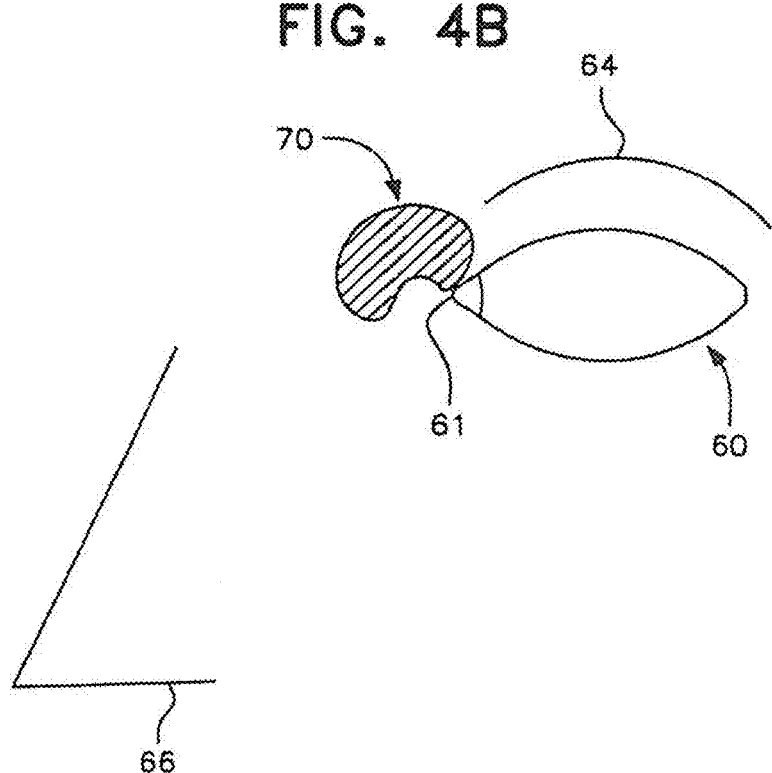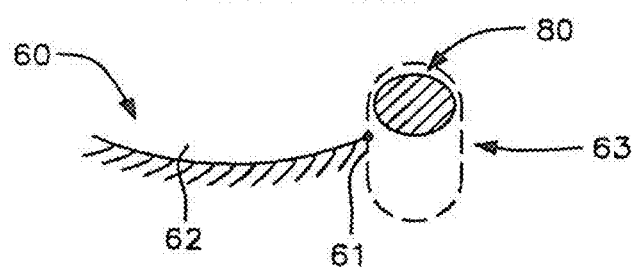

FIG. 6A
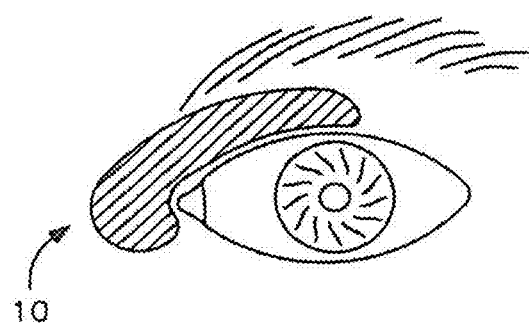
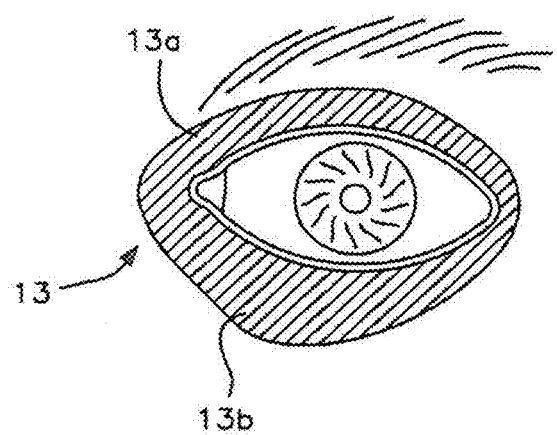

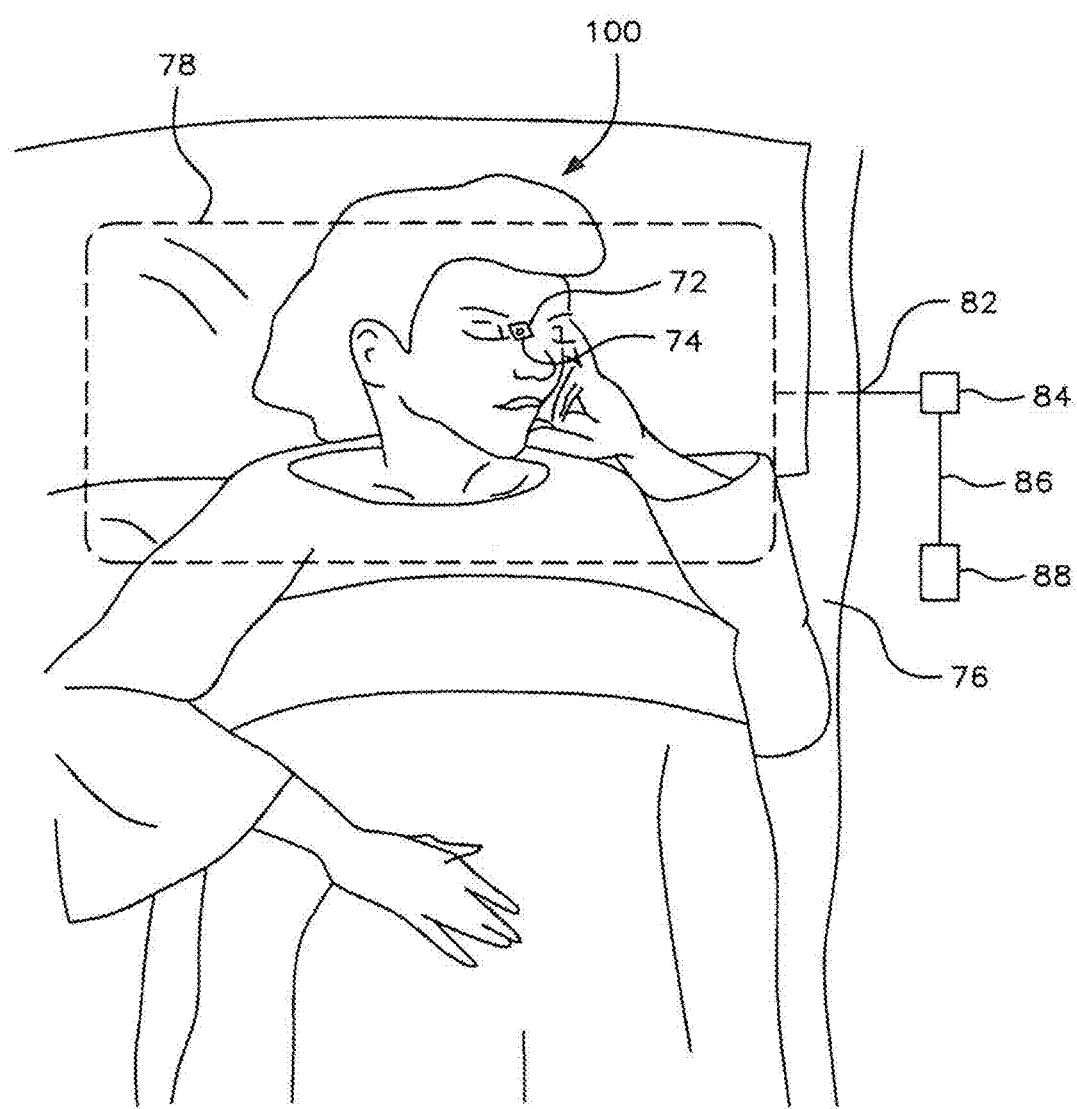

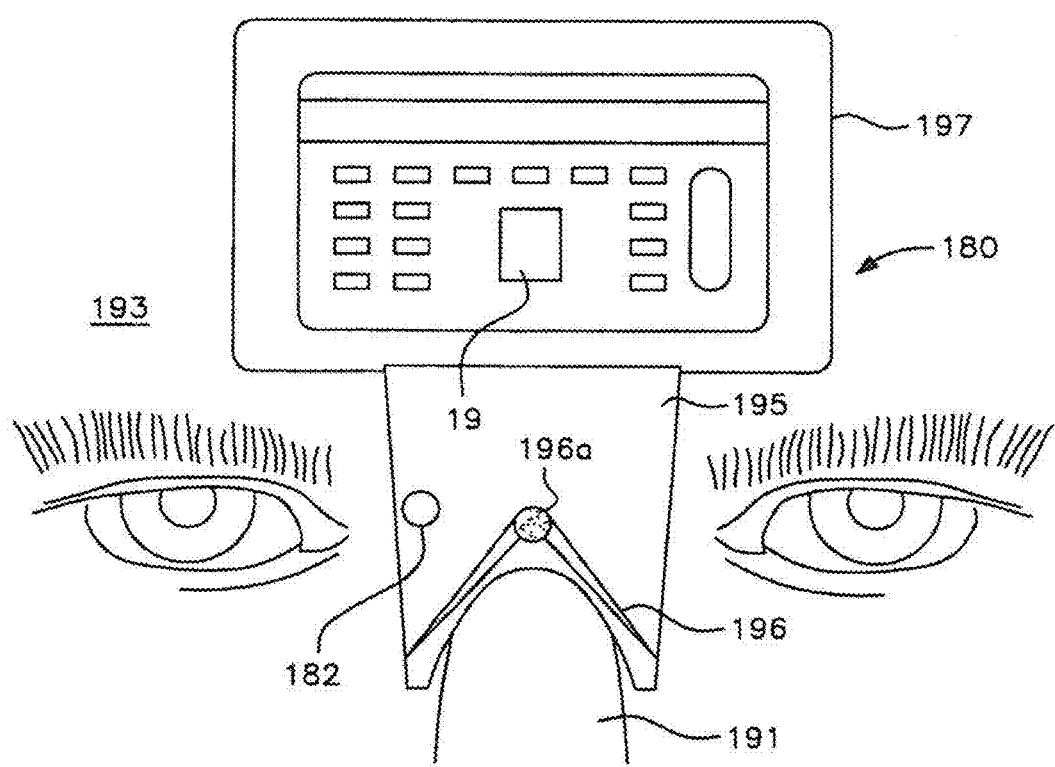

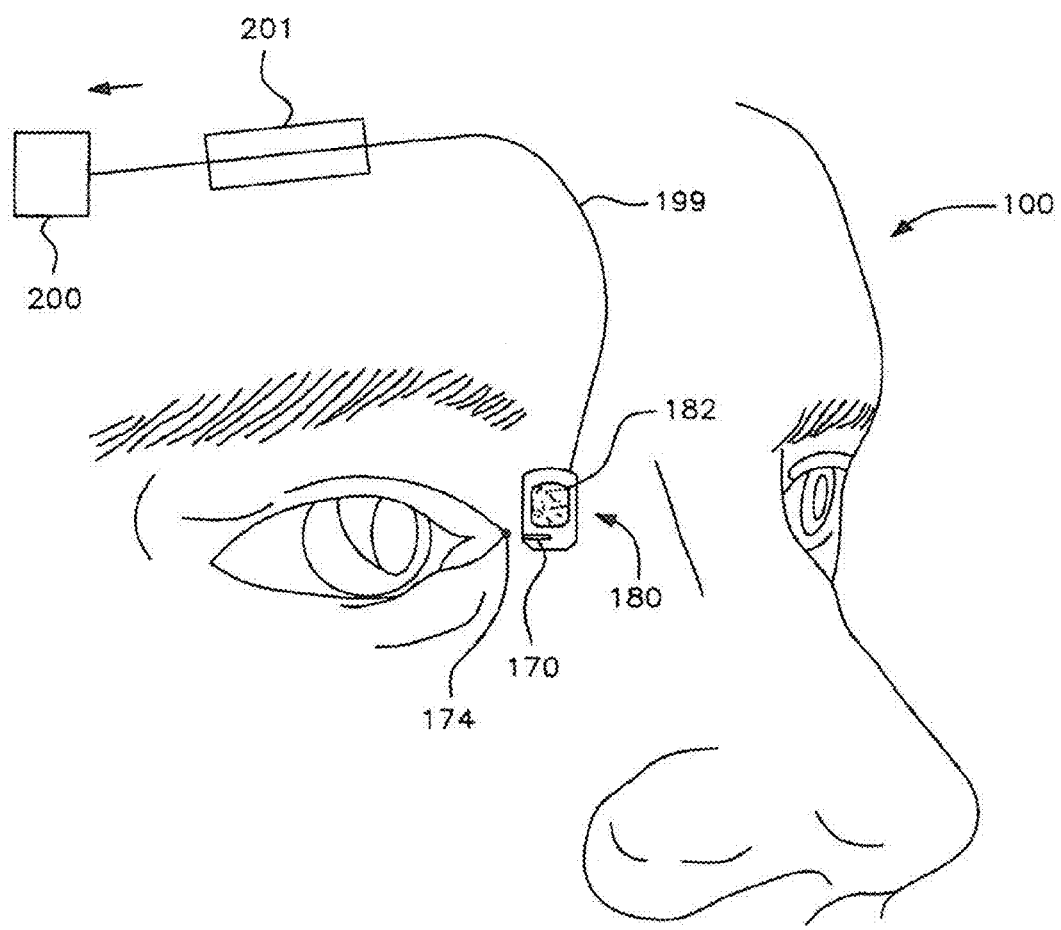

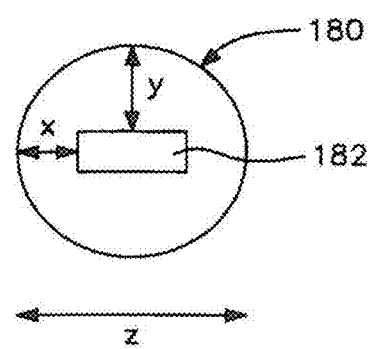
FIG. 19A1
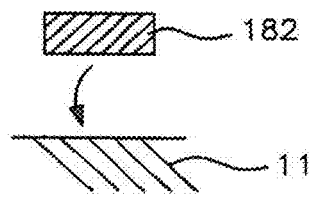
FIG. 19A2
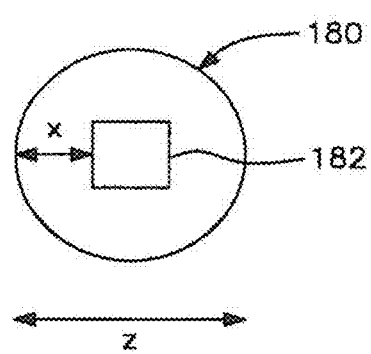
FIG. 19B
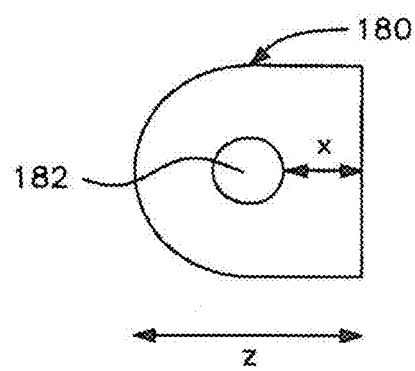
FIG. 19C
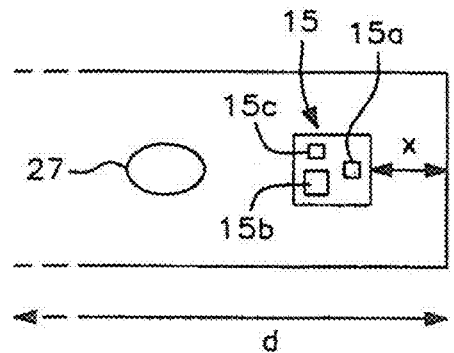
FIG. 19D

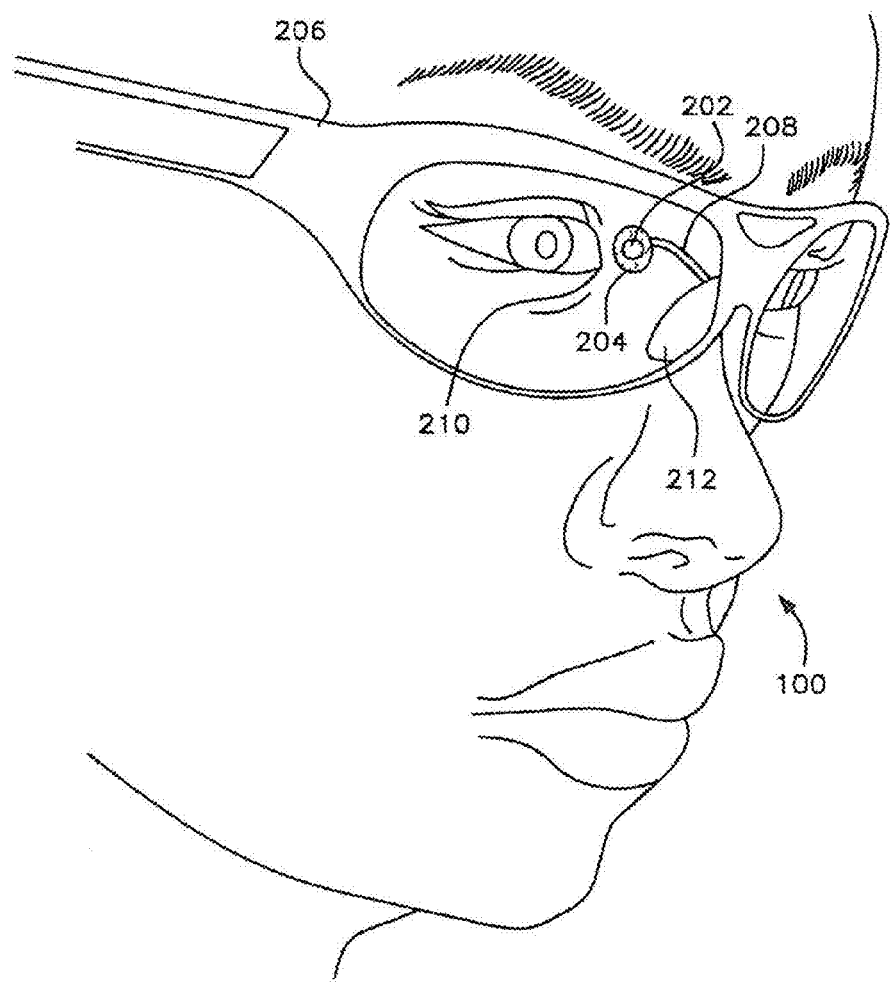

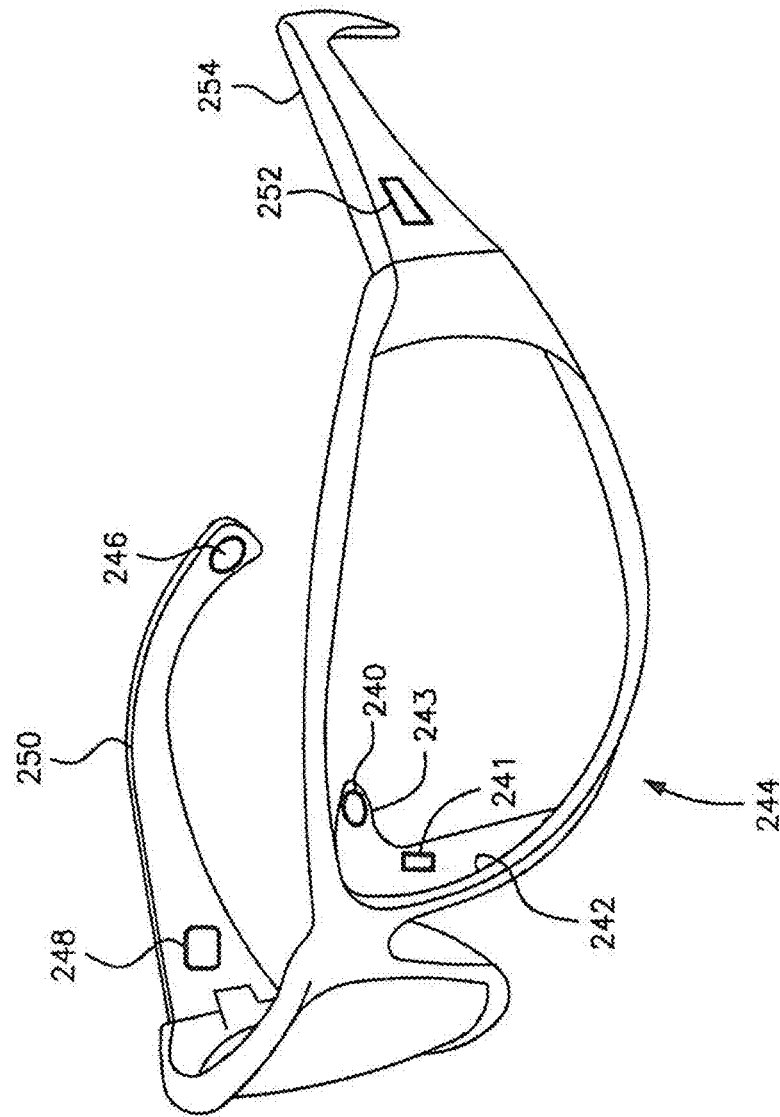

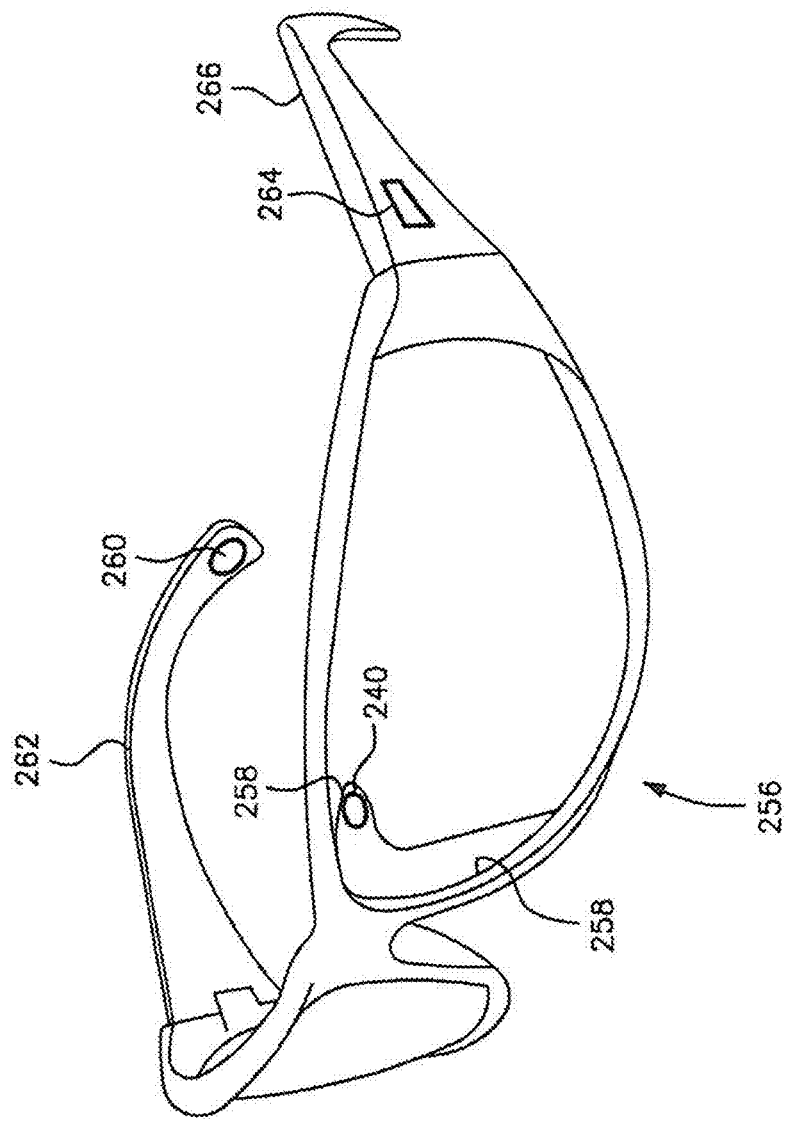

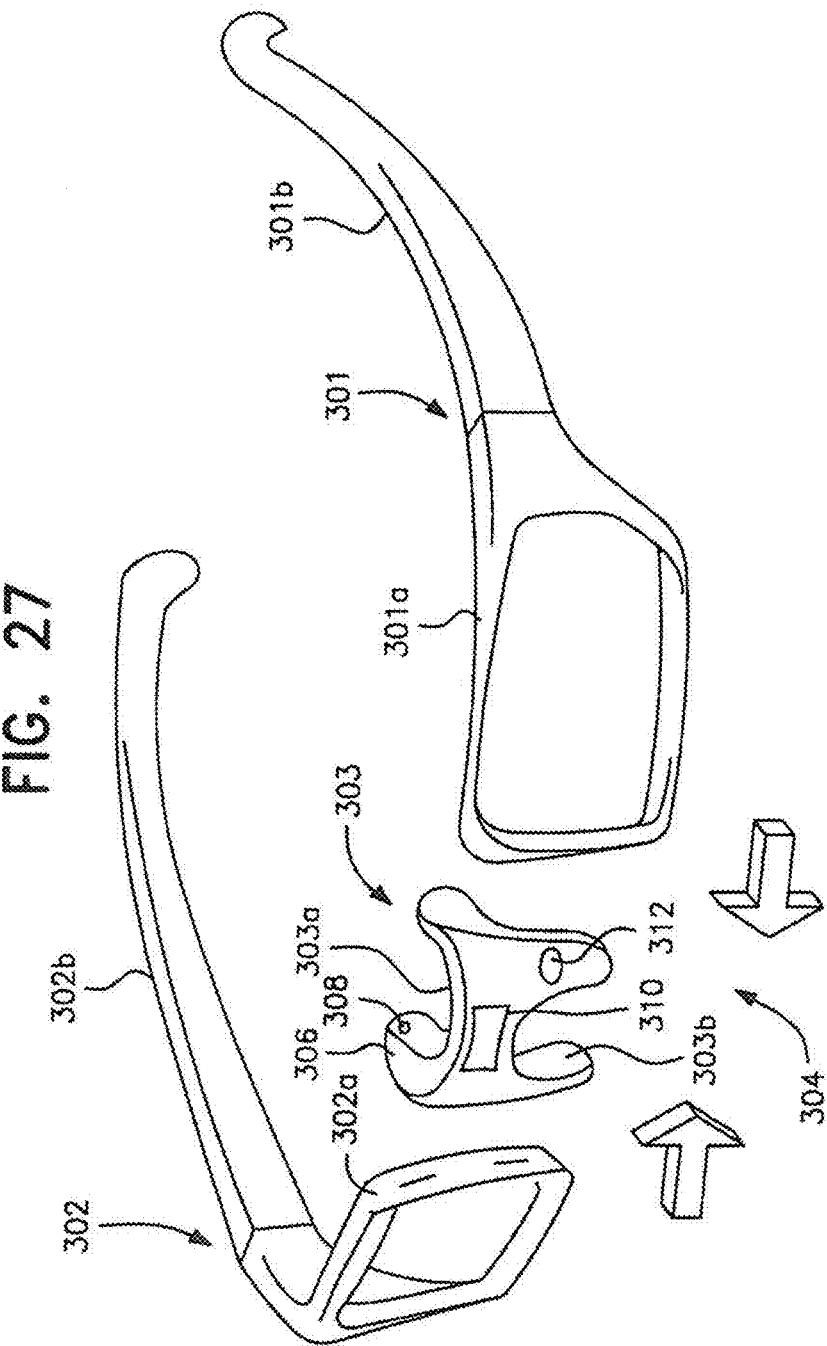

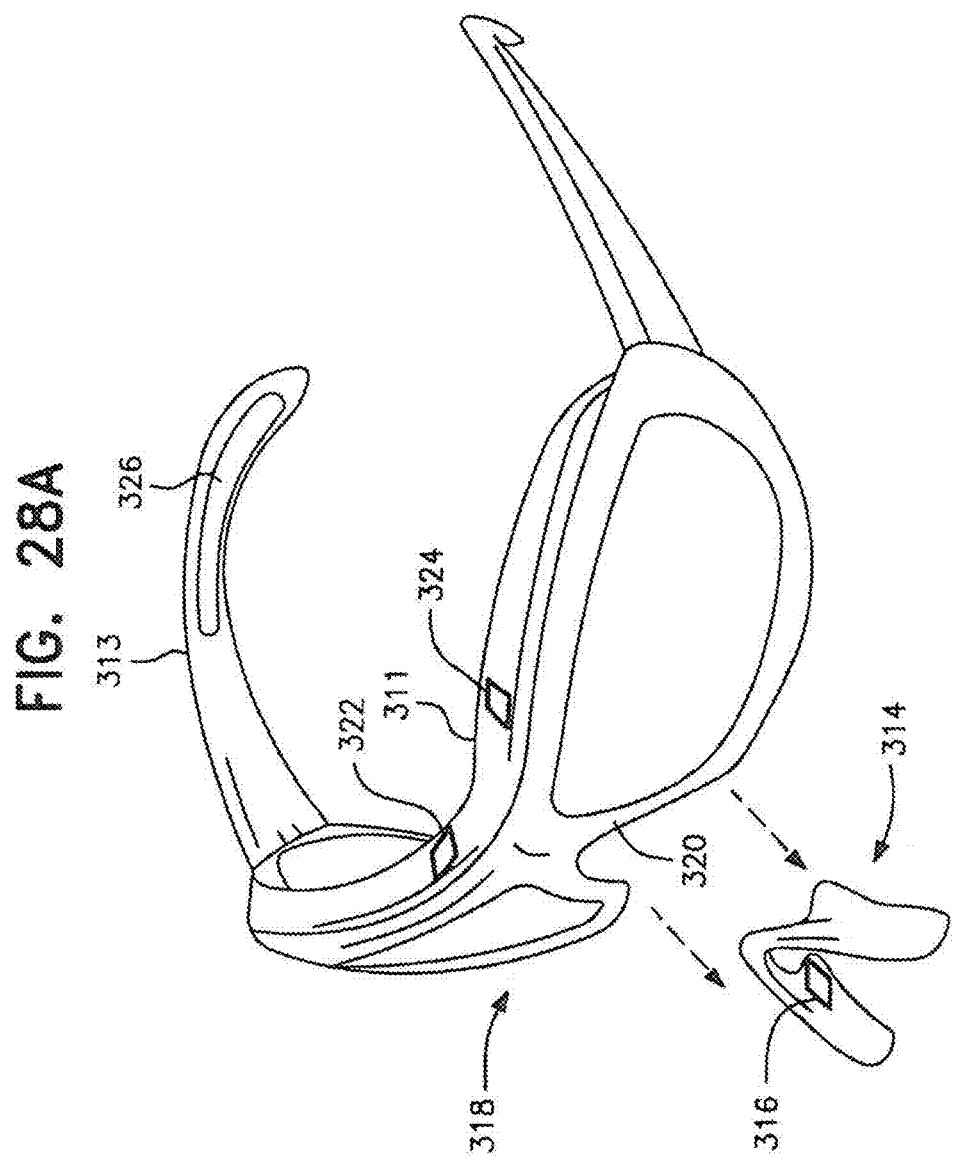

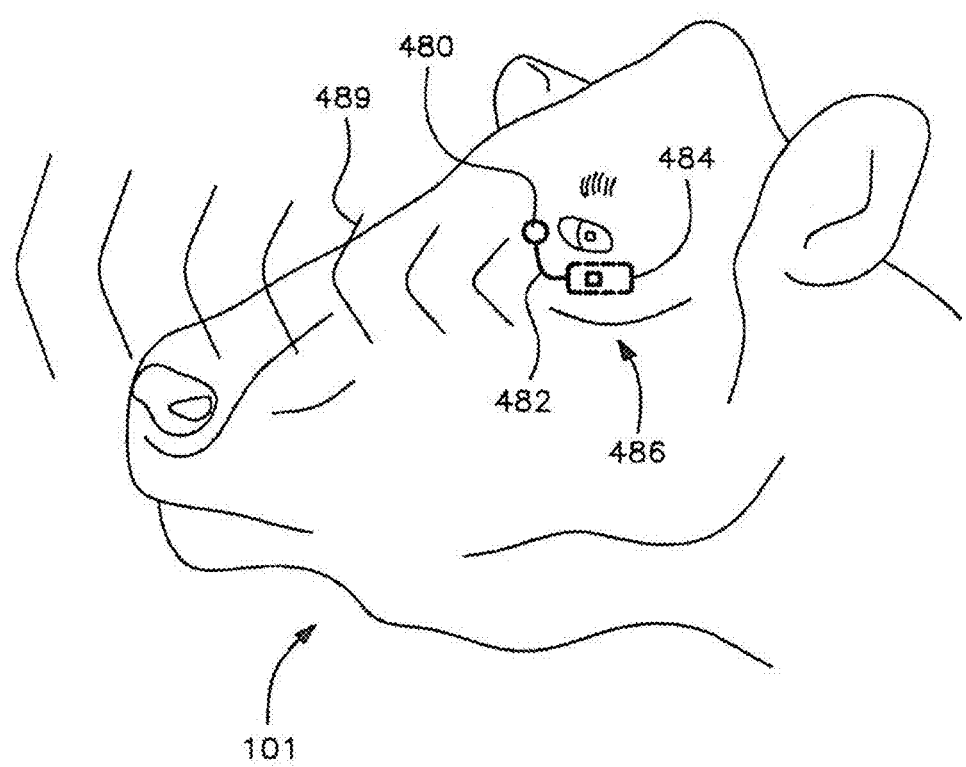

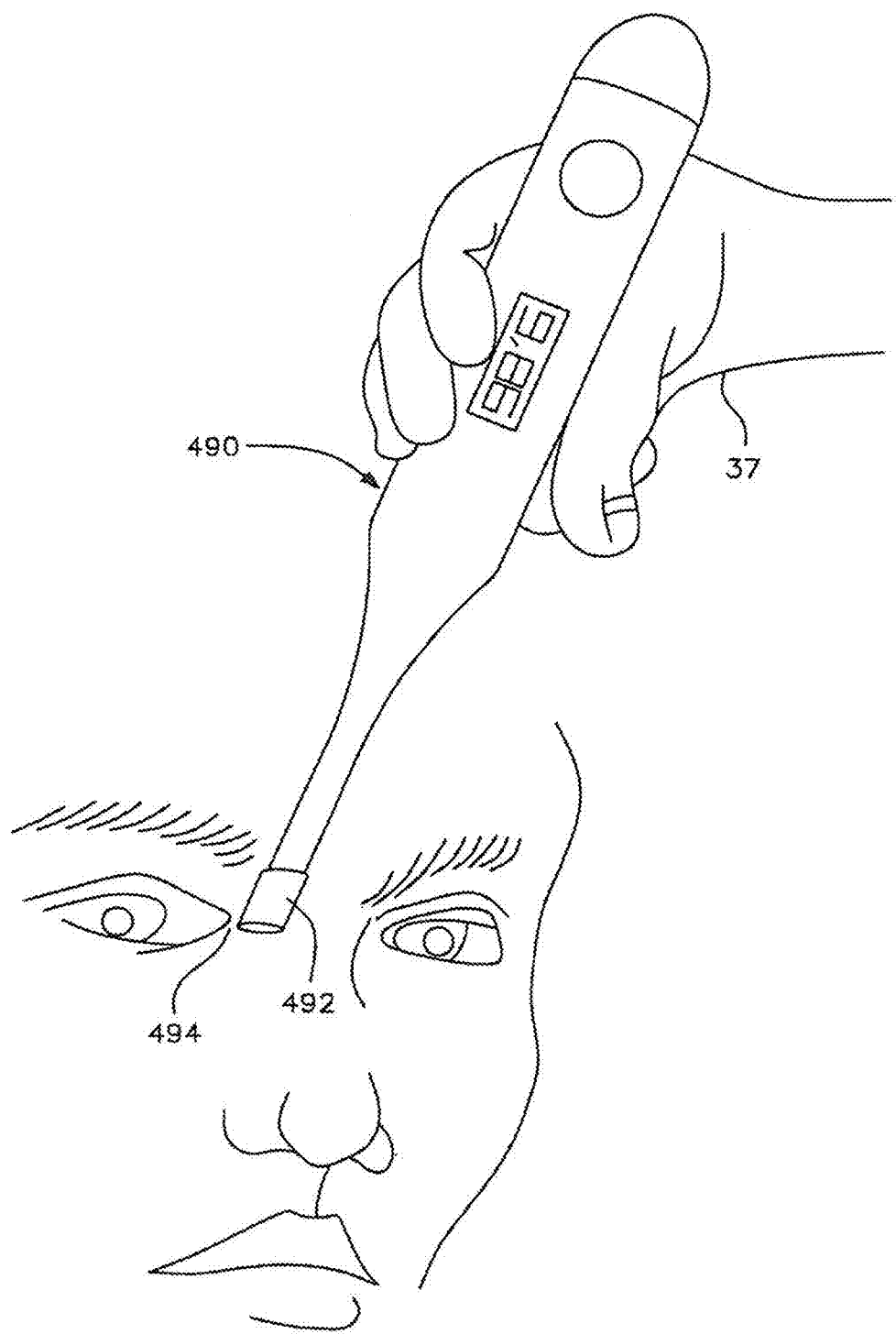

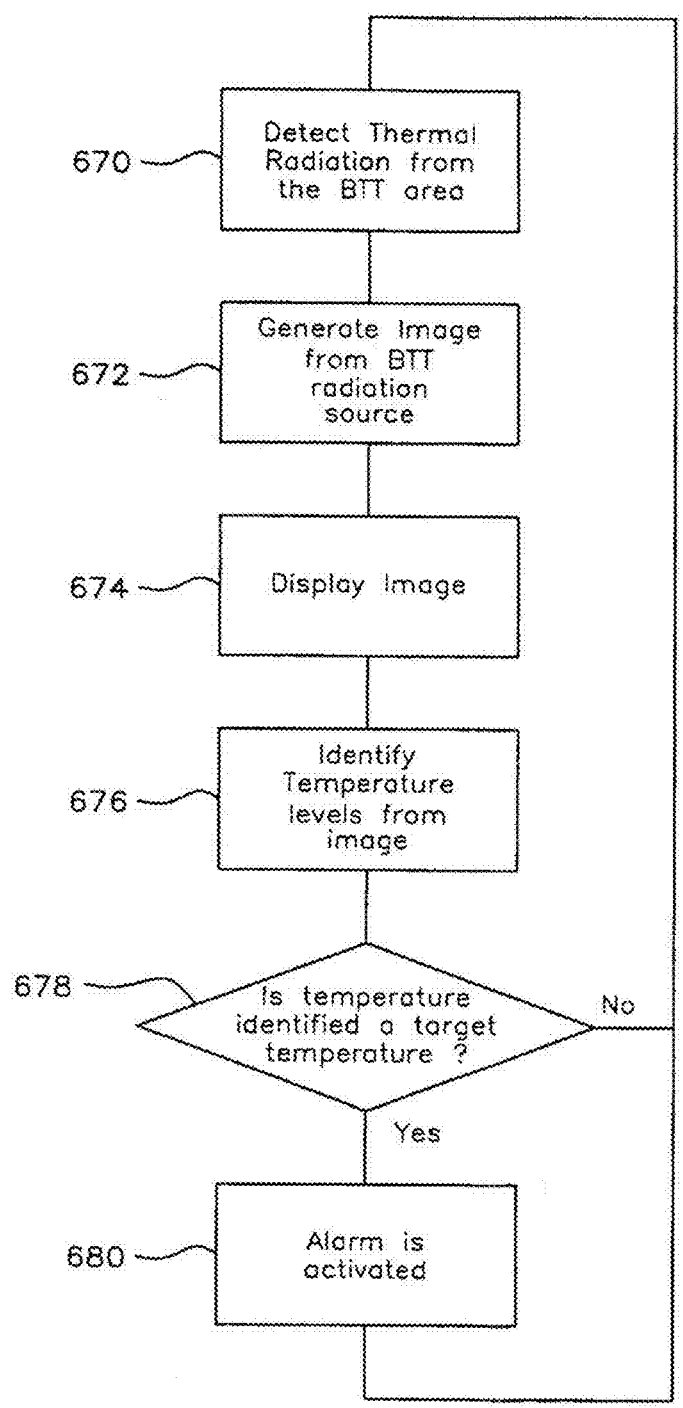

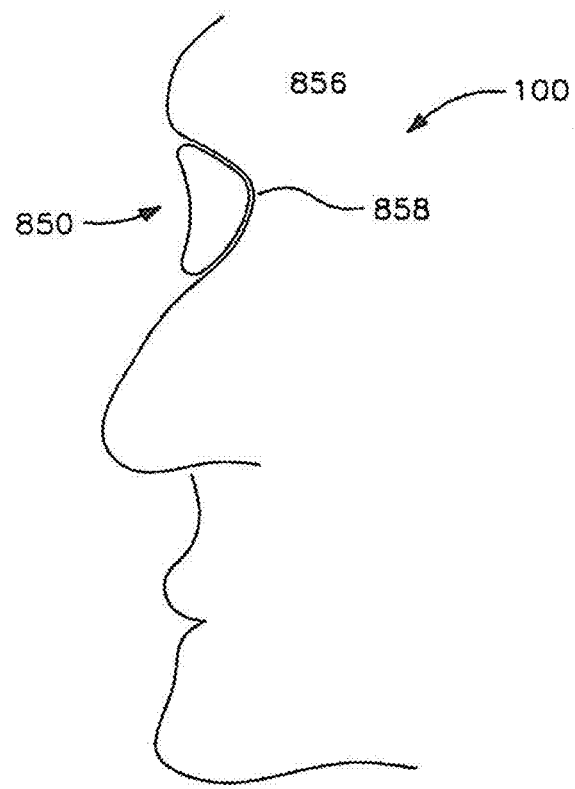
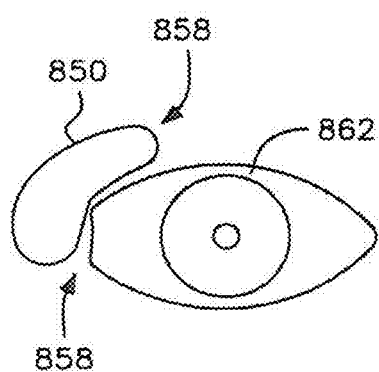

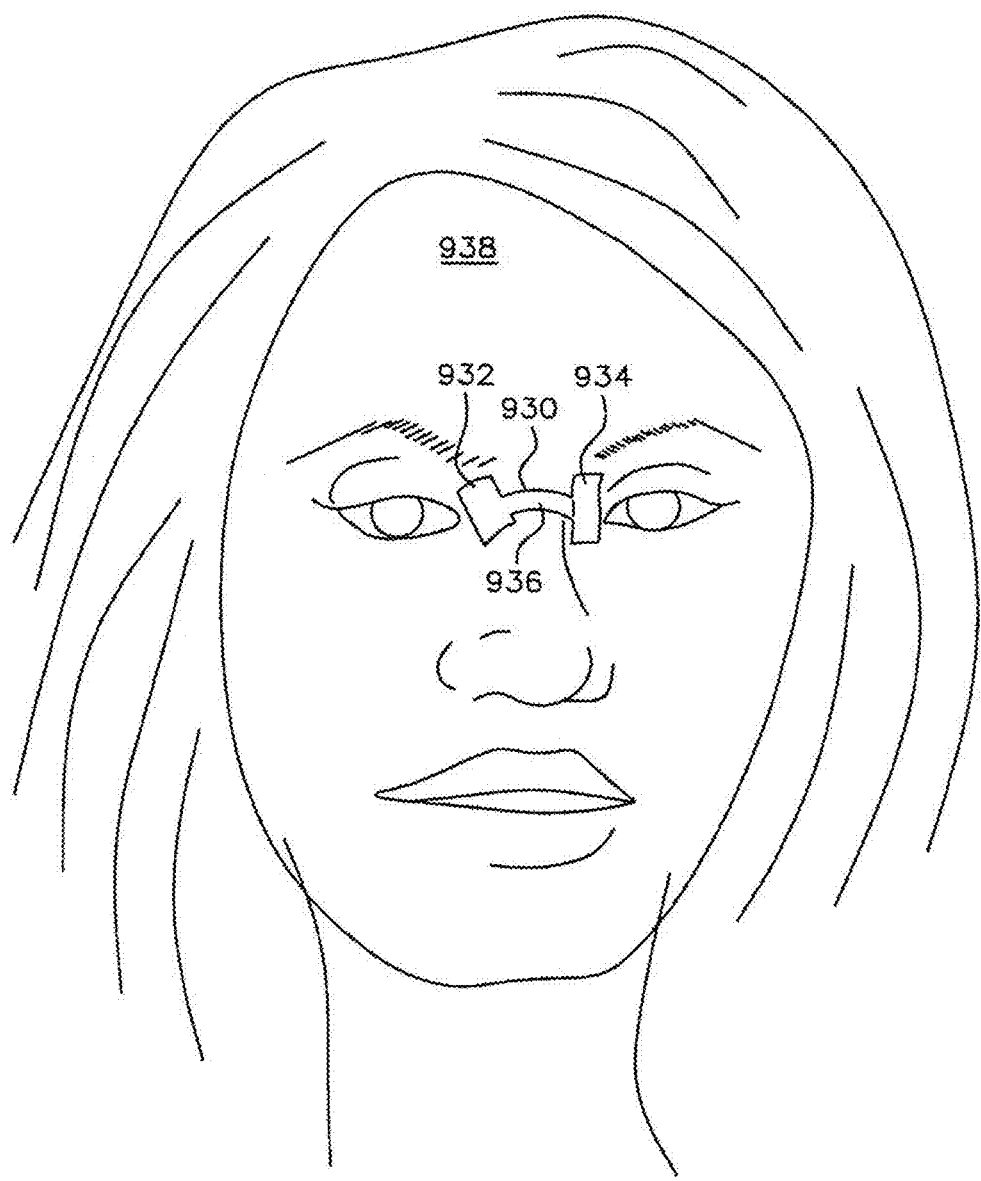

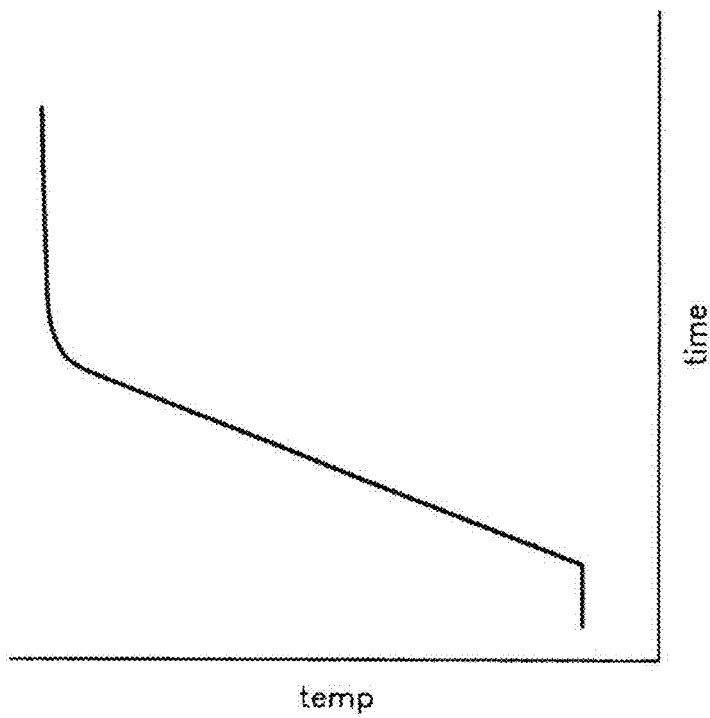

FIRST STEP: C. SCREEN

SECOND STEP: RADIO RCV DIRECTION FINDER

APPARATUS AND METHOD FOR MEASURING BIOLOGIC PARAMETERS

This application is a continuation of U.S. Ser. No. 10/786,623, filed Feb. 26, 2004, which is a continuation-in-part of U.S. Ser. No. 10/420,295, filed Apr. 22, 2003, which claims the benefit of U.S. Provisional Application Ser. No. 60/374,133, filed Apr. 22, 2002, and claims the benefit of the priority of 60/449,800, filed Feb. 26, 2003, 60/475,470, filed Jun. 4, 2003 and 60/497,306, filed Aug. 25, 2003, herein incorporated in their entirety by reference.

FIELD OF THE INVENTION

The present invention includes support and sensing structures positioned in a physiologic tunnel for measuring bodily functions and to manage abnormal conditions indicated by the measurements.

BACKGROUND OF THE INVENTION

Interfering constituents and variables can introduce significant source of errors that prevent measured biologic parameters from being of clinical value. In order to bypass said interfering constituents and achieve undisturbed signals, invasive and semi-invasive techniques have been used. Such techniques have many drawbacks including difficulties in providing continuous monitoring for long periods of time. Non-invasive techniques also failed to deliver the clinical usefulness needed. The placement of a sensor on the skin characterized by the presence of interfering constituents do not allow obtaining clinically useful nor accurate signals due to the presence of said interfering constituents and background noise which greatly exceeds the signal related to the physiologic parameter being measured.

The most precise, accurate, and clinically useful way of evaluating thermal status of the body in humans and animals is by measuring brain temperature. Brain temperature measurement is the key and universal indicator of both disease and health equally, and is the only vital sign that cannot be artificially changed by emotional states. The other vital signs (heart rate, blood pressure, and respiratory rate) all can be influenced and artificially changed by emotional states or voluntary effort.

Body temperature is determined by the temperature of blood, which emits heat as far-infrared radiation. Adipose tissue (fat tissue) absorbs far-infrared and the body is virtually completely protected with a layer of adipose tissue adherent to the skin. Thus measurement of temperature using the skin did not achieve precision nor accuracy because previous techniques used sensors placed on skin characterized by the presence of adipose tissue.

Because it appeared to be impossible with current technology to non-invasively measure brain temperature, attempts were made to determine internal body temperature, also referred to as core temperature. An invasive, artificial, inconvenient, and costly process is currently used to measure internal (core) temperature consisting of inserting a catheter with a temperature sensor in the urinary canal, rectum or esophagus. But such methodology is not suitable for routine measurement, it is painful, and has potential fatal complications.

Semi-invasive techniques have also being tried. Abreu disclosed in U.S. Pat. No. 6,120,460 apparatus and methods for measuring core temperature continuously using a contact lens in the eyelid pocket, but the contact lens is a semi-invasive device which requires prescription by a physician and sometimes it is not easy to place the contact lens in the eye of an infant or even in adults and many people are afraid of touching their eyes.

There are several drawbacks and limitations in the prior art for continuous and/or core measurement of temperature.

Measurement of temperature today is non-continuous, non-core and nurse dependent. Nurses have to stick a thermometer in the patient's mouth, rectum or ear. To get core temperature nurses invasively place a tube inside the body which can cause infection and costly complications.

Measurement of core temperature on a routine basis in the hospital and/or continuously is very difficult and risky because it requires an invasive procedure with insertion of tubes inside the body or by ingesting a thermometer pill. The thermometer pill can cause diarrhea, measure temperature of the fluid/food ingested and not body temperature, and have fatal complications if the pill obstructs the pancreas or liver ducts. Placement of sensors on the skin do not provide clinically useful measurements because of the presence of many interfering constituents including fat tissue.

It is not possible to acquire precise and clinically useful measurements of not only brain temperature, but also metabolic parameters, physical parameters, chemical parameters, and the like by simply placing a sensor on the skin. One key element is the presence of fat tissue. Fat varies from person to person, fat varies with aging, fat content varies from time to time in the same person, fat attenuates a signal coming from a blood vessel, fat absorbs heat, fat prevents delivery of undisturbed far-infrared radiation, fat increases the distance traveled by the element being measured inside the body and an external sensor placed on the surface of the skin.

There is a need to identify a method and apparatus that can non-invasively, conveniently and continuously monitor brain temperature in a painless, simple, external and safe manner with sensors placed on the skin.

There is further a need to identify a method and apparatus that can conveniently, non-invasively, safely and precisely monitor biological parameters including metabolic parameters, physical parameters, chemical parameters, and the like.

There is a need to identify an apparatus and method capable of measuring biological parameters by positioning a sensor on a physiologic tunnel for the acquisition of undisturbed and continuous biological signals.

SUMMARY OF THE INVENTION

The present invention provides methods, apparatus and systems that effectively address the needs of the prior art.

In general, the invention provides a set of sensing systems and reporting means which may be used individually or in combination, which are designed to access a physiologic tunnel to measure biological, physical and chemical parameters. Anatomically and physiologically speaking, the tunnel discovered by the present invention is an anatomic path which conveys undisturbed physiologic signals to the exterior. The tunnel consists of a direct and undisturbed connection between the source of the function (signal) within the body and an external point at the end of the tunnel located on the skin. A physiologic tunnel conveys continuous and integral data on the physiology of the body. An undisturbed signal from within the body is delivered to an external point at the end of the tunnel. A sensor placed on the skin at the end of the tunnel allows optimal signal acquisition without interfering constituents and sources of error.

Included in the present invention are support structures for positioning a sensor on the skin at the end of the tunnel. The present invention discloses devices directed at measuring brain temperature, brain function, metabolic function, hydrodynamic function, hydration status, hemodynamic function, body chemistry and the like. The components include devices and methods for evaluating biological parameters using patches, clips, eyeglasses, head mounted gear and the like with sensing systems adapted to access physiologic tunnels to provide precise and clinically useful information about the physiologic status of the wearer and for enhancing the safety and performance of said wearer, and helping to enhance and preserve the life of said wearer by providing adequate reporting means and alert means relating to the biological parameter being monitored. Other components provide for producing direct or indirect actions, acting on another device, or adjusting another device or article of manufacture based on the biological parameter measured.

The search for a better way to measure biological parameters has resulted in long and careful research, which included the discovery of a Brain Temperature Tunnel (BTT) and other physiologic tunnels in humans and animals. The present invention was the first to recognize the physiologic tunnel in the body. The present invention was yet the first to recognize the end of the tunnel on the skin surface in which an optimal signal is acquired and measurements can be done without the presence of interfering constituents and background noise that exceeds the signal being measured. The present invention was also the first to recognize and precisely map the special geometry and location of the tunnel including the main entry point. The present invention was yet first to recognize the precise positioning of sensing systems at the main entry point for optimal signal acquisition. Careful studies have been undertaken including software development for characterizing infrared radiation to precisely determine the different aspects of the tunnel. This research has determined that the measurement of brain (core) temperature and other body parameters can be accomplished in a non-invasive and continuous manner in humans and animals with sensors positioned in a confined area of the skin at the end of a physiologic tunnel.

The key function and critical factor for life preservation and human performance is brain temperature. Brain tissue is the tissue in the body most susceptible to thermal damage, by both high and low temperature. Brain temperature is the most clinically relevant parameter to determine the thermal status of the body and the human brain is responsible for 18 to 20% of the heat produced in the body, which is an extraordinary fact considering that the brain represents only 2% of the body weight. The great amount of thermal energy generated in the brain is kept in a confined space and the scalp, skull, fat and CSF (cerebral spinal fluid) form an insulating layer. The recognition of the BTT by the present invention bypasses the insulating barriers and provides a direct connection to inside the brain physiology and physics.

Anatomically and physiologically speaking, a Brain Temperature Tunnel consists of a continuous, direct, and undisturbed connection between the heat source within the brain and an external point at the end of the tunnel. The physical and physiological events at one end of the tunnel inside the brain are reproduced at the opposite end on the skin. A BTT enables the integral and direct heat transfer through the tunnel without interference by heat absorbing elements, i.e., elements that can absorb far-infrared radiation transmitted as heat by blood within the brain. There are six characteristics needed to define a BTT. These characteristics are:

1) area without heat absorbing elements, i.e., the area must not contain adipose tissue (fat tissue). This is a key and needed characteristic for defining a temperature tunnel,
2) area must have a terminal branch of a vessel in order to deliver the integral amount of heat,
3) terminal branch has to be a direct branch of a blood vessel from the brain,
4) terminal branch has to be superficially located to avoid heat absorption by deep structures such as muscles,
5) area must have a thin and negligible interface between a sensor and the source of thermal energy to achieve high heat flow, and
6) area must not have thermoregulatory arteriovenous shunts.

All six characteristics are present on the skin on the medial canthal area adjacent to the medial corner of the eye above the medial canthal tendon and in the medial third of the upper eyelid. In more detail the end of BTT area on the skin measures about 11 mm in diameter measured from the medial corner of the eye at the medial canthal tendon and extends superiorly for about 6 mm and then extends into the upper eyelid in a horn like projection for another 22 mm.

The BTT area is the only area in the body without adipose tissue, which is in addition supplied by a terminal branch, which has a superficial blood vessel coming from the brain vasculature, and which has a thin interface and no thermoregulatory shunts. The BTT area is supplied by a terminal branch of the superior ophthalmic vein which is a direct connection to the cavernous sinus, said cavernous sinus being an endothelium-lined system of venous channels inside the brain which collects and stores thermal energy. The blood vessel supplying the BTT area is void of thermoregulatory arteriovenous shunts and it ends on the skin adjacent to the medial corner of the eye and in the superior aspect of the medial canthal area right at the beginning of the upper eyelid. The blood vessels deliver undisturbed heat to the skin on the medial canthal area and upper eyelid as can be seen in the color as well as black and white photos of infrared images shown in FIGS. 1 and 2. The undisturbed thermal radiation from the brain is delivered to the surface of the skin at the end of the tunnel. The heat is delivered to an area of skin without fat located at the end of the tunnel. The blood vessel delivering heat is located just below the skin and thus there is no absorption of infrared radiation by deep structures.

If the blood vessel is located deep, other tissues and chemical substances would absorb the heat, and that can invalidate the clinical usefulness of the measurement. There is direct heat transfer and the skin in the BTT area is the thinnest skin in the body and is void of thermoregulatory arteriovenous shunts. A very important aspect for optimal measurement of temperature is no interference by fat tissue and direct heat transfer.

The absence of fat tissue in this particular and unique area in the body at the end of the tunnel allows the undisturbed acquisition of the signal. The combination of those six elements allows the undisturbed and integral emission of infrared radiation from the brain in the form of direct heat transfer at the BTT area location, which can be seen in the infrared image photographs (FIGS. 1 to 8). The BTT and physiologic tunnels are also referred in this description as the "Target Area".

From a physical standpoint, the BTT is the equivalent of a Brain Thermal Energy tunnel with high total radiant power and high heat flow. The temperature of the brain is determined by the balance between thermal energy produced due to metabolic rate plus the thermal energy delivered by the arterial supply to the brain minus the heat that is removed by cerebral blood flow. Convection of heat between tissue and capillaries is high and the temperature of the cerebral venous blood is in equilibrium with cerebral tissue. Accordingly, parenchymal temperature and thermal energy of the brain can be evaluated by measuring the temperature and thermal energy of the cerebral venous blood. The superior ophthalmic vein has a direct and undisturbed connection to the cavernous sinus and carries cerebral venous blood with a thermal energy capacity of $3.6 \text{ J·ml}^{-1}·(° \text{ C.})^{-1}$ at hematocrit of 45%. Cerebral thermodynamic response, thermal energy, and brain temperature can be evaluated by placing a sensor to capture thermal energy conveyed by the cerebral venous blood at the end of the BTT.

The research concerning BTT and physiologic tunnels involved various activities and studies including: 1) In-vitro histologic analysis of mucosal and superficial body areas; 2) In-vivo studies with temperature evaluation of external areas in humans and animals; 3) In-vivo functional angiographic evaluation of heat source; 4) Morphologic studies of the histomorphometric features of the BTT area; 5) In-vivo evaluation of temperature in the BTT area using: thermocouples, thermistors, and far-infrared; 6) Comparison of the BTT area measurements with the internal eye anatomy and current standard most used (oral) for temperature measurement; 7) Cold and heat challenge to determine temperature stability of BTT; and 8) Infrared imaging and isotherm determination. Software for evaluating geometry of tunnel was also developed and used. Simultaneous measurement of a reference temperature and temperature in the BTT area were done using pre-equally calibrated thermistors. A specific circuit with multiple channels was designed for the experiments and data collection.

The measurement of temperature in the BTT area showed almost identical temperature signal between the BTT area and the internal conjunctival anatomy of the eye, which is a continuation of the central nervous system. Measurement of the temperature in the internal conjunctival anatomy of eye as used in the experiment was described by Abreu in U.S. Pat. Nos. 6,120,460 and 6,312,393. The averaged temperature levels for BTT and internal eye were within 0.1° C. (0.18° F.) with an average normothermia value equivalent of 37.1° C. (98.8° F.) for the BTT and 37° C. (98.6° F.) for the internal eye. Comparison with the standard most used, oral temperature, was also performed. The temperature voltage signal of the BTT area showed an average higher temperature level in the BTT area of an equivalent of 0.3° C. (0.5° F.) when compared to oral.

Subjects underwent cold challenge and heat challenge through exercising and heat room. The lowering and rising of temperature in the BTT area was proportional to the lowering and rising in the oral cavity. However, the rate of temperature change was faster in the BTT area than for oral by about 1.2 minutes, and temperature at the BTT site was 0.5° C. (0.9° F.) higher on few occasions. Subjects of different race, gender, and age were evaluated to determine the precise location of the BTT area across a different population and identify any anatomic variation. The location of the BTT was present at the same location in all subjects with no significant anatomic variation, which can be seen in a sample of infrared imaging of different subjects.

The tunnel is located in a crowded anatomic area and thus the positioning of the sensor requires special geometry for optimal alignment with the end of the tunnel. The clinical usefulness of the tunnel can only be achieved with the special positioning of the sensor in relation to anatomic landmarks and the support structure. The tunnel is located in a unique position with distinctive anatomic landmarks that help define the external geometry and location of the end of the tunnel. The main entry point of the tunnel, which is the preferred location for positioning the sensor, requires the sensor to be preferably placed in the outer edge of a support structure. The preferred embodiment for the measurement of biological parameters by accessing a physiologic tunnel includes sensors positioned in a particular geometric position on the support structure.

The support structure includes patches containing sensors. For the purpose of the description any structure containing an adhesive as means to secure said structure to the skin at the end of the tunnel is referred to as a patch including strips with adhesive surfaces such as a "BAND-AID" adhesive bandage. It is understood that a variety of attachment means can be used including adhesives, designs incorporating spring tension pressure attachment, and designs based on other attachment methods such as elastic, rubber, jelly-pads and the like.

The patches are adapted to position sensors at the end of the tunnel for optimal acquisition of the signal. The patch is preferably secured to the area by having an adhesive backing which lays against the skin, although a combination of adhesive and other means for creating a stable apposition of the sensor to the tunnel can be used such as fastening or pressure.

Support structures also include clips or structures that are positioned at the end of the tunnel with or without adhesive and which are secured to the area by pressure means. Any structure that uses pressure means to secure said structure to the skin at the end of the tunnel is referred as a clip.

Head-mounted structures are structures mounted on the head or neck for positioning sensors on the end of the tunnel and include head bands with accessories that are adjacent to the tunnel, visors, helmets, headphone, structures wrapping around the ear and the like. For the purpose of this description TempAlert is referred herein as a system that measures temperature in the BTT area and has means to report the measured value and that can incorporate alarm devices that are activated when certain levels are reached. Support structures yet include any article that has sensing devices in which said sensing devices are positioned at the end of the tunnel.

Support structures further include medial canthal pieces of eyeglasses. A medial canthal piece is also referred to herein as a medial canthal pad and includes a pad or a piece which positions sensing devices on the skin at the medial canthal area on top of a tunnel, with said medial canthal piece being permanently attached to or mounted to an eyeglass. Any sensing devices incorporated in an eyeglass (fixed or removable) for accessing a tunnel are referred to herein as EyEXT including devices for sensing physical and chemical parameters. Any article of manufacture that has visual function, or ocular protection, or face protection with a part in contact with the tunnel is referred herein as eyeglasses and includes conventional eyeglasses, prescription eyeglasses, reading glasses, sunglasses, goggles of any type, masks (including gas masks, surgical masks, cloth masks, diving masks, eyemask for sleeping and the like) safety glasses, and the like.

For brain temperature evaluation the tunnel area consists of the medial canthal area and the superior aspect of the medial corner of the eye. For brain function evaluation the tunnel area consists of primarily the upper eyelid area. For metabolic function evaluation the tunnel area consists of an area adjacent to the medial corner of the eye and both the upper and lower eyelids.

The measurement of metabolic function, brain function, immunogenic function, physical parameters, physico-chemical parameters and the like includes a variety of support structures with sensors accessing the physiologic tunnels. The sensors are placed in apposition to the skin immediately adjacent to the medial corner of the eye preferably in the superior aspect of the medial canthal area. The sensor can also be positioned in the medial third of the upper eyelid. The sensor is most preferably located at the main entry point of the tunnel which is located on the skin 2.5 mm medial to the corner of the eye and about 3 mm above the medial corner of the eye. The diameter of the main entry point is about 6 to 7 mm. The positioning of the sensor at the main entry point of the tunnel provides the optimum site for measuring physical and chemical parameters of the body.

Besides a sensor that makes contact with the skin at the Target Area, it is understood that sensors which do not make contact with the skin can be equally used. For instance an infrared-based temperature measuring system can be used. The measurement is based on the Stefan-Boltzman law of physics in which the total radiation is proportional to the fourth power of the absolute temperature, and the Wien Displacement law in which the product of the peak wavelength and the temperature are constant. The field of view of the non-contact infrared apparatus of the invention is adapted to match the size and geometry of the BTT area on the skin.

A variety of lenses known in the art can be used for achieving the field of view needed for the application. For example, but not by way of limitation, a thermopile can be adapted and positioned in a manner to have a field of view aimed at the main entry point of the BTT area on the skin. The signal is then amplified, converted into a voltage output and digitized by a MCU (microcontroller).

This infrared-based system can be integrated into a support structure that is in contact with the body such as any of the support structures of the present invention. In addition, it is understood that the infrared-based system of the present invention can be integrated as a portable or hand-held unit completely disconnected from the body. The apparatus of the present invention can be held by an operator that aims said apparatus at the BTT area to perform the measurement. The apparatus further includes an extension shaped to be comfortably positioned at the BTT site for measuring biological parameters without discomfort to the subject. The extension in contact with the skin at the BTT is shaped in accordance with the anatomic landmarks and the geometry and size of the BTT site. The infrared radiation sensor is positioned in the extension in contact with the skin for receiving radiation emitted from the BTT site.

The present invention provides a method for measuring biological parameters including the steps of positioning a sensing device means on the skin area at the end of a tunnel, producing a signal corresponding to the biological parameter measured and reporting the value of the parameter measured.

It is also includes a method to measure biological parameters by non-contact infrared thermometry comprising the steps of positioning an infrared detector at the BTT site with a field of view that encompasses the BTT site and producing a signal corresponding to the measured infrared radiation. The biological parameters include temperature, blood chemistry, metabolic function and the like.

Temperature and ability to do chemical analysis of blood components is proportional to blood perfusion. The present invention recognizes that the tunnel area, herein also referred as a Target Area, has the highest superficial blood perfusion in the head and has a direct communication with the brain, and that the blood vessels are direct branches of the cerebral vasculature and void of thermoregulatory arteriovenous shunts. It was also recognized that the Target Area has the highest temperature in the surface of the body as can be seen in the photographs of experiments measuring infrared emission from the body and the eye.

The Target Area discovered not only has the thinnest and most homogeneous skin in the whole body but is the only skin area without a fat layer. Since fat absorbs significant amounts of radiation, there is a significant reduction of signal. Furthermore other skin areas only provide imprecise and inaccurate signals because of the large variation of adipose tissue from person to person and also great variability of fat tissue according to age. This interference by a fat layer does not occur in the Target Area. Furthermore, the combined characteristics of the Target Area, contrary to the skin in the rest of the body, enable the acquisition of accurate signals and a good signal to noise ratio which far exceeds background noise. In addition, body temperature such as is found in the surface of the skin in other parts of the body is variable according to the environment.

Another important discovery of the present invention was the demonstration that the Target Area is not affected by changes in the environment (experiments included cold and heat challenge). The Target Area provides an optimum location for temperature measurement which has a stable temperature and which is resistant to ambient conditions. The Target Area discovered has a direct connection to the brain, is not affected by the environment and provides a natural, complete thermal seal and stable core temperature. The apparatus and methods of the present invention achieve precision and clinical usefulness needed with the non-invasive placement of a temperature sensor on the skin in direct contact with the heat source from the brain without the interference of heat absorbing elements.

The Target Area is extremely vascularized and is the only skin area in which a direct branch of the cerebral vasculature is superficially located and covered by a thin skin without a fat layer. The main trunk of the terminal branch of the ophthalmic vein is located right at the BTT area and just above the medial canthal tendon supplied by the medial palpebral artery and medial orbital vein. The BTT area on the skin supplied by a terminal and superficial blood vessel ending in a particular area without fat and void of thermoregulatory arteriovenous shunts provides a superficial source of undisturbed biological signals including brain temperature, metabolic function, physical signals, and body chemistry such as glucose level, and the like.

Infrared spectroscopy is a technique based on the absorption of infrared radiation by substances with the identification of said substances according to its unique molecular oscillatory pattern depicted as specific resonance absorption peaks in the infrared region of the electromagnetic spectrum. Each chemical substance absorbs infrared radiation in a unique manner and has its own unique absorption spectra depending on its atomic and molecular arrangement and vibrational and rotational oscillatory pattern. This unique absorption spectra allows each chemical substance to basically have its own infrared spectrum, also referred to as fingerprint or signature which can be used to identify each of such substances. Radiation containing various infrared wavelengths is emitted at the substance to be measured and the amount of absorption of radiation is dependent upon the concentration of said chemical substance being measured according to Beer-Lambert's Law.

Interfering constituents and variables such as fat, bone, muscle, ligaments and cartilage introduce significant source of errors which are particularly critical since the background noise greatly exceeds the signal of the substance of interest. Since those interfering constituents are not present on the skin at the BTT area, the sensing systems positioned at said BTT area can acquire optimal signal with minimal noise including spectroscopic-based measurements.

Spectroscopic devices integrated into support structures disclosed in the present invention can precisely non-invasively measure blood components since the main sources of variation and error, such as fat tissue, are not present in the Target Area. In addition, other key constituents which interfere with electromagnetic energy emission such as muscle, cartilage and bones, are not present in the Target Area either. The blood vessels delivering the infrared radiation are superficially located and the infrared radiation is delivered at the end of the tunnel without interacting with other structures. The only structure to be traversed by the infrared radiation is a very thin skin, which does not absorb the infrared wavelength. The present invention includes infrared spectroscopy means to provide a clinically useful measurement with the precise and accurate determination of the concentration of the blood components at the end of the tunnel.

In addition to spectroscopy in which electromagnetic energy is delivered to the Target Area, the present invention also discloses apparatus and methods for measuring substances of interest through far infrared thermal emission from the Target Area. Yet, besides near-infrared spectroscopy and thermal emission, other devices are disclosed for measurement of substances of interest at the Target Area including electroosmosis as a flux enhancement by iontophoresis or reverse iontophoresis with increased passage of fluid through the skin through application of electrical energy. Yet, transcutaneous optical devices can also be integrated into support structures including medial canthal pieces, modified nose pads, and the frame of eyeglasses, with said devices positioned to access the tunnel.

It is understood that application of current, ultrasonic waves as well as chemical enhancers of flow, electroporation and other devices can be used to increase permeation at the tunnel site such as for example increased flow of glucose with the use of alkali salts. In addition creating micro holes in the target area with a laser, or other means that penetrate the skin can be done with the subsequent placement of sensing devices on the BTT site, with said devices capable of measuring chemical compounds. Furthermore, reservoirs mounted on or disposed within support structures, such as the frame and pads of eyeglasses, can deliver substances transdermally at the BTT site by various devices including iontophoresis, sonophoresis, electrocompression, electroporation, chemical or physical permeation enhancers, hydrostatic pressure and the like.

In addition to measure the actual amount of oxygen in blood, the present invention also discloses devices to measure oxygen saturation and the amount of oxygenated hemoglobin. In this embodiment the medial canthal piece of a support structure or the modified nose pads of eyeglasses contain LEDs emitting at two wave lengths around 940 and 660 nanometers. As the blood oxygenation changes, the ratio of the light transmitted by the two frequencies changes indicating the oxygen saturation. Since the blood level is measured at the end of a physiologic brain tunnel, the amount of oxygenated hemoglobin in the arterial blood of the brain is measured, which is the most valuable and key parameter for athletic purposes and health monitoring.

The present invention also provides a method for measuring biological parameters with said method including the steps of directing electromagnetic radiation at the BTT area on the skin, producing a signal corresponding to the resulting radiation and converting the signal into a value of the biological parameter measured.

Besides using passive radio transmission or communication by cable; active radio transmission with active transmitters containing a microminiature battery mounted in the support structure can also be used. Passive transmitters act from energy supplied to it from an external source. The transensor transmits signals to remote locations using different frequencies indicative of the levels of biological parameters. Ultrasonic micro-circuits can also be mounted in the support structure and modulated by sensors which are capable of detecting chemical and physical changes at the Target Area. The signal may be transmitted using modulated sound signals particularly under water because sound is less attenuated by water than are radio waves.

One preferred embodiment comprises a support structure including a patch adapted to be worn on or attached with adhesives to the tunnel and includes structural support, a sensor for measuring biological parameters, power source, microcontroller and transmitter. The parts can be incorporated into one system or work as individual units. The sensor is located preferably within 7 mm from the outer edge of the patch. The apparatus of the invention can include a temperature sensor located in the outer edge of the patch for sensing temperature. The transmitter, power source and other components can be of any size and can be placed in any part of the patch or can be connected to the patch as long as the sensing part is placed on the edge of the patch in accordance with the principles of the invention. The sensor in the patch is positioned on the skin adjacent to the medial canthal area (medial corner of the eye) and located about 2 mm from the medial canthal tendon. The sensor can preferably include electrically-based sensors, but non-electrical systems can be used such as chemicals that respond to changes in temperature including mylar.

Besides patches, another preferred embodiment for measuring biological parameters at the physiologic tunnel includes a medial canthal pad. The medial canthal piece is a specialized structure containing sensors for accessing the tunnel and adapted to be worn on or attached to eyeglasses in apposition to the tunnel and includes structural support, a sensor for measuring biological parameters, power source, microcontroller and transmitter. The parts can be incorporated into one system or work as individual units. The sensors are positioned on the BTT area. The transmitter, power source, and other components can be placed in the medial canthal pad or in any part of the eyeglasses. A medial canthal piece or extension of nose pads of eyeglasses allow accessing the physiologic tunnel with sensing devices laying in apposition to the BTT area.

The apparatus of the invention include a temperature sensor located in the medial canthal pad. For temperature measurement the sensing system is located on a skin area that includes the medial canthal corner of the eye and upper eyelid. The sensor in the medial canthal pad is preferably positioned on the skin adjacent to the medial canthal area (medial corner of the eye). Although one of the preferred embodiments for measurement of brain temperature consists of medial canthal pads, it is understood that also included in the scope of the invention are nose pads of a geometry and size that reach the tunnel and that are equipped with temperature sensors preferably in the outer edge of said nose pads for measuring brain temperature and other functions. An oversized and modified nose pad containing sensors using a special geometry for adequate positioning at the BTT area is also included in the invention.

With the disclosure of the present invention and by using anatomic landmarks in accordance with the invention the sensor can be precisely positioned on the skin at the end of the tunnel. However, since there is no external visible indication on the skin relating to the size or geometry of the tunnel, accessory means can be used to visualize, map or measure the end of the tunnel on the skin. These accessory means may be particularly useful for fitting medial canthal pads or modified nose pads of eyeglasses.

Accordingly, an infrared detector using thermocouple or thermopiles can be used as an accessory for identifying the point of maximum thermal emission and to map the area. An infrared imaging system or thermography system may be preferably used. In this instance, an optical store selling the eyeglasses can have a thermal imaging system. The optician, technician and the like take an infrared image picture or film the area, and in real time localize the tunnel of the particular user. The medial canthal pads or modified nose pads can then be adjusted to fit the particular user based on the thermal infrared imaging. The eyeglasses are fitted based on the thermal image created. This will allow customized fitting according to the individual needs of the user. Any thermography-based system can be used including some with great visual impact and resolution as a tri-dimensional color thermal wave imaging.

It is also a feature of the invention to provide a method to be used for example in optical stores for locating the tunnel including the steps of measuring thermal infrared emission, producing an image based on the infrared emission, and detecting the area with the highest amount of infrared emission. Another step that can be included is adjusting sensors in support structures to match the area of highest infrared emission.

One of said support structures includes the medial canthal pieces or nose pads of eyeglasses. The thermal imaging method can be used for fitting a patch, but said patch can be positioned at the tunnel by having an external indicator for lining up said indicator with a permanent anatomic landmark such as the medial corner of the eye. Although medial canthal pieces of eyeglasses can have an external indicator for precise positioning, since opticians are used to fit eyeglasses according to the anatomy of the user, the thermal imaging method can be a better fit for eyeglasses than an external indicator on the medial canthal pieces or modified nose pads of eyeglasses.

The source of the signal is key for the clinical usefulness of the measurement. The brain is the key and universal indicator of the health status of the body. The signal coming from the brain or brain area provides the most clinically useful data. In accordance with another embodiment, the measurement of biological parameters will be described. The amount of sodium and other elements in sweat is a key factor for safety and performance of athletes and military, as well as health monitoring.

For instance hyponatremia (decreased amount of sodium) can lead to reduced performance and even death. Hyponatremia can occur due to excess water intake, commonly occurring with intense physical activity and military training. Sweat can be considered as an ultrafiltrate of blood. The blood vessels supplying the skin on the head are branches of the central nervous system vasculature. The amount of chemical substances present in the sweat coming from those blood vessels is indicative of the amount of chemical substances present in the cerebral vasculature. For instance, sodium concentration of sweat from blood vessels in the head changes in relation to the rates of sweating. The apparatus and methods of the present invention can prevent death or harm due to water intoxication, by providing alert signals when the levels of sodium in sweat reach a certain threshold for that particular wearer. The presence of various chemical elements, gases, electrolytes and pH of sweat and the surface of the skin can be determined by the use of suitable electrodes and suitable sensors integrated in the eyeglasses and other support structures mounted on the head or fitted on the head or face. These electrodes, preferably microelectrodes, can be sensitized by several reacting chemicals which are in the sweat or the surface of the skin. The different chemicals and substances can diffuse through suitable permeable membranes sensitizing suitable sensors.

For example but not by way of limitation, electrochemical sensors can be used to measure various analytes such as glucose using a glucose oxidase sensor and the pilocarpine iontophoresis method can be used to measure electrolytes in sweat alone or in conjunction with microfluidics system. Besides the support structures of the present invention, it is also understood that other articles such as watches, clothing, footwear and the like can be adapted to measure concentration of substances such as electrolytes present in sweat, however there is reduced clinical relevance for evaluating metabolic state of an individual outside the central nervous system.

Body abnormalities may cause a change in the pH, osmolarity, and temperature of the sweat derived from brain and neck blood vessels as well as change in the concentration of substances such as acid-lactic, glucose, lipids, hormones, gases, markers, infectious agents, antigens, antibody, enzymes, electrolytes such as sodium, potassium and chloride, and the like. Eyeglasses and any head gear can be adapted to measure the concentration of substances in sweat. Microminiature glass electrodes mounted in the end portion of the temple of eyeglasses sitting behind the ear or alternatively mounted on the lens rim against the forehead can be used to detect divalent cations such as calcium, as well as sodium and potassium ion and pH. Chloride-ion detectors can be used to detect the salt concentration in the sweat and the surface of the skin.

Many agents including biological warfare agents and HIV virus are present in sweat and could be detected with the eyeglasses or support structure on the head or face using sensors coated with antibodies against the agent which can create a photochemical reaction with appearance of colorimetric reaction and/or potential shift with subsequent change in voltage or temperature that can be detected and transmitted to a monitoring station or reported locally by audio or visual means. Electrocatalytic antibodies also can generate an electrical signal when there is an antigen-antibody interaction. It is also understood that other articles such as watches, clothing, footwear, and the like or any article capturing sweat can be adapted to identify antigens, antibody, infectious agents, markers (cancer, heart, genetic, metabolic, drugs, and the like) in accordance with the present invention. However, identification of those elements away from the central nervous system is of reduced clinical relevance.

The different amounts of fluid encountered in sweat can be easily quantified and the concentration of substances calibrated according to the amount of fluid in sweat. The relationship between the concentration of chemical substances and molecules in the blood and the amount of said chemical substances in the sweat can be described mathematically and programmed in a computer.

The present invention also includes eyeglasses or support structures in which a radio frequency transensor capable of measuring the negative resistance of nerve fibers is mounted in the eyeglasses or support structure. By measuring the electrical resistance, the effects of microorganisms, drugs, and poisons can be detected. The system also comprises eyeglasses in which a microminiature radiation-sensitive transensor is mounted in said eyeglasses or support structure.

The brain has a rich vasculature and receives about 15% of the resting cardiac output and due to the absence of fat the tunnel offers an area for optimal signal acquisition for evaluating hemodynamics. Accordingly, change in the viscosity of blood can be evaluated from a change in damping on a vibrating quartz micro-crystal mounted in the eyeglasses or support structure and the invention can be adapted to measure blood pressure and to provide instantaneous and continuous monitoring of blood pressure through an intact wall of a blood vessel from the brain and to evaluate hemodynamics and hydrodynamics. Also, by providing a contact microphone, arterial pressure can be measured using sonic devices.

Pressure can be applied to a blood vessel through a micro cuff mounted in the medial canthal pads, or alternatively by the temples of eyeglasses. Pressure can also be applied by a rigid structure, and the preferred end point is reached when sound related to blood turbulence is generated. The characteristic sound of systole (contraction of the heart) and diastole (relaxation of the heart) can be captured by the microphone. A microphone integrated into the medial canthal pad can be adapted to identify the heart sounds. Pressure transducers such as a capacitive pressure transducer with integral electronics for signal processing and a microphone can be incorporated in the same silicon structure and can be mounted in the medial canthal pad. Motion sensors and/or pressure sensors can be mounted in the medial canthal pad to measure pulse.

Reversible mechanical expansion methods, photometric, or electrochemical methods and electrodes can be mounted in the eyeglasses or support structures of the present invention and used to detect acidity, gases, analyte concentration, and the like. Oxygen gas can also be evaluated according to its magnetic properties or be analyzed by micro-polarographic sensors mounted in the eyeglasses or other support structure. A microminiature microphone mounted in the eyeglasses or other support structure can also be adapted to detect sounds from the heart, respiration, flow, vocal and the environment, which can be sensed and transmitted to a remote receiver or reported by local audio and visual means. The sensors are adapted and positioned to monitor the biological parameters at the end of the tunnel.

The eyeglasses or other support structures can also have elements which produce and radiate recognizable signals and this procedure could be used to locate and track individuals, particularly in military operations. A permanent magnet can also be mounted in the eyeglasses and used for tracking as described above. A fixed frequency transmitter can be mounted in the eyeglasses and used as a tracking device which utilizes a satellite tracking system by noting the frequency received from the fixed frequency transmitter to a passing satellite, or via Global Positioning Systems. Motion and deceleration can be detected by mounting an accelerometer in the eyeglasses. The use of eyeglasses as tracking devices can be useful for locating a kidnapped individual or for rescue operations in the military, since eyeglasses are normally unsuspecting articles.

The use of integrated circuits and advances occurring in transducer, power source, and signal processing technology allow for extreme miniaturization of the components which permits several sensors to be mounted in one unit.

The present invention provides continuous automated brain temperature monitoring without the need for a nurse. The present invention can identify a spike in temperature. Thus, proper diagnosis is made and therapy started in a timely fashion. Time is critical for identifying the temperature spike and organism causing the infection. Delay in identifying spike and starting therapy for the infection can lead to demise of the patient. The invention timely and automatically identifies the temperature spike and prevents the occurrence of complications.

The present invention also alerts the user about overheating or hypothermia to allow:

1. Proper hydration;
2. Increased performance;
3. Increased safety; and
4. Feed back control in treadmills and other exercise machines for keeping proper hydration and performance.

Annually many athletes, construction workers, college students and the general public unnecessarily die due to heatstrokes. Once the brain reaches a certain temperature level such as 40° C., an almost irreversible process ensues. Because there are no specific symptoms and after a certain point there is rapid increase in brain temperature, heatstroke has one of the highest fatality rates. The more severe and more prolonged the episode, the worse the predicted outcome, especially when cooling is delayed. Without measuring core temperature and having an alert system when the temperature falls outside safe levels it is impossible to prevent hyperthermia and heatstroke. The present invention provides a device for continuous monitoring of temperature with alert systems that can prevent dangerous levels to be reached and cooling measures applied if needed. The apparatus can be adapted to be used in an unobtrusive manner by athletes, military, workers and the general population.

All chemical reactions in the body are dependent on temperature. High temperature can lead to enzymatic changes and protein denaturation and low temperature can slow down vital chemical reactions. Hydration is dependent on brain temperature and loss of fluid leads to a rise in brain temperature. Minimal fluctuations in the body's temperature can adversely affect performance and increase risk of illness and of life threatening events. Therefore, it is essential that athletes, sports participants, military personnel, police officers, firefighters, forest rangers, factory workers, farmers, construction workers and other professionals have precise mechanisms to know exactly what is their brain temperature.

When the core temperature rises, the blood that would otherwise be available for the muscles is used for cooling via respiration and perspiration. The body will do this automatically as temperature moves out of the preferred narrow range. It is this blood shifting that ultimately impairs physical performance and thermal induced damage to brain tissue interferes with normal cognitive function. Intense exercise can increase heat production in muscles 20 fold. In order to prevent hyperthermia and death by heat stroke athletes drink water. Because the ingestion of water is done in a random fashion, many times there is water intoxication which can lead to death as occurs to many healthy people including marathon runners and military personnel. Both, excess of water (overhydration) or lack of water (dehydration) can lead to fatal events besides reducing performance. Therefore, it is essential that individuals have precise means to know exactly when and how much to drink. By monitoring brain temperature with the present invention proper hydration can be achieved and athletes and military will know precisely when and how much water to ingest.

Timely ingestion of fluids according to the core temperature allows optimization of cardiovascular function and avoidance of heat strain. Because there is a delay from the time of ingestion of fluid to absorption of said fluid by the body, the method of invention includes signaling the need for ingestion at a lower core temperature such as 38.5° C. to account for that delay, and thus avoid the onset of exhaustion. The temperature threshold can be adjusted according to each individual, the physical activity, and the ambient temperature.

In addition, software can be produced based on data acquired at the BTT site for optimizing fitness, athletic performance, and safety. The upper temperature limit of a particular athlete for maintaining optimal performance can be identified, and the data used to create software to guide said athlete during a competition. For instance, the athlete can be informed on the need to drink cold fluid to prevent reaching a certain temperature level which was identified as reduced performance for said athlete. Brain temperature level for optimal performance identified can be used to guide the effort of an athlete during competition and training. Hyperthermia also affects mental performance and software based on data from the BTT can be produced to optimize mental and physical performance of firefighters in an individual manner. People can have different thresholds for deleterious effects of hyperthermia and thus setting one level for all users may lead to underutilization of one's capabilities and putting others at risk of reduced performance. Likewise, exercise endurance and mental performance is markedly reduced by hypothermia and the same settings can be applied for low temperature situations. Determinations of brain temperature, oxygen and lactic acid levels can also be used for endurance training of athletes, fitness training, and to monitor the effects of training. The system, method, and apparatus of the invention provides a mechanism for enhancing safety and optimizing fitness for athletes and recreational sports participants.

It is a feature of the invention to provide a method for the precise and timely intake of fluids including the steps of measuring brain temperature, reporting the signal measured, and ingesting an amount of fluid based on the signal measured. Other steps can be included such as reporting devices using voice reproduction or visual devices to instruct on what beverage to drink and how much to drink to reduce core temperature. It is understood that the method of the present invention can combine measurement of temperature associated with measurement of sodium in sweat or blood, in accordance with the principles of the invention.

Children do not tolerate heat as well as adults because their bodies generate more heat relative to their size than adults do. Children are also not as quick to adjust to changes in temperatures. In addition, children have more skin surface relative to their body size which means they lose more water through evaporation from the skin. It is understood that different sizes, shapes, and designs of medial canthal pads including children size can be used in the present invention. Children eyeglasses equipped with sensors can have a booster radio transmitter that will transmit the signal to a remote receiver and alert parents about dangerous temperature levels. The eyeglasses can be incorporated with a detecting system to send a signal if the eyeglasses were removed or if the temperature sensor is not capturing signals in a proper manner. By way of illustration, but not of limitation, pressure sensing devices can be incorporated in the end of the temples to detect if the sunglasses are being worn, and an abrupt drop in the pressure signal indicates glasses were removed or misplacement of the sensor can also generate an identifiable signal. An adhesive, a double-sided adhesive tape, or other devices for increasing grip can be used in the medial canthal pads to ensure more stable position. It is understood that the eyeglasses can come equipped with sensors to detect ambient temperature and humidity, which allows for precisely alerting the wearer about any aspect affecting heat conditions.

In the current industrial, nuclear and military settings, personnel may be required to wear protective clothing. Although the protective clothing prevent harm by hazardous agents, the garments increase the rate of heat storage. It is understood that the present invention can be coupled with garments with adjustable permeability to automatically keep the core temperature within safe limits.

In addition, the present invention alerts an individual about risk of thermal damage (risk of wrinkles and cancer) at the beach or during outdoor activities. When one is at the beach, watching a game in a stadium, camping or being exposed to the sun, the radiant energy of the sun is absorbed and transformed into thermal energy. The combination of the different ways of heat transfer to the body lead to an increase in body temperature, which is reflected by the brain temperature. Convection and conduction can also lead to an increase in body temperature through heat transfer in the absence of sun light. The absorption of heat from the environment leads to a rise in the average kinetic energy of the molecules with subsequent increase in core temperature.

The levels of core temperature is related to the risk of thermal damage to the skin. After certain levels of heat there is an increased risk of denaturing protein and breaking of collagen in the skin. This can be compared with changes that occur when frying an egg. After a certain amount of thermal radiation is delivered the egg white changes from fluidic and transparent to a hard and white structure. After the egg white reaches a certain level of temperature the structural change becomes permanent. After a certain level of increase in core temperature during sun exposure, such as a level of 37.7° Celsius to 37.9° Celsius at rest (e.g.; sun bathing), thermal damage may ensue and due to the disruption of proteins and collagen there is an increased risk for wrinkle formation. The increased brain temperature correlates to the amount of thermal radiation absorbed by the body, and the duration of exposure of the temperature level times the level of temperature is an indicator of the risk of thermal damage, wrinkle formation, and skin cancer.

The present invention provides an alarm system that can be set up to alert in real time when it is time to avoid sun exposure in order to prevent further absorption of thermal radiation and reduce the risk of dermatologic changes, as can occur during outdoor activities or at the beach. In addition, thermal damage to the skin prevents the skin from adequately cooling itself and can result in increasing the risk of dehydration which further increases the temperature. The present invention helps preserve the beauty and health of people exposed to sun light and during outdoor activities while allowing full enjoyment of the sun and the benefits of sun light.

By the present invention, a method for timing sun exposure includes the steps of measuring body temperature, reporting the value measured and avoiding sun exposure for a certain period of time based on the level measured.

Hypothermia is the number one killer in outdoor activities in the U.S. and Europe. Hypothermia also decreases athletic performance and leads to injuries. It is very difficult to detect hypothermia because the symptoms are completely vague such as loss of orientation and clumsiness which are indistinguishable from general behavior. Without measuring core temperature and having an alert system when the temperature falls outside safe levels it is impossible to prevent hypothermia due to the vague symptoms. The present invention can alert an individual about hypothermia during skiing, scuba diving, mountain climbing and hiking. The present invention provides means to precisely inform when certain temperature thresholds are met, either too high or too low temperature.

The present invention continuously monitors the brain temperature and as soon as a temperature spike or fever occurs it activates diagnostics systems to detect the presence of infectious agents, which can be done locally in the BTT site, or the infectious agents can be identified in other parts of the body such as the blood stream or the eyelid pocket. The present invention can be also coupled to drug dispensing devices for the automated delivery of medications in accordance with the signal produced at the BTT site including transcutaneous devices, iontophoresis or by injection using a pump.

The invention also includes a tool for family planning. The system can detect spike and changes in basal temperature and identify moment of ovulation and phases of the menstrual cycle. This allows a woman to plan pregnancy or avoid pregnancy. This eliminates the need for invasive devices used for monitoring time for artificial insemination not only for humans but also animals. The invention can yet detect the start of uterine contractions (parturition) and allow a safer birth for animals. Support structures can be equally used in the BTT of animals.

The present invention also includes Automated Climate control according to the value measured at the BTT. The temperature of the user controls the temperature in a car. When the body starts to warm up, the signal from the apparatus of the invention automatically activates the air conditioner according to the user settings, alternatively it activates heat when the body is cold. This automation allows drivers to concentrate on the road and thus can reduce the risk for car crashes. It is understood that other articles that can affect body temperature can be controlled by the present invention including vehicle seats.

Current vehicle climate control systems are dramatically overpowered because they are designed to heat/cool the vehicle cabin air mass from an extreme initial temperature to a standard temperature within a certain period of time. Because people have different thermal needs for comfort, there is a consistent manual change of the temperature settings and said manual further increase consumption of energy. For instance, car temperature is set to remain at 73 F. Some people after 15 minutes may feel that it is too cold and some people may feel it is too hot. Subsequently the passenger changes the setting to 77 and then feels hot after another 10 minutes, and needs to manually change the set points again, and the process goes on. In addition the needs differ for people of different age, people with diabetes and other diseases, and male and female.

Manual frequent adjusting of a vehicle's climate control may increase fuel consumption 20% and increase emissions of pollutants such as carbon monoxide and nitrogen oxides. The present invention provides an automated climate control in which the brain temperature controls the air conditioner and vehicle seats which maximizes comfort and minimizes fuel consumption. The improved fuel economy provided by the present invention protects the environment due to less pollutants affecting the ozone layer; improves public health by decreasing emission of toxic fumes, and increases driver's comfort and safety by less distractions with manually controlling a car's climate control.

Thermal environment inside transportation vehicles can be adjusted according to the temperature at the BTT site including contact sensor measurement and non-contact sensor measurement such as an infrared sensor or thermal image. The temperature at the BTT adjusts any article or device in the car that changes the temperature inside the cabin including air conditioner and heater, vehicle seats, doors, windows, steering wheels, carpets on the floor of the vehicle, and the like. Exemplarily, the temperature at the BTT site adjusts the amount of thermal radiation going through a window of a vehicle, if the BTT sends a signal indicating hot sensation then the windows for instance will darken to prevent further heat from entering the car, and vice versa if cold is perceived the window changing its light transmissibility to allow more heat waves to penetrate the vehicle's cabin. Any article touching the body or in the vicinity of the body can be adapted to change its temperature to achieve thermal comfort for the occupants of the vehicle.

Besides the support structures and thermal imaging systems described in the present invention to monitor and adjust temperature of a cabin of a transportation vehicle, it is understood that a contact lens inside the eyelid pocket with a temperature sensor can also be adapted to adjust the temperature inside the cabin of the vehicle. Exemplary transportation vehicles include cars, trucks, trains, airplanes, ships, boats, and the like.

It is also understood that the sensing system can include sensors in other parts of the body working in conjunction with the temperature sensor measuring temperature and/or thermal radiation at the BTT site. Thermal energy transfer from an article to an occupant of a vehicle can occur by any of radiation, convection, and the like, and any mechanism to transfer deliver, or remove thermal energy can be adjusted based on a temperature signal measured at the BTT.

The present invention provides a more energy-efficient system to achieve thermal comfort of the passengers in any type of transportation vehicle in existence or being developed with any type of sensor alone at the BTT site or in conjunction with sensors in other parts of the body.

Likewise, automated climate control at home, work, or any confined area can be achieved by activating the thermostat directly or via BlueTooth technology based on the temperature measured at the BTT in accordance with the present invention. Besides convenience and comfort, this automation allows saving energy since gross changes manually done in the thermostat leads to great energy expenditure.

It is understood that any body temperature measuring system can provide automated climate control or adjust temperature of articles in accordance with the principles of the present invention.

The present invention yet includes methods for reducing weight. It includes monitoring of temperature during programs for weight reduction based on increasing body heat to reduce said weight. The system alerts athletes on a weight losing program to prevent injury or death by overheating. The system can monitor temperature of people in sauna, steam rooms, spas and the like as part of weight reduction programs in order to prevent injuries and enhance results.

Yet, methods to enhance memory and performance besides preserving health is achieved by providing an automated mechanism to control ambient temperature and surrounding body temperature based on the brain temperature measured by the present invention. Human beings spend about one third of their lives sleeping. Many changes in body temperature occur during sleep. All of the metabolism and enzymatic reactions in the body are dependent on adequate level of temperature. The adequate control of ambient temperature which matches the needs of body temperature such as during sleeping have a key effect on metabolism. Adequate ambient temperature and surrounding temperature of objects which matches body temperature allow not only for people to sleep better, but also to achieve improved efficiency of enzymatic reactions which leads to improved mental ability and improved immune response. A variety of devices such as blankets, clothing, hats, mattress, pillows, or any article touching the body or in the vicinity of the body can be adapted to automatically increase or decrease temperature of said articles according to the temperature signal from the present invention.

The body naturally becomes cooler during the night and many people have restless sleep and turn continuously in bed because of that temperature effect. Since the tossing and turning occurs as involuntary movements and the person is not awake, said person cannot change the stimuli such as for instance increasing room temperature or increasing temperature of an electric blanket. The present invention automatically changes the ambient temperature or temperature of articles to match the temperature needs of the person. This is particularly useful for infants, elderly, diabetics, neurodisorders, heart disease, and a variety of other conditions, since this population has reduced neurogenic response to changes in body temperature, and said population could suffer more during the night, have increased risk of complications besides decreased productivity due to sleep deprivation. Accordingly, the temperature of an electrical blanket or the ambient temperature is adjusted automatically in accordance with the temperature at the BTT. When low temperature at the BTT is detected by the apparatus of the invention a wireless or wired signal is transmitted to the article to increase its temperature, and in the case of an electrical blanket or heating system, the thermostat is automatically adjusted to deliver more heat.

The invention also provides devices and methods to be used with bio feedback activities. A brain temperature signal from the sensor at the BTT site produces a feedback signal as an audio tone or visual display indicating temperature and a series of tones or colors identify if the brain temperature is increasing (faster frequency and red) or decreasing (lower frequency and blue). The display devices can be connected by wires to the support structure holding the sensor at the BTT site.

Head cooling does not change brain temperature. Athletes, military, firefighters, construction workers and others are at risk of heatstroke despite pouring cold water on their head or using a fan. Medically speaking that is a dangerous situation because the cool feeling sensed in the head is interpreted as internal cooling and the physical activity is maintained, when in reality the brain remains at risk of thermal induced damage and heatstroke. Other medical challenges related to temperature disturbances concern response time. The brain has a slower recovery response to temperature changes than core temperature (internal temperature measured in rectum, bladder, esophagus, and other internal mechanisms). Thus, internal measurement may indicate stable temperature while the brain temperature remains outside safe levels, with risk of induced damage to cerebral tissue, either due to hypothermia or hyperthermia. The only medically acceptable way to prevent cerebral tissue damage due to temperature disturbances is by continuous monitoring brain temperature as provided by the present invention.

The present invention utilizes a plurality of active or passive sensors incorporated in support structures for accessing a physiologic tunnel for measuring biological parameters. The present invention preferably includes all functions in a miniature semiconductor chip, which as an integrated circuit, incorporates sensor, processing and transmitting units and control circuits.

Additional embodiments include temperature measurement and mass screening for fever and temperature disturbances (hyperthermia and hypothermia) comprising a body radiation detector, herein referred as a BTT ThermoScan, which comprises a thermal imaging system acquiring a thermal image of the end of the BTT. The BTT ThermoScan of the present invention has sufficient temperature and isotherm discrimination for monitoring temperature at all times and without the possibility of the measurement to be manipulated by artificial influences.

The BTT ThermoScan detects the brain temperature and provides an image corresponding to the BTT area or an image that includes the BTT area.

The BTT ThermoScan comprises a camera that converts thermal radiation into a video image that can be displayed on a screen, such as the images seen in FIGS. 1A, 1B, 3A, 4A, 5A, 5C, 7A, 7B, 8A, 8B, 9A and 9B (for animals), and most preferably the image seen in FIG. 1B. The radiant energy emitted from the body and the BTT area is detected and imaged within the visible range.

Human skin at the BTT site has a high emissivity (e in the Stefan-Boltzman formula) in the infrared range, nearly equal to a black body. A video image of people walking by and looking at the BTT ThermoScan lens is captured and a customized software is adapted to display a colored plot of isotherm lines, as the software used to acquire the image of FIG. 1B in which any point at 99 degrees Fahrenheit is seen as yellow. For detection of SARS the software is adapted to display in yellow any point in the BTT area above 100 degrees Fahrenheit. When the yellow color appears on the screen, the software is adapted to provide an automatic alarm system. Therefore when the Brain Temperature Tunnel area appears as yellow on the screen the alarm is activated. It is understood that any color scheme can be used. For instance, the threshold temperature can be displayed as red color.

As shown in FIGS. 7A and 7B, cold challenge experiments were performed and demonstrated the stability of thermal emission in the BTT area. The cold challenge consisted of continuous capturing thermal infrared images while a subject is exposed to cold including facing a cold air generator (eg., air conditioner and fans), drinking cold liquids, body immersion in cold water, and spraying alcohol on the skin. Despite artificial means used to artificially change the body temperature the radiation from the BTT area remained intact, and can be seen as the bright white spots in the BTT area. Contrary to that, the face gradually became darker indicating cooling of the face during the exposure to cold. FIG. 7B shows a darker face compared to the face in FIG. 7A, but without any change in the thermal radiation from the BTT area.

In addition to cold challenges, hot challenges was performed in order to artificially increase body temperature and included exercise, people with sunburn, facing a heater, alcohol ingestion, cigarette smoking and body immersion in hot water. In all of those experiments the BTT area remained stable, but the remaining of the face had a change of temperature reflecting skin temperature, not internal brain temperature. As seen in FIGS. 2A to 2C the brain is completely insulated from the environment, with the exception of the end of the BTT. The current technology will have too many false positives and someone could be stopped at an airport or at customs just for drinking some alcohol or smoking a cigarette, making the devices in the prior art ineffective. Therefore, the present invention provides a system and method that eliminates or reduces both false negatives and false positives when using thermal imaging detection systems.

Many useful applications can be achieved including mass screening for fever, screening for hyperthermia in athletes at the end of a sports event (e.g., marathon), screening for hypothermia or hyperthermia for military personnel so as to select the one best fit physiologically for battle, and any other temperature disturbance in any condition in which a BTT ThermoScan can be installed.

One particular application consists of prevention of a terrorist attack by a terrorist getting infected with a disease (e.g., SARS—Severe Acute Respiratory Syndrome) and deceiving thermometers to avert detection of fever when entering the country target for the terrorist attack.

SARS could potentially become a high terrorist threat because it cannot be destroyed. By being naturally created, SARS could become a weapon of mass destruction that cannot be eliminated despite use of military force or diplomatic means. A terrorist can get the infection with the purpose of spreading the infection in the target country. With current technology any device can be deceived and current devices would measure normal temperature when indeed fever is present. Simple means can be used by a terrorist, such as washing their face with cold water or ice or by immersion in cold water, to manipulate any device in the prior art used for measuring fever including current infrared imaging systems and thermometers. The thermal physiology of the body, as it is measured and evaluated by the prior art, can be manipulated and the measurement performed can give a false negative for fever.

A terrorist with SARS could easily spread the disease by many ways including individually by shaking hands with clerks on a daily basis on a mass scale by spending time in confined environments such as movie theater, a concert, grocery store, a government building, and others, or by contaminating water or drinking fountains. All of those people infected do not know they caught the disease and start to spread SARS to family members, co-workers, friends and others, who subsequently will infect others, leading to an epidemic situation.

From a medical standpoint, intentional spread of SARS can have immeasurable devastating effects. People not knowing they have the disease may go to a hospital for routine checks or people not feeling good may go to a hospital for routine checks. Patients and others coming to the hospital can then acquire the disease. Admitted patients, who are debilitated, can easily acquire SARS. Spread of SARS in a hospital environment can be devastating and the hospital may need to shut down. Therefore, one person with SARS can lead to the shut down of a whole hospital. Considering that people infected with the disease may go to different hospitals, several hospitals could get contaminated and would have to be partially or completely shut down. This could choke the health care system of a whole area, and patients would have to be transported to other hospitals. Those patients may have acquired SARS as well as perpetuating the transmission cycle. If this is done in several areas by a concerted terrorist effort, much of the health care system of a country could be choked, besides countless doctors and nurses could become infected with SARS which would further cripple the health care system by shortage of personnel.

The key to prevent the catastrophic effects of a terrorist attack is preparedness. The apparatus and methods of the present invention can detect SARS and cannot be manipulated by artificial means. Placement of the BTT ThermoScan of the present invention at the borders, ports and airports of a country can prevent the artificial manipulation of the temperature measurement and a possible terrorist attack. The system of the present invention can identify at all times and under any circumstances the presence of SARS and other diseases associated with fever.

In addition, mass screening of athletes could be performed with a BTT ThermoScan installed at the finish line. An alert is activated for any athlete who crosses the finish line with a high level of hyperthermia. Therefore immediate care can be delivered allowing for the best clinical outcome since any delay in identifying hyperthermia could lead to heatstroke and even death. The BTT ThermoScan is adapted to view at least a portion of the BTT area. BTT ThermoScan detects the brain temperature and provides an image corresponding to or that includes the BTT area. Despite athletes pouring water on their head, the BTT ThermoScan precisely detects the thermal status of the body by detecting the temperature at the BTT.

Temperature disturbances such as hyperthermia and hypothermia can impair mental and physical function of any worker. Drivers and pilots in particular can have reduced performance and risk of accidents when affected by temperature disturbances. The BTT ThermoScan can be mounted in the visor of a vehicle or plane to monitor body temperature with the camera of the BTT ThermoScan capturing a thermal image of the BTT of the driver or pilot and providing an alert whenever a disturbance is noticed. It is understood that any thermal imaging system can be mounted in a vehicle or airplane to monitor body temperature and alert drivers and pilots.

The BTT ThermoScan also includes monitoring mass screening of children and people at risk during flu season. With the shortage of nurses an automated screening can greatly enhance the delivery of health care to the ones in need. When a student walking by the infrared camera is identified as having a temperature disturbance (e.g., fever) a conventional digital camera is activated and takes a picture of the student. The picture can be emailed to the school nurse that can identify the student in need of care or automatically by using stored digital pictures.

Hospitals, factories, homes, or any location that can benefit from automated mass or individual screening of temperature disturbances can use the thermal imaging apparatus in accordance with the present invention.

It is understood that an apparatus comprised of a radiation source emitting a wavelength around 556 nm at the BTT site can be used for determining the concentration of hemoglobin. The hemoglobin present in the red blood cells at the terminal end of the BTT strongly absorbs the 556 nm wavelength and the reflected radiation acquired by a photodetector determines the amount of hemoglobin. Blood flow can be evaluated by knowing the amount with thermal radiation, the higher amount of the thermal radiation indicating higher blood flow in accordance to a mathematical model.

Positioning of contact sensors, non-contact sensors, and thermal imaging camera are facilitated by external visible anatomic aspects that may be present. The cerebral venous blood can be seen under the skin in the medial canthal area next to the corner of the eye. Therefore a method for measuring temperature includes the step of visually detecting the blue or bluish color of the skin at the BTT area and positioning the sensor on or adjacent to the blue or bluish area. For subjects of darker skin, a distinctive feature of difference skin texture in the BTT area next to the medial corner of the eye can be used as the reference for measurement.

The present invention includes devices for collecting thermal radiation from a BTT site, devices for positioning temperature sensitive devices to receive thermal radiation from the BTT site and devices for converting said thermal radiation into the brain temperature. The present invention also provides methods for determining brain temperature with said methods including the steps of collecting the thermal emission from the BTT site, producing a signal corresponding to the thermal emission collected, processing the signal and reporting the temperature level. The invention also includes devices and methods for proper positioning of the temperature sensor in a stable position at the BTT site.

It is also an object of the present invention to provide support structures adapted to position a sensor on the end of a tunnel on the skin to measure biological parameters.

It is an object of the present invention to provide apparatus and methods to measure brain temperature including patches, adhesives strips, elastic devices, clips and the like containing sensors positioned on a physiologic tunnel.

It is an object of the present invention to provide apparatus and methods to measure brain temperature including thermal imaging systems containing infrared sensors sensing infrared radiation from the BTT.

It is an object of the present invention to provide multipurpose eyeglasses equipped with medial canthal pads containing sensors positioned on a physiologic tunnel for measuring biological parameters It is another object of the present invention to provide new methods and apparatus for measuring at least one of brain temperature, chemical function and physical function.

It is yet an object of the invention to provide apparatus that fit on both adults and children.

It is also an object of the invention to provide apparatus that report the signal produced at the tunnel by at least one of wired connection to reporting devices, wireless transmission to reporting devices and local reporting by audio, visual or tactile devices such as by vibration incorporated in support structures.

It is yet another object of the present invention to provide apparatus that allow the wearer to avoid dehydration or overhydration (water intoxication).

It is a further object of the present invention to provide methods and apparatus that allows athletes and sports participants to increase their performance and safety.

It is yet an object of the present invention to provide support structure positioned sensors on a tunnel which can be worn at least by one of athletes during practice and competition, military during training and combat, workers during labor and the general public during regular activities.

It is another object of the present invention to increase safety and comfort in vehicles by providing automated climate control and vehicle seat control based on the core temperature of the occupants of the vehicle.

It is an object of the present invention to provide methods and apparatus that act on a second device based on the level of the biological parameter measured.

It is another object of the invention to provide methods and apparatus to preserve skin health, reduce risk of wrinkles and reduce the risk of skin cancer by preventing sun damage by thermal radiation and alerting the wearer when the temperature has reached certain thresholds.

It is also an object of the invention to provide methods and apparatus for achieving controlled weight loss based on heat-based weight loss approach.

It is also an object of the invention to provide methods and apparatus to alert athletes in a weight losing program based on increasing body temperature to prevent injury or death by overheating.

It is also an object of the invention to provide methods and apparatus that allow monitoring fever and spikes of temperature.

It is also an object of the invention to provide a device for family planning by detecting time of ovulation.

It is a further object of the invention to provide methods and apparatus for the delivery of medications in accordance with the signal produced at the tunnel.

It is yet an object of the invention to provide methods and apparatus that enhance occupational safety by continually monitoring biological parameters.

It is also an object of the invention to provide an article of manufacture with a sensing apparatus positioned on a tunnel for monitoring biological parameters that can be fitted or mounted in at least one of the frame of eyeglasses, the nose pads of eyeglasses, the structure of a head mounted gear and clothing.

The invention also features transmitting the signal from the support structure to act on at least one of exercise equipment, bikes, sports gear, protective clothing, footwear and medical devices.

It is yet an object of the invention to provide support structures that transmit the signal produced at the tunnel to treadmills and other exercise machines for keeping proper hydration and preventing temperature disturbances of the user.

It is yet another object of the invention to provide apparatus and methods for monitoring biological parameters by accessing a physiologic tunnel using active or passive devices.

The invention yet features transmission of the signal from the support structures to watches, pagers, cell phones, computers, and the like.

These and other objects of the invention, as well as many of the intended advantages thereof, will become more readily apparent when reference is made to the following description taken in conjunction with the accompanying drawings.

BRIEF DESCRIPTION OF THE DRAWINGS

FIG. 4B is a schematic diagram of the image in FIG. 4A.

FIG. 5B is a schematic diagram of the image in FIG. 5A.

FIG. 6A is a schematic diagram showing the brain temperature tunnel and the metabolic tunnel.

FIG. 10 is a perspective view of a preferred embodiment showing a person wearing a support structure comprised of a patch with a passive sensor positioned on the skin at the end of the tunnel in accordance with the present invention.

FIG. 17 is a perspective view of another preferred embodiment showing a person wearing a support structure incorporated as a clip with a sensor positioned on the skin at the end of the tunnel in accordance with the present invention.

FIG. 18 is a perspective view of another preferred embodiment showing a person wearing a support structure with a sensor positioned on the skin at the end of the tunnel and connected by a wire.

FIGS. 19A1, 19A2, 19B, 19C and 19D are schematic diagrams of preferred geometry and dimensions of support structures and sensing devices.

FIGS. 22A to 22C are perspective views of preferred embodiments showing a person wearing a support structure incorporated as a medial canthal pad with a sensor positioned on the skin at the end of the tunnel in accordance with the present invention.

FIGS. 23A and 23B are perspective views of an alternative embodiment showing a support structure comprised of modified nose pads with a sensor positioned on the skin at the end of the tunnel in accordance with the present invention.

FIG. 27 is an exploded perspective view of another preferred embodiment showing a three piece support structure.

FIG. 28A is an exploded perspective view of one preferred embodiment of support structure showing a removable medial canthal piece.

FIG. 40 is a perspective view of a preferred embodiment for animal use.

FIGS. 41A and 41B are perspective views of an alternative embodiment of a portable support structure with a sensor positioned at the tunnel.

FIG. 53 shows a flowchart illustrating a method used in the present invention.

FIG. 64A is a side cross-sectional schematic view of a head of a person with a BTT thermal pack.

FIG. 64B is a frontal schematic view of the eye area with BTT thermal pack of FIG. 64A.

FIG. 68B shows a perspective frontal view of a BTT thermal pack supported by support structure comprised of a clip.

FIGS. 75A to 75E are graphs showing thermal signatures.

FIGS. 81C and 81D are perspective diagrams showing a support structure of FIG. 81A.

DETAILED DESCRIPTION OF THE PREFERRED EMBODIMENTS

Figure 1A:
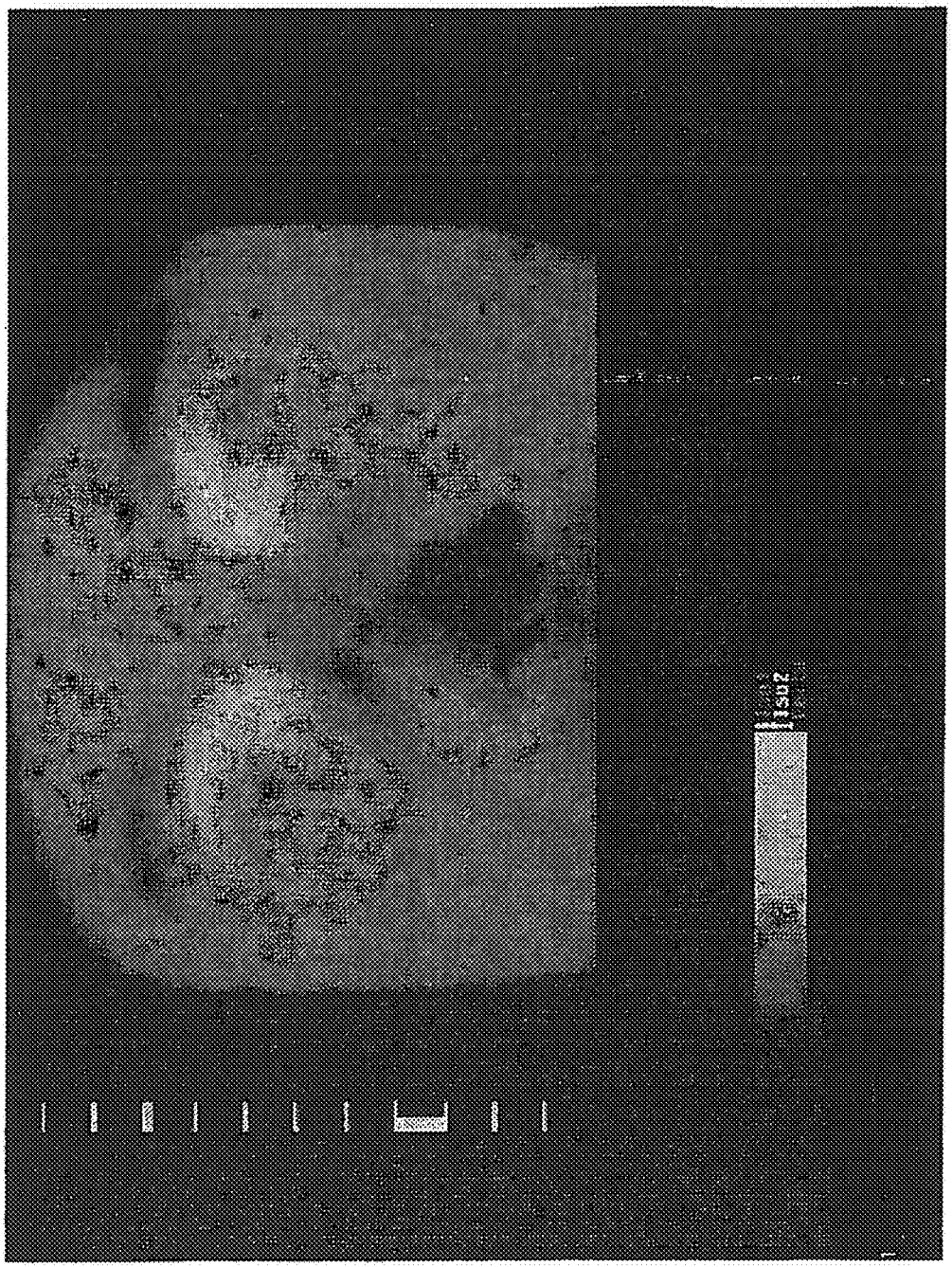
FIG. 1A is a thermal infrared image of the human face showing the brain temperature tunnel.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

FIG. 1A shows a thermal infrared image of the human face showing a physiologic tunnel. The figure shows an image of the end of the brain temperature tunnel (BTT) depicted as white bright spots in the medial canthal area and the medial half of the upper eyelid. The end of the BTT on the skin has special geometry, borders, and internal areas and the main entry point is located on the supero-medial aspect of the medial canthal area diametrically in position with the inferior portion of the upper eyelid and 4 mm medial to the medial corner of the eye. From there the boundary goes down in the medial canthal area diametrically in position with the medial corner of the eye and within 5 mm down from the medial corner of the eye, and proceeding up to the upper eyelid with the lateral boundary beginning at the mid-part of the upper eyelid as a narrow area and extending laterally in a fan-like shape with the superior boundary beginning in the mid-half of the upper eyelid.

The scale indicates the range of temperature found in the human face. The hottest spots are indicated by the brightest white spots and the coldest areas are black. Temperature between the hottest and coldest areas are seen in different hues in a gray scale. The nose is cold (seen as black) since it is primarily composed of cartilage and bones, and consequently has a lower blood volume. That is the reason why frostbite is most common in the nose.

The surrounding periocular area of the upper and lower eyelids (seen as gray) is hotter because of high vascularization and the reduced amount of adipose tissue. The skin underneath the eyelids is very thin and does not have adipose tissue either. However, the other conditions necessary to define a brain temperature tunnel are not present in this area.

The BTT requirements also include the presence of a terminal branch to deliver the total amount of heat, a terminal branch that is a direct branch from a vessel from the brain, a terminal branch that is superficially located to avoid far-infrared radiation absorption by other structures, and no thermoregulatory arteriovenous shunts. Thus, the BTT, i.e., the skin area in the medial corner of the eye and upper eyelid, is the unique location that can access a brain temperature tunnel. The skin around the eyelids delivers undisturbed signals for chemical measurements using spectroscopy and is defined as a metabolic tunnel with optimal acquisition of signals for chemical evaluation, but not for evaluation of the total radiant power of the brain.

Figure 1B:
FIG. 1B is a computer generated thermal infrared color image of the human face showing the brain temperature tunnel.

FIG. 1B is a computer generated thermal infrared color plot image of the human face showing in detail the geometry and different areas of the brain temperature tunnel and surrounding areas. Only few creatures such as some beetles and rattle snakes can see this type of radiation, but not humans. The infrared images make the invisible into visible. Thus the geometry and size of the tunnel can be better quantified. The color plot of the isothermal lines show the peripheral area of the tunnel in red and the central area in yellow-white with the main entry point at the end of the BTT located in the supero-medial aspect of the medial canthal area above the medial canthal tendon.

The main entry point is the area of most optimal signal acquisition. The image also shows the symmetry of thermal energy between the two BTT sites. Since other areas including the forehead do not have the aforementioned six characteristics needed to define a BTT, said areas have lower total radiant power seen as light and dark green. Thus the forehead is not suitable to measure total radiant power. The whole nose has very little radiant power seen as blue and purple areas, and the tip of the nose seen as brown has the lowest temperature of the face. Thus, the nose area is not suitable for measuring biological parameters.

Figure 2A:
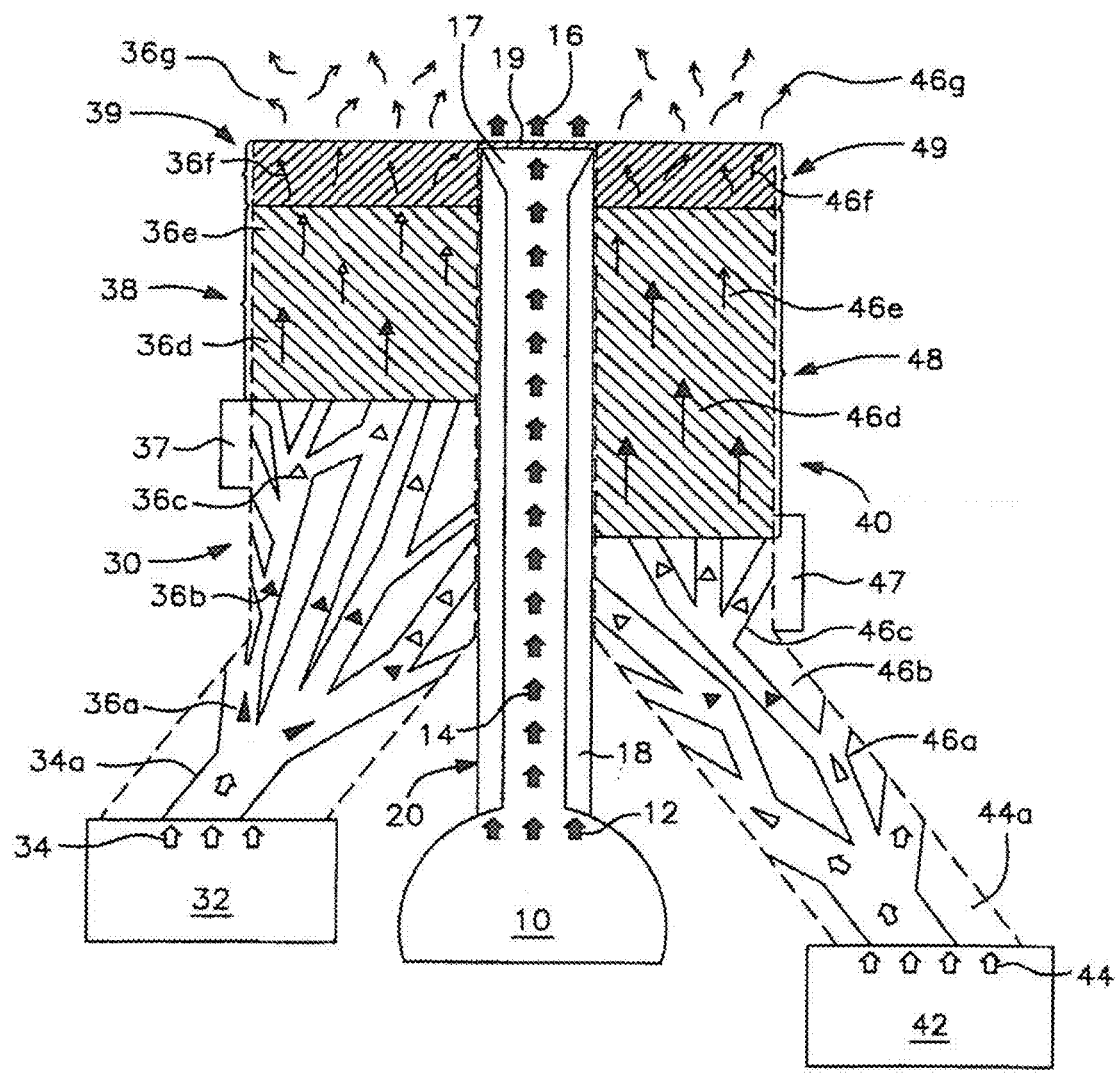
FIG. 2A is a schematic diagram showing a physiologic tunnel.

FIG. 2A is a schematic diagram of a physiologic tunnel, more particularly a Brain Temperature Tunnel. From a physical standpoint, the BTT is a brain thermal energy tunnel characterized by a high total radiant power and high heat flow and can be characterized as a Brain Thermal Energy tunnel. The tunnel stores thermal energy and provides an undisturbed path for conveying thermal energy from one end of the tunnel in the cavernous sinus inside of the brain to the opposite end on the skin with the thermal energy transferred to the surface of the skin at the end of the tunnel in the form of far-infrared radiation. High heat flow occurs at the end of tunnel which is characterized by a thin interface, and the heat flow is inversely proportional to the thickness of the interface.

The total radiated power (P) at the end of the tunnel is defined by $P=\sigma*e*A*T^4$, where $\sigma$ is the Stefan-Boltzman constant with a value $\sigma=5.67\times10^{-8}$ $W\cdot m^{-2}\cdot K^{-4}$ and e is the emissivity of the area. Since the end of the tunnel provides an optimal area for radiation, the total power radiated grows rapidly as the temperature of the brain increases because of the $T^4$ term in the equation. As demonstrated in the experiments in the present invention mentioned, the radiated power in the BTT occurred at a faster rate than the radiated power in the tongue and oral cavity.

The BTT site on the skin is a very small area measuring only less than 0.5% of the body surface area. However, this very small skin region of the body provides the area for the optimal signal acquisition for measuring both physical and chemical parameters.

FIG. 2A shows the brain 10 with the thermal energy 12 stored in its body. The BTT 20 includes the brain 10, the thermal energy 12 stored in the brain 10, the thermal energy stored in the tunnel 14 and the thermal energy 16 transferred to the exterior at the end of the tunnel. The thermal energy 12, 14, 16 is represented by dark arrows of same size and shape. The arrows have the same size indicating undisturbed thermal energy from one end of the tunnel to the other and characterized by equivalent temperature within the tunnel.

Thermal energy from the sinus cavernous in the brain 10 is transferred to the end of the tunnel 16 and a rapid rate of heat transfer occurs through the unimpeded cerebral venous blood path. The tunnel also has a wall 18 representing the wall of the vasculature storing the thermal energy with equivalent temperature and serving as a conduit from the inside of the body 10 to the exterior (skin surface) 19 which ends as a terminal vessel 17 transferring the total amount of thermal energy to said skin 19.

The skin 19 is very thin and allows high heat flow. The thickness of skin 19 is negligible compared to the skin 39, 49 in non-tunnel areas 30 and 40 respectively. Due to the characteristics of skin 19, high heat flow occurs and thermal equilibrium is achieved rapidly when a sensor is placed on the skin 19 at the end of the BTT 20.

In other areas of skin in the face and in the body in general, and in the exemplary non-tunnel areas 30 and 40 of FIG. 2 several interfering phenomena occur besides the lack of direct vasculature connection to the brain, and includes self-absorption and thermal gradient. 1. Self-absorption: This relates to the phenomena that deep layers of tissue selectively absorb wavelengths of infrared energy prior to emission at the surface. The amount and type of infrared energy self-absorbed is unknown. At the surface those preferred emissions are weak due to self-absorption by the other layers deriving disordered thermal emission and insignificant spectral characteristic of the substance being analyzed being illustratively represented by the various size, shapes and orientations of arrows 34a to 36g and 44a to 46g of FIG. 2. Self-absorption in non-tunnel areas thus naturally prevents useful thermal emission for measurement to be delivered at the surface. 2. Thermal gradient: there is a thermal gradient with the deeper layers being warmer than the superficial layers, illustratively represented by thicker arrows 36d and 46d in the deeper layers compared to thinner arrows 36e and 46e located more superficially. There is excessive and highly variable scattering of photons when passing through various layers such as fat and other tissues such as muscles leading to thermal loss.

Contrary to that, the tunnel area 20 is homogeneous with no absorption of infrared energy and the blood vessels are located on the surface. This allows undisturbed delivery of infrared energy to the surface of the skin 19 and to a temperature detector such as an infrared detector placed in apposition to said skin 19. In the BTT area there is no thermal gradient since there is only a thin layer of skin 19 with terminal blood vessel 17 directly underneath said thin interface skin 19. The thermal energy 16 generated by the terminal blood vessel 17 exiting to the surface skin 19 corresponds to the undisturbed brain (true core) temperature of the body. The preferred path for achieving thermal equilibrium with brain tissue temperature is through the central venous system which exits the brain and enters the orbit as the superior ophthalmic vein. The arterial blood is 0.2 to 0.3 degrees Celsius lower when compared to the central venous blood, and said arterial blood is not the actual equivalent of the brain temperature. Thus although arterial blood may be of interest in certain occasions, the venous system is the preferred carrier of thermal energy for measurement of brain temperature. Arterial blood temperature may be of interest to determine possible brain cooling by the arterial blood in certain circumstances.

Non-tunnel areas 30 and 40 are characterized by the presence of heat absorbing elements. The non-tunnel areas, 30 and 40 are defined by broken lines characterizing the vulnerability of interference by heat absorbing constituents and by the disorganized transferring of heat in said non-tunnel areas 30 and 40. Various layers and other constituents in non-tunnel areas 30 and 40 selectively absorb infrared energy emitted by the deeper layers before said energy reaches the surface of skin, and the different thermal energy and the different areas are represented by the different shapes and sizes of arrows and arrow heads.

Non-tunnel area 30 can be representative of measuring temperature with a sensor on top of the skin anatomically located above the heart 32. White arrows 34 represent the thermal energy in the heart 32. Non-tunnel area 30 includes the heart 32 and the various blood vessels and its branches 36a, 36b, 36c, 36d storing thermal energy.

Different amounts of heat are transferred and different temperatures measured depending on the location and anatomy of blood vessels 36a, 36b, 36c. The blood vessels branch out extensively from the main trunk 34a. The non-tunnel area 30 also includes heat absorbing structures 37 such as bone and muscles which thermal energy 34 from the heart 32 need to be traversed to reach the skin 39. The non-tunnel area 30 also includes a variable layer of fat tissue 38 which further absorbs thermal energy. The reduced amount of thermal energy reaching the skin surface due to the presence of fat 38 is represented by the arrows 36d and 36e, in which arrow 36d has higher temperature than arrow 36e. Non-tunnel area 30 also includes a thick skin 39 with low heat flow represented by arrows 36f.

The thick skin 39 corresponds to the skin in the chest area and fat layer 38 corresponds to the variable amount of fat present in the chest area. Arrows 36g represent the disordered and reduced total radiant power delivered after said thermal energy traverses the interfering constituents in the non-tunnel area including a thick interface and heat absorbing structures. In addition, BTT 20 has no fat layer as found in non-tunnel areas 30 and 40. Lack of a thick interface such as thick skin and fat, lack of thermal barriers such as fat, and lack of heat absorbing elements such as muscles allows undisturbed emission of radiation at the end of the BTT.

Lack of a thick interface such as thick skin and fat, lack of thermal barriers such as fat, and lack of heat absorbing elements such as muscles allowed undisturbed emission of radiation at the end of the BTT.

Yet referring to FIG. 2, non-tunnel area 40 can be representative of measuring temperature with a sensor on top of the skin in the arm 42. The heat transfer in non-tunnel area 40 has some similarity with non-tunnel area 30 in which the end result is a disordered and reduced total radiant power not representative of the temperature at the opposite end internally. The blood vessels branch out extensively from the main trunk 44a. Thermal energy and temperature in blood vessels 46a, 46b, 46c is different than in areas 36a, 36b, 36c. The structures that thermal energy 44 needs to traverse to reach the skin are also different compared to non-tunnel 30. The amount of heat absorbing structures 47 is different and thus the end temperature at non-tunnel 40 is also different when compared to non-tunnel area 30. The amount of fat 48 also varies which changes the energy in areas 46d and 46e, wherein area 46d is deeper than area 46e. Thick skin 49 also reduces heat flow and the temperature of the area 46f. Reduction of radiant power indicated by arrow 46g when compared to radiant power 36g is usually quite different, so different skin temperature is measured depending on the area of the body. This applies to the whole skin surface of the body, with the exception of the skin at the end of the BTT.

Measurements of internal temperature such as rectal do not have the same clinical relevance as measurement in the brain. Selective brain cooling has been demonstrated in a number of mammalian species under laboratory conditions and the same process could occur in humans. For instance the temperature in bladder and rectum may be quite different than the brain. High or low temperature in the brain may not be reflected in the temperature measured in other internal organs.

Figure 2B:
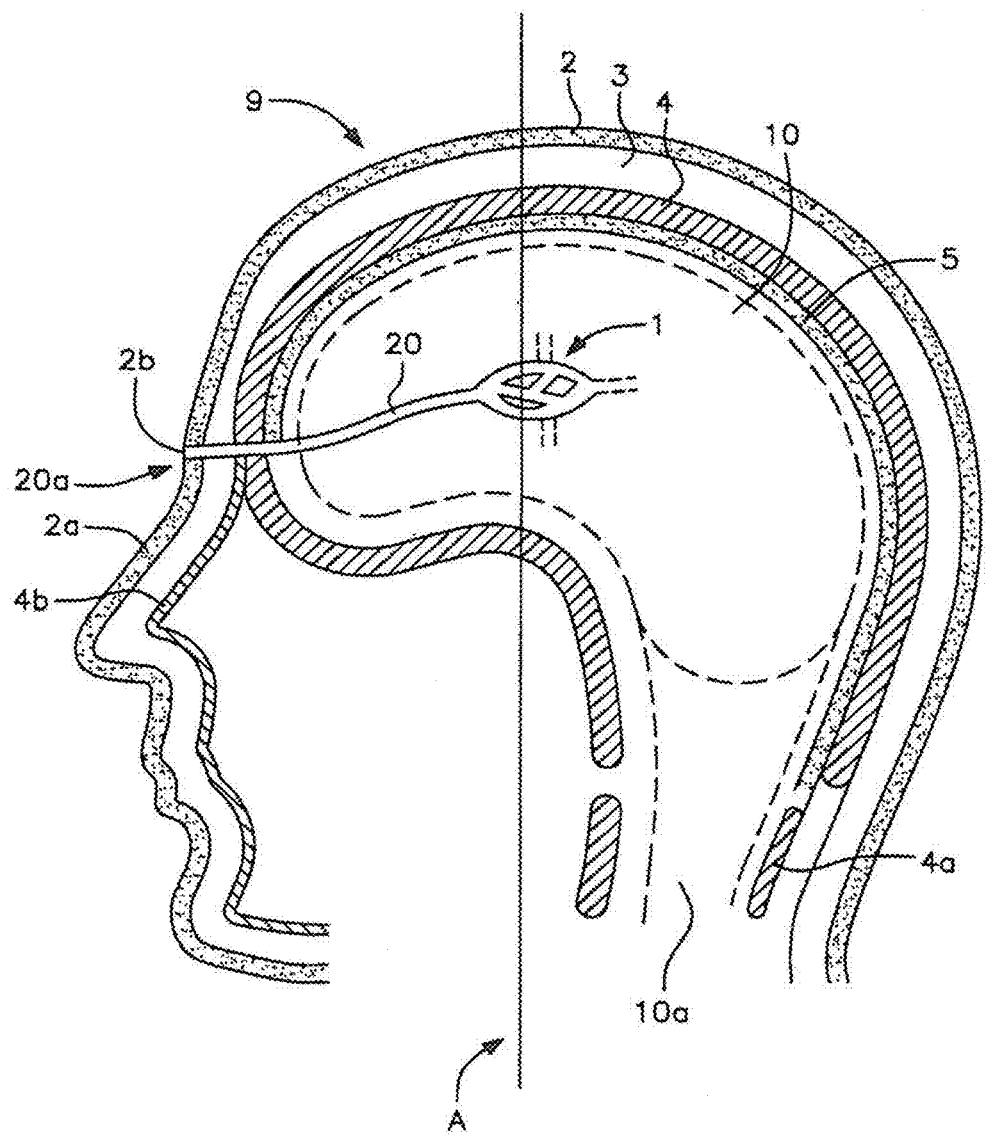
FIG. 2B is a cross-sectional schematic diagram of the human head showing the tunnel.

FIG. 2B is a cross-sectional schematic diagram of the human head 9 showing the brain 10, spinal cord 10a, the tunnel 20 represented by the superior ophthalmic vein, the cavernous sinus 1, which is the thermal energy storage compartment for the brain, and the various insulating barriers 2, 2a, 3, 4, 4a, 4b, 5 that keep the brain as a completely thermally insulated structure. Insulating barriers include skin 2 corresponding to the scalp, skin 2a corresponding to the skin covering the face, fat 3 covering the whole surface of the skull and face, skull bone 4, spinal bone 4a surrounding spinal cord 10a, facial bone 4b covering the face, and cerebral spinal fluid (CSF) 5. The combined thickness of barriers 2, 3, 4, 5 insulating the brain can reach 1.5 cm to 2.0 cm, which is a notable thickness and the largest single barrier against the environment in the whole body. Due to this completely confined environment the brain cannot remove heat efficiently and heat loss occurs at a very low rate. Skin 2 corresponds to the scalp which is the skin and associated structure covering the skull and which has low thermal conductivity and works as an insulator. Fat tissue 3 absorbs the majority of the far-infrared wavelength and works as a thermal buffer. Skull bone 4 has low thermal conductivity and the CSF works as a physical buffer and has zero heat production.

The heat generated by metabolic rate in the brain corresponds to 20% of the total heat produced by the body and this enormous amount of heat is kept in a confined and thermally sealed space. Brain tissue is the most susceptible tissue to thermal energy induced damage, both high and low levels of thermal energy. Because of the thermal insulation and physical inability of the brain to gain heat or lose heat, both hypothermic (cold) and hyperthermic (hot) states can lead to brain damage and death can rapidly ensue, as occur to thousands of healthy people annually besides seizures and death due to high fever in sick people. Unless appropriate and timely warning is provided by continuously monitoring brain temperature anyone affected by cold or hot disturbances is at risk of thermal induced damage to the brain.

FIG. 2B also shows a notably small entry point 20*a* measuring less than 0.5% of the body surface which corresponds to the end of the tunnel 20 on the skin 2*b*. The skin 2*b* is extremely thin with a thickness of 1 mm or less compared to the skin 2 and 2*a* which are five fold or more, thicker than skin 2*b*.

The tunnel 20 starts at the cavernous sinus 1 which is a conduit for venous drainage for the brain and for heat transfer at the end of the tunnel 20 as a radiant energy. Tunnel 20 provides an unobstructed passage to the cavernous sinus 1, a structure located in the middle of the brain, and which is in direct contact with the two sources of heat to the brain: 1) thermal energy produced due to metabolic rate by the brain and carried by the venous system; and 2) thermal energy delivered by the arterial supply from the rest of the body to the brain. This direct contact arrangement is showed in detail in FIG. 2C, which is a coronal section of FIG. 2B corresponding to the line marked "A".

Figure 2C:
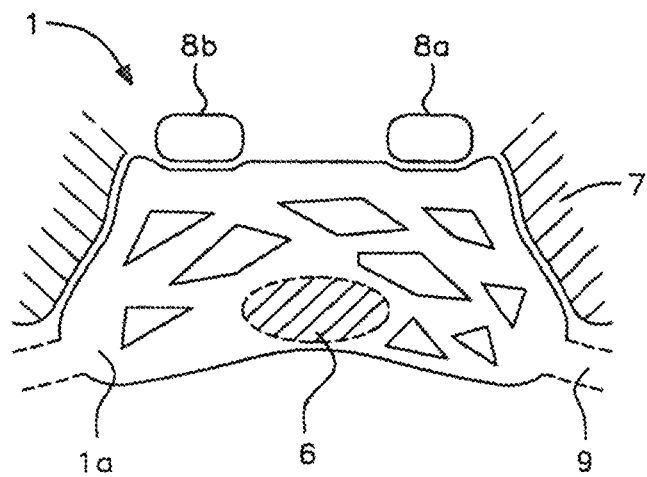
FIG. 2C is a coronal section schematic diagram showing the cavernous sinus of FIG. 2B.

FIG. 2C is a coronal section through the cavernous sinus 1 which is a cavity-like structure with multiple spaces 1*a* filled with venous blood from the veins 9 and from the superior ophthalmic vein 6. Cavernous sinus 1 collects thermal energy from brain tissue 7, from arterial blood of the right and left internal carotid arteries 8*a*, 8*b*, and from venous blood from vein 9. All of the structures 7, 8*a*, 8*b*, 9 are disposed along and in intimate contact with the cavernous sinus 1. A particular feature that makes the cavernous sinus 1 of the tunnel a very useful gauge for temperature disturbances is the intimate association with the carotid arteries 8*a*, 8*b*. The carotid arteries carry the blood from the body, and the amount of thermal energy delivered to the brain by said vessels can lead to a state of hypothermia or hyperthermia. For instance during exposure to cold, the body is cold and cold blood from the body is carried to the brain by internal carotid arteries 8*a*, 8*b*, and the cavernous sinus 1 is the entry point of those vessels 8*a*, 8*b* to the brain.

As soon as cold blood reaches the cavernous sinus 1 the corresponding thermal energy state is transferred to the tunnel and to the skin surface at the end of the tunnel, providing therefore an immediate alert even before the cold blood is distributed throughout the brain. The same applies to hot blood for instance generated during exercise which can lead to a 20 fold heat production compared to baseline. This heat carried by vessels 8*a*, 8*b* is transferred to the cavernous sinus 1 and can be measured at the end of the tunnel. In addition, the thermal energy generated by the brain is carried by cerebral venous blood and the cavernous sinus 1 is a structure filled with venous blood.

Figure 3B:
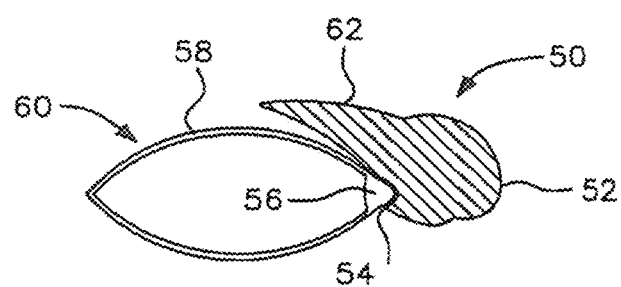
FIG. 3B is a schematic diagram of the image in FIG. 3A showing the geometry at the end of the tunnel.
Figure 3A:
FIG. 3A is a thermal infrared image of the human face showing the tunnel.

FIG. 3A is a thermal infrared image of the human face in which the geometry of the end of the tunnel on the skin can be visualized. The white bright spots define the central area of the tunnel. FIG. 3B is a schematic diagram of an exemplary geometry on the skin surface at the end of the tunnel. The medial aspect 52 of the tunnel 50 has a round shape. The lateral aspect 54 borders the upper lid margin 58 and caruncle 56 of the eye 60. The tunnel extends from the medial canthal area 52 into the upper eyelid 62 in a horn like projection.

Figure 4A:
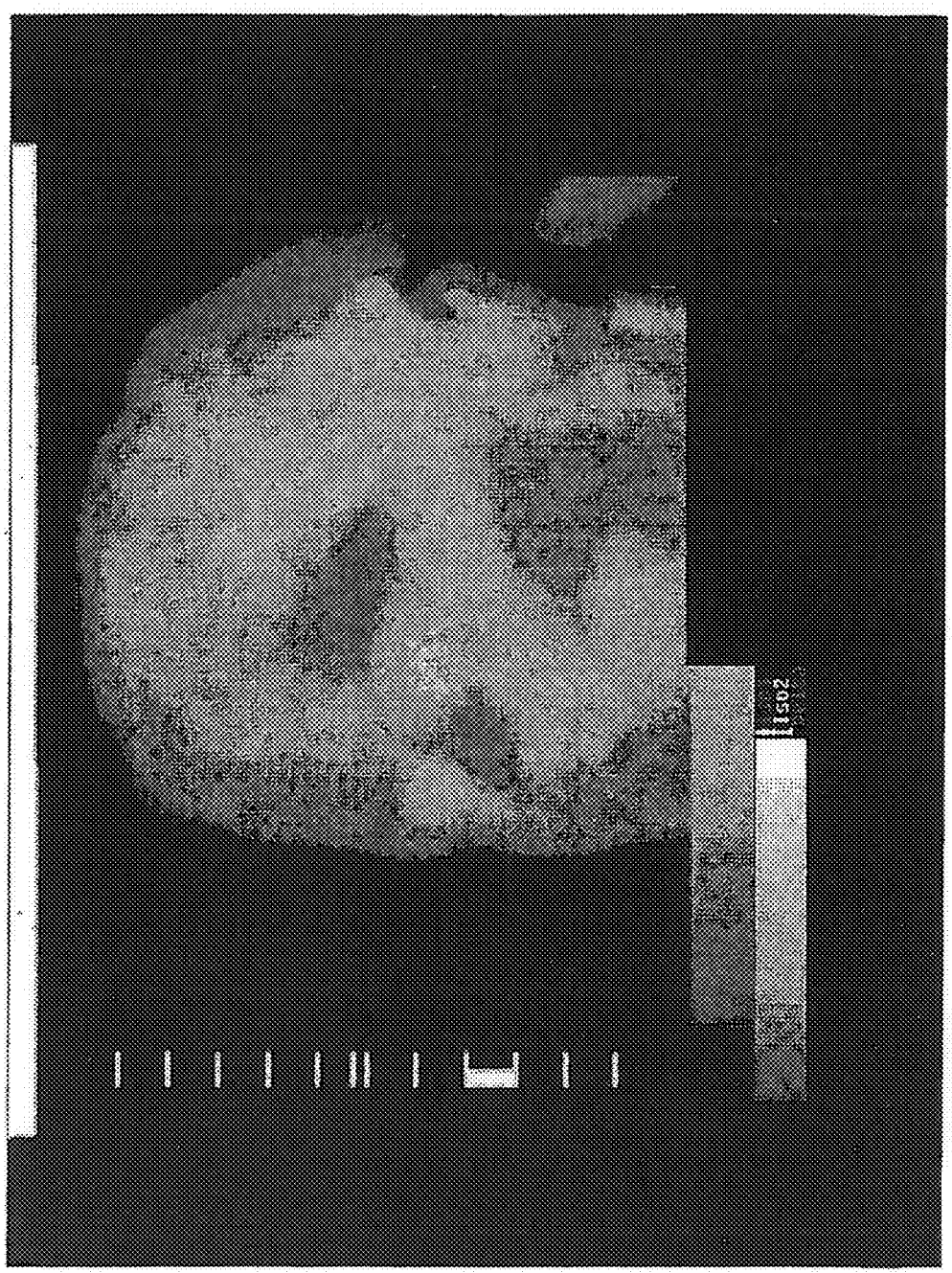
FIG. 4A is a thermal infrared image of the side of the human face showing a general view of the main entry point of the brain temperature tunnel.

The internal areas of the tunnel 50 include the general area for the main entry point and the main entry point as shown in FIGS. 4A to 5D. FIG. 4A is a thermal infrared image of the side of the human face showing a general view of the main entry point of the brain temperature tunnel, seen as white bright points located medial and above the medial canthal corner. FIG. 4B is a diagram showing the general area 70 of the main entry point and its relationship to the eye 60, medial canthal corner 61, eyebrow 64, and nose 66. The general area 70 of the main entry point provides an area with more faithful reproduction of the brain temperature since the area 70 has less interfering elements than the peripheral area of the tunnel.

Figure 5A:
FIG. 5A is a thermal infrared image of the front of the human face showing the main entry point of the brain temperature tunnel.

FIG. 5A is a thermal infrared image of the front of the human face with the right eye closed showing the main entry point of the brain temperature tunnel seen as white bright spots above and medial to the medial canthal corner. With closed eyes it is easy to observe that the radiant power is coming solely from the skin at the end of BTT.

FIG. 5B is a diagram showing the main entry point 80 and its relationship to the medial canthal corner 61 of closed eye 60 and eyelids 62. The main entry point 80 of the tunnel provides the area with the most faithful reproduction of the brain temperature since the area 80 has the least amount of interfering elements and is universally present in all human beings at an equivalent anatomical position. The main entry point 80 has the highest total radiant power and has a surface with high emissivity. The main entry point 80 is located on the skin in the superior aspect of the medial canthal area 63, in the supero-medial aspect of the medial canthal corner 61.

Figure 5C:
FIG. 5C is a thermal infrared image of the side of the human face in FIG. 5A showing the main entry point of the brain temperature tunnel.

FIG. 5C is a thermal infrared image of the side of the human face in FIG. 5A with the left eye closed showing a side view of the main entry point of the brain temperature tunnel, seen as bright white spots. It can be observed with closed eyes that the radiant power is coming solely from the skin at the end of BTT.

Figure 5D:
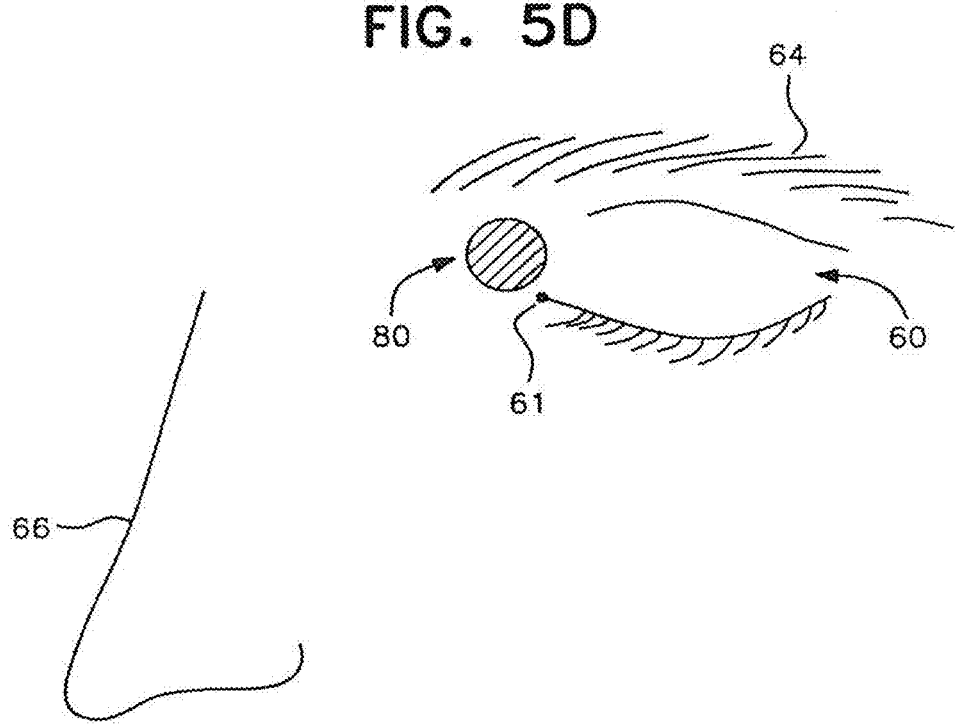
FIG. 5D is a schematic view of the image in FIG. 5C.

FIG. 5D shows the main entry point 80 in the superior aspect of the medial canthal area above the medial canthal corner 61, and also shows the position of main entry point in relation to the eye 60, eyebrow 64 and nose 66. Support structures can precisely position sensing devices on top of the main entry point of the tunnel because the main entry point is completely demarcated by anatomic landmarks. In general the sensor is positioned on the medial canthal skin area above the medial canthal corner and adjacent to the eye. Although indicators can be placed on support structures to better guide the positioning of the sensor, the universal presence of the various permanent anatomic landmarks allows the precise positioning by any non-technical person.

The main entry point is the preferred location for the positioning of the sensor by the support structure, but the placement of a sensor in any part of the end of the tunnel including the general entry point area and peripheral area provides clinically useful measurements depending on the application. The degree of precision needed for the measurement will determine the positioning of the sensor. In cases of neurosurgery, cardiovascular surgery, or other surgical procedures in which the patient is at high risk of hypothermia or malignant hyperthermia, the preferred position of the sensor is at the main entry point. For recreational or professional sports, military, workers, fever detection at home, wrinkle protection in sunlight, and the like, positioning the sensor in any part of the end of the tunnel area provides the precision needed for clinical usefulness.

Figure 6:
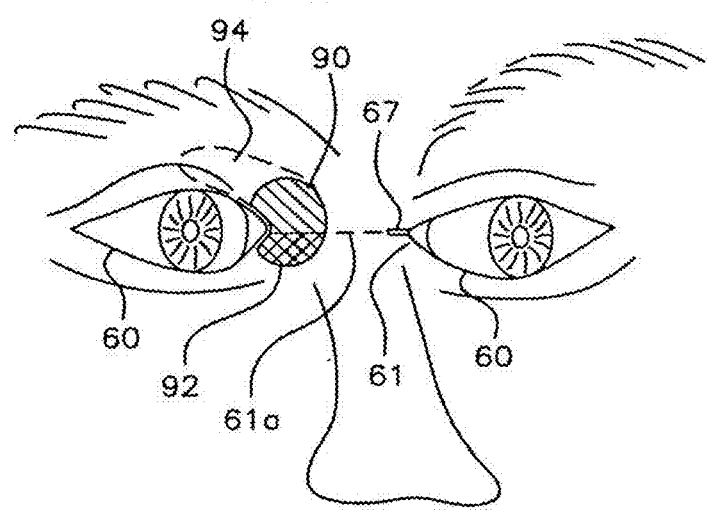
FIG. 6 is a schematic view of the face showing the general area of the main entry point of the tunnel and peripheral parts.

In accordance with the present invention, FIG. 6 is a schematic view of the face showing the general area of the main entry point of the tunnel 90 and the overall area of the end of the tunnel and its relationship to the medial canthal tendon 67. The end of the tunnel includes the general main entry point area 90 and the upper eyelid area 94. The area 90 has a peripheral portion 92. Both medial canthal areas have a medial canthal tendon and the left eye is used to facilitate the illustration. The medial canthal tendon 67 arises at the medial canthal corner 61 of eye 60. The left medial canthal tendon 67 is diametrically opposed to the right medial canthal tendon as shown by broken lines 61a which begins at the medial corner of the eye 61. Although the main entry point is above the medial canthal tendon 67, some of the peripheral area 92 of the tunnel is located below tendon 67.

FIG. 6A is a schematic diagram showing two physiologic tunnels. The upper figure shows the area corresponding to the BTT 10. The lower figure shows an area corresponding to a metabolic tunnel 13 which includes the upper eyelid area 13a and lower eyelid area 13b seen as light blue areas in FIG. 1B. For measuring the concentration of chemical substances the total radiant power is not mandatory. The key aspect for clinical useful spectroscopic measurements is signal coming from the cerebral area and the reduction or elimination of interfering constituents, and the main interfering constituent is adipose tissue. By removing adipose tissue and receiving spectral information carried by a vasculature from the brain, precise and clinical measurements can be achieved. The sensors supported by support structure are adapted to have a field of view that matches in total or in part the metabolic tunnel 13 for capturing thermal radiation from said tunnel 13.

Figure 7A:
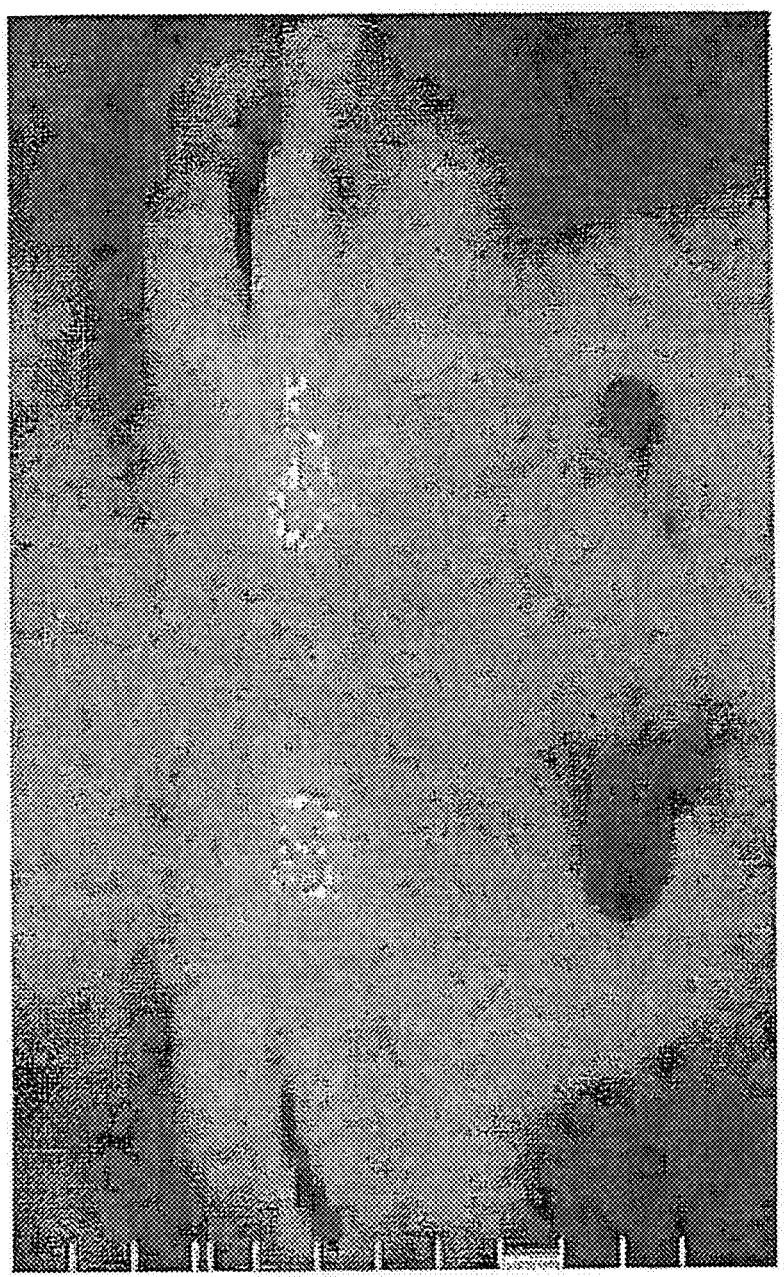
FIGS. 7A and 7B are thermal infrared images of the human face before and after cold challenge.
Figure 7B:

To determine the thermal stability of the tunnel area in relation to environmental changes, cold and heat challenge tests were performed. FIGS. 7A and 7B are thermal infrared images of an exemplary experiment showing the human face before and after cold challenge. In FIG. 7A the face has a lighter appearance when compared to FIG. 7B which is darker indicating a lower temperature. The nose in FIG. 7A has an overall whitish appearance as compared to the nose in FIG. 7B which has an overall darker appearance. Since the areas outside the tunnel have thermoregulatory arteriovenous shunts and interfering constituents including fat, the changes in the temperature of the environment are reflected in said areas. Thus measurements in those non-tunnel areas of the face reflect the environment instead of the actual body temperature. The non-tunnel areas of the skin in the face and body can change with the changes in ambient temperature. The radiant power of the tunnel area remains stable and there is no change in the amount of thermal energy demonstrating the stability of the thermal emission of the BTT area. Changes of thermal radiation at the tunnel area only occur when the brain temperature changes, which provides the most reliable measurement of the thermal status of the body.

Figure 8A:
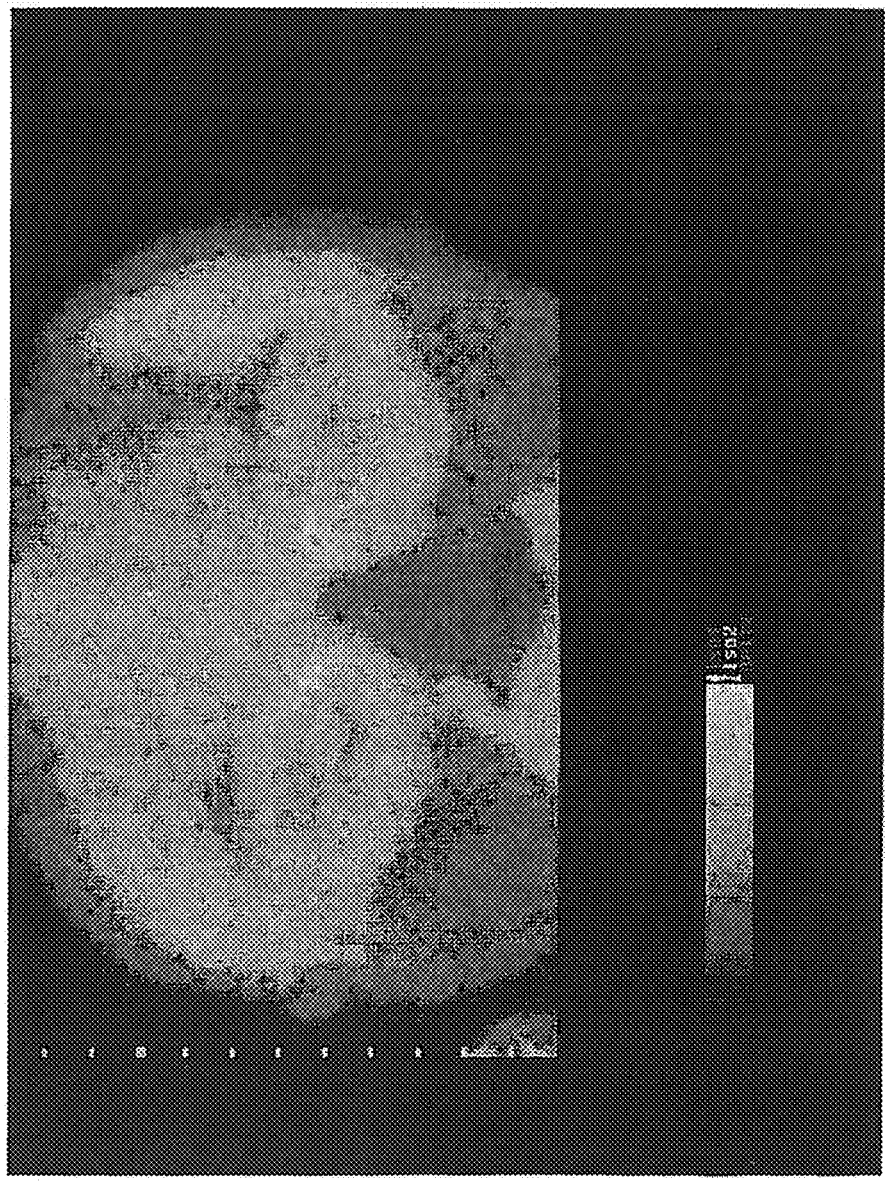
FIGS. 8A and 8B are thermal infrared images of the human face of different subjects showing the tunnel.
Figure 8B:
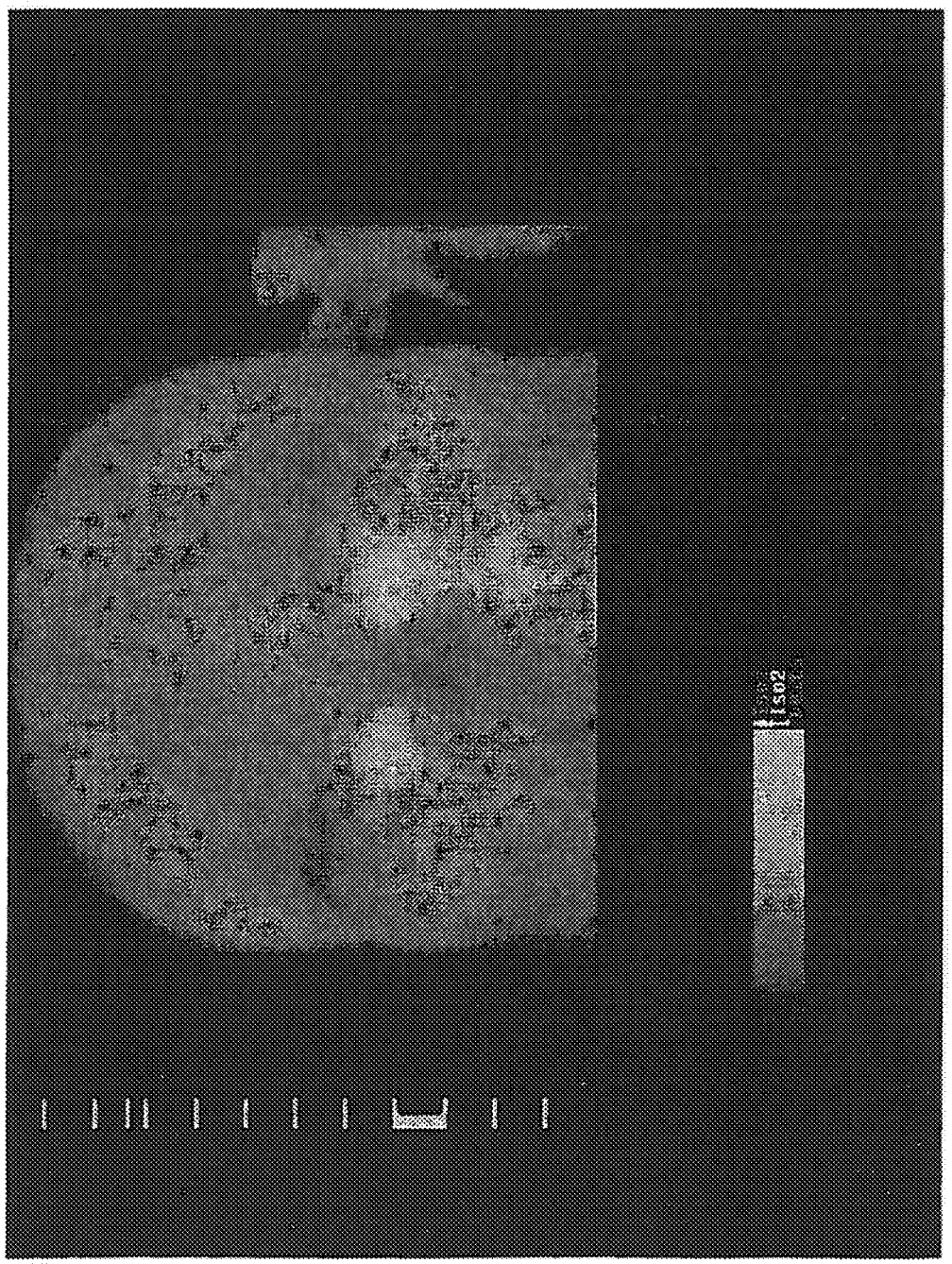
Figure 9A:
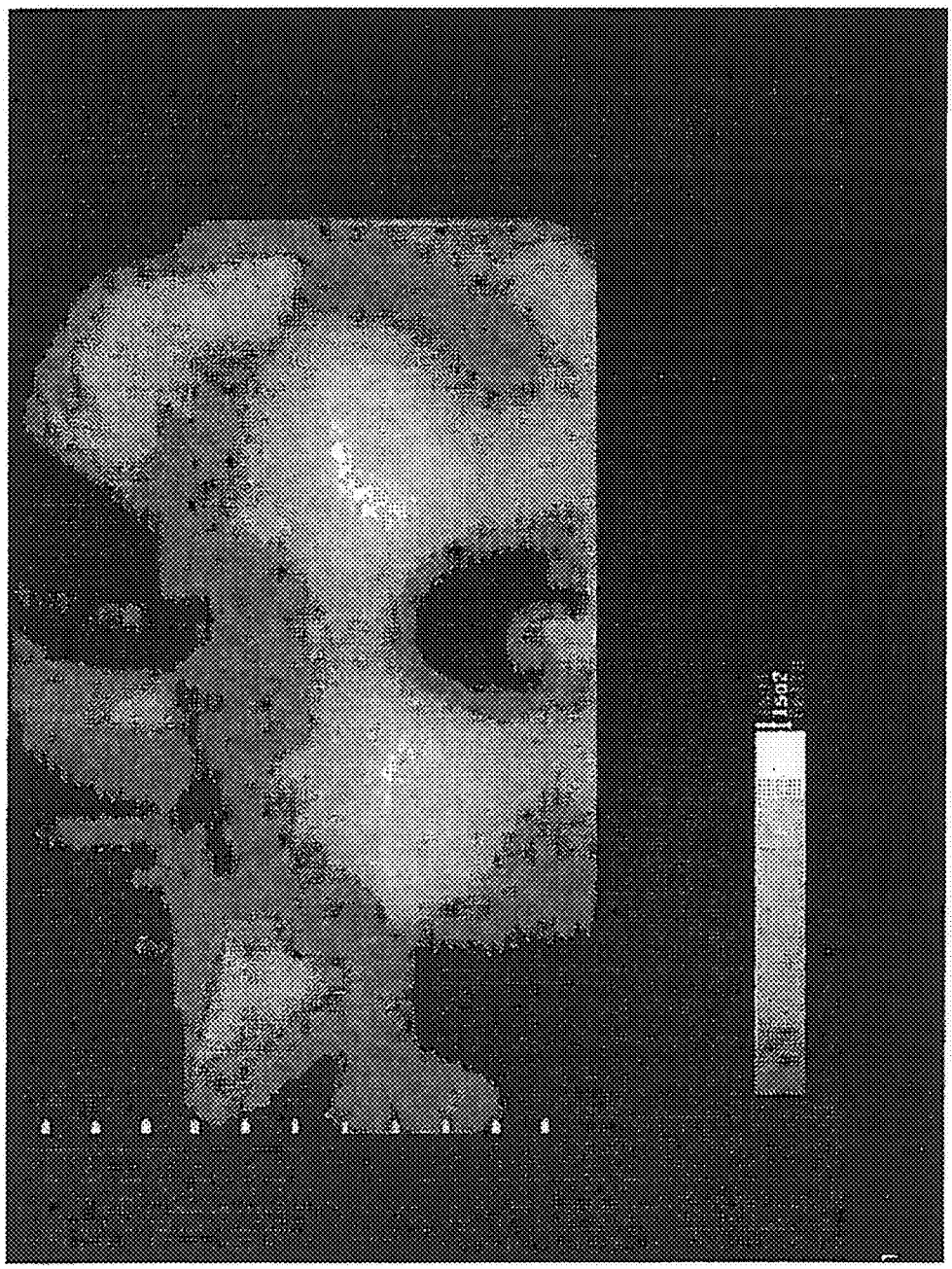
FIGS. 9A and 9B are thermal infrared images of animals showing a tunnel.
Figure 9B:
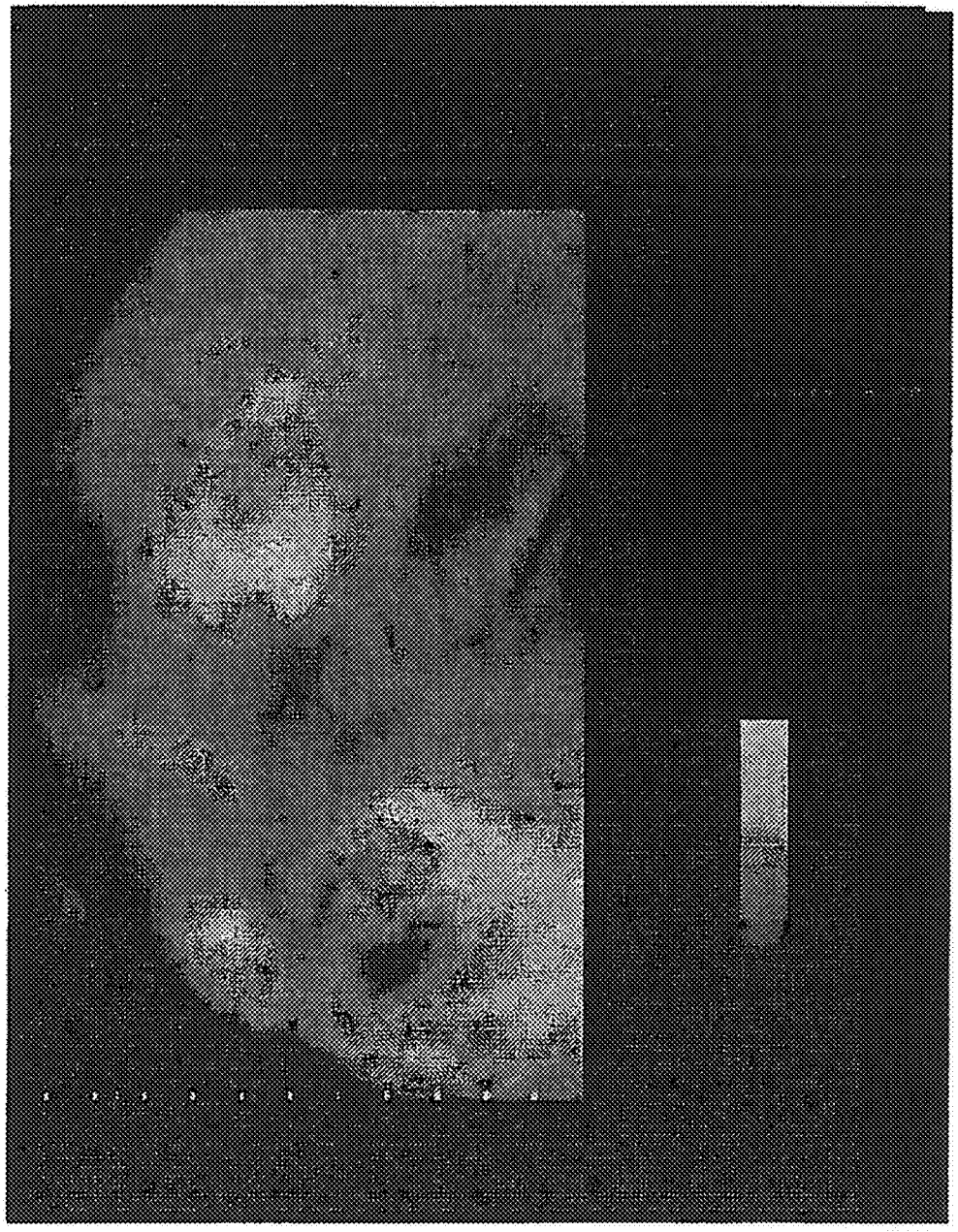

FIGS. 8A and 8B are thermal infrared images of the human face of different subjects showing the tunnel seen as bright white spots in the medial canthal area. The physiologic tunnel is universally present in all individuals despite anatomic variations and ethnic differences. FIGS. 9A and 9B are thermal infrared image showing that the tunnel seen as bright white spots are equally present in animals, illustrated here by a cat (FIG. 9A) and a dog (FIG. 9B).

A preferred embodiment includes a temperature sensor with measurement processing electronics housed in a patch-like support structure which positions a passive sensor directly in contact with the skin over the brain temperature tunnel site. Accordingly, FIG. 10 is a perspective view of a preferred embodiment showing a person 100 wearing a support structure comprised of a patch 72 with a passive sensor 74 positioned on the skin at the end of the tunnel. Person 100 is laying on a mattress 76 which contains antenna 78. Wire 82 extends from antenna 78 to controller unit 84 with said controller 84 communicating with device 88 by communication line 86. Exemplary device 88 includes a decoding and display unit at the bedside or at the nursing station. It is understood that controller unit 84 besides communicating by cable 86, can also contain a wireless transmission device to wirelessly transmit the signal acquired to a remote station. This inductive radio frequency powered telemetry system can use the same antenna 78 to transfer energy and to receive the signal.

The antenna 78 can be secured to a mattress, pillow, frame of a bed, and the like in a removable or permanent manner. The preferred embodiment includes a thin flat antenna encapsulated by a flexible polymer that is secured to a mattress and is not visible to the user. Alternatively an antenna can be placed in any area surrounding the patient, such as on a night stand.

The antenna 78 and controller unit 84 works as a receiver/interrogator. A receiver/interrogator antenna 78 causes RF energy to radiate to the microcircuit in the patch 72. This energy would be stored and converted for use in the temperature measurement process and in the transmission of the data from the patch 72 to the antenna 78. Once sufficient energy has been transferred, the microcircuit makes the measurement and transmits that data to the receiver/interrogator antenna 78 with said data being processed at controller 84 and further communicated to device 88 for display or further transmission. The switching elements involved in the acquisition of the sensor data (measurement of the energy) is done in a sequence so that the quantitized answer is available and stored prior to the activation of the noise-rich transmission signal. Thus the two inherently incompatible processes successfully coexist because they are not active simultaneously.

The capability of the RF link to communicate in the presence of noise is accomplished by "spreading" the spectral content of the transmitted energy in a way that would inherently add redundancy to the transmission while reducing the probability that the transmission can ever be interpreted by the receiver/interrogator 78 as another transmission or noise that would cause the receiver/interrogator 78 to transmit and display incorrect information. This wireless transmission scheme can be implemented with very few active elements. The modulation purposely spreads the transmission energy across the spectrum and thus provides noise immunity and the system can be ultimately produced via batch processing and thus at a very low cost.

Since the energy to operate sensor 74 in patch 72 comes from the antenna 78, the microcircuit in said patch 72 can be very small and ultra-thin. Size of the patch 72 would be further minimized to extremely small dimensions by the design approach that places all the processing function of the RF link in the controller unit 84 working as a receiver. RF messaging protocol and the control of the sensor 74 resides in the receiver/interrogator controller powered by commercially available batteries or by AC current. Thus the RF messaging protocol and the control of the sensor 74 is directly controlled by the MCU of controller 84. The circuit resident in the patch 72 is preferably completely self-contained. The sensing system 74 in the patch 72 is preferably a silicon microcircuit containing the circuits needed to support the sensor, quantatize the data from the sensor, encode the data for radio frequency transmission, and transmit the data, besides power conditioning circuits and digital state control. Sensor, support circuitry, RF power and communications are all deposited on a micro-chip die allowing the circuit to be built in large quantities and at very low cost.

This scheme is preferably used for both passive and active devices.

The operational process can consist of two modes, manual or automated. In the manual mode, an operator such as a nurse activates the system and RF energy radiated to the microcircuit in the patch 72 would be stored and converted for use in the temperature measurement process and in the transmission of the data from the end of the BTT to the antenna 78. Once sufficient energy has been transferred (less than 1 second) the microcircuit would make the measurement and transmit the data to the antenna 78 receiver and controller 84 to be displayed for example on a back-lit LCD display at the nursing station. An audio "beep" will signal that the data had been received and is ready for view. In the automated mode, the process is done automatically and continuously by interrogation at preset frequency and an alarm being activated when the reading is outside the specified range. A tri-dimensional antenna can also be used and the controller 84 set up to search the three dimensions of the antenna to assure continued and proper connection between antenna 78 and sensing means 74. It is also understood that the sensor can modulate reflected RF energy. Accordingly, the energy will trigger the unit to acquire a temperature measurement, and then the unit will modulate the reflected energy. This reflected energy and information will be received at the interrogator and displayed as above.

The present invention also provides a method for monitoring biological parameters, which comprises the steps of: securing a passive sensor to the body; generating electromagnetic radiation from a device secured to at least one of a mattress, a pillow and the frame of a bed; generating a signal from said passive sensor; receiving said signal by a device secured to at least one of a mattress, a pillow and the frame of a bed; and determining the value of the biological parameter based on said signal.

It is understood that a variety of external power sources such as electromagnetic coupling can be used including an ultra-capacitor charged externally through electromagnetic induction coupling and cells that can be recharged by an external oscillator. It is also understood that the sensing system can be remotely driven by ultrasonic waves.

Figure 11:
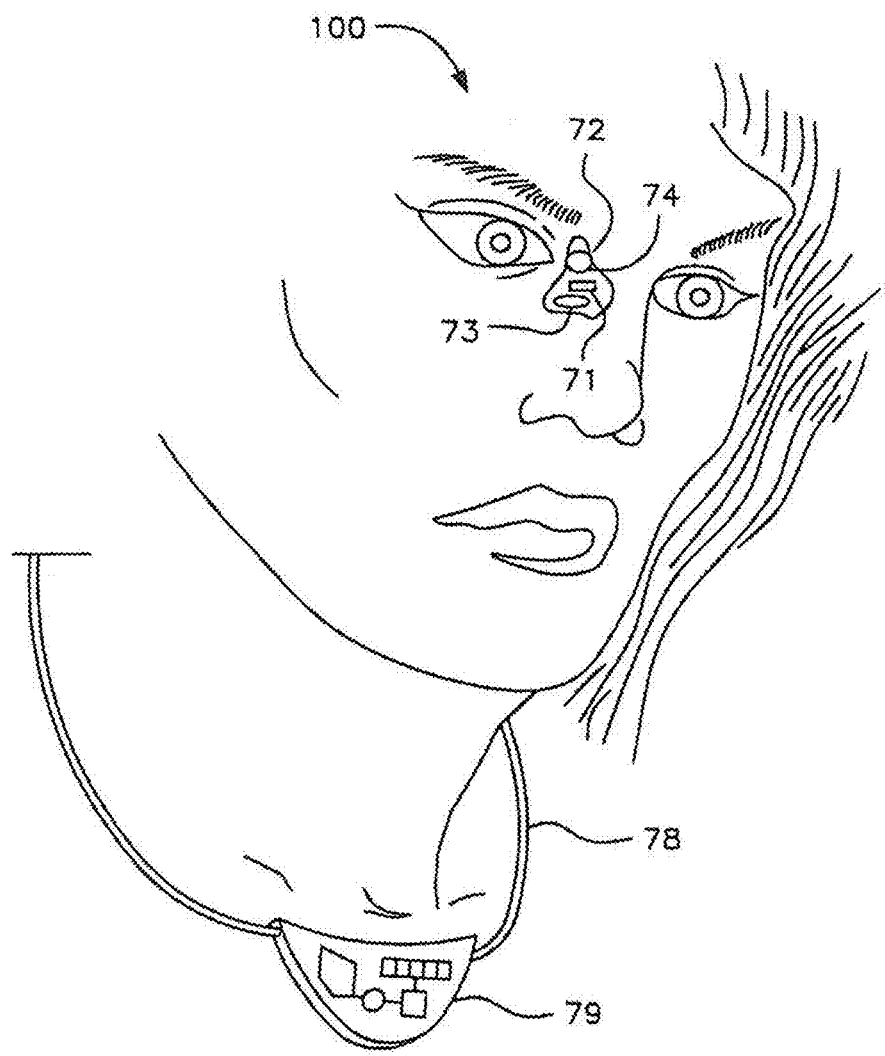
FIG. 11 is a perspective view of another preferred embodiment showing a person wearing a support structure comprised of a patch with a passive sensor positioned on the skin at the end of the tunnel in accordance with the present invention.

FIG. 11 is a perspective view of another preferred embodiment showing in closer detail a person 100 wearing a support structure comprised of patch 72 with a sensor 74, transmitter 71, and digital converter and control 73 positioned on the skin at the end of the tunnel. Person 100 is wearing a necklace which works as antenna 78 and a pendant in the necklace works as the controller unit and transmitting unit 79. Solar cells and/or specialized batteries power unit 79. Patients are used to carrying Holter monitoring and cards with cords around their necks and this embodiment can fit well with those currently used systems. It is understood that, besides a necklace, a variety of articles including clothing and electric devices can be used as a receiver/interrogator and this capability can be easily incorporated into cell phones, note book computers, hand held computers, internet appliances for connecting to the internet, and the like, so a patient could use his/her cell phone or computer means to monitor his/her brain temperature.

The preferred embodiments shown in FIGS. 10 and 11 can preferably provide continuous monitoring of fever or temperature spikes for any surgery, for any patient admitted to a hospital, for nursing home patients, in ambulances, and to prevent death or harm by hospital infection. Hospital infection is an infection acquired during a hospital stay. Hospital infection is the fourth cause of death in the U.S. and kills more than 100,000 patients annually and occurs primarily due to lack of early identification of fever or temperature spikes. The present invention provides timely identification and therapy of an infection due to 24 hour automated monitoring of temperature. If there is a spike in temperature an alarm can be activated. This will allow timely identification and treatment of an infection and thus prevent death or costly complications such as septic shock that can occur due to delay in treating infectious processes. Besides, said preferred embodiments provide means for continuous fever monitoring at home including during sleeping for both children and adults.

Figure 12A:
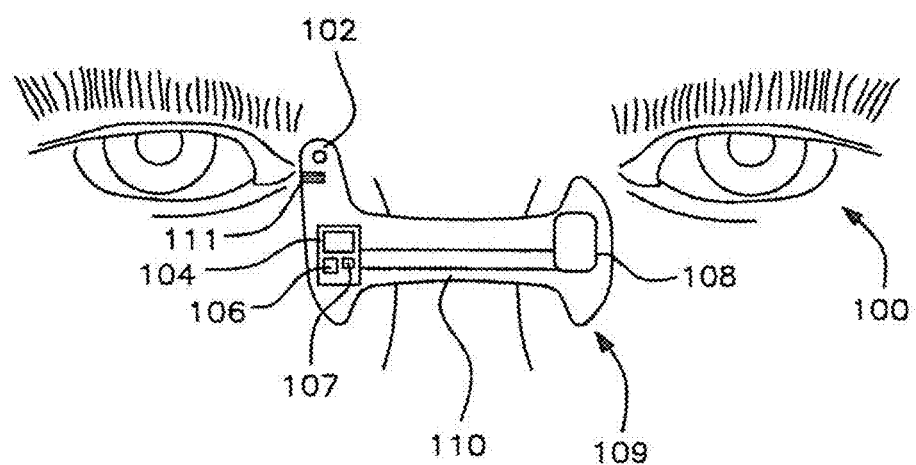
FIG. 12A is a front perspective view of a person wearing a support structure comprised of a patch with an active sensor positioned on the skin at the end of the tunnel in accordance with the present invention.
Figure 12B:
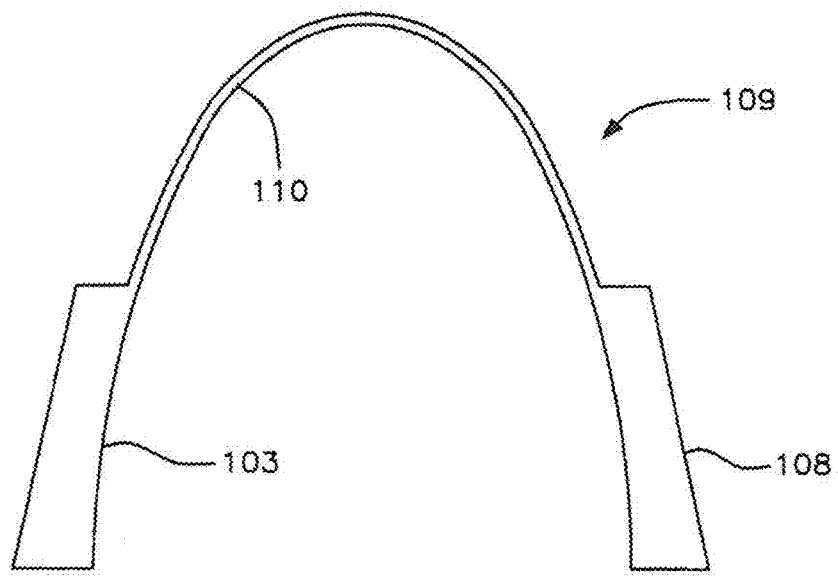
FIG. 12B is a side schematic view showing the flexible nature of the support structure shown in FIG. 12A.

FIG. 12A is a front perspective view of a preferred embodiment showing a person 100 wearing a support structure comprised of a patch 109 with indicator lines 111 and containing an active sensor 102 positioned on the skin at the end of the tunnel. The preferred embodiment shown in FIG. 12 provides a transmitting device 104, a processing device 106, AD converter 107 and a sensing device 102 connected by flexible circuit 110 to power source 108. For example the transmitting module can include RF, sound or light. FIG. 12B is a side schematic view showing the flexible nature of the support structure in FIG. 12A with flexible circuit 110 connecting microelectronic package 103 which contains a transmitting device means, a processing device and a sensing device in the right side of the patch 109 and the power source 108 in the left side of said patch 109. Exemplary embodiments will be described.

In accordance with this exemplary embodiment for temperature measurement, the thermal energy emitted by the BTT is sensed by the temperature sensor 102 such as a miniature thermistor which produces a signal representing the thermal energy sensed. The signal is then converted to digital information and processed by processor 106 using standard processing for determining the temperature. An exemplary sonic-based system for brain temperature measurement comprises a temperature sensor, input coupling circuit, signal processing circuit, output coupling circuit and output display circuit. A temperature sensor 102 (e.g., thermistor) in a patch 109 placed on the surface of the skin at the medial canthal area responds to variations in brain temperature which is manifested as a DC voltage signal.

This signal, coupled to a Signal Processor Circuit via an Input Coupling Circuit is used to modulate the output of an oscillator, e.g., a multivibrator circuit, piezoelectric systems operating in or just above the audio frequency range. The oscillator is a primary component of the Signal Processor Circuit. The output of the oscillator is input to an amplifier, which is the second primary component of the Signal Processor.

The amplifier increases the output level from the oscillator so that the output of the Signal Processor is sufficient to drive an Output Display Circuit. Depending on the nature of the Output Display Circuit, e.g., an audio speaker, a visual LED display, or other possible display embodiment, an Output Coupling Circuit is utilized to match the signal from the Signal Processor Circuit to the Output Display Circuit. For an Output Display Circuit that requires a digital input signal, the Output Coupling Circuit might include an analog to digital (A/D) converter circuit. A DC power supply circuit is the remaining primary component in the Signal Processor Module. The DC power supply is required to support the operation of the oscillator and the amplifier in the Signal Processing Circuit. Embodiments of the DC power supply can include ultra miniature DC batteries, a light sensitive DC power source, or some combination of the two, and the like.

The micro transducers, signal processing electronics, transmitters and power source can be preferably constructed as an Application Specific Integrated Circuit or as a hybrid circuit alone or in combination with MEMS (micro electrical mechanical systems) technology.

The thermistor voltage is input to a microcontroller unit, i.e., a single chip microprocessor, which is pre-programmed to process the thermistor voltage into a digital signal which corresponds to the patient's measured temperature in degrees C. (or degrees F.) at the BTT site. It is understood that different programming and schemes can be used. For example, the sensor voltage can be directly fed into the microcontroller for conversion to a temperature value and then displayed on a screen as a temperature value, e.g., 98.6° F. On the other hand the voltage can be processed through an analog to digital converter (ADC) before it is input to the microcontroller.

The microcontroller output, after additional signal conditioning, serves as the driver for a piezoelectric audio frequency (ultrasonic) transmitter. The piezoelectric transmitter wirelessly sends digital pulses that can be recognized by software in a clock radio sized receiver module consisting of a microphone, low-pass audio filter, amplifier, microcontroller unit, local temperature display and pre-selected temperature level alert mechanism. The signal processing software is pre-programmed into the microcontroller unit of the receiver. Although the present invention provides means for RF transmission in the presence of noise, this particular embodiment using a microphone as the receiving unit may offer additional advantages in the hospital setting since there is zero RF interference with the many other RF devices usually present in said setting. The microcontroller unit drives a temperature display for each patient being monitored. Each transmitter is tagged with its own ID. Thus one receiver module can be used for various patients. A watch, cell phone, and the like adapted with a microphone can also work as the receiver module.

In another embodiment the output of the microcontroller is used to drive a piezo-electric buzzer. The microcontroller output drives the piezo-electric buzzer to alert the user of the health threatening situation. In this design the output of the microcontroller may be fed into a digital-to-analog converter (DAC) that transforms the digital data signal from the microcontroller to an equivalent analog signal which is used to drive the buzzer.

In yet another embodiment the output from the (DAC) is used to drive a speech synthesizer chip programmed to output an appropriate audio warning to the user, for instance an athlete at risk of heatstroke. For a sensed temperature above 39 degrees Celsius the message might be: "Your Body temperature is High. Seek shade. Drink cold liquid. Rest." For temperature below 36 degrees Celsius the message might be: "Your Body temperature is Low. Seek shelter from the Cold. Drink warm liquid. Warm up."

In another embodiment the output is used to drive a light transmitter programmed to output an appropriate light signal. The transmitter consists of an infrared light that is activated when the temperature reaches a certain level. The light signal will work as a remote control unit that activates a remote unit that sounds an alarm. This embodiment for instance can alert the parents during the night when the child is sleeping and has a temperature spike.

An exemplary embodiment of the platform for local reporting consists of three electronic modules mechanically housed in a fabric or plastic holder such as patch 109, which contain a sensor 102 positioned on the skin at the BTT site. The modules are: Temperature Sensor Module, Microcontroller Module, and Output Display Module in addition to a battery. An electronic interface is used between each module for the overall device to properly function. The configuration of this system consists of a strip such as patch 109 attached to the BTT area by a self-adhesive pad. A thermistor coupled to a microcontroller drives an audio frequency piezoelectric transmitter or LED. The system provides local reporting of temperature without a receiver. An audio tone or light will alert the user when certain thresholds are met. The tone can work as a chime or reproduction of human voice.

Another exemplary embodiment for remote reporting consists of four electronic modules: Sensor Module, Microcontroller Module, Output Transmitter Module and Receiver/Monitor Module. From a mechanical viewpoint the first three modules are virtually identical to the first embodiment. Electronically the Temperature Sensor and Microprocessor Modules are identical to the previous embodiment. In this embodiment an Output Transmitter Module replaces the previous local Output Display Module. Output Transmitter Module is designed to transmit wirelessly the temperature results determined by the Microprocessor Module to a remotely located Receiver/Monitor Module. An electronic interface is used between each module for proper function. This device can be utilized by patients in a hospital or home setting. On a continuous basis temperature levels can be obtained by accessing data provided by the Receiver/Monitor Module.

A variety of temperature sensing elements can be used as a temperature sensor including a thermistor, thermocouple, or RTD (Resistance Temperature Detector), platinum wire, surface mounted sensors, semiconductors, thermoelectric systems which measure surface temperature, optic fiber which fluoresces, bimetallic devices, liquid expansion devices, and change-of-state devices, heat flux sensor, crystal thermometry and reversible temperature indicators including liquid crystal Mylar sheets. A preferred temperature sensor includes thermistor model 104JT available from Shibaura of Japan.

Figure 13:
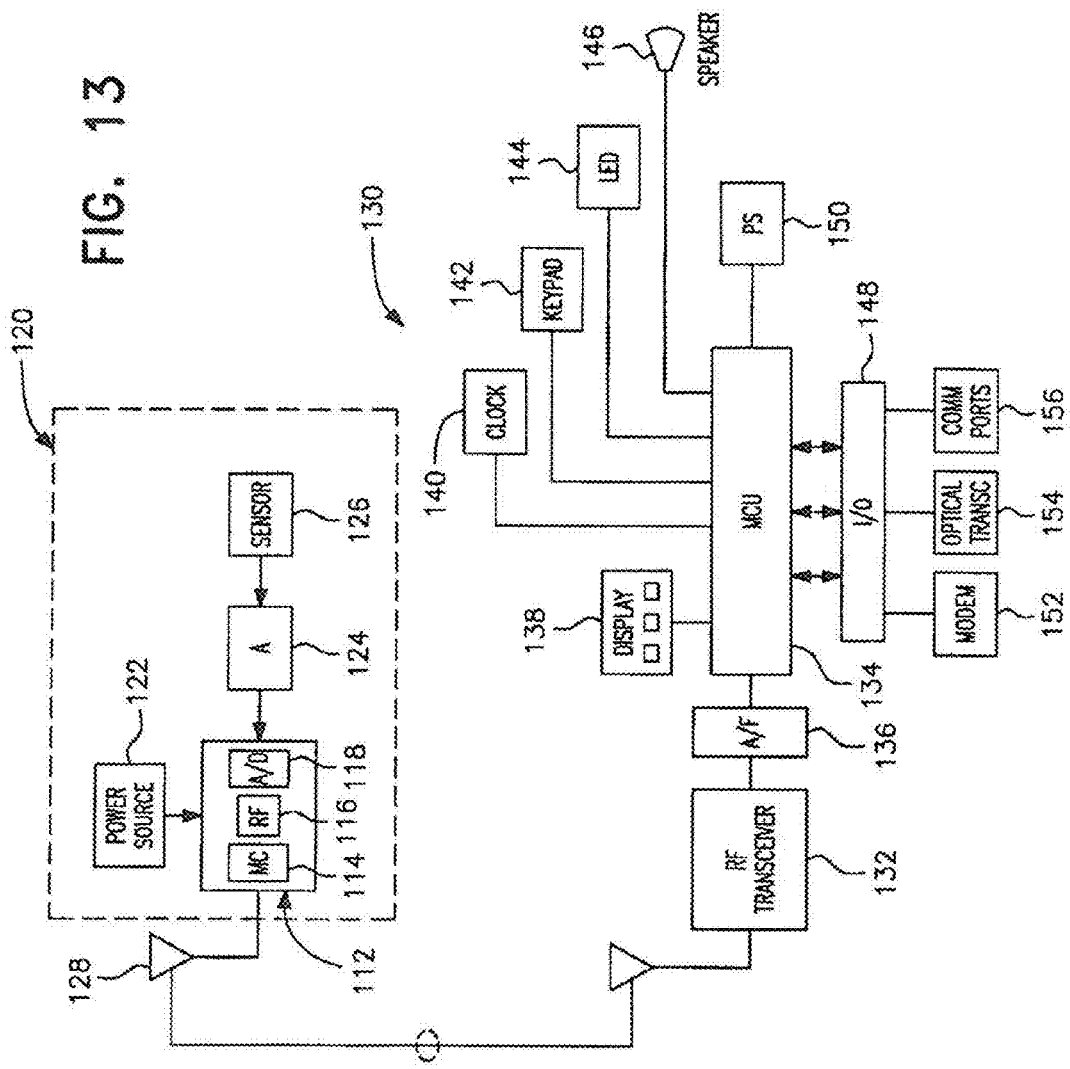
FIG. 13 is a schematic block diagram of one preferred embodiment.

FIG. 13 shows a block diagram of a preferred embodiment of the present invention linking transmitter 120 to receiver 130. Transmitter 120 preferably includes a chip 112 incorporating a microcontroller (MCU) 114, a radio frequency transmitter (RF) 116 and a A/D converter 118 in addition to a power source 122, amplifier (A) 124, sensor 126, and antenna 128, preferably built-in in the chip. Exemplary chips include: (1) rfPIC12F675F, (available from Microchip Corporation, Arizona, USA) this is a MCU+ADC+433 Mhz Transmitter (2) CC1010, available from Chipcon Corporation of Norway.

Receiver 130 preferably includes a chip RF transceiver 132 (e.g., CC1000 available from Chipcon Corporation), a microcontroller unit (MCU) 134, amplifier and filtering units (A/F) 136, display 138, clock 140, keypad 142, LED 144, speaker 146, in addition to a power source 150 and input/output units (I/O) 148 and associated modem 152, optical transceiver 154 and communication ports 156.

A variety of devices can be used for the transmission scheme besides the commercially available RF transmitter chips previously mentioned. One simple transmission devices include an apparatus with a single channel transmitter in the 916.48 MHz band that sends the temperature readings to a bed side receiver as a frequency proportional to the reading. The thermistor's resistance would control the frequency of an oscillator feeding the RF transmitter data input. If the duty cycle is less than 1%, the 318 MHz band would be usable. Rather than frequency, a period measurement technique can be used. The model uses a simple radio frequency carrier as the information transport and modulating that carrier with the brain temperature information derived from a transduction device capable of changing its electrical characteristics as a function of temperature (e.g.; thermistor). Either frequency or amplitude of the carrier would be modulated by the temperature information so that a receiver tuned to that frequency could demodulate the changing carrier and recover the slowly moving temperature data.

Another transmission technique suitable to transmit the signal from a sensor in a support structure is a chirp device. This means that when activated, the transmitter outputs a carrier that starts at a lower frequency in the ISM band and smoothly increases frequency with time until a maximum frequency is reached. The brain temperature information is used to modify the rate of change of frequency of the chirp. The receiver is designed to measure the chirp input very accurately by looking for two or more specific frequencies. When the first of the frequencies is detected, a clock measures the elapsed time until the second frequency is received. Accordingly, a third, fourth, etc., frequency could be added to aid in the rejection of noise. Since virtually all the direct sequence spread spectrum transmitters and frequency hopping transmitters are spread randomly throughout their part of the ISM band, the probability of them actually producing the "right" sequence of frequencies at exactly the right time is remote.

Once the receiver measured the timing between the target frequencies, that time is the value that would represent the brain temperature. If the expected second, third, or fourth frequency is not received by the receiver within a "known" time window, the receiver rejects the initial inputs as noise. This provides a spread spectrum system by using a wide spectrum for transmitting the information while encoding the information in a way that is unlike the expected noise from other users of the ISM band. The chirp transmitter is low cost and simple to build and the brain temperature transducer is one of the active elements that controls the rate of change of frequency.

Other preferred embodiments for local reporting include a sensor, an operational amplifier (LM358 available from National Semiconductor Corporation) and a LED in addition to a power source. It is understood that the operational amplifier (Op Amp) can be substituted by a MCU and the LED substituted by a piezoelectric component.

Figure 14:
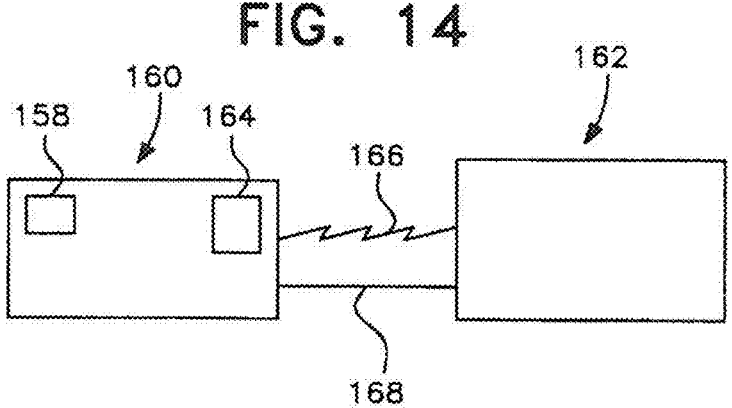
FIG. 14 is a schematic diagram of one preferred embodiment of the invention interacting with devices and articles of manufacture.

FIG. 14 is a schematic diagram showing the support structure 160 to a sensor 158, and MCU 164 controlling and/or adjusting unit 162. Communication between MCU 164 and unit 162 is achieved by wires 168 or wirelessly 166. By way of example, but not by limitation, exemplary units 162 include climate control units in cars, thermostats, vehicle seats, furniture, exercise machines, clothing, footwear, medical devices, drug pumps, and the like. For example, MCU 164 is programmed with transmit the temperature level to receiver unit 162 in the exercise machine. MCU in the exercising machine unit 162 is programmed to adjust speed or other settings in accordance with the signal generated by MCU 164.

The preferred embodiment allows precise positioning of the sensing apparatus by the support structure on the BTT site. The support structure is designed to conform to the anatomical landmarks of the BTT area which assures proper placement of the sensor at all times. The corner of the eye is considered a permanent anatomic landmark, i.e., it is present in the same location in all human beings. The BTT area is also a permanent anatomic landmark as demonstrated by the present invention. To facilitate consistent placement at the BTT site, an indicator in the support structure can be used as shown in FIGS. 15A to 15E.

Figure 15A:
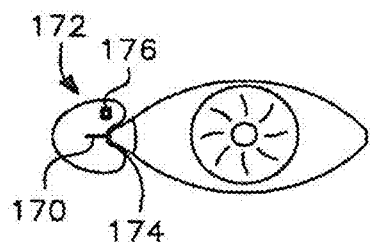
FIGS. 15A to 15E are schematic views showing preferred embodiments of the invention using indicators.

FIG. 15A shows a Guiding Line 170 placed on the outside surface of the support structure 172. The Guiding Line 170 is lined up with the medial corner of the eye 174. The sensor 176 is located above the Guiding Line 170 and on the outer edge of the support structure 172, so once the Guiding Line 170 of the support structure 172 is lined up with the medial corner of the eye 174, the sensor 176 is positioned on the main entry point of the tunnel. Thus the support structure 172 can be precisely and consistently applied in a way to allow the sensor 176 to cover the BTT area at all times.

Figure 15B:
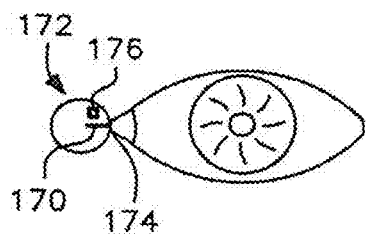

FIG. 15B shows a different design of the patch 172 but with the same Guiding Line 170 lined up with the medial corner of the eye 174, thus allowing consistent placement of sensor 176 at the BTT site despite the difference in design.

Figure 15C:
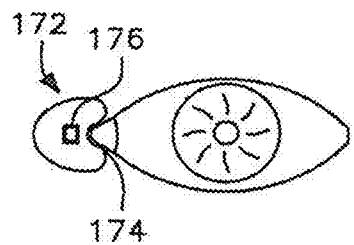

FIG. 15C is another preferred embodiment showing the sensor 176 lined up with medial corner 174. Thus in this embodiment a Guiding Line is not required and the sensor 176 itself guides the positioning.

Figure 15D:
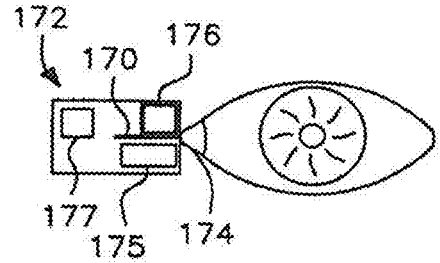

In FIG. 15D the MCU 175 and cell 177 of patch 172 are located outside of the BTT site while sensor 176 is precisely positioned at the BTT site. It is understood that any type of indicator on the support structure can be used to allow proper placement in the BTT area including external marks, leaflets, cuts in the support structure, different geometry that lines up with the corner of the eye, and the like.

Figure 15E:
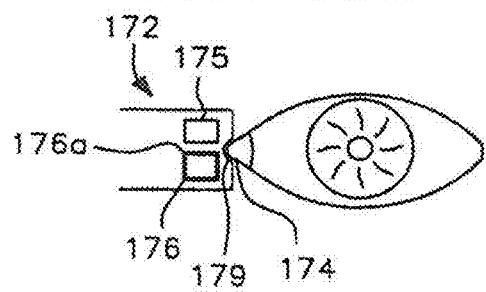

FIG. 15E is another preferred embodiment showing the superior edge 176a of sensor 176 lined up with medial corner 174 and located in the inferior aspect of the medial canthal area while microchip controller 175 is located in the superior aspect of the medial canthal area. Support structure 172 has a geometric indicator 179 comprised of a small recess on the support structure 172. It is understood that a strip working as support structure like an adhesive bandage can have the side opposite to the sensor and hardware made with tear off pieces. The sensor side is first attached to the skin and any excess strip can be easily torn off. Two sizes, adult and children cover all potential users.

The material for the support structure working as a patch can be soft and have insulating properties such as are found in polyethylene. Depending on the application a multilayer structure of the patch can include from the external side to the skin side the following: thinsulate layer; double foam adhesive (polyethylene); sensor (thermistor); and a Mylar sheet. The sensor surface can be covered by the Mylar sheet, which in turn is surrounded by the adhesive side of the foam. Any soft thin material with high thermal resistance and low thermal conductivity can be preferably used as an interface between the sensor and the exterior, such as polyurethane foam (K=0.02 W/m·C). Any support structure can incorporate the preferred insulation material.

A preferred power source for the patch includes natural thermoelectrics as disclosed by the present invention. In addition, standard lightweight thin plastic batteries using a combination of plastics such as fluorophenylthiophenes as electrodes can be used, and are flexible allowing better conformation with the anatomy of the BTT site. Another exemplary suitable power source includes a light weight ultra-thin solid state lithium battery comprised of a semi-solid plastic electrolyte which are about 300 microns thick.

The system can have two modes: at room temperature the system is quiet and at body temperature the system is activated. The system can also have an on/off switch by creating a circuit using skin resistance, so only when the sensor is placed on the skin is the system activated. The patch can also have a built-in switch in which peeling off a conductive backing opens the circuit (pads) and turn the system on. In addition, when removed from the body, the patch can be placed in a case containing a magnet. The magnet in the case acts as an off switch and transmission is terminated when said patch is in the case.

Figure 16A:
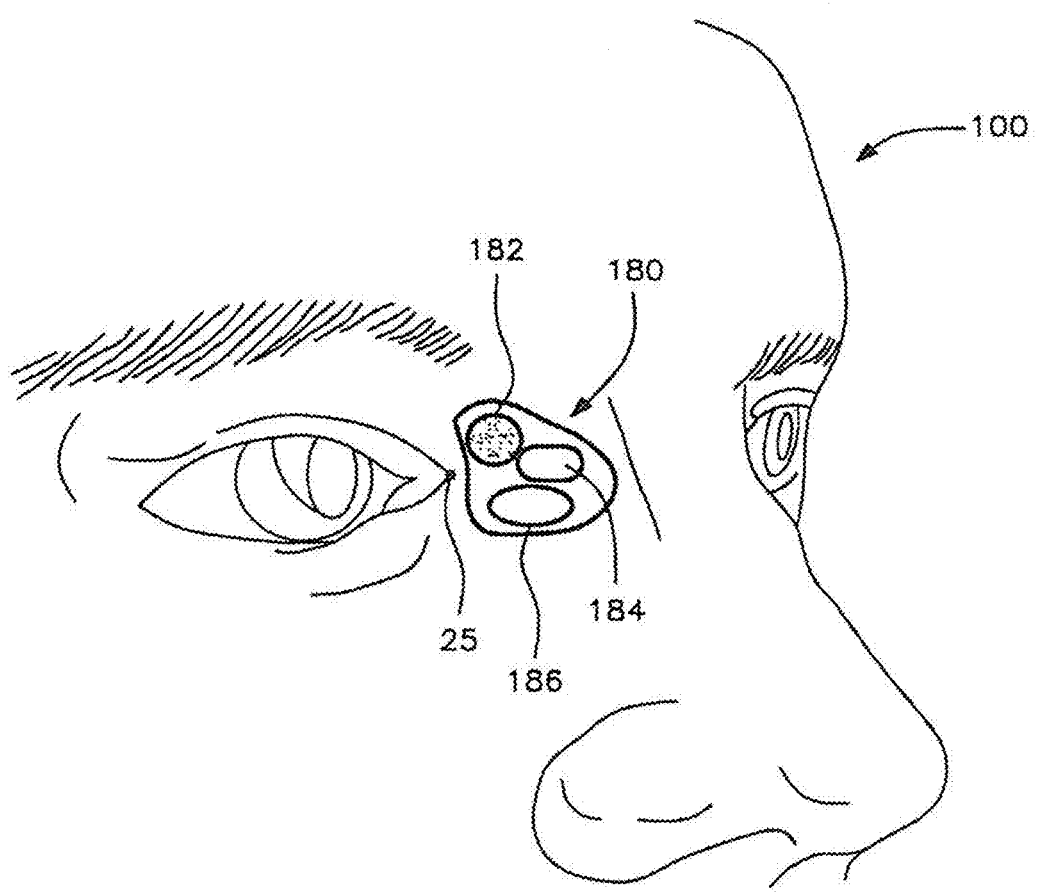
FIGS. 16A to 16C are perspective views of a preferred embodiment showing a person wearing support structures incorporated as patches.
Figure 16B:
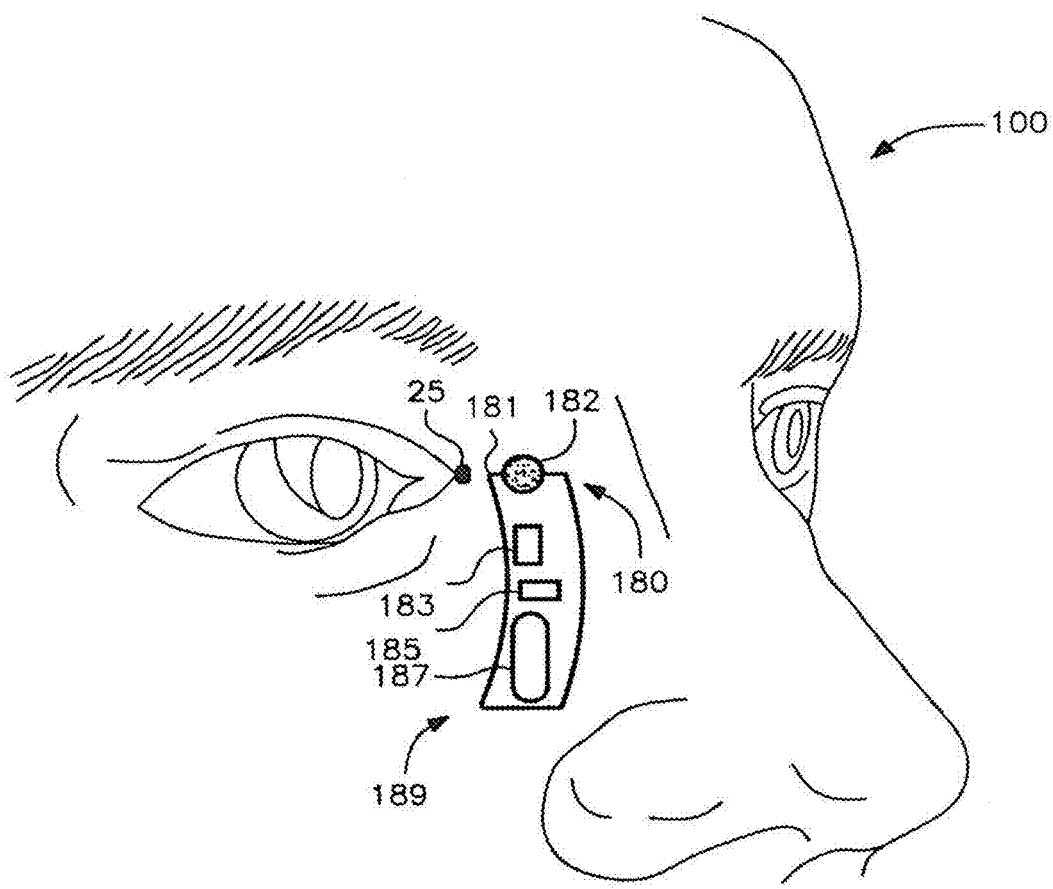
Figure 16C:
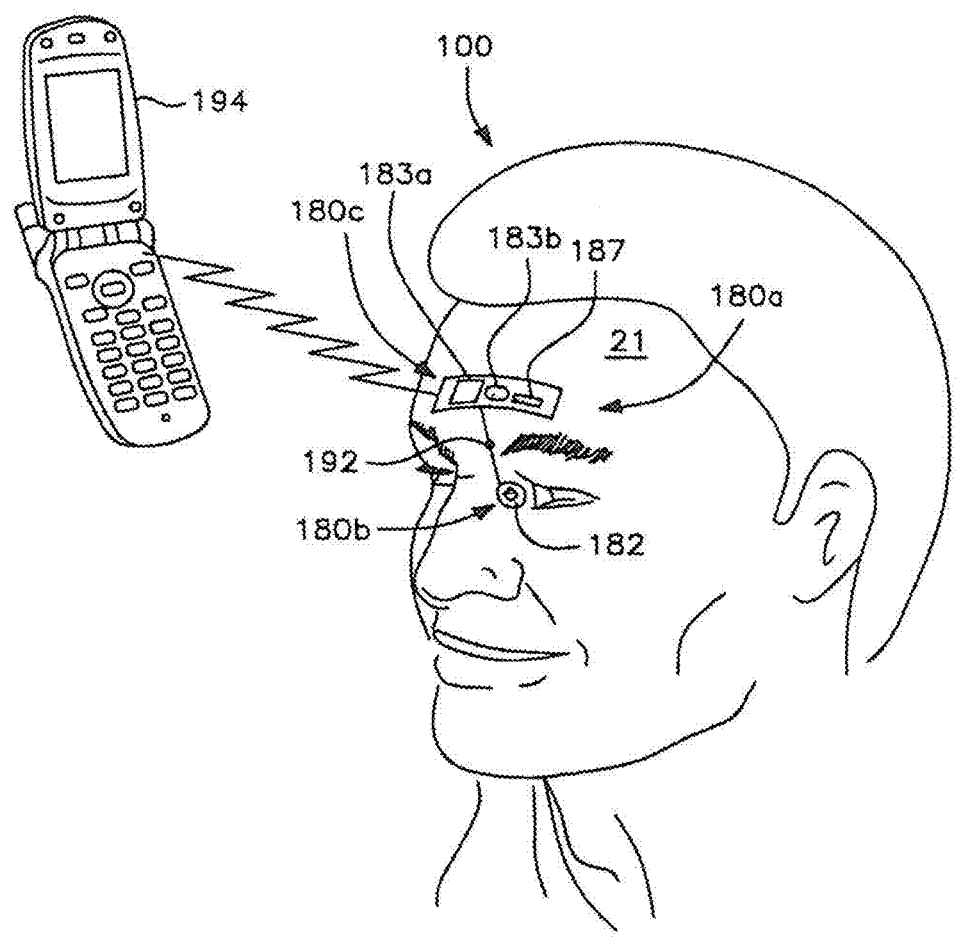

FIG. 16A to 16C are perspective views of preferred embodiments showing a person 100 wearing support structures 180 incorporated as patches. In a preferred embodiment shown in FIG. 16A, the support structure 180 contains LED 184, cell 186, and sensor 182. Sensor 182 is positioned at a main entry point on the superior aspect of the medial canthal area adjacent to the medial corner of the eye 25. LED 184 is activated when a signal reaches certain thresholds in accordance with the principles of the invention. FIG. 16B is another preferred embodiment showing a person 100 wearing support structure 180 with sensor 182 positioned at the general area of the main entry point of the tunnel with the superior edge 181 of support structure 180 being lined up with the corner of the eye 25. Support structure 180 contains an extension that rests on the cheek area 189 and houses transmitting means 183 for wireless transmission, processing means 185 and power source 187. FIG. 16C is an exemplary preferred embodiment showing person 100 wearing a two piece structure 180a comprised of support structure 180b and housing structure 180c connected by wires 192, preferably a flexible circuit. Support structure 180b contains the sensor 182 which is positioned at the BTT site. Housing structure 180c which can comprise an adhesive strip on the forehead 21 houses processing device 183a, transmitting device 183b and power source 187 for transmitting the signal to unit 194, for example a cell phone.

FIG. 17 is a schematic view of another preferred embodiment showing the support structure 180 with sensor 182 being held at the nose 191 by a clip 196. Support structure 180 extends superiorly to the forehead 193. Housing 195 of support structure 180 contains pressure attachment means such as clip 196. Housing 197 on the forehead contains the transmitting device and power source. Clip 196 uses a spring based structure 196a to apply gentle pressure to secure support structure 180 and sensor 182 in a stable position. Housing 197 can also have a LCD display 19. The LCD 19 can have an inverted image to be viewed in a mirror by the user, besides LCD 19 can have a hinge or be foldable to allow proper positioning to allow the user to easily view the numerical value displayed.

FIG. 18 is a perspective view of another preferred embodiment showing a person 100 wearing a support structure 180 comprised of a patch with sensor 182 positioned on the skin at the end of the tunnel and connected by a wire 199 to a decoding and display unit 200. Support structure 180 has a visible indicator 170 lined up with the medial corner of the eye 174. Wire 199 includes an adhesive tape 201 within its first 20 cm, and most preferably adhesive tape connected to wire 199 is in the first 10 cm of wire from sensor 182.

FIGS. 19A1 to 19D are schematic views of preferred geometry and dimensions of support structures 180 and sensing device 182. Special geometry and dimension of sensors and support structure is necessary for the optimal functioning of the present invention. The dimensions and design for the support structure 180 are made in order to optimize function and in accordance with the geometry and dimensions of the different parts of the tunnel.

FIG. 19A1 shows support structure 180 working as a patch. The patch 180 contains sensor 182. The patch 180 may contain other hardware or solely the sensor 182. Exemplary sensor 182 is a flat thermistor or surface mount thermistor. The preferred longest dimension for the patch referred to as "z" is equal or less than 12 mm, preferably equal to or less than 8 mm, and most preferably equal to or less than 5 mm. The shortest distance from the outer edge of the sensor 182 to the outer edge of the patch 180 is referred to as "x". "x" is equal to or less than 11 mm, preferably equal to or less than 6 mm and most preferably equal to or less than 2.5 mm. For illustrative purposes the sensor 182 has unequal sides, and distance "y" corresponds to the longest distance from outer edge of the sensor to outer edge of the patch 180. Despite having unequal sides, the shortest distance "x" is the determining factor for the preferred embodiment. It is understood that the whole surface of the sensor 182 can be covered with an adhesive and thus there is no distance between the sensor and an outer edge of a support structure.

An exemplary embodiment for that includes a sensor in which the surface touching the skin at the BTT site is made with Mylar. The Mylar surface, which comprises the sensor itself, can have an adhesive in the surface that touches the skin. In this case, the support structure that can include a piece of glue or an adhesive may be constructed flush in relation to the sensor itself. Accordingly in FIG. 19E support structure 171 comprised of a piece of glue supports sensor 182 in position against the BTT area. Sensor 182 can include a Mylar, a thermistor, thermocouple and the like, and the sensor 182 can be preferably at the edge of the support structure 171 such as a piece of glue or any support structure, and said sensor 182 can be preferably further insulated in its outer surface with a piece of insulating material 173, such as polyethylene.

As shown in FIG. 19A2, the sensor 182 has adhesive in its surface, to be secured to skin 11. The sensor then can be applied to the BTT site in accordance with the principles of the invention. The preferred distance "x" equal to or less than 2.5 mm allows precise pinpoint placement of sensor 182 at the main entry site of the tunnel and thus allows the most optimal signal acquisition, and it should be used for applications that require greatest precision of measurements such as during monitoring surgical procedures. Although a patch was used as support structure for the description of the preferred dimensions, it is understood that the same dimensions can be applied to any support structure in accordance with the principle of the invention including clips, medial canthal pads, head mounted gear, and the like.

FIG. 19B is an exemplary embodiment of a round patch 180 with a flat sensor 182. Preferred dimensions "x" and "z" apply equally as for FIG. 19A1. FIG. 19C is an exemplary embodiment of a patch 180 with a bead-type sensor 182. Preferred dimensions "x" and "z" apply equally as for FIG. 19A1. FIG. 19D is an exemplary embodiment of a support structure 180 with a sensor-chip 15. Sensor chip 15 comprises a sensor that is integrated as part of a chip, such as an Application Specific Integrated Circuit (ASIC). For example sensor chip 15 includes sensor 15a, processor 15b, and transmitter 15c. Preferred dimension "x" apply equally as for FIG. 19A1. Other hardware such as power source 27 may be housed in the support structure 180 which can have a long dimension referred to as "d" that does not affect performance as long as the dimension "x" is preserved.

The support structure and sensor are adapted to match the geometry and dimensions of the tunnel, for either contact measurements or non-contact measurements, in which the sensor does not touch the skin at the BTT site.

Figure 20A:
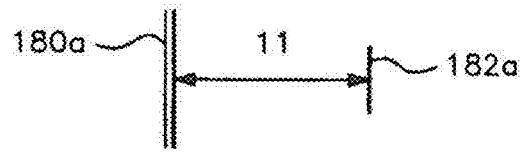
FIGS. 20A to 20C are schematic diagrams of preferred dimensions of the outer edge of support structures in relation to the outer edge of sensing devices.
Figure 20B:
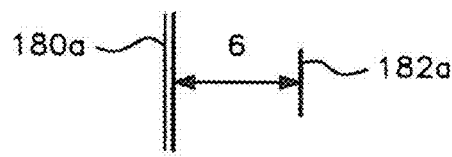
Figure 20C:
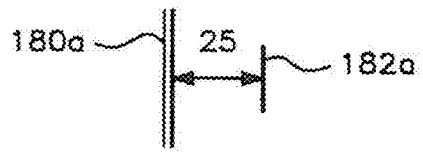

FIGS. 20A to 20C show the preferred dimensions "x" for any support structure in accordance with the present invention. The distance from the outer edge 180a of the support structure to outer edges of sensor 182a is 11 mm, as shown in FIG. 20A. Preferably, the distance from the outer edge 180a of support structure to outer edges of sensor 182a is 6 mm, as shown in FIG. 20B. Most preferably, the distance from the outer edge 180a of the support structure to outer edges of sensor 182a is 2.5 mm, as shown in FIG. 20C.

Figure 21A:
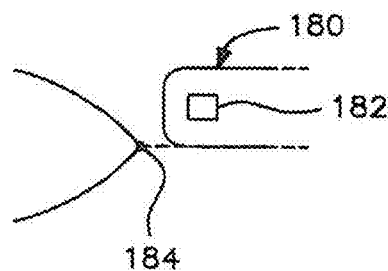
FIGS. 21A and 21B are schematic diagrams of preferred positions of sensing devices.
Figure 21B:
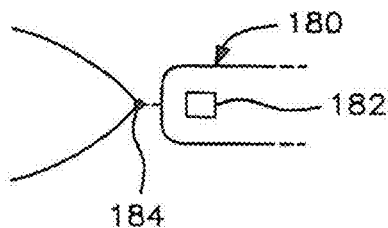

Preferred positions of sensors 182 in relation to the medial corner of the eye 184 are shown in FIGS. 21A and 21B. Support structure 180 positions sensor 182 lined up with medial corner 184 (FIG. 21B). Preferably, as shown in FIG. 21A, support structure 180 positions the sensor 182 above the medial corner 184.

The preferred embodiments of support structures incorporated as patches and clips are preferably used in the hospital setting and in the health care field including continuous monitoring of fever or temperature spikes. Support structures incorporated as medial canthal pads or head mounted gear are preferred for monitoring hyperthermia, hypothermia and hydration status of recreational athletes, professional athletes, military, firefighters, construction workers and other physically intensive occupations, occupational safety, and for preventing wrinkle formation due to thermal damage by sun light.

Figure 22B:
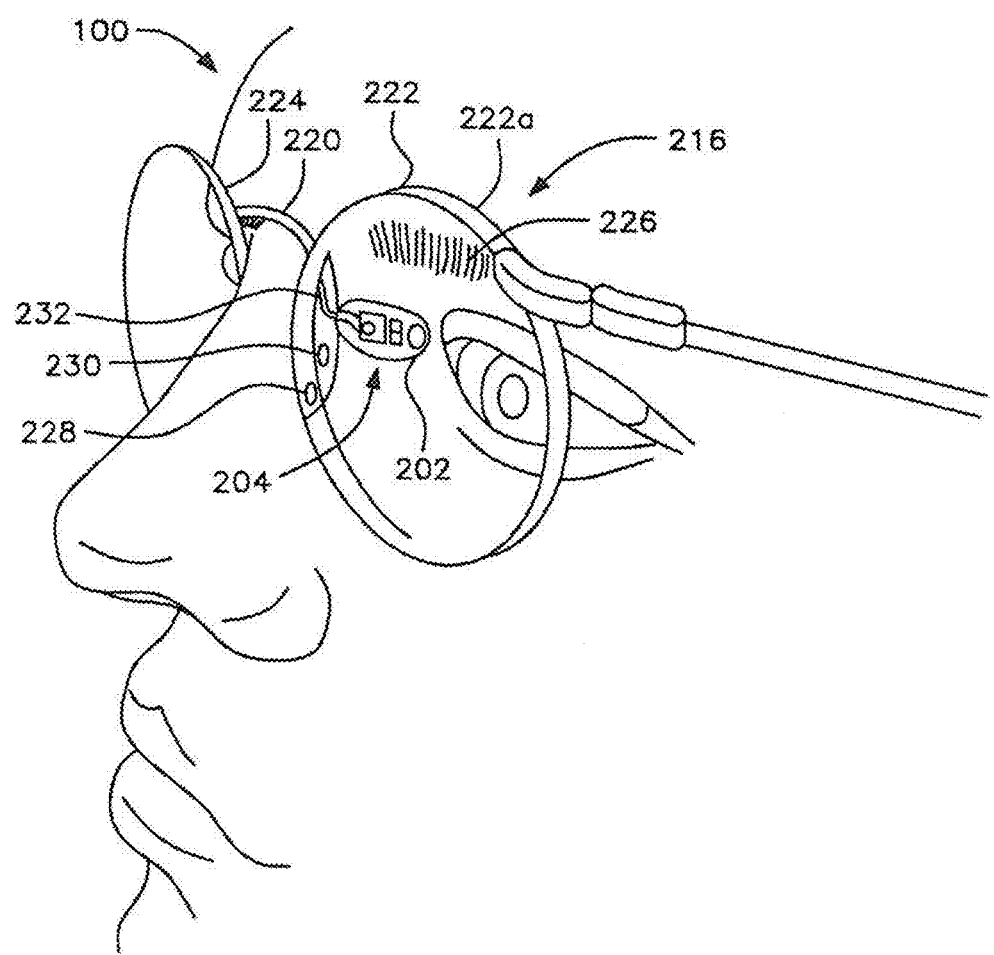
Figure 22C:
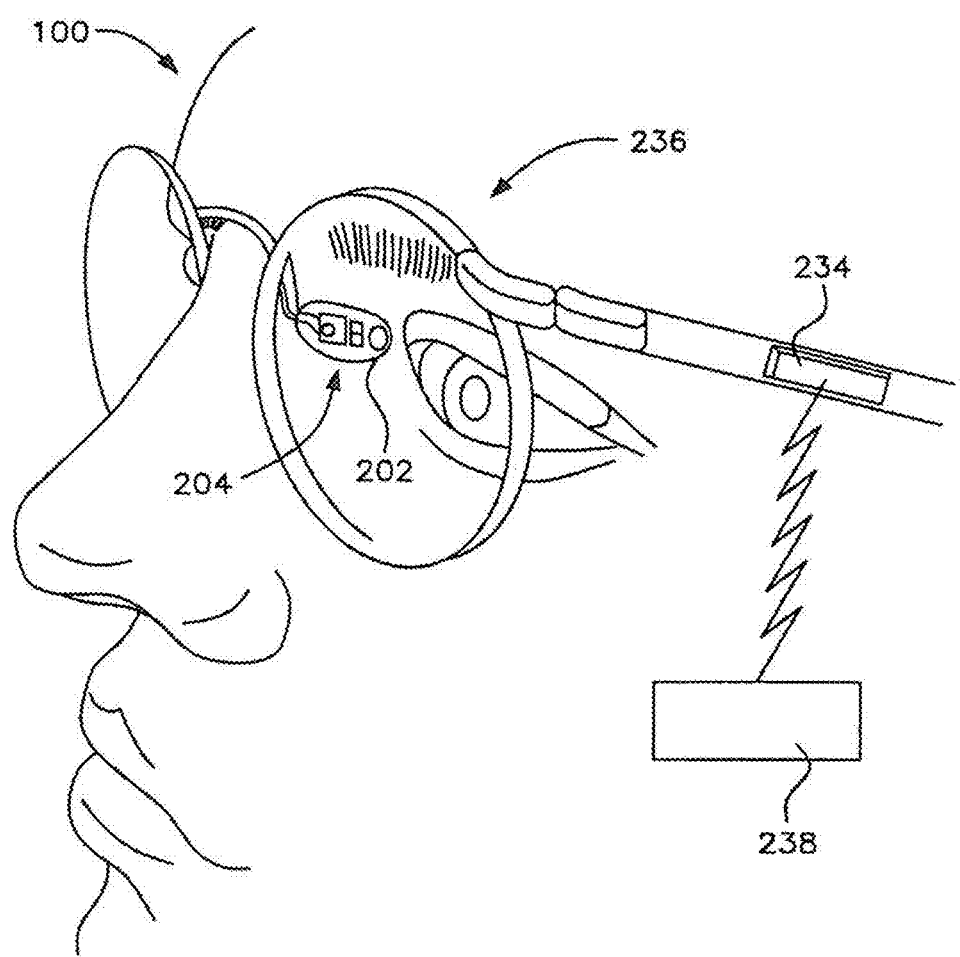

FIGS. 22A to 22C are perspective views of preferred embodiments showing a person 100 wearing support structures incorporated as a medial canthal pad 204 of eyeglasses 206. In a preferred embodiment shown in FIG. 22A, the medial canthal pad 204 contains sensor 202. Connecting arm 208 connects medial canthal pad 204 to eyeglasses frame 206 next to regular nose pads 212. Sensor 202 is positioned on the superior aspect of the medial canthal area adjacent to the medial corner of the eye 210.

FIG. 22B is an exemplary preferred embodiment showing person 100 wearing support structure incorporated as medial canthal pads 204 with sensor 202 integrated into specially constructed eyeglasses frame 216 and containing LEDs 228, 230. Connecting piece 220 which connects the left lens rim 222 and right lens rim 224 is constructed and positioned at a higher position than customary eyeglasses construction in relation to the lens rim 222, 224. Due to the higher position of connecting piece 220 and the special construction of frame 216, the upper edge 222a of left lens rim 222 is positioned slightly above the eyebrow 226. This construction allows medial canthal pad 204 to be positioned at the BTT site while LEDs 228,230 are lined up with the visual axis. Arm 232 of medial canthal pad 204 can be flexible and adjustable for proper positioning of sensor 202 on the skin at the BTT site and for moving away from the BTT site when measurement is not required. The LED 228 is green and LED 230 is red, and said LEDs 228, 230 are activated when a signal reaches certain thresholds.

FIG. 22C is an exemplary preferred embodiment showing person 100 wearing support structure incorporated as medial canthal pads 204 with sensor 202. Signal from sensor 202 is transmitted wirelessly from transmitter 234 housed in the temple of eyeglasses 236. Receiving unit 238 receives a signal from transmitter 234 for processing and displaying. Exemplary receiving units 238 include watch, cell phone, pagers, hand held computers, and the like.

FIGS. 23A to 23B are perspective views of alternative embodiments showing support structures incorporated as a modified nose pad 242 of eyeglasses 244. FIG. 23A is a perspective view showing eyeglasses 244 containing a modified nose pad 242 with sensor 240 and processor 241, sweat sensor 246 and power source 248 supported by temple 250, and transmitter 252 supported by temple 254, all of which are electrically connected. Modified nose pads 242 are comprised of oversized nose pads with a horn like extension 243 superiorly which positions sensor 240 on top of the end of the tunnel.

FIG. 23B is a perspective view showing eyeglasses 256 containing an oversized modified nose pad 258 with sensor 240, sweat sensor 260 supported by temple 262, and transmitter 264 supported by temple 266. Modified oversized nose pad 258 measures preferably 12 mm or more in its superior aspect 258a and contains sensor 240 in its outer edge in accordance with the dimensions and principles of the present invention.

Figure 24:
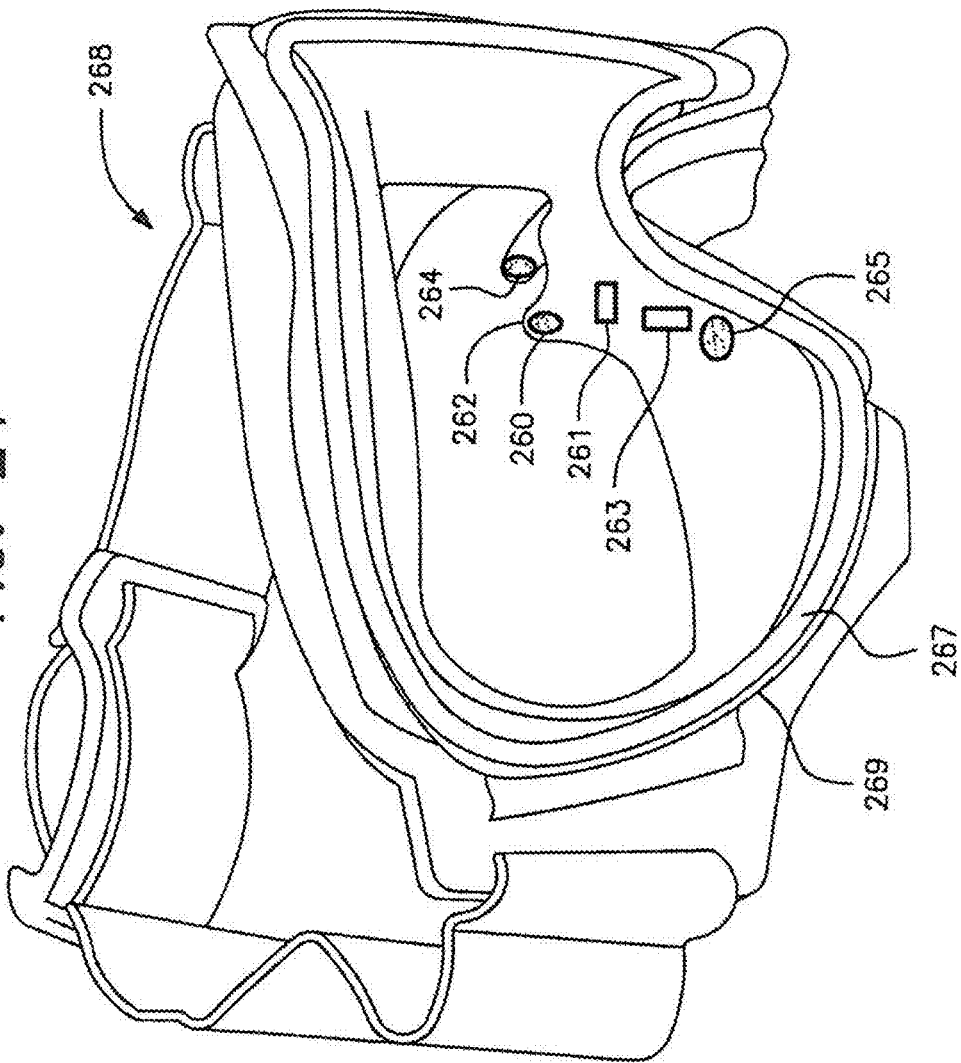
FIG. 24 is a perspective view of another preferred embodiment of support structure in accordance with the invention.

Another preferred embodiment of the invention, shown in FIG. 24, provides goggles 268 supporting medial canthal pads 260 adapted to position sensor 262, 264 at the tunnel site on the skin. As shown, goggles 268 also support transmitting device 261, power source 263, local reporting device 265 such as LED and an antenna 267 for remote reporting. Antenna 267 is preferably integrated as part of the lens rim 269 of goggles 268.

Figure 25:
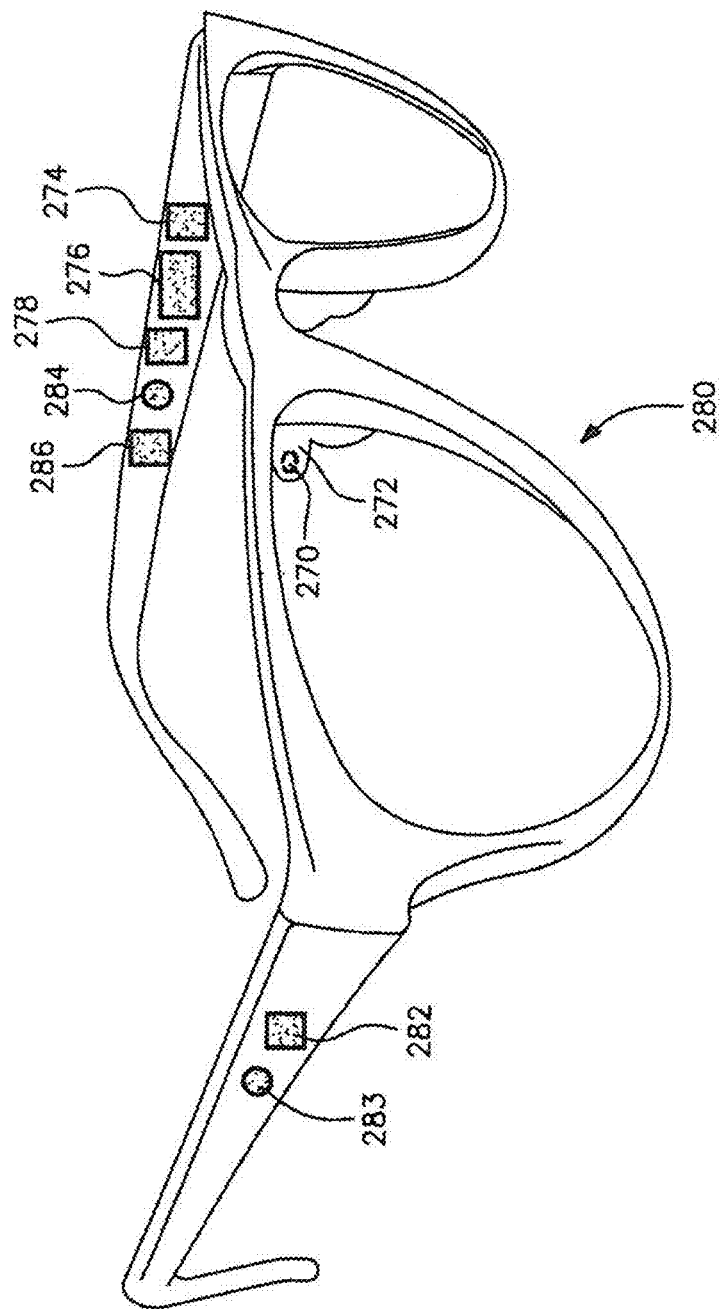
FIG. 25 is a perspective view of one preferred embodiment of support structure showing additional structures for including a sensor.

As shown in FIG. 25, additional device related to the signal generated by sensor 270 in medial canthal pad 272 include power switch 274, set switch 276 which denotes a mode selector, transmitter 278 for wireless transmission of signals, a speaker 282, piezoelectric device 283, input device 284 and processing device 286. The device 274, 276, 278, 282, 284, and 286 are preferably supported by any portion of the frame of eyeglasses 280. It is understood that a variety of devices, switches and controlling devices to allow storage of data, time and other multiple function switches can be incorporated in the apparatus in addition to wires for wired transmission of signals.

Figure 26A:
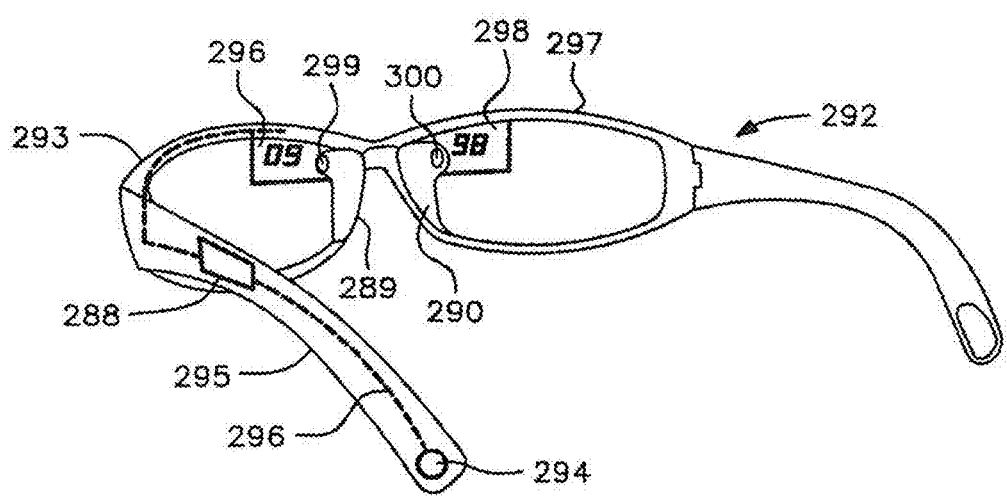
FIG. 26A is a rear perspective view of one preferred embodiment of a support structure with a display device.

FIG. 26A is a rear perspective view of one preferred embodiment showing sensors 299, 300 supported by medial canthal pads 290, 289 of eyeglasses 292 and includes lens rim 297 and display 298 in addition to transmitter 288, sweat sensor 294 and wires 296 disposed within temple 295 and lens rim 293 of said eyeglasses 292 and connected to display device 296.

Figure 26B:
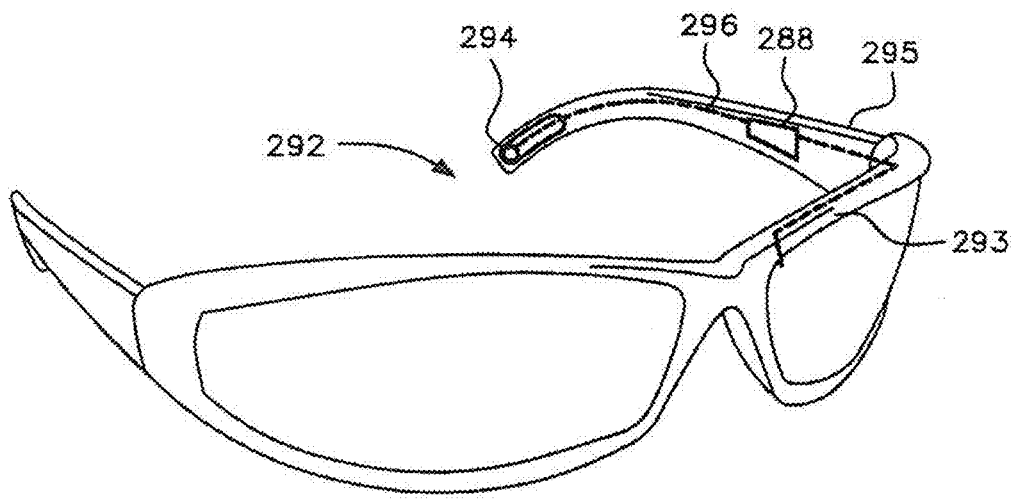
FIG. 26B is a front perspective view of one preferred embodiment of a support structure with a display device.

FIG. 26B is a front perspective view of eyeglasses 292 including sweat sensor 294, transmitter 288 and wires 296 disposed within temple 295 and lens rim 293 of eyeglasses 292 and connected to a display device. In this embodiment sweat sensor 294 produces a signal indicating the concentration of substances in sweat (e.g., sodium of 9 mmol/L) which is displayed on left side display 296 and sensor 300 supported by medial canthal pad 290 produces a signal indicative of, for example, brain temperature of 98 degrees F. which is displayed on the right side display 298. Sweat sensor can be porous or microporous in order to optimize fluid passage to sensors when measuring chemical components.

A variety of display devices and associated lenses for proper focusing can be used including liquid crystal display, LEDs, fiber optic, micro-projection, plasma devices, and the like. It is understood that a display device can be attached directly to the lens or be an integral part of the lens. It is also understood that a display device can include a separate portion contained in the lens rim or outside of the lens rim. Further, the two lenses and displays 296, 298 held within the lens rims 293, 297 can be replaced with a single unit which can be attached directly to the frame of eyeglasses 292 with or without the use of lens rim 293, 297.

FIG. 27 is a perspective view of another preferred embodiment showing a three piece support structure 304 and preferably providing a medial canthal pad connecting piece 303 adapted as an interchangeable connecting piece. This embodiment comprises three pieces. Piece 301 comprises left lens rim 301a and left temple 301b. Piece 302 comprises right lens rim 302a and right temple 302b. Piece 303 called the medial canthal piece connector comprises the connecting bridge of eyeglasses 303a and the pad structure 303b of eyeglasses. Pad piece 303 is particularly adapted to provide medial canthal pads 306 for positioning a sensor 308 at the BTT site. In reference to this embodiment, the user can buy three piece eyeglasses in accordance with the invention in which the connector 303 has no sensing capabilities, and it is thus a lower cost. However, the three piece eyeglasses 304 offers the versatility of replacing the non-sensing connector 303 by a connector 303 with sensing capabilities. As shown in FIG. 27 connector 303 with medial canthal pads 306 and sensor 308 includes also radio frequency transmitter 310 and cell 312. Therefore, connector 303 provides all the necessary hardware including devices for sensing, transmitting, and reporting the signal. Any devices for attachment known in the art can be used including pressure devices, sliding devices, pins, and the like.

Another preferred embodiment, as shown in FIG. 28A, provides a removable medial canthal piece 314 supporting sensor 316. As shown, connecting bridge 320 of eyeglasses 318 are attached to medial canthal piece 314 in a releasable manner. Eyeglasses 318 further includes sweat sensor 322, 324 supported by front part 311 and transmitting device 326 supported by temple 313. Front part 311 of eyeglasses 318 defines a front brow portion and extends across the forehead of the wearer and contains sweat sensor 322, 324. Sweat fluid goes through membranes in the sensor 322, 324 and reaches an electrode with generation of current proportional to the amount of analyte found in the sweat fluid.

Figure 28B:
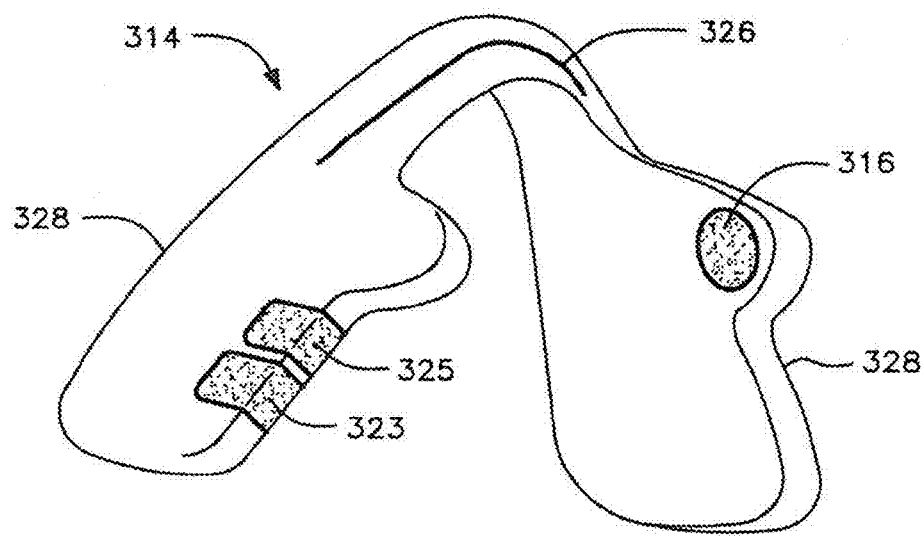
FIG. 28B is a rear perspective view of the removable medial canthal piece of FIG. 28A.
Figure 28C:
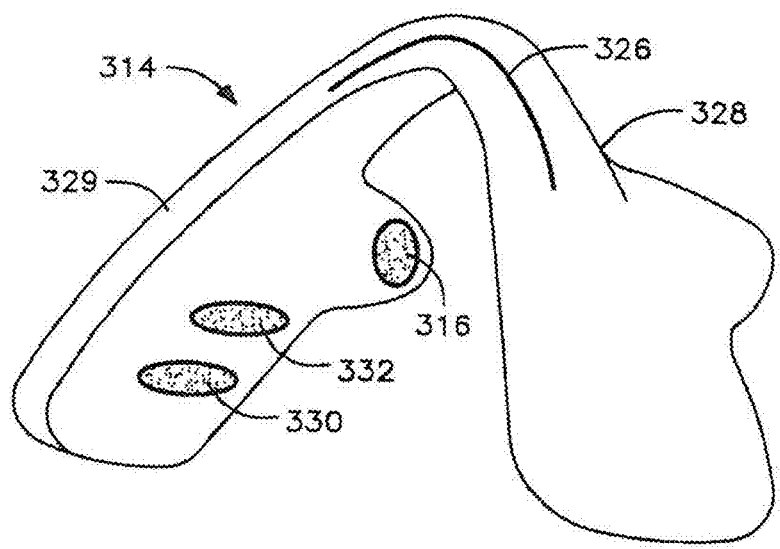
FIG. 28C is a front perspective view of the removable medial canthal piece of FIG. 28B.

FIG. 28B is a rear perspective view of the removable medial canthal piece 314 showing visual reporting devices 323, 325 such as a green LED and a red LED in left arm 328 and sensor 316 adapted to be positioned at the end of the tunnel, and wire 326 for electrically connecting right arm 329 and left arm 328 of medial canthal piece 314. FIG. 28C is a front perspective view of the removable medial canthal piece 314 showing power source 330, transmitter 332 and sensor 316 in right arm 329 and wire 326 for electrically connecting right arm 329 and left arm 328 of medial canthal piece 314. Medial canthal piece 314 can be replaced by a non-sensing regular nose pad which would have the same size and dimension as medial canthal piece 314 for adequate fitting with connecting bridge 320 of eyeglasses 318 of FIG. 28A. The removable medial canthal piece can have, besides LED, a built-in LCD display for displaying a numerical value and/or RF transmitter. Therefore, the removable medial canthal piece can have one or various reporting devices integrated as a single sensing and reporting unit.

Figure 29:
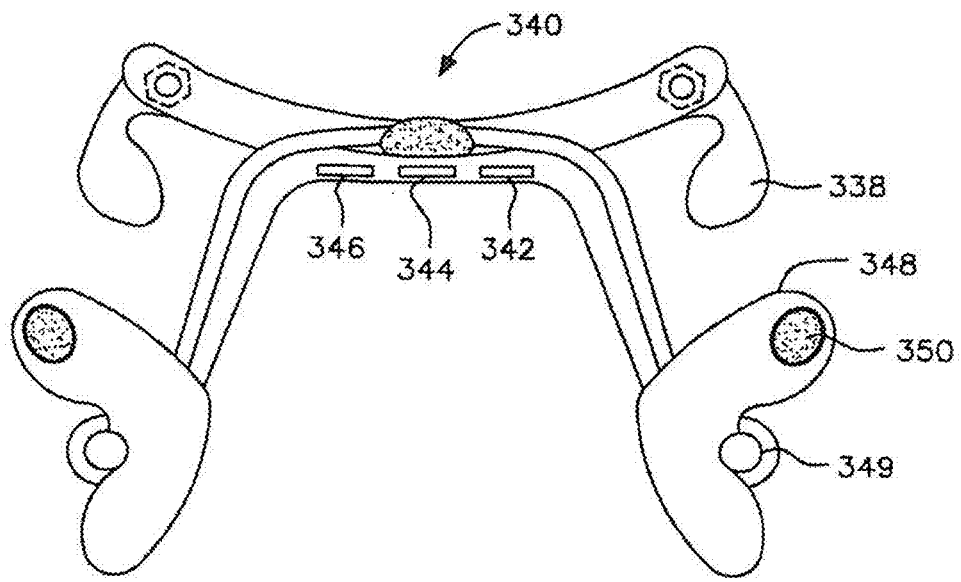
FIG. 29 is a rear perspective view of one preferred embodiment of a support structure incorporated as a clip-on for eyeglasses.

FIG. 29 is a rear perspective view of one preferred embodiment of a support structure incorporated as a clip-on 340 for eyeglasses and includes attachment device 338 such as a hook or a magnet, transmitting device 342, processing device 344, power source 346, medial canthal pad 348 mounted on a three axis rotatable structure 349 for proper positioning at the BTT site, and sensor 350. Clip-on 340 is adapted to be mounted on regular eyeglasses and to fit the medial canthal pad 348 above the regular nose pads of eyeglasses.

Figure 30:
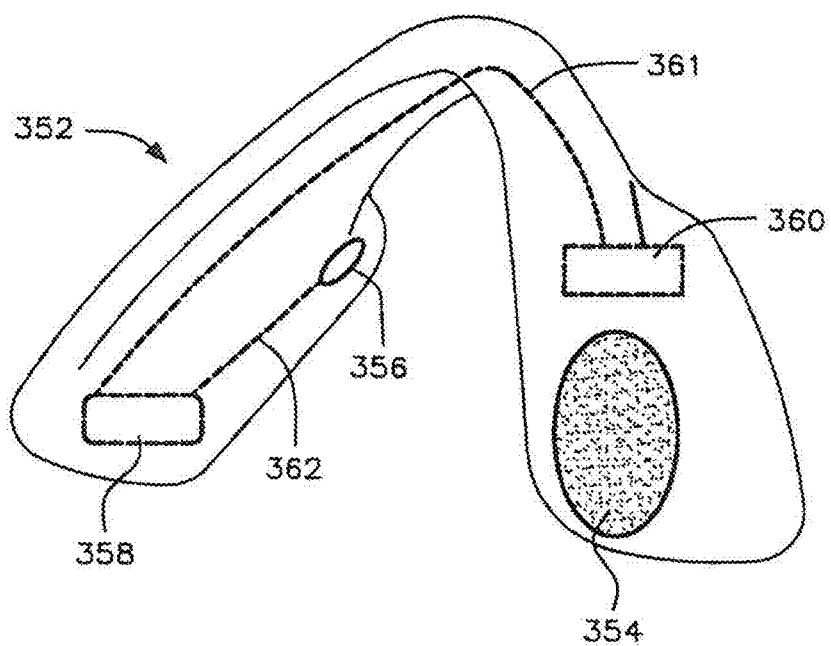
FIG. 30 is a perspective view of one alternative embodiment of a support structure with medial canthal pads that uses an adhesive backing for securing to another structure.

Sensing medial canthal pads can be preferably connected to attachment structure such as eyeglasses independent of the presence of specialized connecting or attachment devices mounted in said eyeglasses such as grooves, pins, and the like. This embodiment provides means for the universal use of sensing medial canthal pads in any type or brand of attachment structure. FIG. 30 shows a front perspective view of medial canthal pads 352 comprising an adhesive backing 354 for securing pad 352 to an attachment structure such as eyeglasses or another support structure. Adhesive surface 354 is adapted to match an area of eyeglasses that allow securing medial canthal pad 352 to said eyeglasses, such as for instance the area corresponding to regular nose pads of eyeglasses. Medial canthal pad 352 works as a completely independent unit and contains sensor 356, power source 358 and reporting device 360 electrically connected by wire 361, 362. Reporting device 360 includes local reporting with visual devices (e.g., LED), audio devices (e.g., piezoelectric, voice chip Or speaker) and remote reporting with wireless transmission.

Figure 31A:
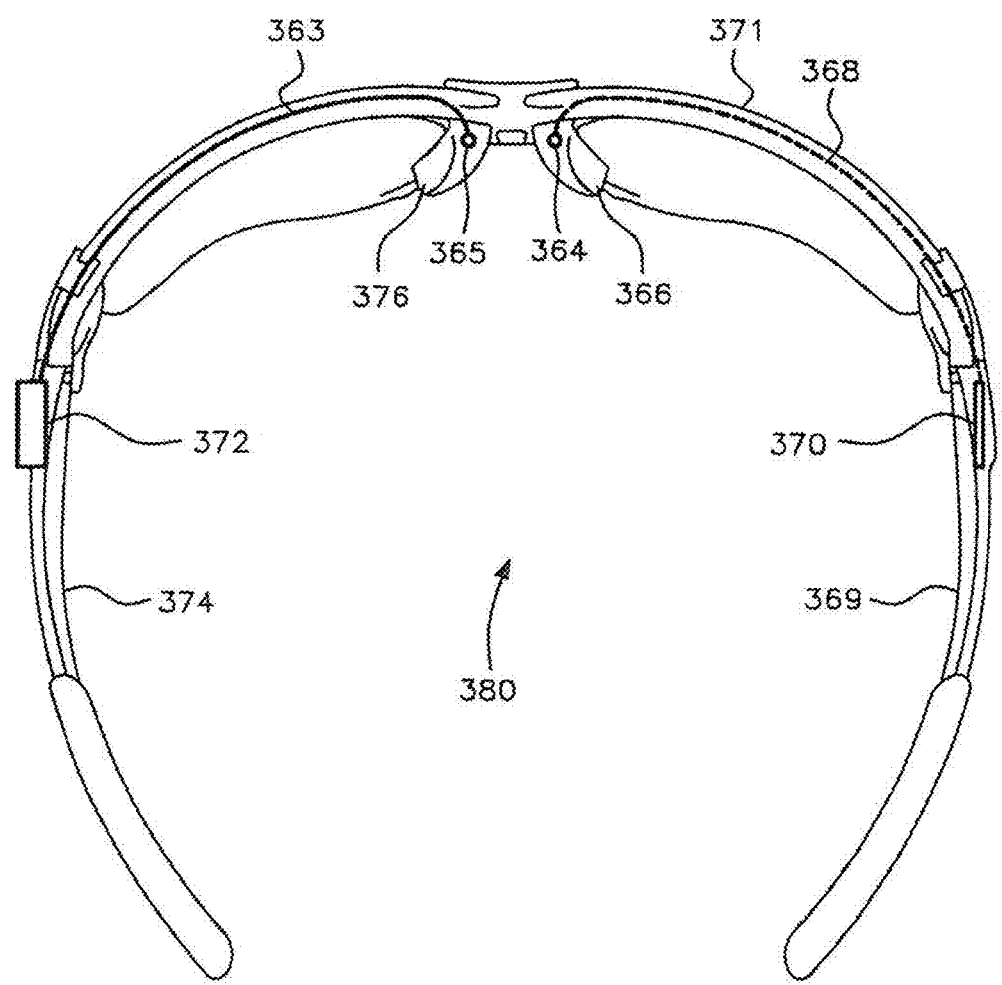
FIG. 31A is a top perspective view of one alternative embodiment of a support structure with holes for securing medial canthal pads.
Figure 31B:
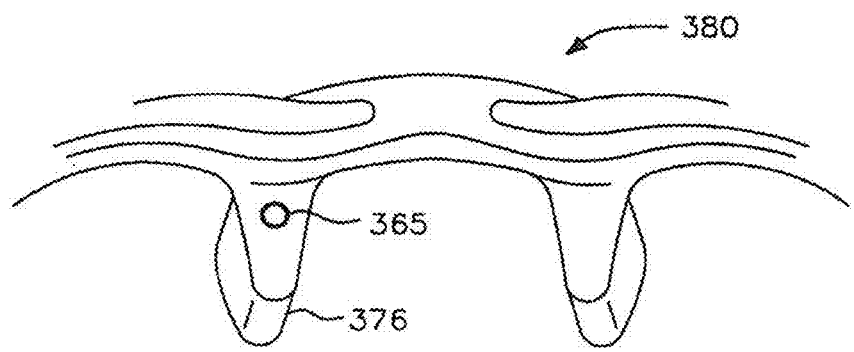
FIG. 31B is a magnified perspective view of part of the support structure of FIG. 31A.
Figure 31D:
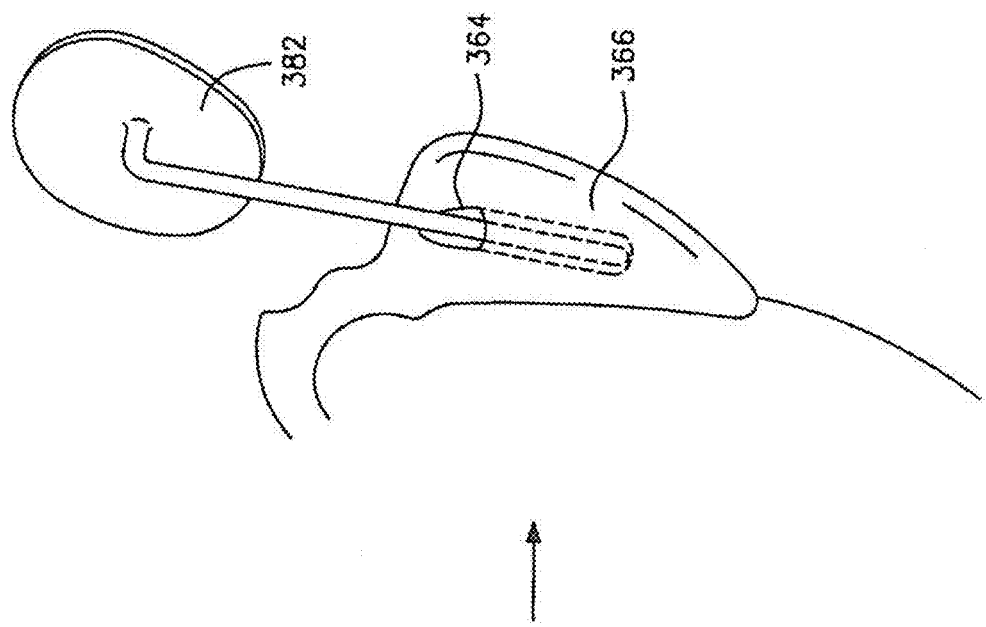
FIG. 31D is a side perspective view of a medial canthal piece secured at the support structure.
Figure 31C:
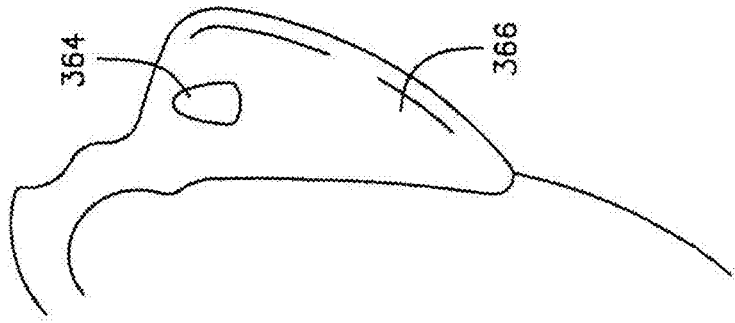
FIG. 31C is a side perspective view of part of the support structure of FIG. 31B.

FIG. 31A is a top perspective view of one alternative embodiment of a support structure incorporated as eyeglasses 380 with holes 364, 365 in regular nose pads 366, 376 for securing specialized medial canthal pads. Eyeglasses 380 includes wire 368 disposed within the right lens rim 371 of the frame of eyeglasses 380 with said wire 368 connecting transmitter 370 housed inside the right temple 369 to nose pad 366. Eyeglasses 380 further includes wire 363 mounted on top of left lens rim 365 with said wire 363 connecting transmitter 372 mounted on top of the left temple 374 to nose pad 376. FIG. 31B is a magnified perspective view of part of the support structure 380 with hole 365 in regular nose pad 376. FIG. 31C is a side perspective view of regular nose pad 366 with hole 364. FIG. 31D is a side perspective view of a medial canthal piece 382 secured to hole 364 of regular nose pad 366.

Figure 32A:
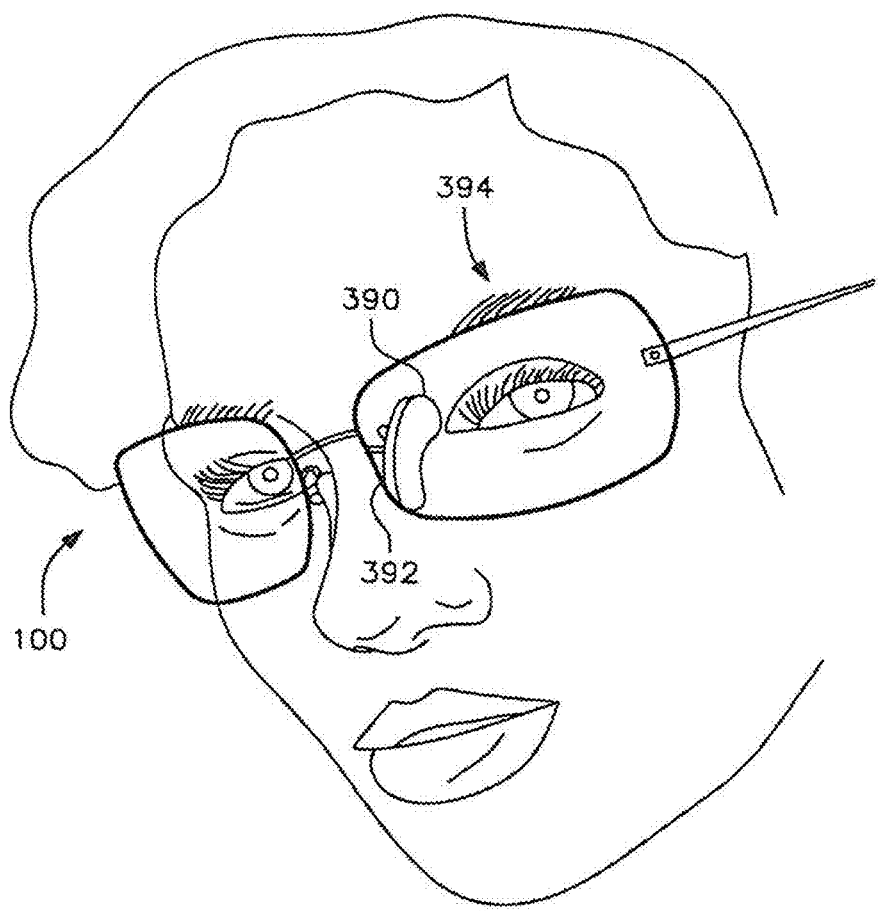
FIG. 32A is a perspective view of a person wearing a support structure comprised of medial canthal caps secured on top of a regular nose pad of eyeglasses.
Figure 32B:
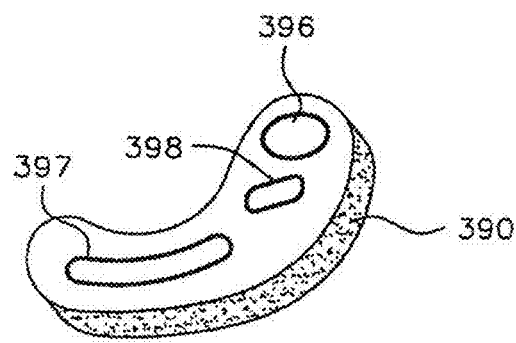
FIG. 32B is a perspective view of the medial canthal cap of FIG. 32A.

FIG. 32A is a perspective view of a person 100 wearing a support structure comprised of medial canthal caps 390 secured on top of a regular nose pad 392 of eyeglasses 394. FIG. 32B is a perspective rear view of the medial canthal cap 390 showing sensor 396, transmitter chip 398 and opening 397 for securing cap 390 to nose pads.

Figure 33A:
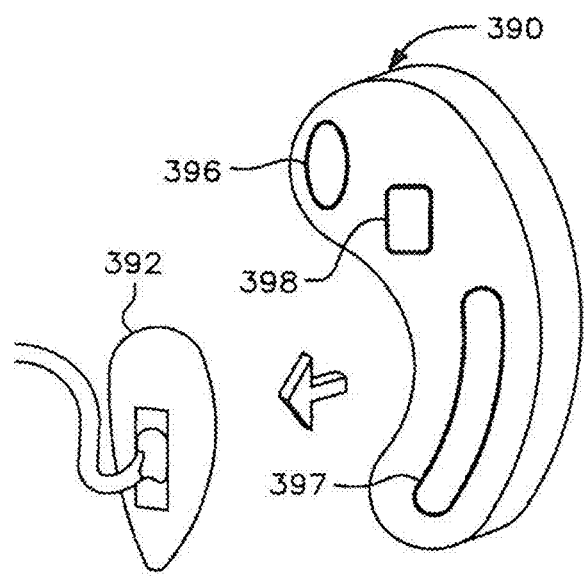
FIG. 33A is an exploded perspective view of a medial canthal cap being secured to the nose pad.
Figure 33B:
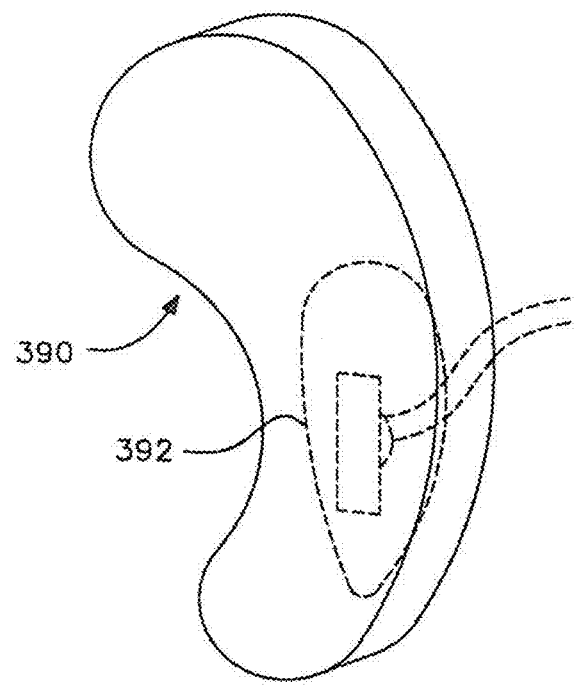
FIG. 33B is a perspective view of the end result of the medial canthal cap secured to the nose pad.

FIG. 33A is a perspective view of a medial canthal cap 390 being secured to the nose pad 392. Medial canthal cap 390 contains sensor 396, transmitter chip 398 and opening 397. FIG. 33B is a perspective view showing the end result of the medial canthal cap 390 secured to the nose pad 392.

Figure 34:
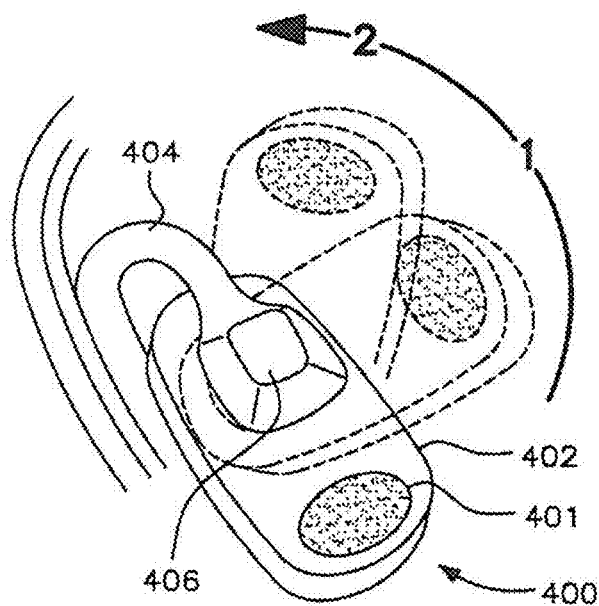
FIG. 34 is a perspective view of a modified rotatable nose pad to position a sensor on the skin at the end of the tunnel in accordance with the present invention.

Special nose pads are provided by the present invention for proper positioning a sensor at the BTT site. FIG. 34 is a perspective view of a modified left side rotatable nose pad 400 adapted to position a sensor on the skin at the end of the tunnel and includes nose pad 402 with sensor 401, arm 404, house 406 which houses a gear that allows rotation of a nose pad as a dial for positioning sensor 401 on different regions of the tunnel identified as 1 and 2. Position 1 places the sensor in line with the medial canthal corner and reaches the general area of the main entry point of the tunnel and position 2 places the sensor above the medial canthal corner right at the main entry point of the tunnel. This embodiment allows automated activation of the sensing system and takes advantage of the fact that the nose bridge is cold as seen in FIG. 1 (nose is dark) and FIG. 2 (nose is purple and blue). When the pad is in its resting position ("zero"), the sensor 401 rests in a cold place with temperature of 35.7° C. corresponding to the regular position of nose pads on the nose. In position "zero" the sensor is in Sleep Mode (temperature of 35.8° C. or less). Changing the sensor to a hot region such as the general area (position 1) or the main entry point (position 2) automatically activates the sensor which goes into Active Mode and start sensing function.

It is understood that numerous special nose pads and medial canthal pads can be used in accordance with the principles of the invention including a pivotal hinge that allows pads to be foldable in total or in part, self-adjusting pads using a spring, pivoting, sliding in a groove, and the like as well as self-adjusting mechanisms which are adaptable to anatomic variations found in different races. It is understood that the modified nose pads are preferably positioned high in the frame, most preferably by connecting to the upper part of the lens rim or within 6 mm from the upper edge of the lens rim.

A variety of materials can be used including materials with super-adherent properties to allow intimate apposition of sensing devices to the BTT site. A variety of metallic wires exhibiting super-elastic properties can be used as the hinge assembly mechanism for allowing proper positioning of a sensing device with the BTT site. Medial canthal pads can be made of a flexible synthetic resin material such as a silicon rubber, conductive plastic, conductive elastomeric material, metal, pliable material, and the like so that appropriate apposition to the BTT site at the medial canthal area and proper functioning is achieved. It is also understood that the medial canthal pads can exhibit elastic and moldable properties and include material which when stressed is able to remain in the stressed shape upon removal of the stress. Any type of rubber, silicone, and the like with shape memory can also be used in the medial canthal pads and modified nose pad.

By greatly reducing or eliminating the interfering constituents and providing a high signal to noise ratio with a sensor adapted to capture thermal radiation from the BTT, the present invention provides the devices needed for accurate and precise measurement of biological parameters including chemical components in vivo using optical devices such as infrared spectroscopy. Moreover, the apparatus and methods of the present invention by enhancing the signal allows clinical useful readings to be obtained with various techniques and using different types of electromagnetic radiation. Besides near-infrared spectroscopy, the present invention provides superior results and higher signal to noise ratio when using other forms of electromagnetic radiation such as for example mid-infrared radiation, radio wave impedance, photoacoustic spectroscopy, Raman spectroscopy, visible spectroscopy, ultraviolet spectroscopy, fluorescent spectroscopy, scattering spectroscopy and optical rotation of polarized light as well as other techniques such as fluorescent (including Maillard reaction, light induced fluorescence and induction of glucose fluorescence by ultraviolet light), colorimetric, refractive index, light reflection, thermal gradient, Attenuated Total Internal Reflection, molecular imprinting, and the like. A sensor adapted to capture thermal energy at the BTE (Brain Thermal Energy) tunnel site provides optimal means for measurement of biological parameters using electromagnetic devices. The BTE tunnel is the physical equivalent to the physiologic BTT and is used herein to characterize the physics of the tunnel. The geometry and dimension on the skin surface are the same for the BTT and BTE tunnel.

The following characteristics of the BTE tunnel allow optimal signal acquisition. Skin at the end of the BTE tunnel is thin. With a thick skin radiation may fail to penetrate and reach the substance to be measured. Skin at the BTE tunnel is homogenous with constant thickness along its entire surface. Random thickness of skin as occurs in other skin areas prevent achieving the precision needed. The BTE tunnel has no fat. The intensity of the reflected or transmitted signal can vary drastically from patient to patient depending on the individual physical characteristics such as the amount of fat. A blood vessel in the end of the BTE is superficial, terminal and void of thermoregulatory shunts. In other parts of the skin the deep blood vessels are located deep and vary greatly in position and depth from person to person. The BTE tunnel has no light scattering elements covering its end such as bone, cartilage and the like. Thermal radiation does not have to go through cartilage or bone to reach the substance to be measured. The end of the BTE tunnel on the skin has a special but fixed geometry and is well demarcated by permanent anatomic landmarks. In other skin surfaces of the body, inconsistency in the location of the source and detector can be an important source of error and variability.

Far-infrared radiation spectroscopy measures natural thermal emissions after said emissions interact and are absorbed by the substance being measured. The present invention provides a thermally stable medium, insignificant number of interfering constituents, and a thin skin is the only structure to be traversed by the thermal emissions from the BTE tunnel before reaching the detector. Thus there is high accuracy and precision when converting the thermal energy emitted by the BTE tunnel into concentration of the substance being measured.

The natural spectral emission by BTE tunnel changes according to the presence and concentration of chemical substances. The far-infrared thermal radiation emitted follow Planck's Law and the predicted amount of thermal radiation can be calculated. Reference intensity is calculated by measuring thermal energy absorption outside the substance of interest band. The thermal energy absorption in the band of substance of interest can be determined via spectroscopic means by comparing the measured and predicted values at the BTE tunnel site. The signal is then converted to concentration of the substance measured according to the amount of thermal energy absorbed.

A sensor adapted to view the BTE tunnel provides means for measuring a substance of interest using natural brain far-infrared emissions emitted at the BTE tunnel site and for applying Beer-Lambert's law in-vivo. Spectral radiation of infrared energy from the surface of the BTE tunnel site corresponds to spectral information of chemical substances. These thermal emissions irradiated at 38 degrees Celsius can include the 4,000 to 14,000 nm wavelength range. For example, glucose strongly absorbs light around the 9,400 nm band. When far-infrared thermal radiation is emitted at the BTE tunnel site, glucose will absorb part of the radiation corresponding to its band of absorption. Absorption of the thermal energy by glucose bands is related in a linear fashion to blood glucose concentration in the thermally sealed and thermally stable environment present in the BTE tunnel.

The support structure includes at least one radiation source from infrared to visible light which interacts with the substance being measured at the BTE tunnel and a detector for collecting the resulting radiation.

The present invention provides method for measuring biological parameters comprising the steps of measuring infrared thermal radiation at the BTE tunnel site, producing output electrical signals representative of the intensity of the radiation, converting the resulting input, and sending the converted input to a processor. The processor is adapted to provide the necessary analysis of the signal to determine the concentration of the substance measured and for displaying the results.

The present invention includes means for directing preferably near-infrared energy into the surface of the skin at the end of the BTE tunnel, means for analyzing and converting the reflectance or back scattered spectrum into the concentration of the substance measured and support structure for positioning the light source and detector device adjacent to the surface of the skin at the BTE tunnel site.

The present invention also provides methods for determining the concentration of a substance with said methods including the steps of directing electromagnetic radiation such as near-infrared at the skin at the BTE tunnel site, detecting the near-infrared energy radiated from said skin at the BTE tunnel site, taking the resulting spectra and providing an electrical signal upon detection, processing the signal and reporting concentration of the substance of interest according to said signal. The invention also includes device and methods for positioning the light sources and detectors in stable position and with stable pressure and temperature in relation to the surface to which radiation is directed to and received from.

The present invention further includes devices for directing infrared energy through the nose using medial canthal pads, devices for positioning radiation source and detector diametrically opposed to each other, and devices for analyzing and converting the transmitted resulting spectrum into the concentration of the substance measured. The present invention also provides methods for measuring biological parameters with said methods including the steps of directing electromagnetic radiation such as near-infrared through the nose using medial canthal pads, collecting the near-infrared energy radiated from said nose, taking the resulting spectra and providing an electrical signal upon detection, processing the signal and reporting concentration of the substance measured according to said signal. The invention also includes means and methods for positioning the radiation sources and detectors in a stable position and with stable pressure and temperature in relation to the surface to which radiation is directed through.

The present invention yet includes devices for collecting natural far-infrared thermal radiation from the BTE tunnel, devices for positioning a radiation collector to receive said radiation, and devices for converting the collected radiation from the BTE tunnel into the concentration of the substance measured. The present invention also provides methods for measuring biological parameters with said methods including the steps of using the natural far-infrared thermal emission from the BTE tunnel as the resulting radiation for measuring the substance of interest, collecting the resulting radiation spectra, providing an electrical signal upon detection, processing the signal and reporting the concentration of the substance measured according to said signal.

A drug dispensing system including an infusion pump can be activated according to the level of the substance measured at the BTE tunnel, for example insulin can be injected automatically as needed to normalize glucose levels as an artificial pancreas.

Any substance present in blood which is capable of being analyzed by electromagnetic devices can be measured at the BTE tunnel. For example but not by way of limitation such substances can include exogenous chemicals such as drugs and alcohol as well as endogenous chemicals such as glucose, oxygen, lactic acid, cholesterol, bicarbonate, hormones, glutamate, urea, fatty acids, triglycerides, proteins, creatinine, aminoacids and the like. Values such as pH can also be calculated as pH can be related to light absorption using reflectance spectroscopy.

Figure 35:
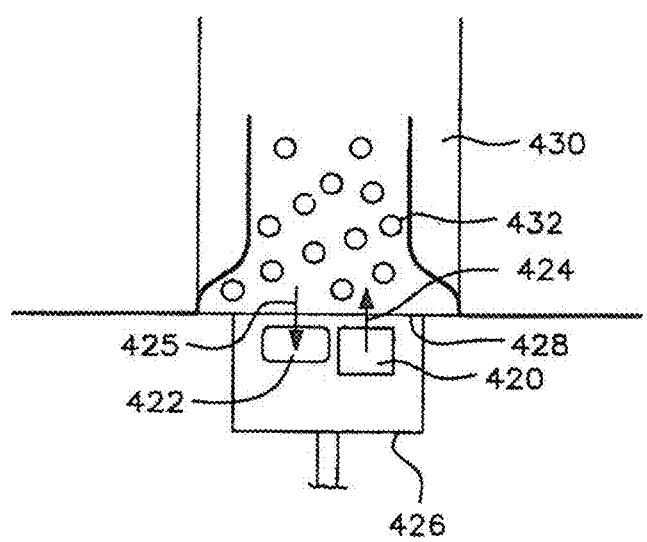
FIG. 35 is a schematic view of another preferred embodiment of the present invention using spectral reflectance.

In accordance with FIG. 35 a schematic view of one preferred reflectance measuring apparatus of the present invention is shown. FIG. 35 shows a light source 420 such as an infrared LED and a photodetector 422 located side-by-side and disposed within support structure 426 such as a medial canthal pad or modified nose pads of eyeglasses directing radiation 424 at the BTE tunnel 430 with said light source 420 laying in apposition to the skin 428 at the BTE tunnel 430. The light source 420 delivers the radiation 424 to the skin 428 at the BTE tunnel which is partially absorbed according to the interaction with the substance 432 being measured resulting in attenuated radiation 425. Part of the radiation 424 is then absorbed by the substance 432 and the resulting radiation 425 emitted from BTE tunnel 430 is collected by the photodetector 422 and converted by a processor into the blood concentration of the substance 432. Thin skin 428 is the only tissue interposed between radiation 424, 425 and the substance 432 being measured. The concentration of the substance 432 is accomplished by detecting the magnitude of light attenuation collected which is caused by the absorption signature of the substance being measured.

Infrared LEDs (wavelength-specific LEDs) are the preferred light source for this embodiment because they can emit light of known intensity and wavelength, are very small in size, low-cost, and the light can be precisely delivered to the site. The light source 420 emits preferably at least one near-infrared wavelength, but alternatively a plurality of different wavelengths can be used. The light source emits radiation 424, preferably between 750 and 3000 nm, including a wavelength typical of the absorption spectrum for the substance 432 being measured. The preferred photodetector includes a semiconductor photodiode with a 400 micron diameter photosensitive area coupled to an amplifier as an integrated circuit.

Figure 36:
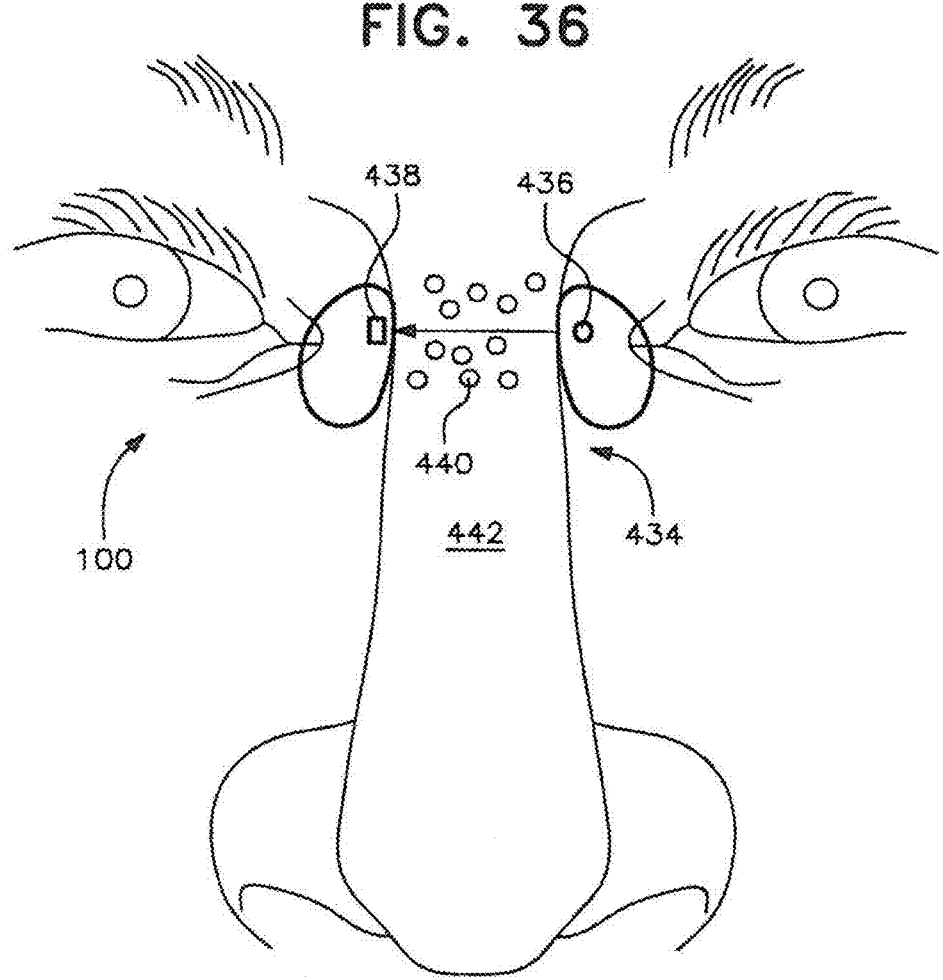
FIG. 36 is a schematic view of a person showing another preferred embodiment in accordance with the present invention using spectral transmission.

FIG. 36 shows a schematic view of a person 100 wearing a support structure 434 and light source 436 and detector 438 adapted to measure biological parameters using spectral transmission device. The light source 436 and photodetector 438 are positioned diametrically opposed to each other so that the output of the radiation source 436 goes through the nasal interface 442 containing the substance 440 being measured before being received by the detector 438. Photodetector 438 collects the resulting transmitted radiation which was directed through the nasal interface 442. A variety of LEDs and optical fibers disposed within the support structure 434 such as the medial canthal pads, nose pads and frames of eyeglasses are preferably used as a light delivery for the light source 436 and the light detector 438.

Arms of support structures 434 such as medial canthal pads are moveable and can be adjusted into different positions for creating a fixed or changeable optical path. Preferred substances measured include oxygen and glucose. The brain maintains constant blood flow, whereas flow in extremities change according to cardiac output and ambient conditions. The oxygen levels found in the physiologic tunnel reflects central oxygenation. The oxygen monitoring in a physiologic tunnel is representative of the general hemodynamic state of the body. Many critical conditions such as sepsis (disseminated infection) or heart problems which alter perfusion in most of the body can be monitored. Oxygen in the BTE tunnel can continuously monitor perfusion and detect early hemodynamic changes.

Figure 37:
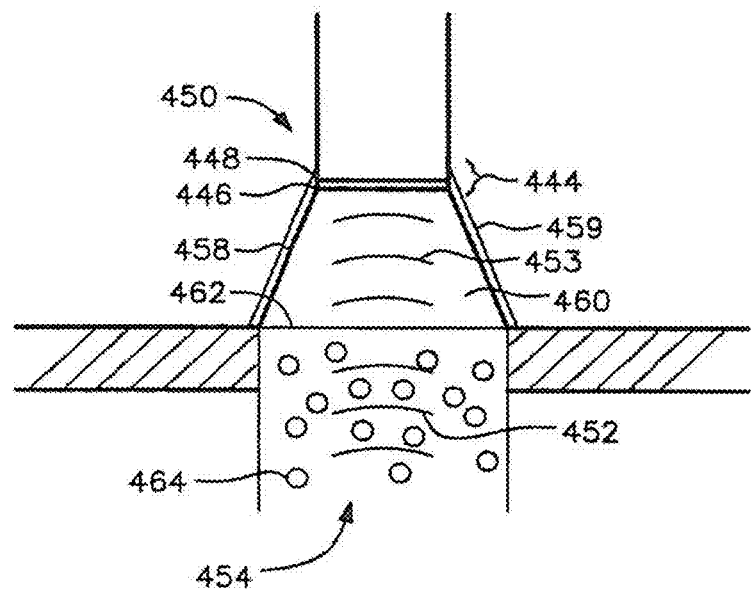
FIG. 37 is a schematic cross-sectional view of another preferred embodiment of the present invention using thermal emission.

FIG. 37 is a schematic cross-sectional view of another preferred embodiment of the present invention using thermal emission from the BTE tunnel. FIG. 37 shows a support structure 450 housing a thermal infrared detector 444 which has a filter 446 and a sensing element 448 with said sensing element 448 being preferably a thermopile and responding to thermal infrared radiation 452 naturally emitted by the BTE tunnel 454. The support structure 450 is adapted to have sensing device 448 with a field of view that corresponds to the geometry and dimension of the skin 462 at the end of the BTE tunnel 454. Support structure 450 provides walls 456, 458 which are in contact with the skin 462 with said walls creating a cavity 460 which contains thermal radiation 453 which has already passed through thin skin 462.

For example in the thermally sealed and thermally stable environment in the BTE tunnel 454, at 38° Celsius spectral radiation 453 emitted as 9,400 nm band is absorbed by glucose in a linear fashion according to the amount of the concentration of glucose due to the carbon-oxygen-carbon bond in the pyrane ring present in the glucose molecule. The resulting radiation 453 is the thermal emission 452 minus the absorbed radiation by the substance 464. The resulting radiation 453 enters the infrared detector 444 which generates an electrical signal corresponding to the spectral characteristic and intensity of said resulting radiation 453. The resulting radiation 453 is then converted into the concentration of the substance 464 according to the amount of thermal energy absorbed in relation to the reference intensity absorption outside the substance 464 band.

The same principles disclosed in the present invention can be used for near-infrared transmission measurements as well as for continuous wave tissue oximeters, evaluation of hematocrit, blood cells and other blood components. The substance measured can be endogenous such as glucose or exogenous such as alcohol and drugs including photosensitizing drugs.

Figure 38:
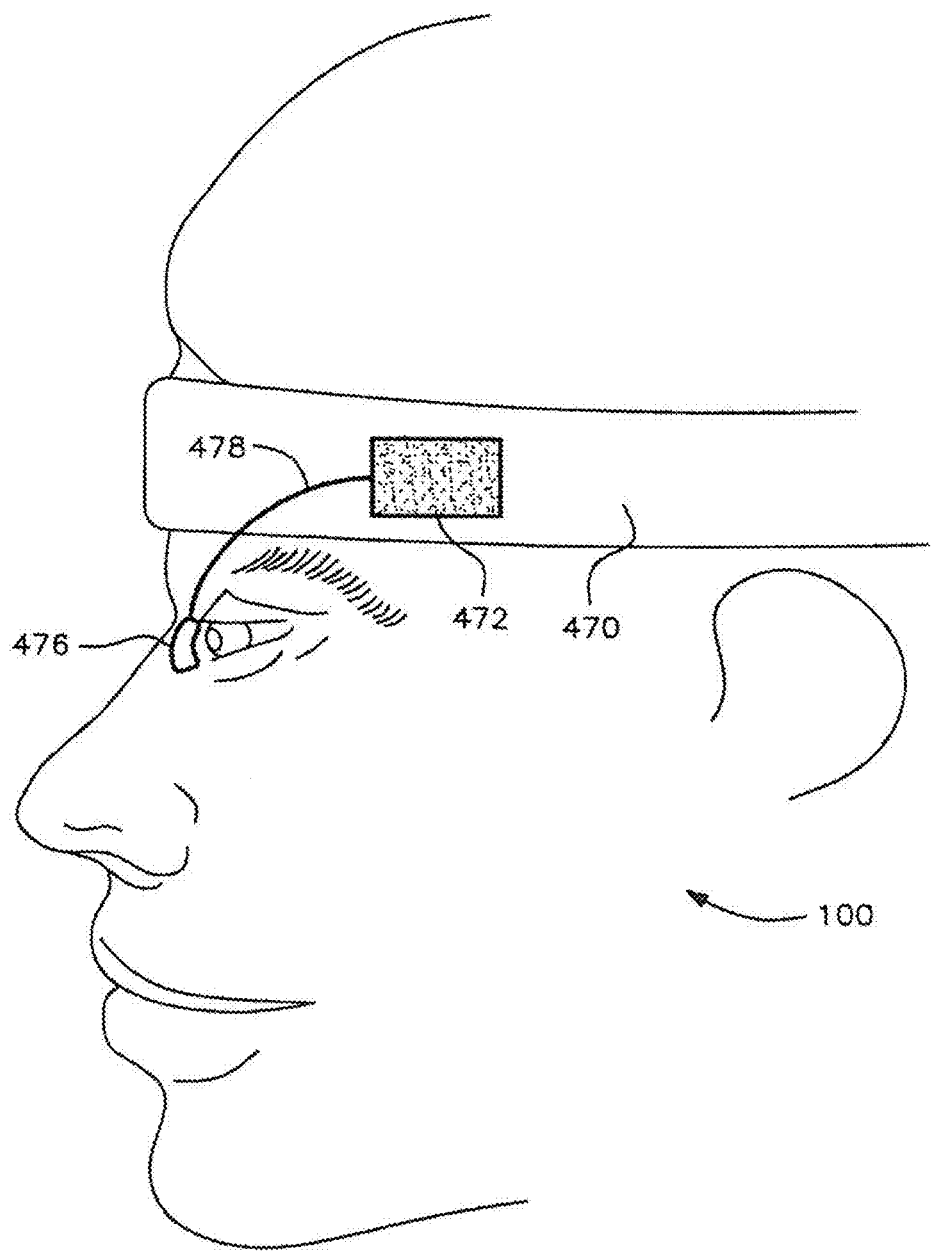
FIG. 38 is a side perspective view of an alternative embodiment using head mounted gear as a support structure.

Numerous support structures can position sensors at the BTT site for measuring biological parameters. Accordingly, FIG. 38 is a side perspective view of an alternative embodiment showing a person 100 using head mounted gear 470 as a support structure positioning with wires 478 and sensor 476 on the skin at the BTT site. A microelectronic package 472 containing transmitting means, processing means, and power source is disposed within or mounted on head band 470, with said head band 470 providing wire 478 from microelectronic package 472 for connection with sensing device 476 on the skin at the BTT site.

It is understood that the sensing device can be an integral part of the support structure or be connected to any support structures such as using conventional fasteners including screw, pins, a clip, a tongue-groove relationship, interlocking pieces, direct attachment, adhesives, mechanical joining, and the like; and said support structures include patches, clips, eyeglasses, head mounted gear, and the like.

Figure 39:
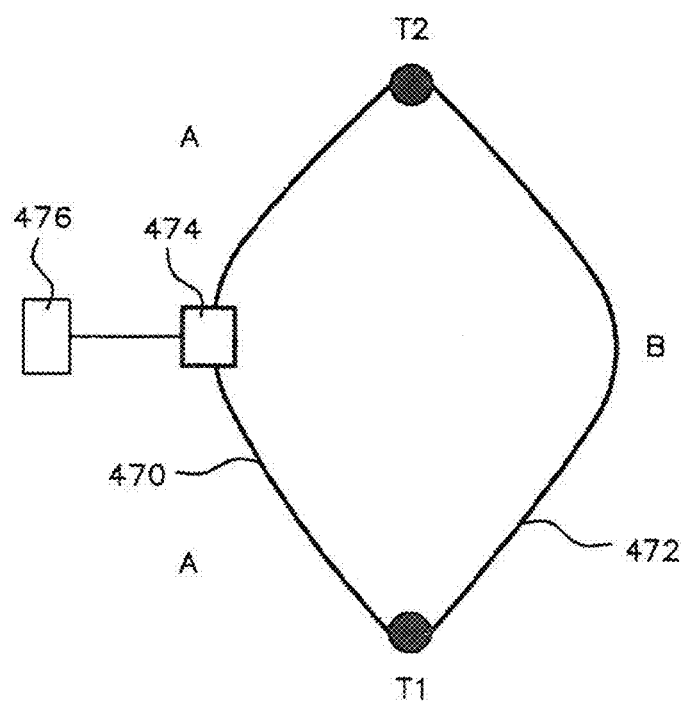
FIG. 39 is a schematic diagram of a preferred embodiment for generating thermoelectric energy to power the sensing system.

Various means to provide electrical energy to the sensing system were disclosed. The BTE tunnel offers yet a new way for natural generation of electrical energy. Accordingly, FIG. 39 is a schematic diagram of a preferred embodiment for generating thermoelectric energy from the BTE tunnel to power the sensing system. The generator of the invention converts heat from the tunnel into electricity needed to power the system. A thermoelectric module is integrated into the support structure to power the sensing system. The thermoelectric module preferably includes a thermopile or a thermocouple which comprises dissimilar metallic wires forming a junction. As heat moves from the tunnel through the thermoelectric module an electric current is generated. Since the BTE tunnel is surrounded by cold regions, the Seebeck effect can provide means for generating power by inducing electromotive force (emf) in the presence of a temperature gradient due to distribution of electric charges at the surface and interface of the thermoelectric circuit generated by the temperature at the BTE tunnel.

Accordingly, FIG. 39 shows the junctions T1 and T2 of metallic wire A 470 and metallic wire B 472 kept at different temperatures by placing junction T1 at the main entry point of the tunnel and junction T2 in a cold area such as the nose bridge (denoted in blue or purple in FIG. 1B, and referred herein as blue-purple nose). Metallic wires A 470 and B 472 are made of different materials and electric current flows from the hot to the cold region due to the thermal gradient with a magnitude given by the ratio of the thermoelectric potential. The potential U is given by $U=(Q_a-Q_b)*(T_1-T_2)$, where $Q_a$ and $Q_b$ denote the Seebeck coefficient (thermoelectric power) of metal A and metal $B_2$ and $T_1$ denotes temperature at the entry point of the BTE tunnel and $T_2$ denotes temperature at the blue-purple nose. The thermoelectric potential generated can power the sensing system and a capacitor 474 inserted into the system can be used to collect and store the energy and MCU 476 is adapted to control the delivery of energy as needed for measuring, processing and transmitting the signal.

It is understood that other means to convert thermal energy from the BTE tunnel into electricity can be used. It is also understood that the surface of the eye and caruncle in the eye can provide a thermal gradient and Seebeck effect, however it is much less desirable than using the skin at the end of the BTE tunnel since hardware and wires touching the surface of the eye and/or coming out of the eye can be quite uncomfortable and cause infection. It is yet understood that the cold end can include any relatively cold article including the frame of the glasses as well as the air.

Contrary to that numerous support structures disclosed in the present invention including eyeglasses can easily be adapted to provide in an unobtrusive manner the power generating system of the invention, for example by using a support structure such as eyeglasses for positioning the hot junction at the BTE site using medial canthal pads and positioning the cold junction on the nose using regular nose pads of eyeglasses. It is also understood that although the power generating system using Brain Thermal Energy was designed for powering the sensing system of the present invention, any other electrical device could be adapted to be supplied with energy derived from the Brain Thermal Energy tunnel.

Additional embodiments include support structures to position the sensor at the BTT site of animals. Many useful applications can be achieved, including enhancing artificial insemination for mammalian species by detecting moment of ovulation, monitoring herd health by continuous monitoring of brain temperature, detection of parturition and the like.

Accordingly, FIG. 40 is a perspective view of a preferred embodiment showing an animal 101 with sensor 480 positioned at the BTT site with wire 482 connecting sensor 480 with a microelectronic package 484 containing a transmitting device, a processing device, and power source in the eyelid pocket 486 of animal 101. Signal from microelectronic package 484 is preferably transmitted as radio waves 489. The signal from the transmitter in package 484 can be conveyed to a GPS collar allowing the identification of the animal having a high temperature associated with the localization of said animal by GPS means. Whenever there is an increase in brain temperature identified by the sensing device 480, the signal of high temperature activates the GPS collar to provide the localization of the affected animal. Alternatively the remote radio station receiving waves 489 activate the GPS system when the abnormal signal is received. In this case, the transmitter in package 484 only sends the signal to the remote station, but not to the GPS collar.

FIG. 41A is a perspective view of a portable support structure 490 positioning sensor 492 in contact with the skin 494 at the BTT site for measuring biological parameters.

Figure 41B:
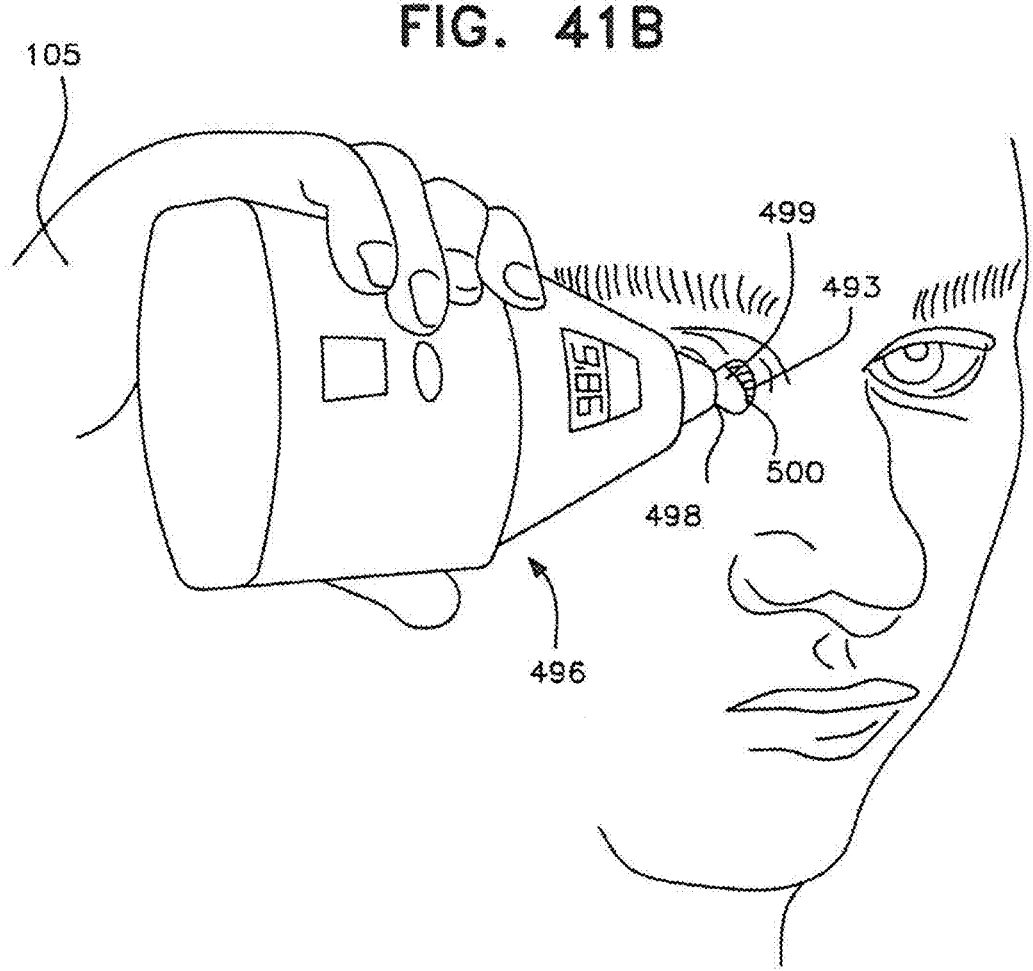

Support structure 490 incorporated as a thermometer with a contact sensor 492 is held by a second person 17 for positioning the sensor 492 on the skin 494 and performing the measurement. FIG. 41B is a perspective view of a portable support structure 496 with walls 500 positioning non-contact sensor 498 such as a thermopile with a field of view that matches in total or in part the geometry and dimension of the skin area at the end of the BTT. Support structure 496 incorporated as an infrared thermometer is held by a second person 105 for positioning the sensor 498 and measuring biological parameters. Although it is understood that pointing an infrared detector to the BTT site can be used in accordance with the invention, the temperature measured is not as clinically useful because of the ambient temperature. Therefore, the support structure 496 contains walls 500 that create a confined environment for thermal radiation to reach sensor 498 from the skin over the tunnel. Walls 500 of the support structure are adapted to match the geometry of the tunnel and to provide a cavity 499 with the boundaries consisting of the sensor surface 492 and the skin area 493 viewed by said sensor 498, in a similar manner as described for FIG. 37.

Figure 42A:
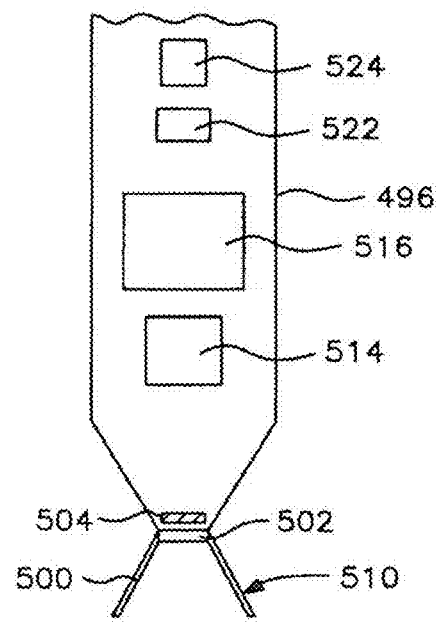
FIGS. 42A and 42B are schematic diagrams showing a non-contact sensor in accordance with the present invention.
Figure 42B:
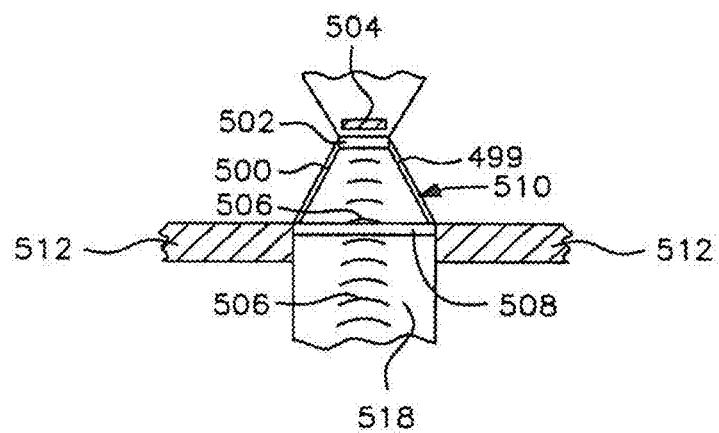

Now, with reference to FIGS. 42A and 42B, FIG. 42A is a schematic diagram showing the support structure 496, also referred to herein as a housing, a window 502 and radiation sensor 504 contained in the housing 496 and an extension 510 secured to the housing adapted for temperature measurement at the BTT area. In a preferred embodiment, the extension 510 has walls 500 and is substantially conical in shape and secured to a housing 496 adapted to be held by a hand 105 as shown in FIG. 41B. To measure the temperature, a user 105 positions the extension 510 adjacent to the BTT site such that the walls 500 of the extension 510 lie on the skin at the BTT area and the radiation sensor 504 views the BTT area. FIG. 42B is a schematic view showing the walls 500 of extension 510 creating a cavity 499 wherein thermal radiation 506 emitted from the skin 508 at the BTT area 518 is received by the radiation sensor 504. BTT area 506 is surrounded by the thick skin and fat in non-BTT areas 512. BTT temperature measurements are obtained from the output of the radiation sensor 504 contained in the housing 496. Electronics 514 within the housing 496 convert the received radiation to a temperature level which is displayed on a housing display 516 as illustratively shown in FIG. 41B.

The radiation sensor 504 views at least a portion of the BTT surface skin area 508 through an infrared radiation transparent window 502 and detect infrared radiation 506 from the BTT skin surface 508. The radiation sensor 504 is preferably a thermopile, but other radiation sensors may also be used such as pyroelectric detectors or any other radiation sensors that detect heat flux from the surface being evaluated. Exemplary window 502 materials include silicon and germanium. The sensor 504 is preferably mounted in an extension 510 which is shaped to match the dimension and geometry of the BTT area 508. The extension 510 can easily be positioned such that only the skin area 508 at the end of the BTT 518 may be viewed by the radiation sensor 504 wherein the skin area 508 is at substantially the same temperature as the brain temperature. Once in a position for the sensor 504 to view the BTT skin area 508, a button 522 is pressed to begin a measurement and the processing 514 within the housing 496 determines the brain temperature and display the value in a liquid crystal display 516 coupled to a sound device 524 for emitting an audio signal. A disposable cover may be used to cover any part of the apparatus in contact with the skin.

Although the temperature at the end of the BTT is substantially equivalent to the brain temperature based on the temperature of the cavernous sinus and cerebral blood, a variety of mathematical calculations and means can be used to determine the temperature at the BTT area including arterial heat balance, venous heat balance, and ambient temperature. It is understood that the BTT detector can contain a sensor for measuring ambient temperature and said measured ambient temperature be used for calculating temperature of the subject.

The temperature at the BTT area can be used as a reference for adjusting measurement acquired in other parts of the body outside the BTT area. The electrical equivalent of the BTT tunnel is an area of high voltage but low current, in which the voltage representing the temperature is virtually equal at the two ends of the tunnel. The high perfusion in the end of the BTT keeps a high temperature at the skin at the end of said end of the BTT.

The present invention also provides a method for detecting body temperature including the steps of providing a temperature detector positioned adjacent to the BTT during temperature detection and determining the temperature based on the radiation sensed at the BTT area. It is understood that the detector can remain in one position or move around the BTT area to identify the surface with the highest temperature.

A further method of detecting body temperature includes the steps of scanning a temperature detector across the BTT area and other areas in the head or in the contra-lateral BTT area and selecting the highest temperature, preferably selecting the highest temperature by scanning the right and the left BTT areas with the processor in the BTT detector determining and selecting the highest temperature.

Another method for identifying the highest temperature point in the BTT area can be found by scanning a radiation detector over the BTT area and having a processor adapted to select the highest reading and indicate that with an audio signal. The temperature detector 20 provides an audible beep with each peak reading.

Figure 43A:
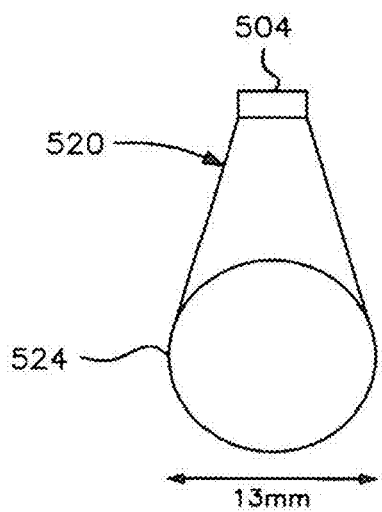
FIG. 43A to 43C are diagrams showing preferred embodiments for the diameter of the cone extension
Figure 43B:
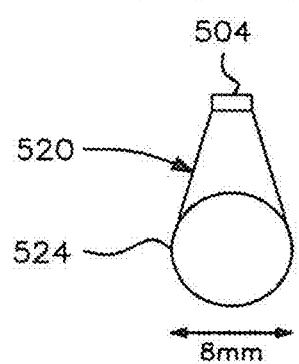
Figure 43C:
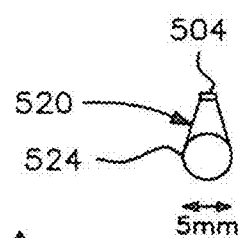

FIG. 43A to 43C are diagrams showing preferred embodiments for the diameter of the cone extension 510 at the end of the housing 496 in contact with the skin 508 at the BTT site 518. It is understood that although any shape can be used for the extension, the extension takes preferably the form of a cone with a radiation sensor positioned to view the BTT area. The cup 520 has an outer diameter at its end which is equal to or less than the BTT area. In FIG. 43A, for the radiation sensor 504 viewing the general area of the BTT site 508 the preferred outer diameter of the end 524 of the cup 520 is equal to or less than 13 mm. In FIG. 43B for the radiation sensor 504 viewing the general main entry point of the BTT site 508 the preferred outer diameter of the end 524 of the cup is equal to or less than 8 mm. In FIG. 43C, for the radiation sensor 504 viewing the main entry point the preferred outer diameter of the end 524 of the cup 520 is equal to or less than 5 mm. It is understood that although the preferred geometry of the radiation sensor and extension is round and has a substantially conical shape, any other shape of the radiation sensor and/or extension can be used including oval, square, rectangular, and the like. It is understood that the diameter and geometry is preferably chosen to match the geometry of the BTT area. It is also understood that the dimension of the sensor 504 is adapted to match the dimension of the cup 520 to the viewing area of the skin 508.

In accordance with a further aspect of the present invention, the extension is adapted to fit on top of the eyelids. The portion of the extension 510 of the housing 496 in contact with the skin 508 can also have an inner concave surface that matches the eyelid contour. Alternatively, the portion of the conical extension 510 in contact with the skin 508 can have a convex surface to match the medial canthal area and upper lid above the medial corner of the eye.

It is also understood that the dimensions for pediatric use are about two thirds of the dimension for adult size, or even half or less than half of adult size especially in small children. Accordingly, the preferred sizes of the outer diameter of the extension for children are: for the radiation sensor viewing the general area the preferred outer diameter of the extension is equal to or less than 9 mm for viewing the general area of the BTT, equal to or less than 6 mm for viewing the general main entry point of the BTT, and equal to or less than 4 mm for viewing the main entry point of the BTT.

Figure 44A:
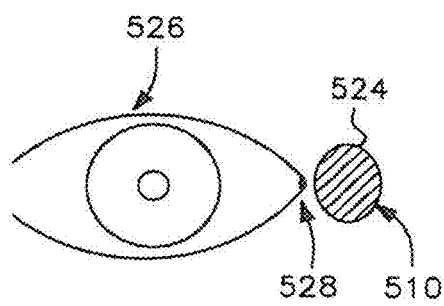
FIGS. 44A and 44B shows alternative geometries and shapes of an end of the extension.
Figure 44B:
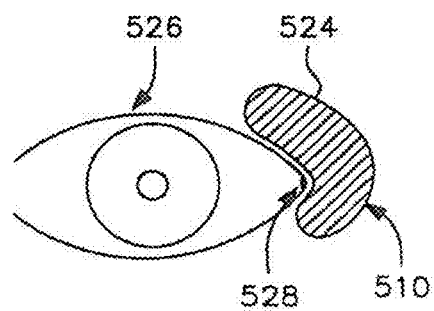

Besides the preferred round shape for the end 524 of extension 510, FIGS. 44A and 44B shows alternative geometries and shapes of end 524 extension 510 for non-contact sensor with said sensor viewing at least a portion of the BTT area next to the corner 528 of the eye 526. In FIG. 44A, the outer shape of the end 524 of extension 510 is shown as an oval shape. FIG. 44B shows an elliptical, banana or half moon shape of end 524 of extension 510 for viewing the medial canthal area and the upper eye lid area.

Figure 45A:
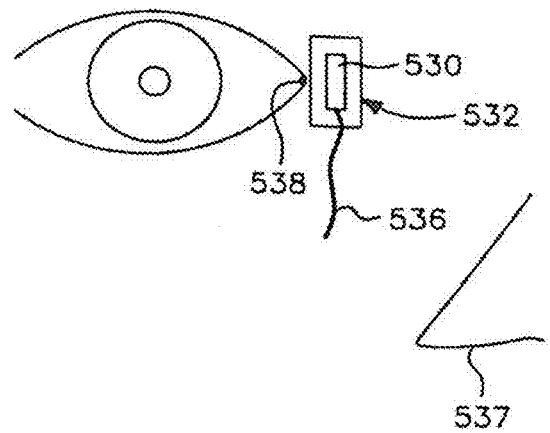
FIGS. 45A and 45B shows exemplary geometries and shapes for a support structure containing a contact sensor.
Figure 45B:
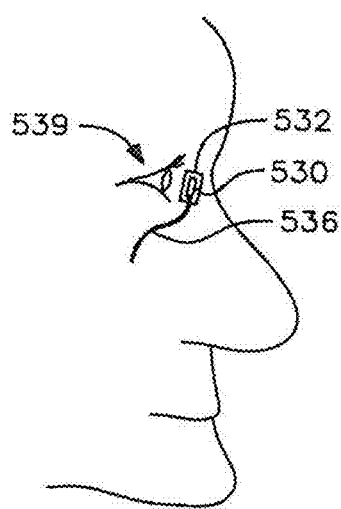

FIGS. 45A and 45B shows exemplary geometries and shapes for a support structure containing a contact sensor with said sensor positioned on the skin at the BTT area. FIG. 45 is a schematic frontal view showing a temperature sensor 530 in the shape of a rod contained in a patch 532 and positioned vertically on the BTT area 534 next to the corner of the eye 538 and nose 537 with a cord 536 extending from the distal end of the sensor 530. FIG. 45B is a side view of FIG. 45A showing sensor 530 with cord 536 contained in patch 532 next to the eye 539. A sensor is placed centrally in the patch, wherein the patch measures less than 11 mm in diameter.

Figure 46A:
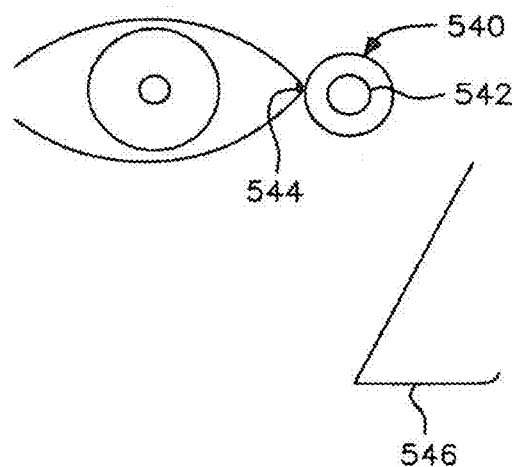
FIGS. 46A to 46D shows exemplary geometries and shapes for medial canthal pads or modified nose pads.
Figure 46B:
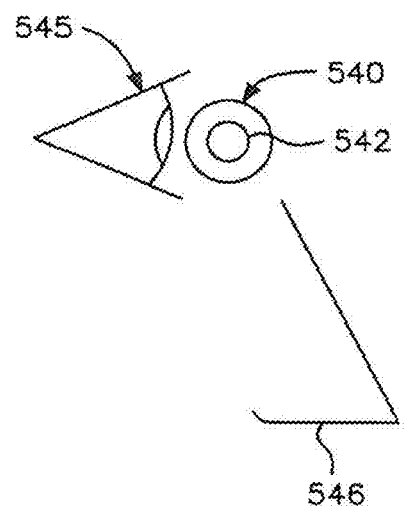
Figure 46C:
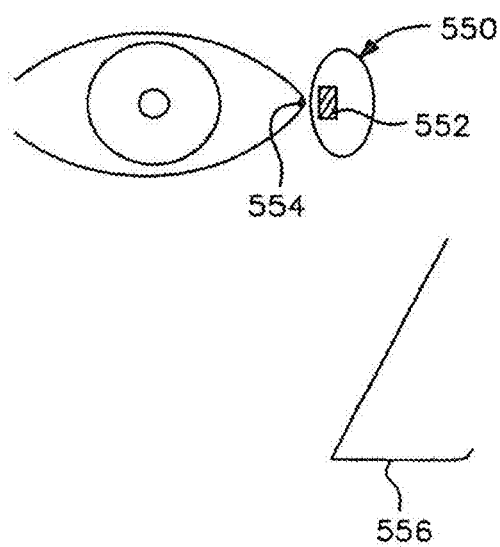
Figure 46D:
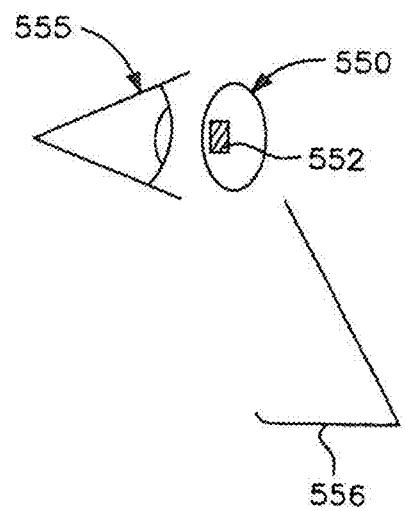

FIGS. 46A to 46D shows exemplary geometries and shapes for medial canthal pads or modified nose pads and their relation to the medial corner of the eye. FIG. 46A, shows a frontal view of a modified nose pad 540 containing a sensor 542 located centrally in said nose pad 540 wherein the sensor 542 is positioned on the skin at the BTT area next to the corner of the eye 544 and nose 546. FIG. 46B is a side view showing the eye 545 and nose 546 and the modified nose pad 540 with the sensor 542 positioned at the BTT site. FIG. 46C show a frontal view of a modified nose pad 550 having a sensor 552 located in its outer edge and positioned on the skin area at the BTT site next to the corner of the eye 554 and nose 556. FIG. 46D is a side view showing the eye 555 and nose 556 and the modified nose pad 550 with the sensor 552 positioned at the BTT site. It is understood that although an extension is the preferred embodiment with the sensor not contacting the skin, an infrared sensor probe adapted to touch the skin at the BTT area can also be used.

Figure 47:
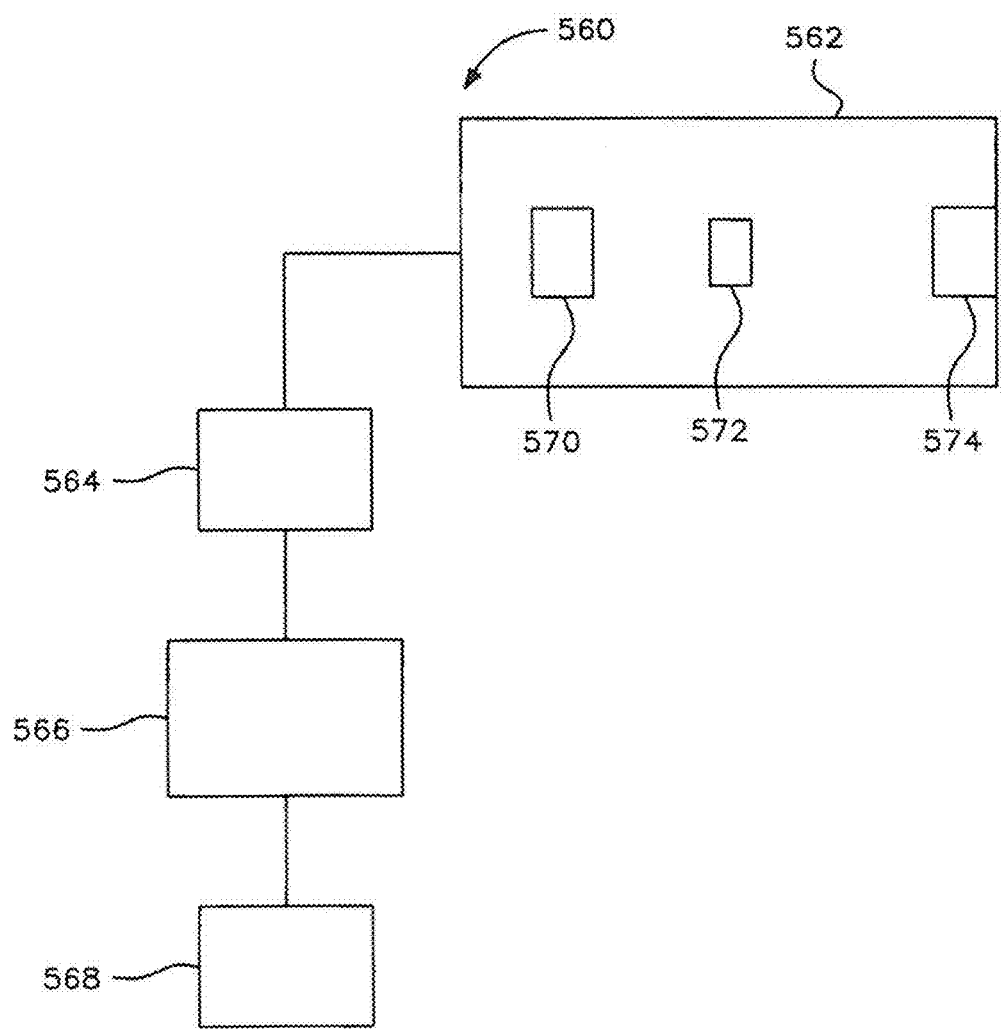
FIG. 47 is a schematic block diagram showing a preferred embodiment of the infrared imaging system of the present invention.

Now in reference to the thermal imaging systems of the present invention, FIG. 47 is a schematic block diagram showing a preferred embodiment of the infrared imaging system of the present invention. FIG. 47 shows a BTT ThermoScan 560 comprising a camera 562, a microprocessor 564, a display 566, and a power source 568. The system further includes proprietary software and software customized for the precise measurement and mapping of the BTT area. The BTT ThermoScan 560 includes a camera 562 with a lens 574, an optical system 572 that can contain mirrors, filters and lenses for optimizing image acquisition, and a photodetector 570, also referred to herein as a radiation sensor or a radiation detector, to quantify and record the energy flux in the far infrared range. The display unit 566 displays the thermal image of the BTT being viewed by the lens 574 in the camera. Radiation detector materials known in the art can be used in the photodetector 570 including alloys of indium-antimonide, mercury-cadmiun-telluride, Copper doped Germanium, Platinum Silicide, Barium Strontium Titanate, and the like.

The infrared radiation detector converts the incident radiation that includes the BTT area into electrical energy which is amplified. The detector 570 is responsive to infrared radiation to provide an output signal and discrete points related to the intensity of the thermal energy received from the BTT area and the surrounding area around the BTT area.

The discrete points are imaged and each point source must have enough energy to excite the radiation detector material to release electrons. Any point size can be used, but preferably with a size between 1 and 2 mm in diameter. When using an angle of 1.3 mrads, the BTT ThermoScan can capture an instantaneous image from a point size of approximately 1 mm diameter at a distance of 1 m from the detector. It is understood that any spatial resolution for optimal capturing of the BTT image can be used, but it is preferably between 1.0 and 1.6 mrad. The camera 562 of the BTT ThermoScan 560 has a field of view adapted to view the BTT area. Discrete points are further converted into an image of the face that includes the BTT area in the medial corner of the eye and upper eyelid. The screening function of the BTT ThermoScan is based on the temperature at the BTT area, either absolute temperature or the differential temperature of the BTT area in relation to a reference.

The electrical response to the thermal radiation can be displayed on the monitor as intensity, with a strong signal producing a bright (white) point as seen in FIG. 1A with said white point being representative of the highest radiant energy from the source. In FIG. 1A the source is the human face and the highest intensity of radiation is found in the BTT area. Calibration of the display screen result in a continuum shades of gray, from black (0 isotherm) to bright white (1 isotherm). Each point is digitally stored for further processing and analysis.

It is understood that a variety of lenses, prisms, filters, Fresnel lenses, and the like known in the art can be used to change the angle of view or optimize signal acquisition and capture of thermal energy flux from the face and the BTT area. The lens of the BTT ThermoScan 560 is preferably perpendicular to the plane of the human face or of the BTT area being viewed.

The radiation detector material in the BTT ThermoScan 560 is preferably sensitive to radiation with wavelength ranging from 8 to 12 μm. The BTT ThermoScan 560 has a temperature span set between 2 to 5 degrees Celsius and is extremely sensitive and adapted to discern temperatures to within 0.008 degrees Celsius to 0.02 at a range of 1 meter. Temperature measurements can be based on radiometric means with built-in electronics or by differential using a reference such as a black body. Although the system can be uncooled, to maximize the efficiency of the detector and achieve an optimum signal to noise ratio the detector can be cooled using solid state means, liquid nitrogen, evaporation of compressed argon gas, piezoelectric components, and the like.

Many radiation detectors capable of detecting infrared waves are being developed including silicon based, solid state systems, and microbolometers, and all said systems new or to be developed in the future can be used in the apparatus of the present invention to detect thermal radiation from the BTT with the display of a corresponding image of the BTT in a monitor.

An exemplary infrared detector system includes a microbolometer which is fabricated on silicon substrates or integrated circuits containing temperature sensitive resistive material that absorbs infrared radiation, such as vanadium oxide. The incident infrared radiation from the BTT area is absorbed by the microbolometer producing a corresponding change in the resistance and temperature. Each microbolometer functions as a pixel and the changes in electrical resistance generate an electrical signal corresponding to thermal radiation from the BTT area that can be displayed in a screen of a computer.

The display of the image of the BTT is the preferred embodiment of the invention, but the present invention can be implemented without display of an image. Radiation coming from the BTT can be acquired by the radiation sensors aforementioned and the temperature of the BTT area can be calculated based on the electrical signal generated by the radiation sensor using a reference. Any means to detect thermal radiation and/or temperature from the BTT area can be used in accordance with the principles of the invention.

Besides the easy manipulation of temperature at the skin level outside the BTT area, significantly lower temperatures are found in the areas outside the BTT as shown in the image on the screen, and depicted in the photos of FIGS. 1A and 1B. The lower and more unstable temperature outside the BTT area results in generating a non-clinically significant temperature level or thermal image when said areas outside the BTT are used for sensing thermal radiation and/or measuring temperature.

It is understood that a variety of signal conditioning and processing can be used to match the temperature areas outside the BTT area to a value that corresponds to the BTT area, and those methods also fall in the scope of the invention. Image outside the BTT area as seen more like a blur compared to the BTT area and superimposition of images that include the BTT area can also be used for achieving higher level of accuracy during temperature measurements. Comparing a radiation pattern outside the BTT area with the BTT area without necessarily creating an image of the BTT area can also be used for accurate and precise temperature measurement and evaluation of the thermal status of the body in accordance with the principles of the invention. Any method or device used for temperature evaluation or evaluation of the thermal status that is based on the temperature level or thermal radiation present in the BTT area by generating or not generating an image falls within the scope of the present invention.

Figure 48:
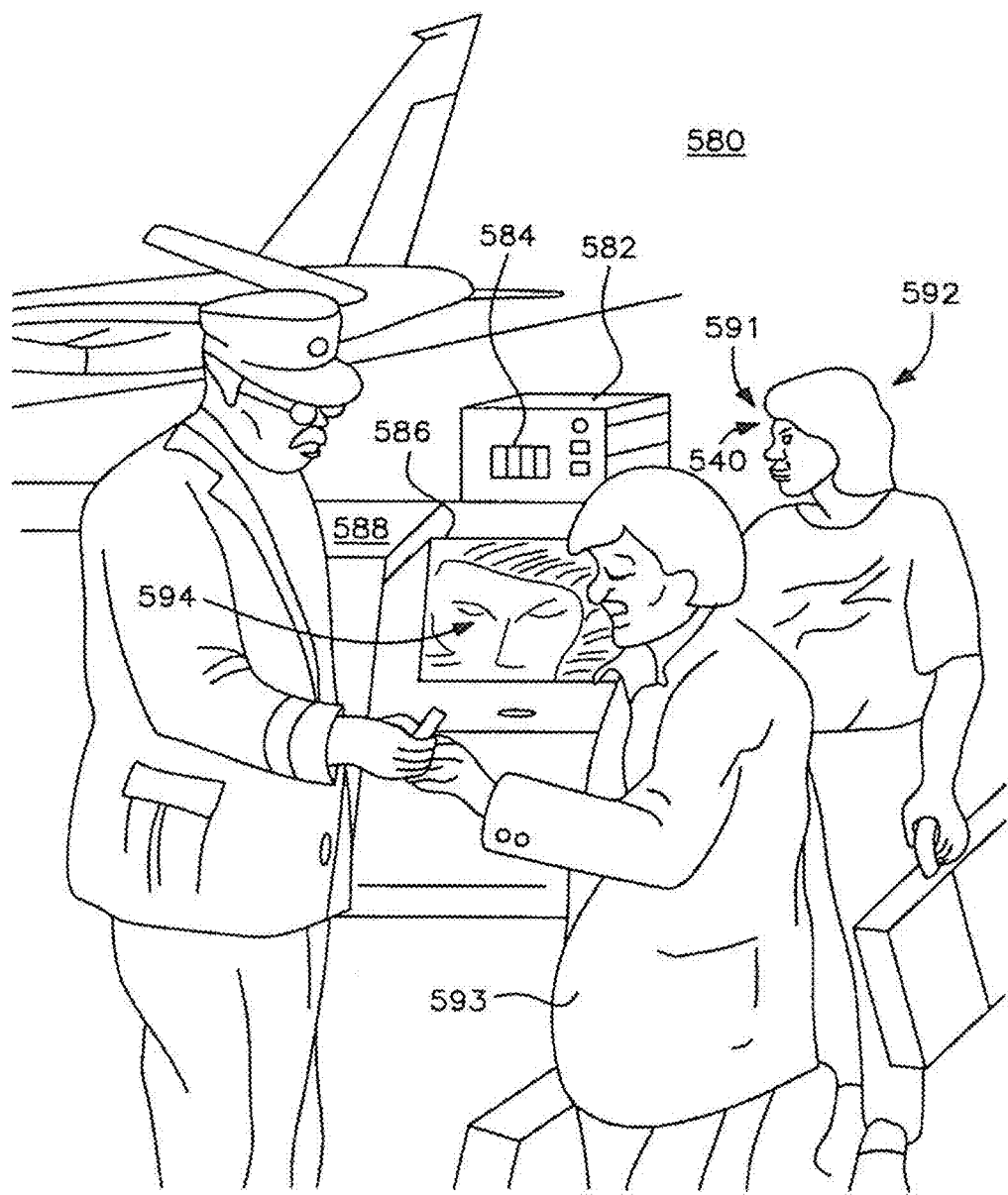
FIGS. 48 to 51 are schematic views showing the infrared imaging system of the present invention mounted in a support structure in different locations for screening people for temperature changes.

FIG. 48 is a schematic view showing the thermal imaging system 560 of the present invention adapted to be used in an airport 580 including an infrared camera 582, a processor 584, and a display 586 which are mounted in a support structure 588 at an airport 580. Camera 582 scans the BTT area present in the medial corner of the eye 590 in a human face 591 and provides an output signal to a signal processor 584. The output signal is an electronic signal which is related to the characteristic of the thermal infrared energy of the BTT 590 in the human face 591 when people 592, 593 walking by look at or are viewed by the camera 582. The processor 584 processes the output signal so that an image of the BTT area 594 can be formed by the display 586 such as a computer monitor.

Exemplarily, passenger 592 is looking at the camera 582 for sensing the thermal radiation from the BTT area 590, with said passenger 582 holding his/her eyeglasses since for the camera 582 to precisely view the BTT area 590 the eyeglasses have to be removed. If someone goes by the camera 582 without a thermal image of the BTT 590 being acquired an alarm will be activated. Likewise, if someone has a temperature disturbance an alert indicative of said temperature disturbance is activated.

Figure 49:
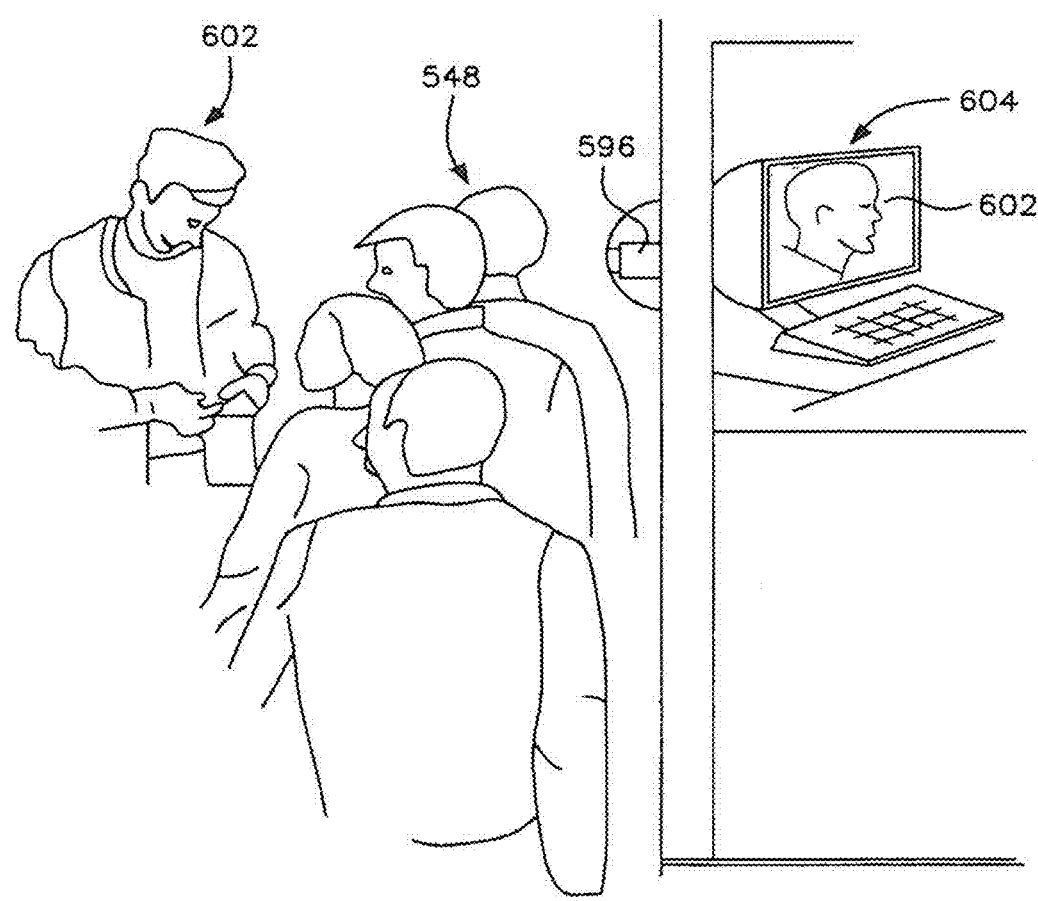

FIG. 49 is a schematic view showing the thermal imaging system 560 of the present invention adapted to be used in any facility that has a gathering of people such as a movie theater, a convention, stadium, a concert, a trade show, schools, and the like. In FIG. 49 the infrared camera 596 of the BTT Thermoscan 560 is located at the entrance of the aforementioned facilities and while people 598 show their identification or ticket to an agent 602, the BTT ThermoScan 560 scans the side of the face of the people 598 to capture a thermal image 600 and temperature at the BTT tunnel which is displayed in a remote computer display 604. The camera 596 has adjustable height and a tracking system to track the heat, and therefore said camera 596 can position itself for sensing thermal radiation from people 598 at different distances and of different height. It is also understood that the BTT Thermoscan 560 can be used in any facility including optical stores for adjusting positioning of sensors in eyeglasses.

Figure 50:
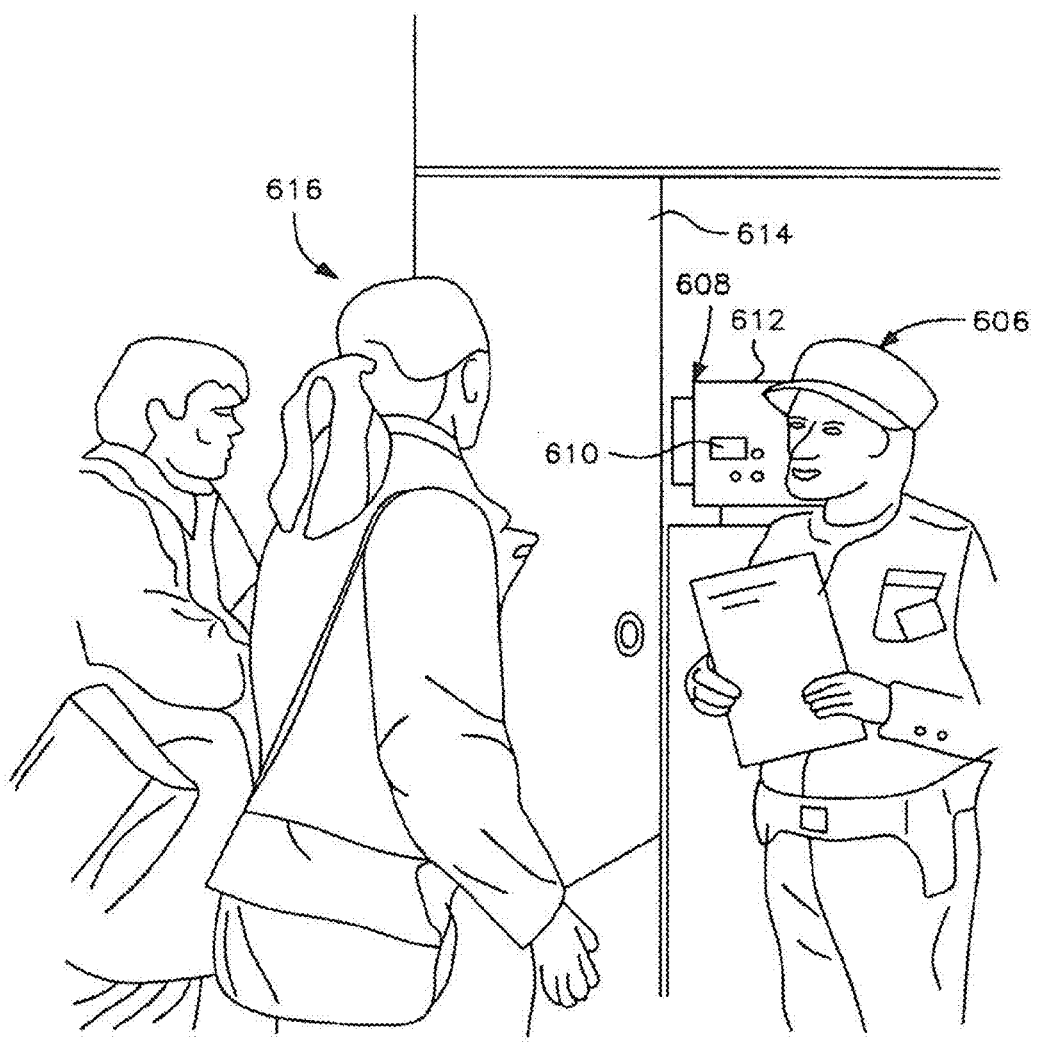

A facility that is of strategic importance such as a government building, military bases, courts, certain factories and the like can also benefit from screening for temperature disturbances. As shown in FIG. 50, a guard 606 is standing by an infrared detector camera 608 for sensing thermal radiation from the BTT area and preferably including a card slot 610 in its housing 612. Although a guard 606 is shown, the BTT ThermoScan of the present invention can work in an unguarded entrance. In this embodiment the BTT thermal image 560 works as a key to automatically open a door 614. Accordingly, employee 616 scan her Company Identification card in the slot 610 which then prompts the user to look at the camera 608 for capturing the thermal image of the BTT area. If the temperature of the BTT is within acceptable limits, the processor of the ThermoScan 608 is adapted to open the door 614. If the BTT temperature shows fever indicating a possible infection the employee is directed to a nurse. This will greatly help safety procedures in facilities dealing with food products in which one employee having a contagious disease can contaminate the whole lot of food products.

Figure 51:
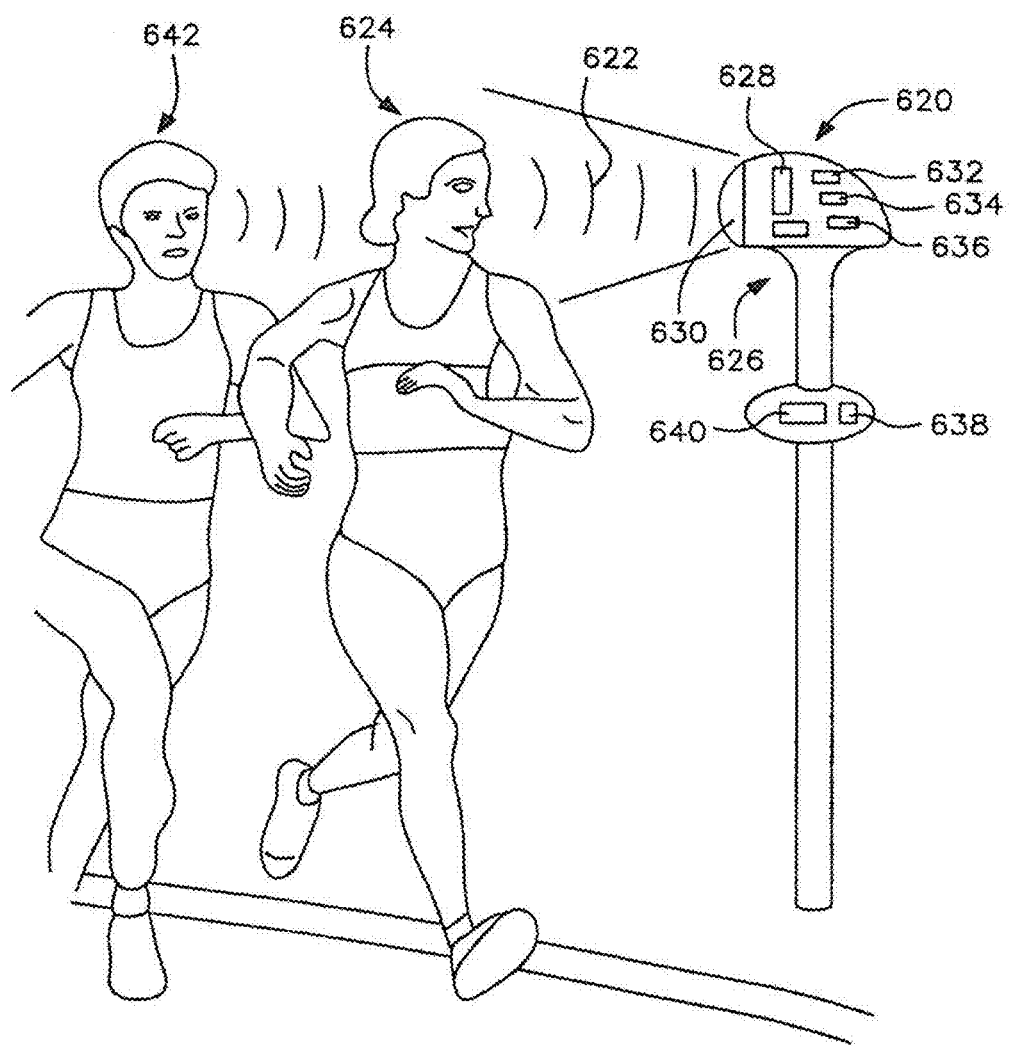

FIG. 51 is a schematic view of another embodiment of the present invention to monitor temperature disturbances during physical activity such as sports events, military training, and the like, showing infrared thermal detector 620 sensing thermal radiation 622 from an athlete 624. The infrared thermal detector 620 includes a detector head 626 which contains an infrared sensor 628, a digital camera, 630 and a set of lights, red 632, yellow 634 and green 636 indicating the thermal status of the athlete with the red light 632 indicating temperature that can reduce safety or performance of the athlete, a red light 632 flashing that indicates temperature outside safe levels, a yellow light 634 indicating borderline temperature, a green light 636 indicating safe temperature levels, and a green light 636 flashing indicating optimum thermal status for enhancing performance. The infrared sensor 628 detects the thermal radiation 622 and if the red light 632 is activated the digital camera 626 takes a picture of the scene to identify the number of the athlete at risk for heatstroke or heat illness. The infrared detector 620 further includes a processor 638 to process and a transmitter 640 to transmit the signal wired or wirelessly. It is understood that a wider field of view can be implemented with multiple BTT signals being acquired simultaneously as shown by BTT radiation from a second athlete 642 being sensed by the infrared detector head 626.

Figure 52A:
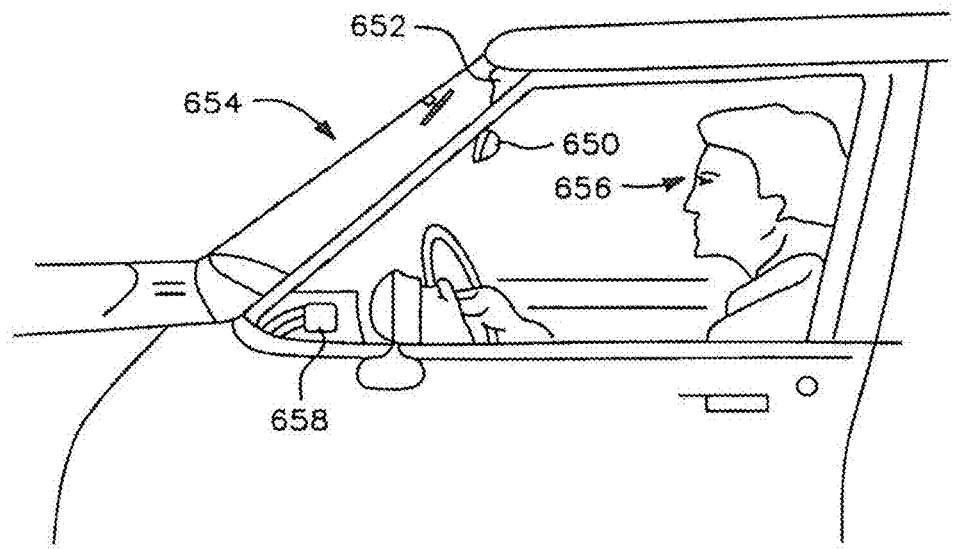
FIG. 52A is a schematic view showing the infrared imaging system of the present invention mounted in a vehicle.

Now referring to FIG. 52A, the BTT ThermoScan of this embodiment preferably includes a micro solid state infrared detector 650 which is mounted on a visor 652 of a vehicle 654 for sensing thermal radiation from the BTT of a driver 656 and of ambient radiation monitored by processor 658 mounted in the dashboard of the vehicle to determine whether the driver 656 is at risk of temperature disturbance (hyperthermia or hypothermia) which hampers mental and physical function and can lead to accidents. In addition the temperature at the BTT site of the driver 656 can be used for automated climate control and seat temperature control of vehicle 654. When the image of the BTT site indicates high body temperature the air conditioner is automatically activated.

Figure 52B:
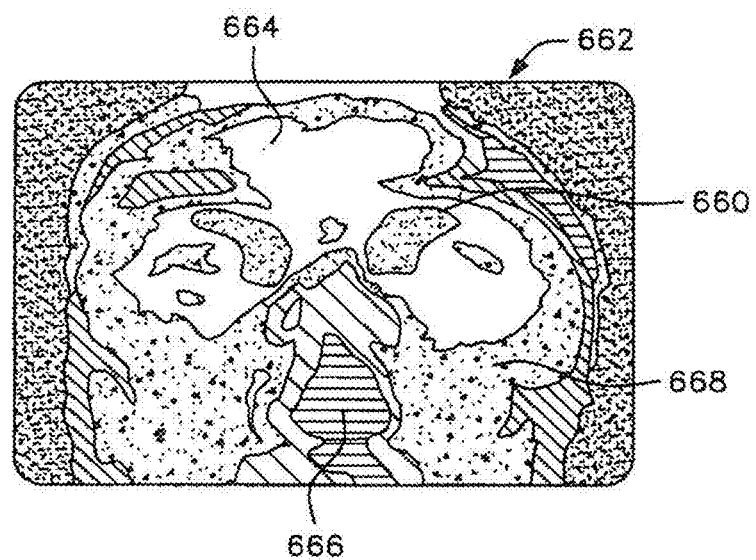
FIG. 52B is a representation of an illustrative image generated with the infrared imaging system of FIG. 52A.

FIG. 52B is a representation of an image generated by the detector 650 showing the BTT area 660 on a display 662. FIG. 48 is a representation of an illustrative image generated with the infrared imaging system of the present invention. FIG. 52B shows a frontal view of the human face and the BTT area 660 displayed on a screen 662 as well as the other areas outside the BTT area present in the human face such as forehead 664, nose 666, and cheeks 668. Please note that FIG. 1B shows an actual photo of the geometry of the general entry point of the BTT displayed on a screen and FIG. 4A shows a side view of the human face and of the BTT area displayed on a screen.

FIG. 53 shows an illustrative method of the present invention represented in a flowchart. It is to be understood that the method may be accomplished using various signal processing and conditioning with various hardware, firmware, and software configurations, so the steps described herein are by way of illustration only, and not to limit the scope of the invention. The preferred embodiment includes detecting thermal radiation from a source that includes at least a portion of the BTT area (step 670). At step 672 an image from a radiation source that includes at least a portion of the BTT area is generated. At step 674 the image generated at step 672 is displayed. Step 676 identifies temperature levels from the image displayed at step 674. Step 678 determines whether the temperature identified at step 676 matches a temperature target. The temperature target can be indicative of a temperature disturbance or indicative of the need to change the climate control level of the vehicle. Considering a temperature disturbance, if yes and there is a match between the detected temperature at the BTT and the stored target temperature, then an alarm is activated at step 680 informing the subject of the temperature disturbance (e.g., fever, hyperthermia, and hypothermia) and processing continues at step 670. If there is no match, step 678 proceeds to the next operation at step 670.

To enhance the image generated by the BTT ThermoScan, the method further includes aligning the BTT area with the field of view of the infrared detector and by removing eyeglasses during thermal detection of the BTT area.

Figure 54A:
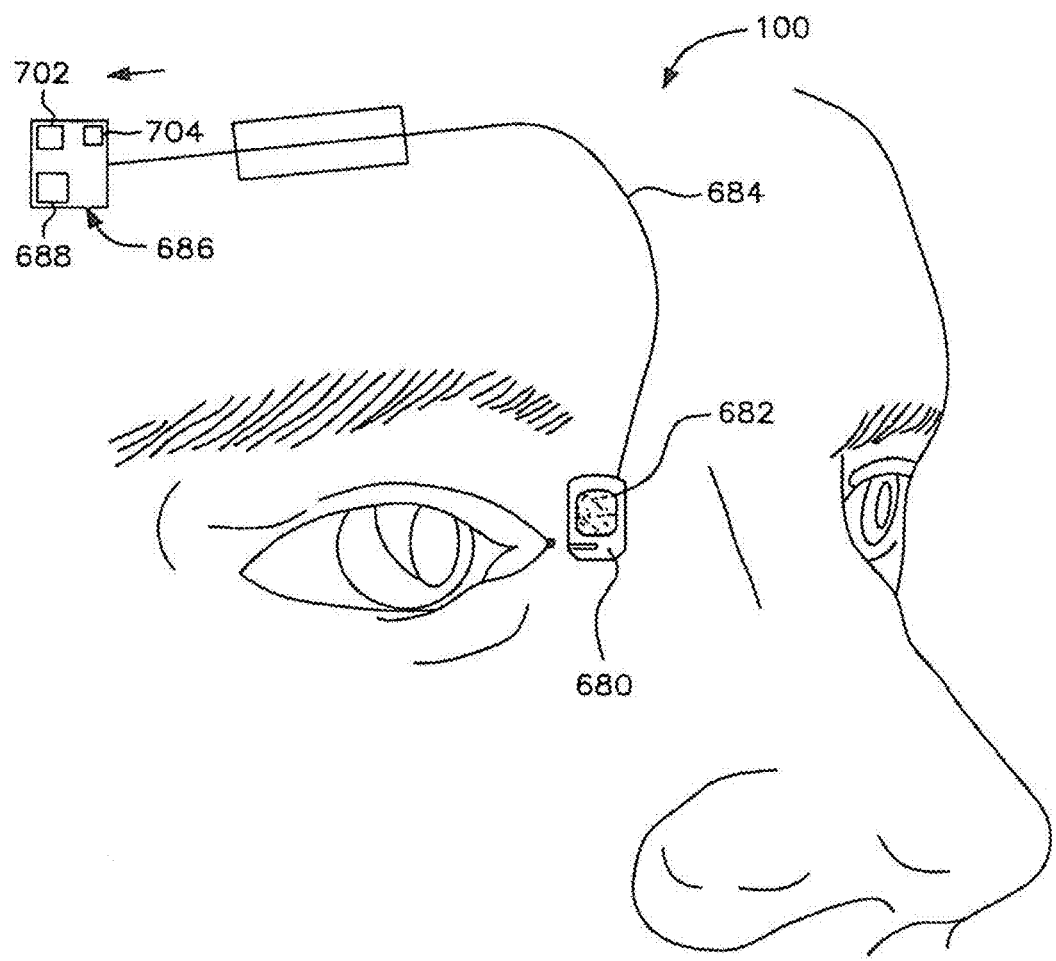
FIGS. 54A and 54B are perspective views of a preferred embodiment coupled to a head gear.
Figure 54B:
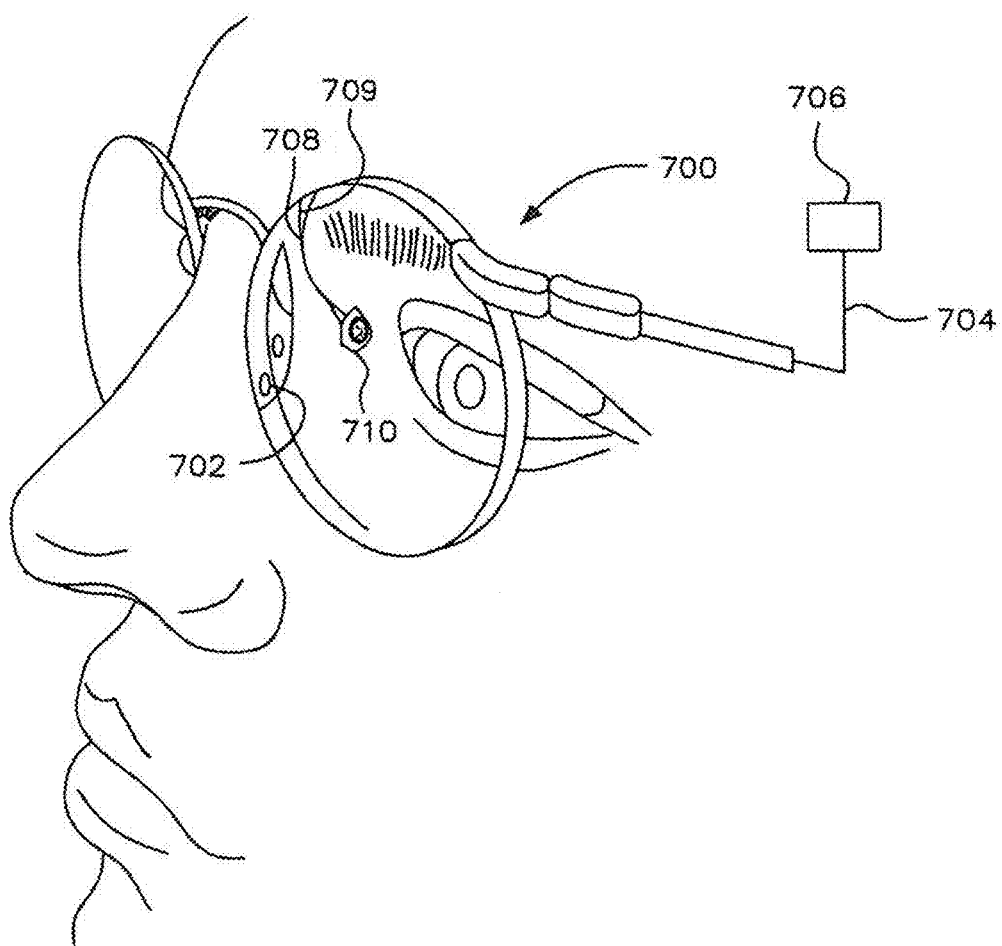

FIG. 54A is a perspective view of another preferred embodiment showing a person 100 wearing a support structure 680 comprised of a patch with sensor 682 positioned on the skin at the end of the tunnel and connected by a wire 684 to a helmet 686 which contains the decoding and processing hardware 688, transmitter 702 and display unit 704. Exemplary helmets include ones known in the art for the practice of sports, military, firefighters, and the like. Alternatively, as shown in FIG. 54B the support structure includes eyewear 700 with a warning light 702 and sensor 710 of eyewear 700 connected by wire 704 to the head mounted gear, such as a helmet 706. Sensor 710 has an arm 708 with a spring mechanism 709 for positioning and pressing the sensor 710 against the skin at the BTT area.

Figure 55:
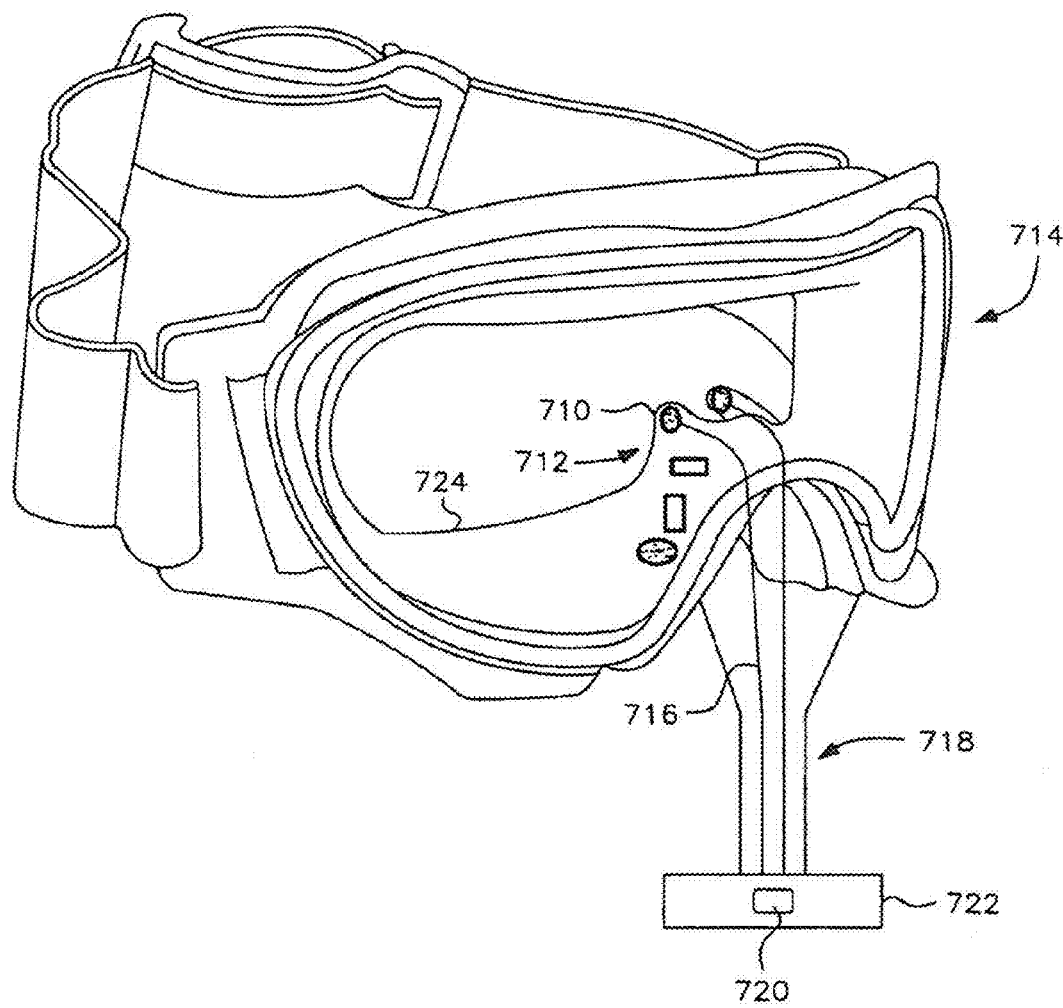
FIG. 55 is a perspective view of a preferred embodiment comprised of a mask and an air pack.

Now in reference to FIG. 55, the temperature sensor 710 can be mounted on nose pieces 712 of masks 714, for example a mask for firefighters. Wire 716 from mask 714 is mounted in an insulated manner, such as being positioned within the structure of mask 714 and air tube 718 that connects mask 714 to air pack 722. Wire 716 connects sensor 710 to radio transmitter 720 located in the air pack 722. Alternatively, wire 716 can be mounted external to the air tube 718. A warning light 724 in the mask 714 alerts the firefighter about high or low temperature.

Figure 56A:
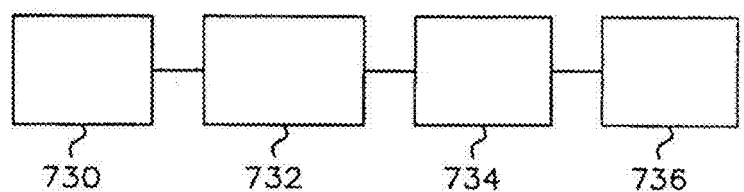
FIGS. 56A and 56B are schematic diagrams showing a BTT entry point detection system in accordance with the present invention.
Figure 56B:
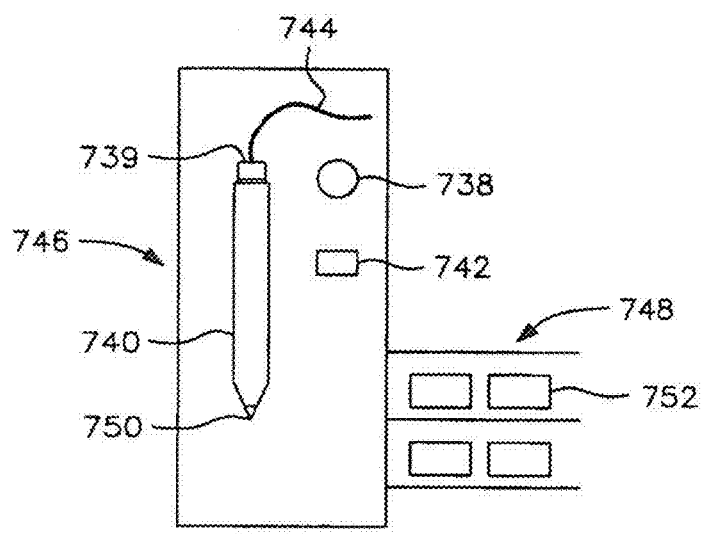

FIG. 56A is a diagram showing a BTT entry point detection system, which corresponds to the area with the highest temperature in the surface of the body, including temperature sensor 730, amplifier 732, processor 734, and pager 736. Processor 734 is adapted to drive the pager 736 to emit a high frequency tone for a high temperature and a low frequency tone for a low temperature. Scanning of the BTT area with the sensor 730 allows precise localization of the main entry point of the BTT, which corresponds to the highest frequency tone generated during the scanning. Another preferred embodiment for detection of the main entry point of the BTT includes replacing a buzzer or pager emitting sound or vibration by a light warning system. Exemplarily, FIG. 56B shows a pen 740, a LED 738 mounted on a board 746 and a LED 739 mounted on said pen 740, a sensor 750, and a processor 742. Wire 744 connects the pen 740 to board 746. The processor 742 is adapted to activate light 738, 739, when during scanning the BTT area, the highest temperature is found. By way of example, as shown in FIG. 56B, this pen 740 can be mounted on a board 746 next to a shelf 748 where TempAlert thermometers 752 are sold, allowing a customer to precisely locate the main entry point of the BTT. Sensor 750 of pen 740 can be for example a non-contact sensor (e.g., Thermopile) or a contact sensor (e.g., Thermistor).

Figure 57:
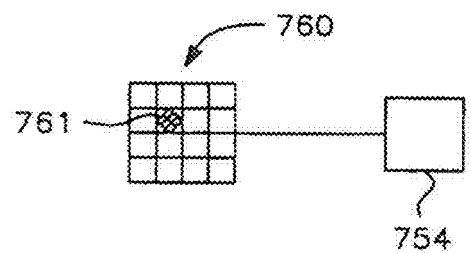
FIG. 57 is a schematic diagram showing an automated BTT entry point detection system.

The detection of the main entry point of the BTT can also be done automatically. Accordingly, FIG. 57 shows a 4 by 4 sensor array 760 placed at the BTT. The sensor array 760 contains 16 temperature sensors, which measure the temperature at the BTT site. Each temperature sensor T1 to T16 in the array 760 provides a temperature output. Sensor array 760 is connected to microprocessor 754 which is adapted to identify the sensor in sensor array 760 with the highest temperature output, which corresponds to the main entry point of the tunnel. For example temperature sensor T6 761 is identified as providing the highest temperature output, then the temperature of sensor T6 is displayed. The processor 754 continually searches for the highest temperature output of sensor array 760 in an automated manner and the highest temperature is continuously displayed.

Figure 58A:
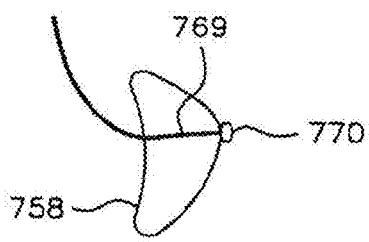
FIGS. 58A to 58C are schematic views showing alternative support structures in accordance with the present invention.
Figure 58B:
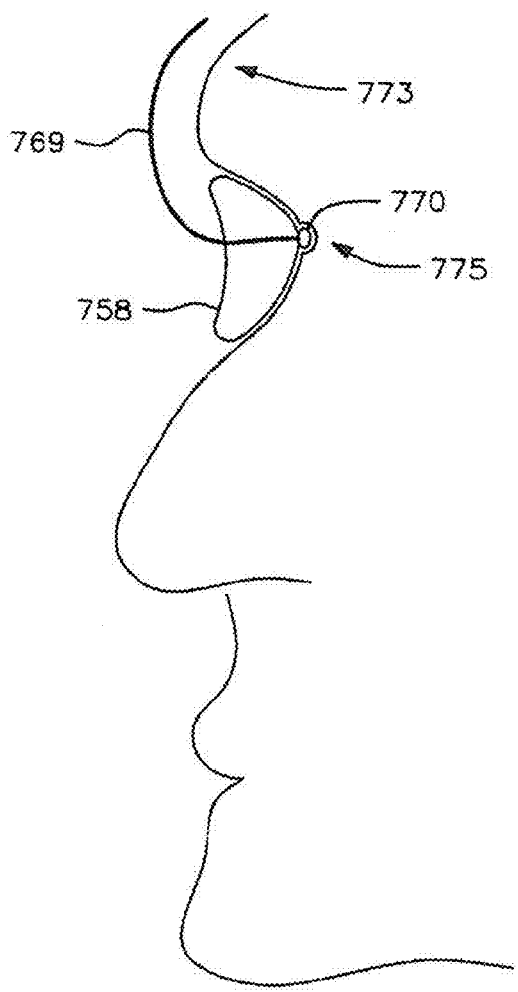
Figure 58C:
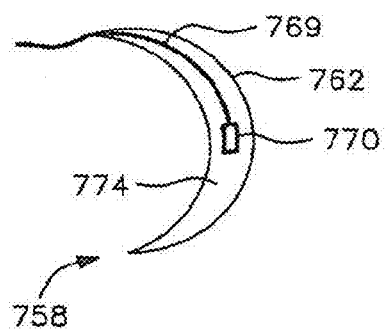

FIG. 58A is an alternative embodiment showing support structure 758 comprised of a piece of silicone molded to fit the BTT area with said support structure 758 containing wire 769 and sensor 770 in its structure. FIG. 58B shows the support structure 758 with sensor 770 positioned at the BTT area 775 with wire 769 exiting the molded piece of silicone structure 758 toward the forehead 773. Now referring to FIG. 58C, support structure 758 can alternatively include a multilayer structure comprised of a Mylar surface 762, sensor 770 with wire 769, and silicone piece 774 in the shape of a cup that encapsulates sensor 770, allowing proper and stable positioning of sensor 770 at the BTT area.

Figure 59:
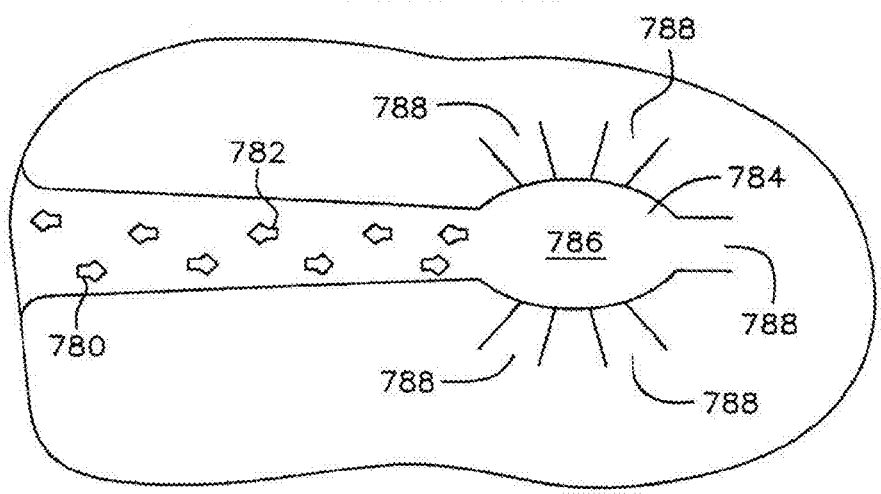
FIG. 59 is a schematic diagram showing bidirectional flow of thermal energy in the BTT.

It is also an object of the invention to provide methods and devices for treating and/or preventing temperature disturbances. As shown in FIG. 2B the brain is completely insulated on all sides with the exception at the entrance of the BTT. The BTT is a thermal energy tunnel in which thermal energy can flow in a bidirectional manner and therefore heat can be removed from the brain or delivered to the brain by externally placing a device at the entrance of the BTT that either delivers heat or removes heat. Accordingly, FIG. 59 shows the bidirectional flow of thermal energy represented by arrows 780 carrying heat to the brain and arrow 782 removing heat from the brain with the distribution of heat to and from the brain 784 occurring via the thermal storage area 786, with said thermal storage area shown in FIG. 2B in the center of the brain. From the thermal storage area 786 the thermal energy represented as hot or cold blood is distributed throughout the brain tissue 784 by the blood vessels 788, for treating and/or preventing hyperthermia (heatstroke) or hypothermia.

Accordingly, another object of this invention is to provide a new and novel BTT thermal pad for the application of cold or heat to the BTT area for cooling or heating the brain.

A further object of this invention is to provide a new and novel BTT thermal pad which covers the entrance of the BTT area, which may extend to other areas of the face. However, since the brain is insulated on all other sides but at the BTT entrance, the cooling is only external and does not reach the brain, which could be at "frying" temperature despite the external cooling sensation. Considering that, a preferred embodiment includes an extended BTT thermal pad covering the face in which only the BTT area is exposed to the cold and the remainder of the extended BTT thermal pad covering the face is insulated, preventing the warming up of the gel or ice placed inside the bag. The BTT thermal pad container can include a radiant heat-reflecting film over various portions thereof, and an insulator over the same or other portions and which together facilitate directional cooling. Thus, only heat conducted by the BTT is absorbed as the BTT is cooled.

The BTT thermal device applied to the BTT area promotes selective brain cooling or selective brain heating for treating hyperthermia and hypothermia respectively. The brain, which is the most sensitive organ to thermally induced damage, can be protected by applying heat via the BTT during hypothermia or removing heat during hyperthermia. The cooling or heating is selective since the temperature of the remaining body may not need to be changed, this is particularly important when cooling the brain for treating patients with stroke or any brain damage. The majority of the brain tissue is water and the removal or application of heat necessary to cool or heat the brain can be precisely calculated using well known formulas based on BTU (British thermal unit). A BTU is the amount of energy needed to raise the temperature of a pound of water 1 degree F., when a pound of water cools 1 F, it releases 1 BTU.

The BTT thermal pad for therapeutic treatment of excessive heat or excessive cold in the brain preferably includes a bag having a substantially comma, banana, or boomerang shape, with said bag in complete overlying relationship with the entire entrance of the BTT, said bag including an outer wall and an inner wall defining a sealed cavity to be filled with ice, gel-like material, solid material, and the like, for cooling or heating the BTT skin area overlying the entrance of the BTT.

An exemplary brain cooling or brain heating device includes hot and cold pad or pack adapted to fit and match the special geometry of the entrance of the BTT and comprising a preferably flexible and sealed pad and a gel within said pad, said gel being comprised of a mixture of water, a freezing point depressant selected from the group consisting of propylene glycol, glycerine, and mixtures thereof associated with other compounds such as sodium polyacrylate, benzoate of soda, hydroxibenzoate, and mixtures thereof and a thickening agent. Any other cooling or heating device or chemical compounds and gels including a combination of ammonium nitrate and water can be used as cooling agent as well as heating agents such as a combination of iron powder, water, activated carbon, vermiculite, salt and Purge natural mineral powder. Those compounds are commercially available from many vendors (e.g., trade name ACE from Becton-Dickson).

Figure 60A:
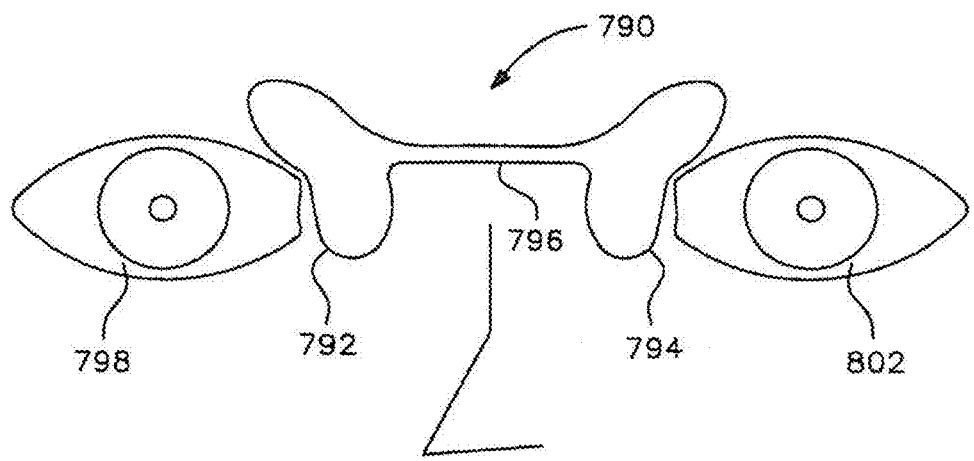
FIGS. 60A to 60C show diagrammatic views of a preferred BTT thermal pack.
Figure 60B:
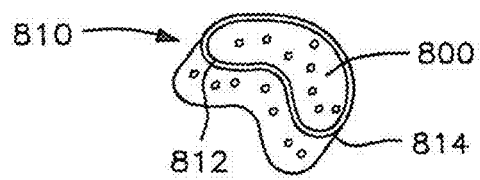
Figure 60C:
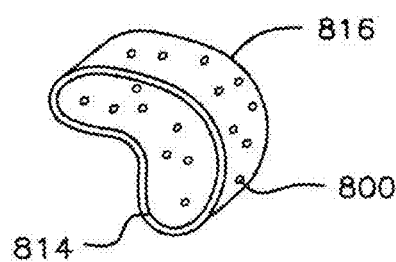

FIG. 60A shows a diagrammatic view of a preferred dual BTT thermal pad also referred to herein as BTT cold/hot pack 790 located next to eye 798, 802 including a dual bag system 792, 794 for both the right and left sides connected by connector 796. FIG. 60B shows in more detail a perspective view of the single bag BTT cold/hot pack device 810, represented by a device to be applied to the left-side, comprising preferably a generally comma-shape, boomerang-shape or banana-shape pad which is sealed in a conventional fashion at its ends 812 to enclose a quantity of a gel-like material 800 which fills the pad 814 sufficiently to enable said pad 814 to be closely conformed to the special topography of the BTT area in the recess between the eye and nose. FIG. 60C is an opposite perspective view showing an extension 816 that conforms to the recess at the BTT area of pad 814 containing gel 800. The device is referred to herein as BTT cold/hot pad or BTT cold/hot pack. Still in reference to FIG. 60C, perspective view is shown of the BTT cold/heat pack device and which is shown as being formed in a pillow-like configuration which permits the molding of the BTT cold/heat pack into the BTT area.

In use the BTT thermal pad would be put into a freezer or other chilling device for use as a cold compress or would be put into hot water to be used as a hot compress. The BTT thermal pad preferably comprises a tough flexible envelope of plastic material. The material within the BTT thermal pad is preferably a gel which will maintain its gel-like consistency over a wide range of temperatures. There exist many gels which can be cooled to freezing and which absorb heat during warmup. There are a number of different types of such gels. Some of them freeze solid, and some are flexible even at 0 degrees F. Cold packs such as a frozen water-alcohol mixture can also be used. Alternatively, a BTT thermal pad includes a bag having inner and outer walls lined interiorly with plastic which define a cavity to be filled with ice through an opening in the bag. In this instance the bag is preferably sealed with a rubber material.

Although flexible plastic is described as a preferred material for containing the gel, it is understood that any material or fabric can be used including vinyl, cotton, rayon, rubber, thermoplastic, synthetic polymers, mixtures of materials, and the like. The size and shape of the BTT pad structure is adapted to fit the special anatomy of the recess between eye and nose and for matching the special geometry of the entrance of the BTT.

Any cooling or heating device known in the art can be used in the BTT pad treatment device including hot or cold water flowing through tubes that are adapted to carry or deliver heat to the BTT area. The tubes can be mounted in any head gear or the frame of eyeglasses, pumping mechanisms can be mounted in the head gear or eyeglasses for providing a continuous flow of water through the tubes. The BTT pad can be connected to tubes which have connectors for joining to a water temperature control and circulating unit in the head gear or eyeglasses. Hot or cold liquid is circulated through tubes which are in communication with each other and which deliver or remove heat from the BTT.

Elastic band or hook and loop fastener can be used for securing the BTT pad in position. Any of the support structures mentioned herein can be used to secure the BTT pad in position including a piece of glue. For example, the BTT pad can include a clip like mechanism or the BTT thermal pad can be secured to the frame of eyeglasses. Nose pads of eyeglasses or modified nose pads of eyeglasses can include cooling or heating devices for delivering or removing heat from the BTT. A BTT thermal pad can include a stick mounted in the pad that can held by hand and manually placed in the BTT area, for example held by a player during a break in the game to reduce the temperature in the brain, or for warming up the brain of a skier during a winter competition.

An alternative embodiment includes a BTT thermal pad attached to a head gear for supplying water to evaporatively cool the BTT area. In this instance the cold water is generated by evaporative cooling in the headband and forehead and upper portion of a wearer's head.

Any cooling or heating device can be used to cool or heat the BTT area for selective brain cooling or brain heating, preferably using a moldable device that conforms to the anatomy of the region at the entrance of the BTT, with directional temperature control properties for cooling or heating the skin at the entrance of the BTT. Any of the devices for heating or overheating or for cooling, including electrical, chips, semiconductor, polymers, and the like known in the art as well as described by Abreu in U.S. Pat. No. 6,120,460; U.S. Pat. No. 6,312,393 and U.S. Pat. No. 6,544,193, herein incorporated in their entirety by reference, and other pending applications by Abreu can be adapted in support structures for positioning at the BTT entrance and used for cooling or heating the brain.

The present invention provides a moldable BTT thermal pad or BTT thermal pack in a packaging arrangement that can provide surfaces of differing thermal conductivities and heat reflecting properties so as to prolong the useful cooling/heating time thereof. The construction and materials of the BTT thermal pad or BTT thermal pack permits the molding of its shape and the retention thereof to the BTT site on the skin between the eye and nose. The materials disclosed herein can remain flexible plastic for temperatures in the range of −10° C. to 140° C.

Figure 61:
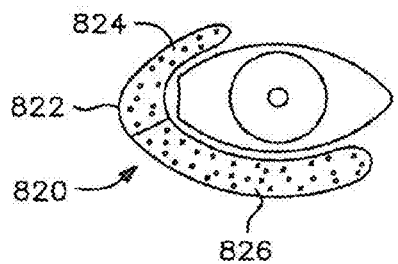
FIG. 61 is a schematic frontal view showing a preferred BTT thermal pack in accordance with the present invention.

Referring to FIG. 61, a frontal view of an alternative embodiment of BTT thermal pack 820 is shown including a bag 822 with gel 800 with said bag having two parts with the first part 824 positioned at the main portion of BTT 824 and containing the highest amount of gel 800 and a second part 826 positioned at the peripheral portion of the BTT and containing a smaller amount of gel.

Figure 62:
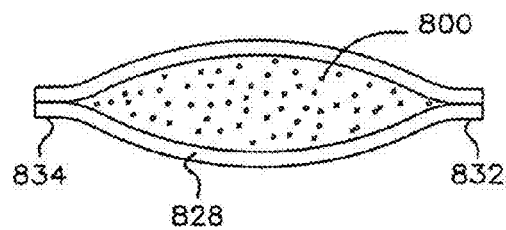
FIG. 62 is a schematic cross sectional view of a BTT thermal pack.

FIG. 62 shows a cross sectional view of the bag 828 of the BTT thermal pack containing gel 800 with said bag sealed in its ends 832, 834.

It is understood that a ring shape surrounding the eye can also be used or a shape that includes other parts of the face/forehead as long as there is conformation and apposition of part of the BTT thermal pack to the BTT area. The preferred shape and dimension matches the special geometry of the BTT area described herein.

Figure 63A:
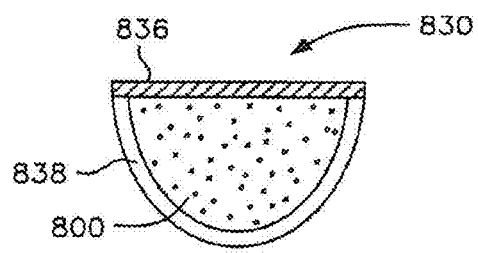
FIG. 63A is a schematic cross sectional view of a BTT thermal pack in its relaxed state.
Figure 63B:
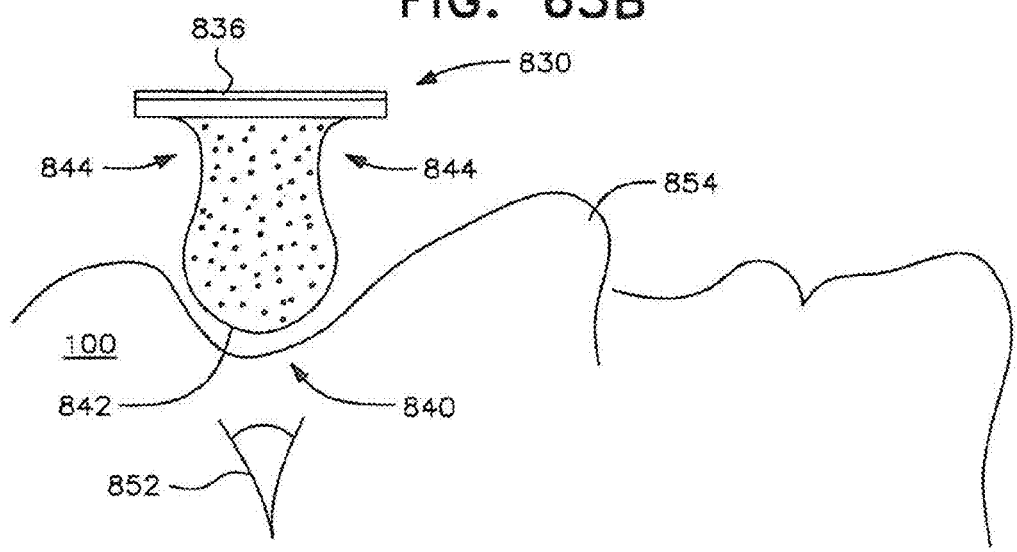
FIG. 63B is a schematic cross sectional view of a BTT thermal pack of FIG. 63A in its compressed state conforming to the BTT area.

FIG. 63A shows a preferred embodiment of the BTT thermal pack 830 in its relaxed state that includes a hard upper part 836 made preferably of hard rubber or plastic attached to a bag 838 made of soft plastic with said bag containing gel 800 and being deformable upon external pressure. As depicted in FIG. 63B, the BTT thermal pack 830 is shown with a centrally formed convex shape 842 at the opposite end of hard upper part 836 upon compression shown by arrows 844 to conform to the BTT anatomy 840 between eye 852 and nose 854 of person 100.

The BTT thermal pack is preferably moldable and the container or bag constructed with materials that are deformable and otherwise pliable over the temperature range of use so as to conform to the anatomy of the BTT area. A central convex area in the pack allows for intimate interaction and thermal energy transfer at the entrance of the BTT, but it is to be recognized that the specific shape of the convex area of the BTT cold/heat pack itself can be slightly varied according to the ethnic group.

FIG. 64A shows a side cross-sectional view of a head 856 of person 100 with BTT thermal pack 850 in a pillow-like configuration located at the BTT site 858. Construction of BTT thermal pack is performed so as to maintain an intimate apposition to the BTT site. FIG. 64B is a frontal view of BTT hot/cold pack 850 shown in FIG. 64A at the BTT site 858 located next to the left eye 862.

Figure 65:
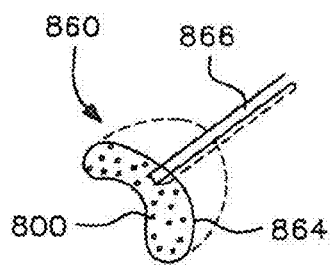
FIG. 65 shows a perspective view of a BTT thermal pack containing a rod 866.
Figure 66:
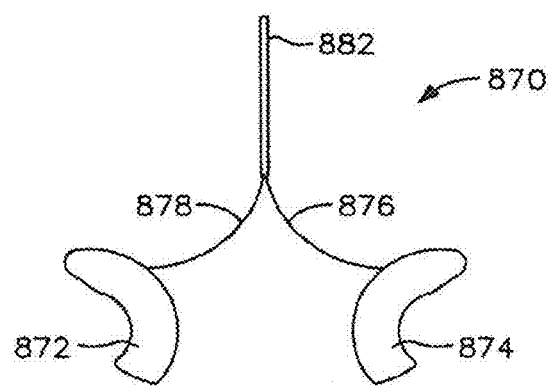
FIG. 66 shows a schematic view of another embodiment of dual bag BTT thermal pack.

FIG. 65 shows a perspective view of a BTT thermal pack 860 that includes a bag 864 containing gel 800 and a rod 866 for manually holding said BTT pack 860 at the BTT site. FIG. 66 shows a frontal view of a dual bag BTT thermal pack 870 with bags 872, 874 connected to a rod 880 by flexible wires 876, 878.

Figure 67A:
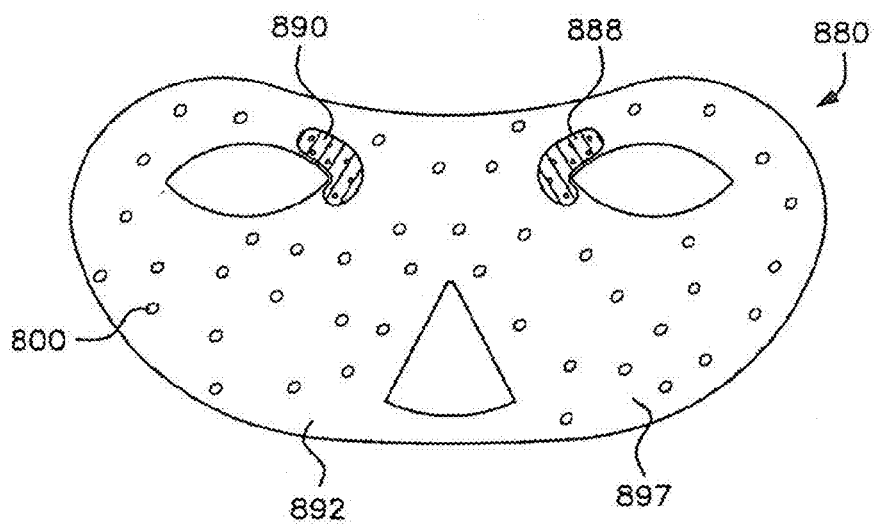
FIG. 67A shows a frontal schematic view of a BTT thermal mask.
Figure 67B:
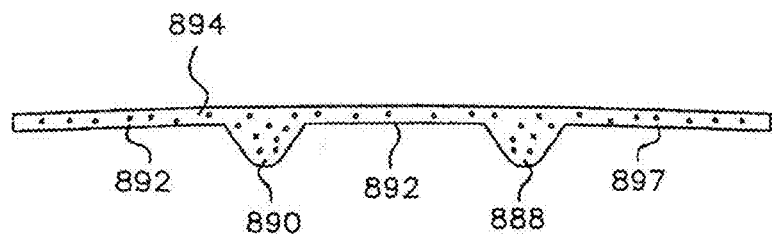
FIG. 67B shows a side cross-sectional schematic view of the BTT thermal mask of FIG. 67A.

FIG. 67A shows a BTT thermal mask 880 with openings 884 for the eyes and 886 for the nose and comprised of a pouch containing gel 800, and including bags 888, 890 for matching the anatomy of the BTT area. The remainder of the mask 880 comprises flat area 892. The flat area 892 is preferably insulated for allowing directional thermal energy flow, so the gel 800 only touches the skin at the BTT area. FIG. 67B is a cross-sectional side view of mask 880 showing pouch 894 with bags 888, 890 and the remaining flat area 892.

Figure 67C:
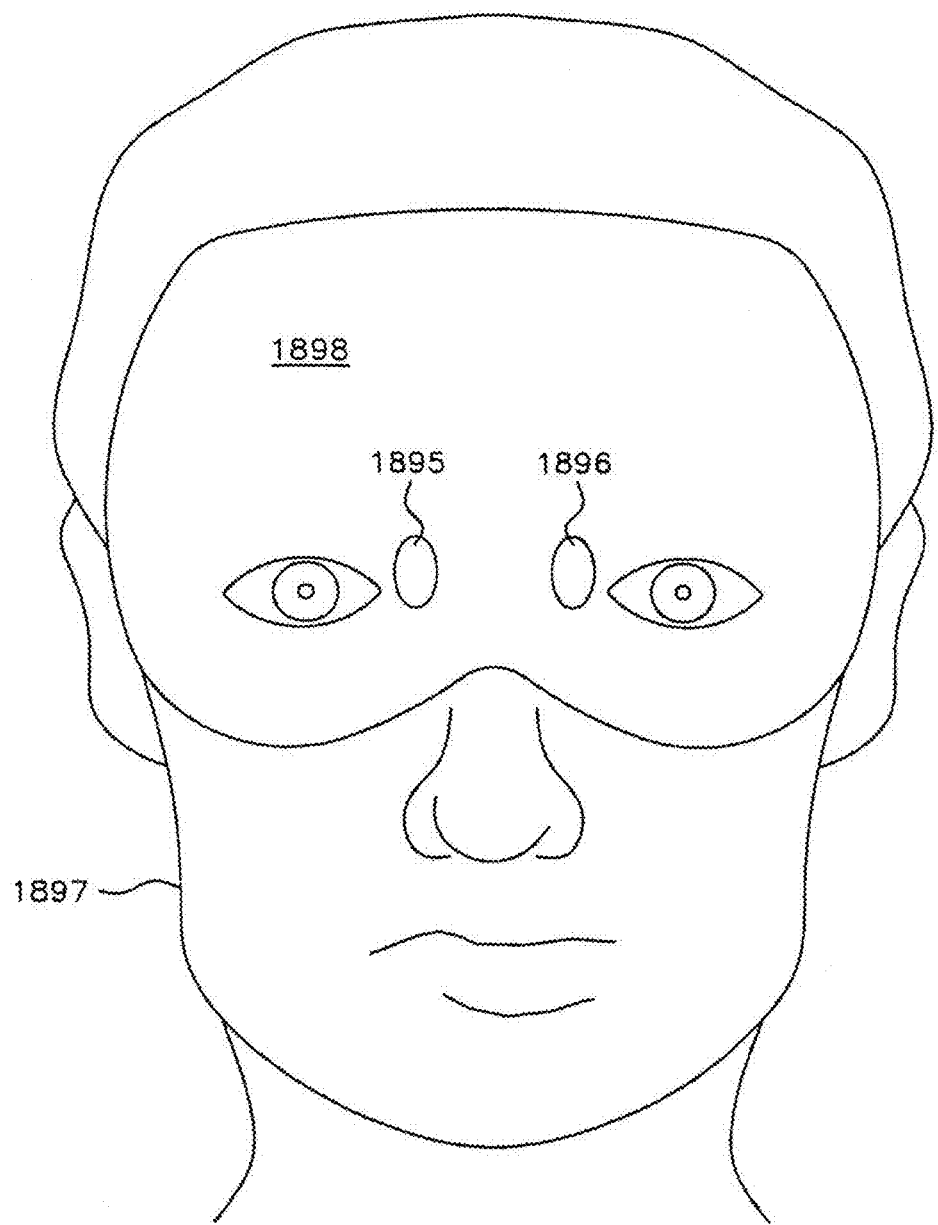
FIG. 67C shows a perspective frontal view of the BTT thermal mask of FIG. 67A on the face and on the BTT.

FIG. 67C is a schematic view of BTT thermal mask 898 with pouches 895, 896 which allow intimate apposition to the BTT area being worn by user 897.

Figure 68A:
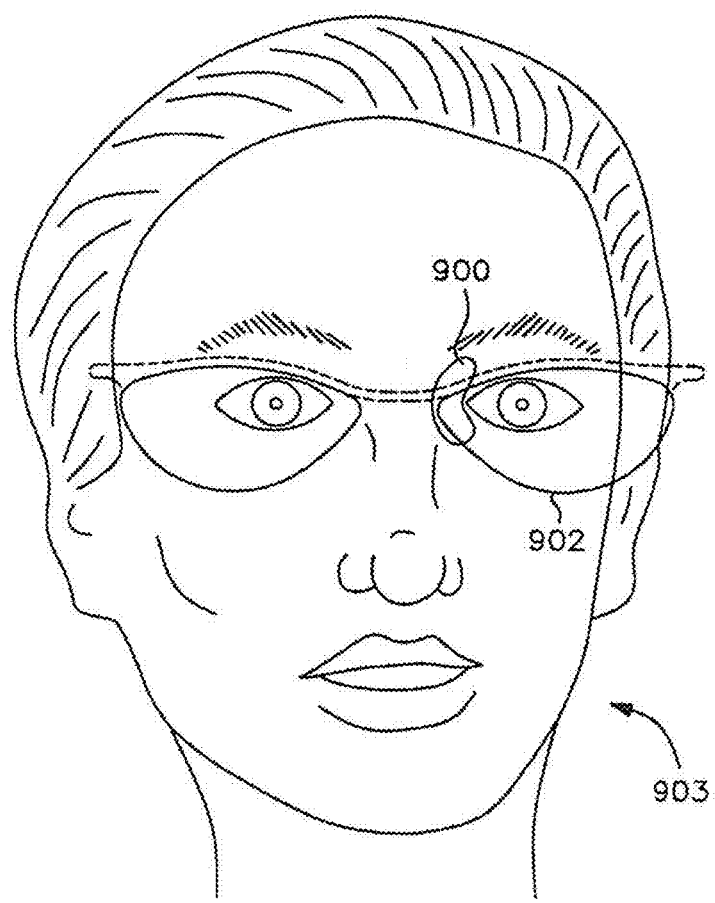
FIG. 68A shows a perspective frontal view of a BTT thermal pack supported by support structure comprised of eyewear.

FIG. 68A is a perspective view showing the BTT thermal pack 900 being applied to the BTT area by support structure comprised of eyewear 902 being worn by user 903. FIG. 68B is a perspective frontal view of a BTT hot/cold pack 930 with dual bags 932, 934 for right and left BTT and connected by an arm 936 working as a clip to secure a hot/cold pack in place on the BTT of user 938.

Figure 69A:
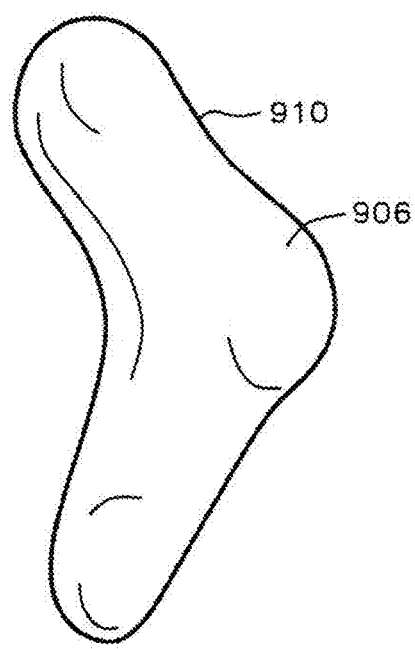
FIGS. 69A to 69C show perspective views of a preferred BTT thermal pack.
Figure 69B:
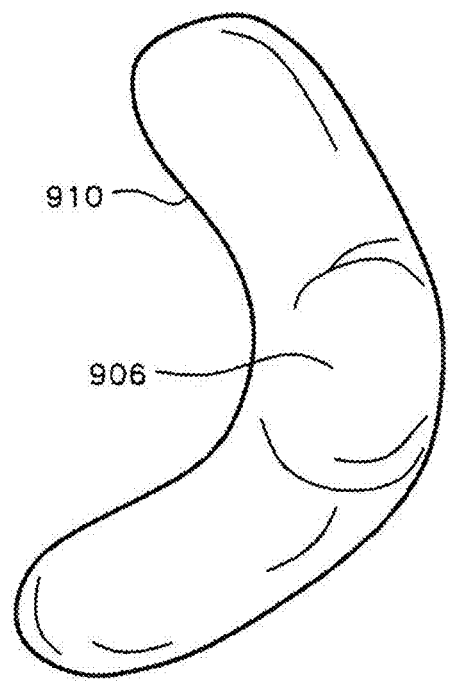
Figure 69C:
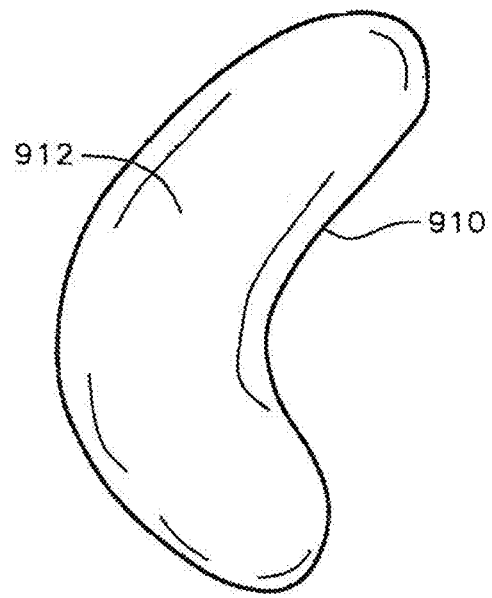
Figure 69D:
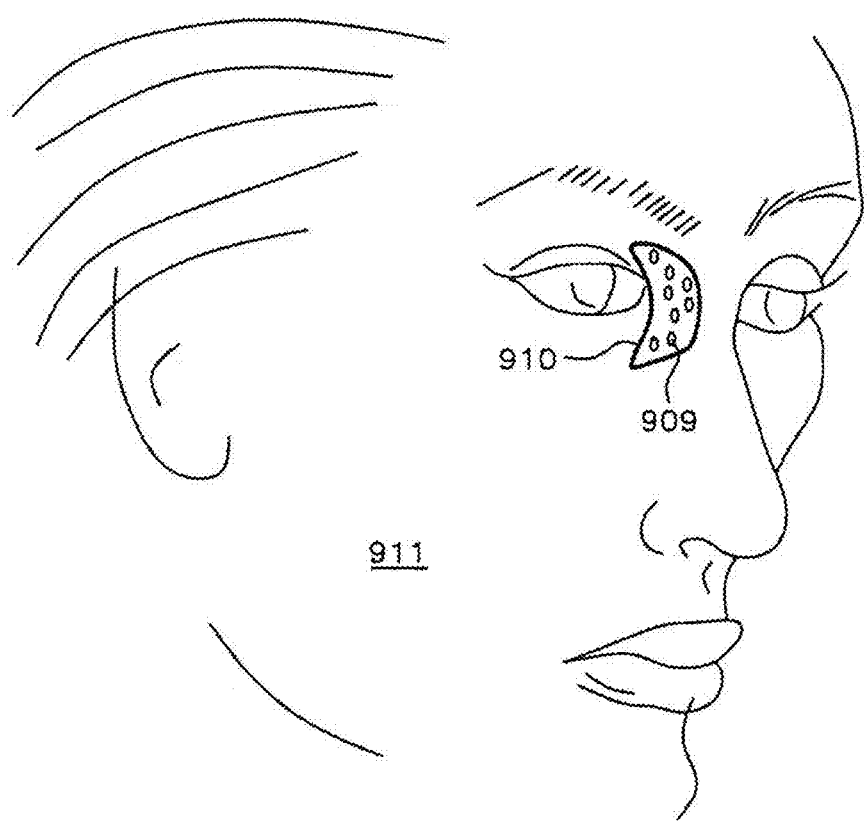
FIG. 69D is a perspective view of a BTT thermal pack of FIG. 69A positioned on the BTT.

The brain cooling or brain heating device in accordance with the principles of the invention includes hot and cold pad or pack adapted to fit and match the special geometry of the entrance of the BTT and comprising a preferably flexible and sealed pad and a gel within said pad, with the surface touching the skin having a substantially convex shape. Accordingly, FIG. 69A is a perspective side view of BTT thermal pack 910 and bulging substantially convex part 906 which rests against the skin and conforms to the anatomy of the BTT. FIG. 69B is a perspective inferior view of BTT hot/cold pack 910 and bulging substantially convex part 906 which rests against the skin and conforms to the anatomy of the BTT. FIG. 69C is a perspective planar view of BTT hot/cold pack 910 and substantially flat part 912 which faces the outside and does not touch the skin. FIG. 69D is a perspective view of hot/cold pack 910 with gel 909 being applied to the BTT area of user 911.

A tube fit to match the special geometry of the BTT site and anatomy of the region with circulating water can also be use for selectively cooling or heating the brain.

The BTT thermal pack can include a bag so as to avoid direct contact with the skin depending on the chemical compound used, such as heating agent to prevent any thermal injury to the skin.

It is understood that a combination temperature sensor and BTT cold/heat pack can be implemented and positioned in place using the support structures described herein such as eyeglasses and any head mounted gear. The nose pads of eyeglasses can have a combination of a heat flow sensor to determine how fast heat is being pulled. The gradient for instance across a thin piece of Mylar indicates the direction of heat flow. It is also understood that the right nose pad of the eyeglasses have a temperature sensor and the left side has the cooling/heating device that applies or removes heat according to the temperature measured on the opposite side.

It is also understood that many variations are evident to one of ordinary skill in the art and are within the scope of the invention. For instance, one can place a sensor on the skin at the BTT site and subsequently place an adhesive tape on top of said sensor to secure the sensor in position at the BTT site. Thus in this embodiment the sensor does not need to have an adhesive surface nor a support structure permanently connected to said sensor.

Figure 70:
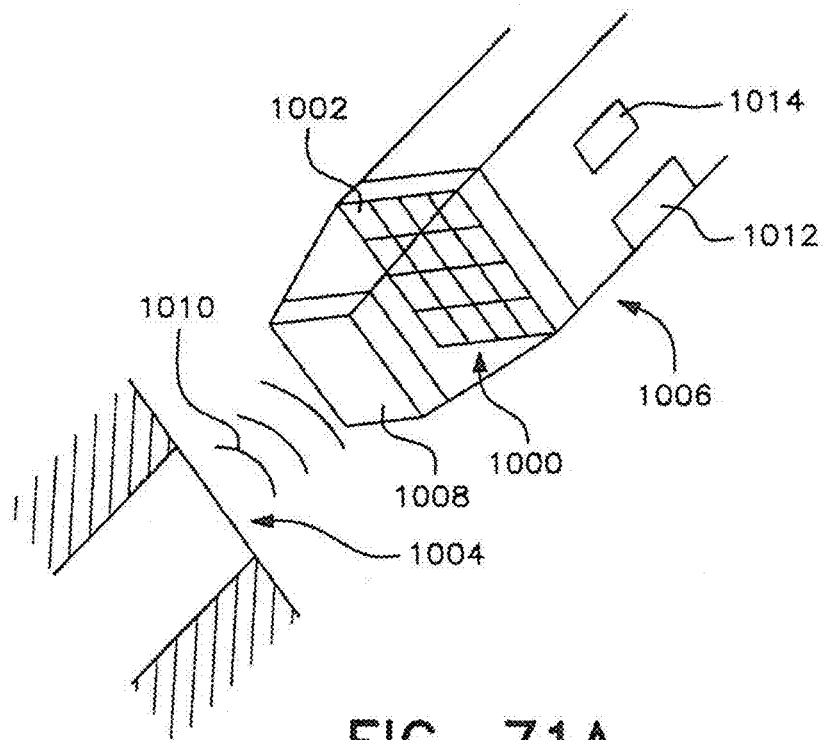
FIG. 70 is a schematic diagram showing a hand held non-contact BTT measuring device.
Figure 71A:
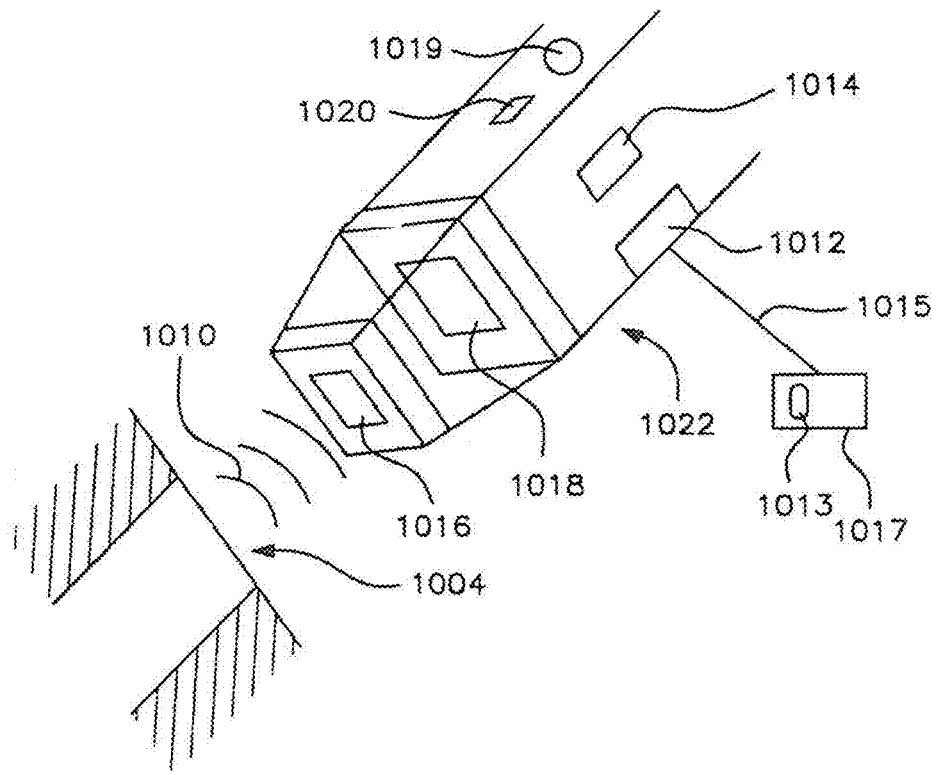
FIGS. 71A to 71C are schematic diagrams showing hand held infrared BTT measuring devices.
Figure 71B:
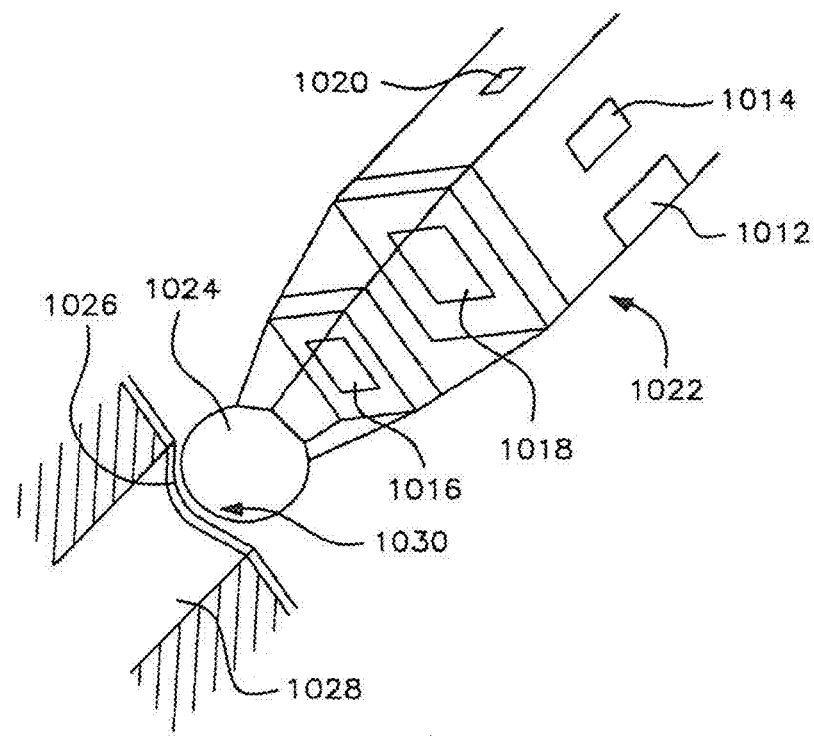

A plurality of hand held devices with non-contact or contact sensors can measure the brain temperature at the BTT for single or continuous measurement and are referred to herein as Brain Thermometers or BrainTemp devices. Accordingly, FIG. 70 shows an array 1000 of infrared sensors 1002 viewing the BTT entrance 1004 which are mounted in a housing 1006 containing a lens 1008 to focus the radiation 1010 on sensor array 1000 in a manner such as that the sensor array 1000 views only the skin at the entrance of the BTT 1004 and a microprocessor 1012 adapted to select the highest temperature value read by an infrared sensor 1002 in the array 1000 with the highest value being displayed on display 1014. Exemplary infrared sensors for the array 1000 include thermopile, thermocouples, pyroelectric sensors, and the like. Processor 1012 processes the signal and displays in display 1014 the highest temperature value measured by the sensor 1002 in the array 1000. FIG. 71A shows another embodiment comprising of a non-contact measuring system that includes a housing 1022 containing a single infrared sensor 1018 (e.g., thermopile), a lens 1016 to focus the radiation 1010 of the BTT area 1004 into the sensor 1018, a transmitter 1019, and an ambient temperature sensor 1020 used to adjust the temperature reading according to the ambient temperature, and processing 1012 and display means 1014 to process the signal and display a temperature value in addition to wire 1015 connected to an external module 1017 with said module including a processor 1013 adapted to further process the signal such as processing spectroscopic measurements, chemical measurements, and temperature measurements with said module 1017 adapted yet to display and transmit the value calculated by processor 1013 including wireless transmission and transmission over a distributed computer network such as the internet. An alternative for the pen-like systems in accordance with the invention and in accordance to FIG. 71A, as shown in FIG. 71B, includes a bulging part 1024 with a substantially convex shape at the end 1030 that touches the skin 1026 and matches the concave anatomy of the skin 1026 entrance of the BTT 1028. The bulging convex end 1024 touching the skin 1026 helps to stretch the skin 1026 and allow better emissivity of radiation in certain skin conditions, allowing the system to measure temperature in the skin of the BTT area at optimal conditions and with any type of skin.

An exemplary lens system for viewing thermal radiation coming from the BTT can include exemplarily 25 sensors for reading at 1 inch from the tip of the sensor to the skin at the BTT entrance and 100 sensor array for reading radiation coming from a distance of 3 inches between skin at the BTT and sensor tip. Preferably a five degree field of view, and most preferably a two to three degree field of view, and yet even a one degree of field view is used to see the main entry point of the BTT. The spot size (view area) of the infrared sensor is preferably between 1 and 20 mm in diameter and most preferably between 3 and 15 mm in diameter which allows the infrared sensor to receive radiation from the BTT entrance area when said sensor is aimed at the BTT entrance area which corresponds to the bright spots in FIG. 1A and the red-yellow area in FIG. 1B. It is understood that an infrared device (thermopile) can be placed at any distance and read the temperature of the BTT entrance area, as long as the sensor is positioned in a manner to view the BTT entrance area and a lens is used focus the radiation on to the temperature sensor.

Figure 73:
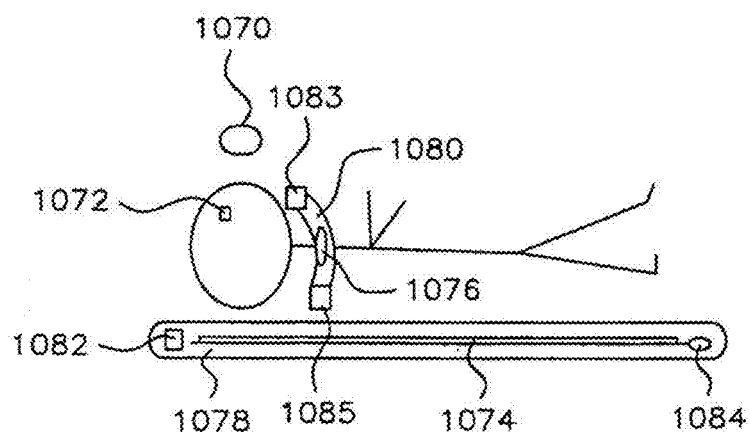
FIG. 73 is a schematic diagram showing heat transfer devices coupled to BTT measuring devices.

The array is adapted to receive the temperature of the BTT area. The temperature signal received is less than the whole face and is not the temperature of the face, nor the temperature of the forehead. The temperature signal comes from the BTT, one particular area of special geometry around the medial corner of the eye and medial aspect of the upper eyelid below the eyebrow. This said temperature signal from the BTT can be acquired by contact sensors (e.g., thermistors), non contact sensors (e.g., thermopile), and infrared thermal imaging. This said temperature signal can be fed into a processor to act upon an article of manufacturing that can remove or transfer heat as shown in FIG. 73. With said article being activated by the temperature level measured at the BTT by a hand held single measuring device, a continuous temperature measuring device, and any of the devices of the present invention. In addition, the temperature level signal can activate another device and activate a function of said device. The temperature level measured by the hand held devices can be automatically transmitted by wireless or wired transmission means to a receiver.

Figure 71C:
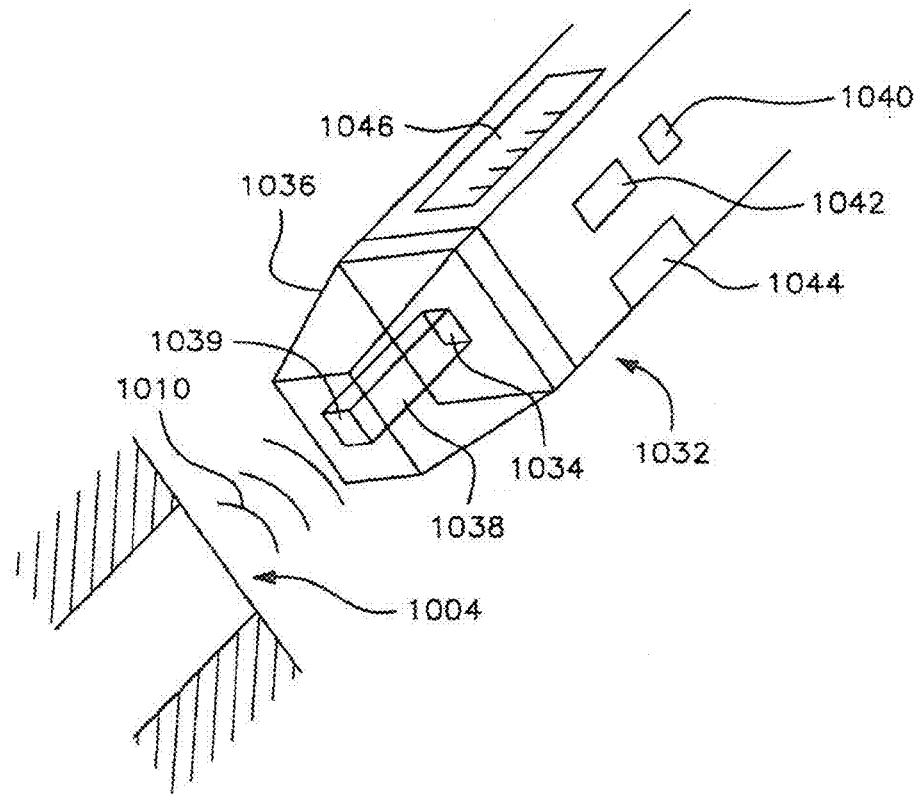

FIG. 71C shows another embodiment comprising a non-contact measuring system that includes a housing 1032 containing a single infrared sensor 1034 (e.g., thermopile), a columnar extension 1036 housing a window 1039 and cavity 1038 to focus the radiation 1010 of the BTT area 1004 into the sensor 1034 which is located about 3 cm from the window 1039 of columnar extension 1036 in addition to an amplifier 1040, processing device 1042 and display device 1044 to process the signal and display the temperature value. The columnar extension may have a widthwise dimension, either as a cylinder, rectangle, or square, of less than 3 mm, preferably less than 2.5 mm and most preferably less than 2.0 mm.

A retractable ruler 1046 is mounted in the housing 1032 and the tip of said ruler can rest on the face and used for assuring proper distance and direction of the housing in relation to the BTT for optimal view of the BTT area. It is understood that any measuring and positioning means for optimizing view of the BTT by the sensor can be used and are within the scope of the present invention. It is understood that any positioning device to establish a fixed relationship between the sensor and BTT are within the scope of the invention.

Figure 72:
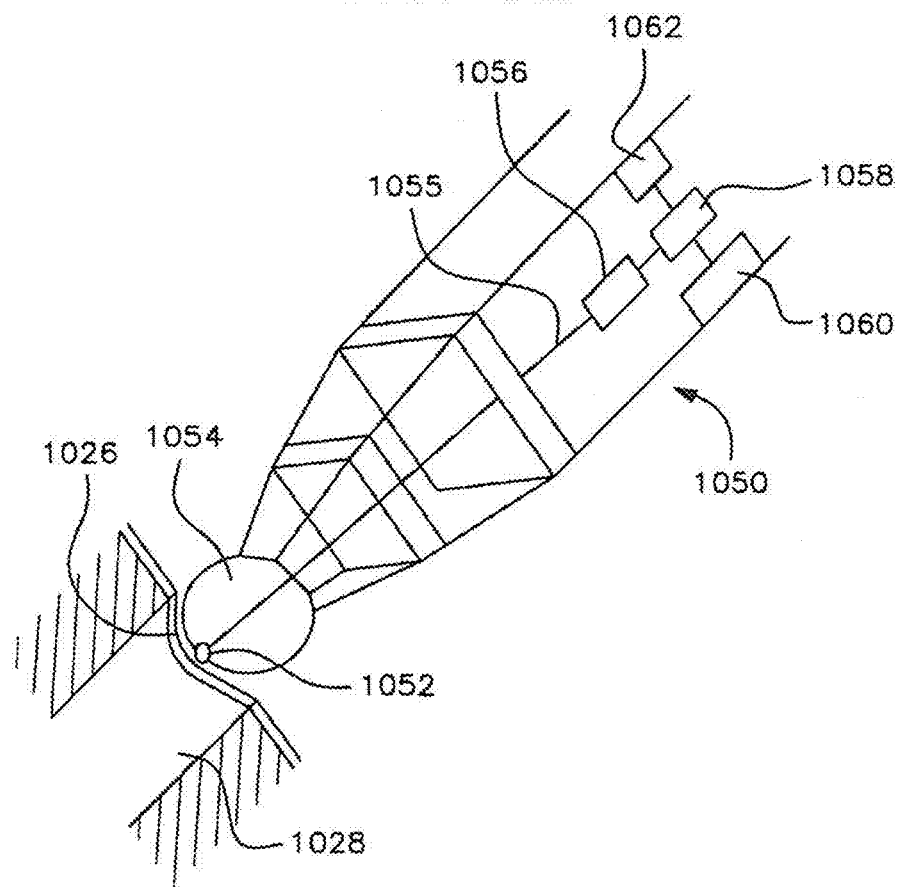
FIG. 72 is a schematic diagram showing a hand held contact sensor measuring device.

FIG. 72 is a schematic view of another embodiment preferably used as a single measurement by touching the skin at the BTT with a contact temperature sensor. Accordingly, FIG. 72 shows a pen-like housing 1050 with a sensor 1052 (e.g., thermistor) encapsulated by an insulating tip 1054 with a substantially convex external shape to conform to the BTT area and further including wire 1055 connecting sensor 1052 to processor 1056, which is in electrical connection to LCD display 1058, LED 1060, and piezoelectric device 1062. In use the sensor 1052 touches the skin at the BTT entrance area 1004 generating a voltage corresponding to the temperature, which is fed into the processor 1056 which in turn activates LED 1060 and device 1062 when the highest temperature over the time of measurement is achieved, and subsequently displays the temperature in display. The sensor 1052 and encapsulating tip 1054 can be covered by the disposable cap with a convex external surface that conforms to the convex tip 1054.

The temperature signal from sensor 1052 can be converted to an audio signal emitted by the piezoelectric device 1062 with said audio frequency proportional to the temperature level measured. In addition processor 1056 in the housing 1050 is adapted to lock in the highest frequency audio signal (which represents the highest temperature) while the user scans the BTT area. Furthermore, LED 1060 in the housing 1050 can be activated when the highest temperature level is reached, and then the value is displayed in display 1058.

It is understood that any article of manufacture that transfers heat or removes heat from the body in a direct or indirect fashion can be used in accordance with the principles of the invention. Accordingly FIG. 73 shows other exemplary embodiments including a sensing device represented by a non-contact sensing device 1070 such a thermopile housed in a hand held device or a contact sensing device 1072 such as a thermistor housed in a patch measuring temperature in the BTT area which are coupled by wires or wireless transmission means shown previously to an article of manufacture such as mattress 1078 or a collar 1080 which can alter its own temperature or the temperature in the vicinity of said articles 1078 and 1080. Exemplary embodiments include a mattress 1078 which is adapted by electrical means to change its temperature in accordance with the signal received from the temperature sensor 1070 and 1072 measuring temperature in the BTT area and an article around the neck such as a collar 1080. Articles 1078 and 1080 are provided with a serpentine tube 1074 and 1076 respectively, which run cold or hot water for removing or delivering heat to the body by mattress 1078 or to the neck and head by collar 1080, with said water system of mattress 1078 having a valve 1082 and of collar 1080 having valve 1083 which is controlled by a processor 1084 and 1085 respectively. Processor 1084 of mattress 1078 and processor 1085 of collar 1080 are adapted to open or close the valve 1082 or 1083 based on the temperature level at the BTT measured by sensor 1070 and 1072. The signal of the temperature sensor 1070 and 1072 controls the valves 1082 and 1083 that will open to allow cold fluid to fill a mattress when the signal from the sensor 1070 or 1072 indicates high body temperature (e.g., temperature equal or higher than 100.5 degrees Fahrenheit). Likewise, when the signal from the sensor 1070 or 1072 indicates low body temperature (e.g., temperature lower than 96.8 degrees Fahrenheit) the signal from said sensors 1070 and 1072 opens the valve 1082 and 1083 that allows warm fluid to fill the mattress 1078 and collar 1080. It is understood that any garment, gear, clothing, helmets, head mounted gear, eyewear, hats, and the like can function as an article of manufacture in which heat is removed or transferred to achieve thermal comfort of the wearer based on the temperature of the BTT area. It is also understood that any sensor, contact (e.g., thermistor) or non-contact (e.g., thermopile or thermal image sensing system), measuring temperature at the BTT can be used to control an article of manufacture removing or transferring heat to a body or physical matter. It is further understood that the article of manufacturing includes infusion lines capable of delivering warm or cold fluid into a vein of a patient in accordance with the temperature at the skin around the medial corner of the eye and eyelid, which corresponds to the entrance of the BTT. Other exemplary articles of manufacture include shoes, floor with heating or cooling systems, electrical draping, in-line fluid warmers, and the like.

In the embodiment in which a contact sensor touching the skin is used, the probe head can be covered with a disposable cap, such as a piece of polymer preferably with good thermal conductivity, with the shape of the disposable cap to match the shape of the various probes in accordance with the principles and disclosure of the present invention.

Figure 74:
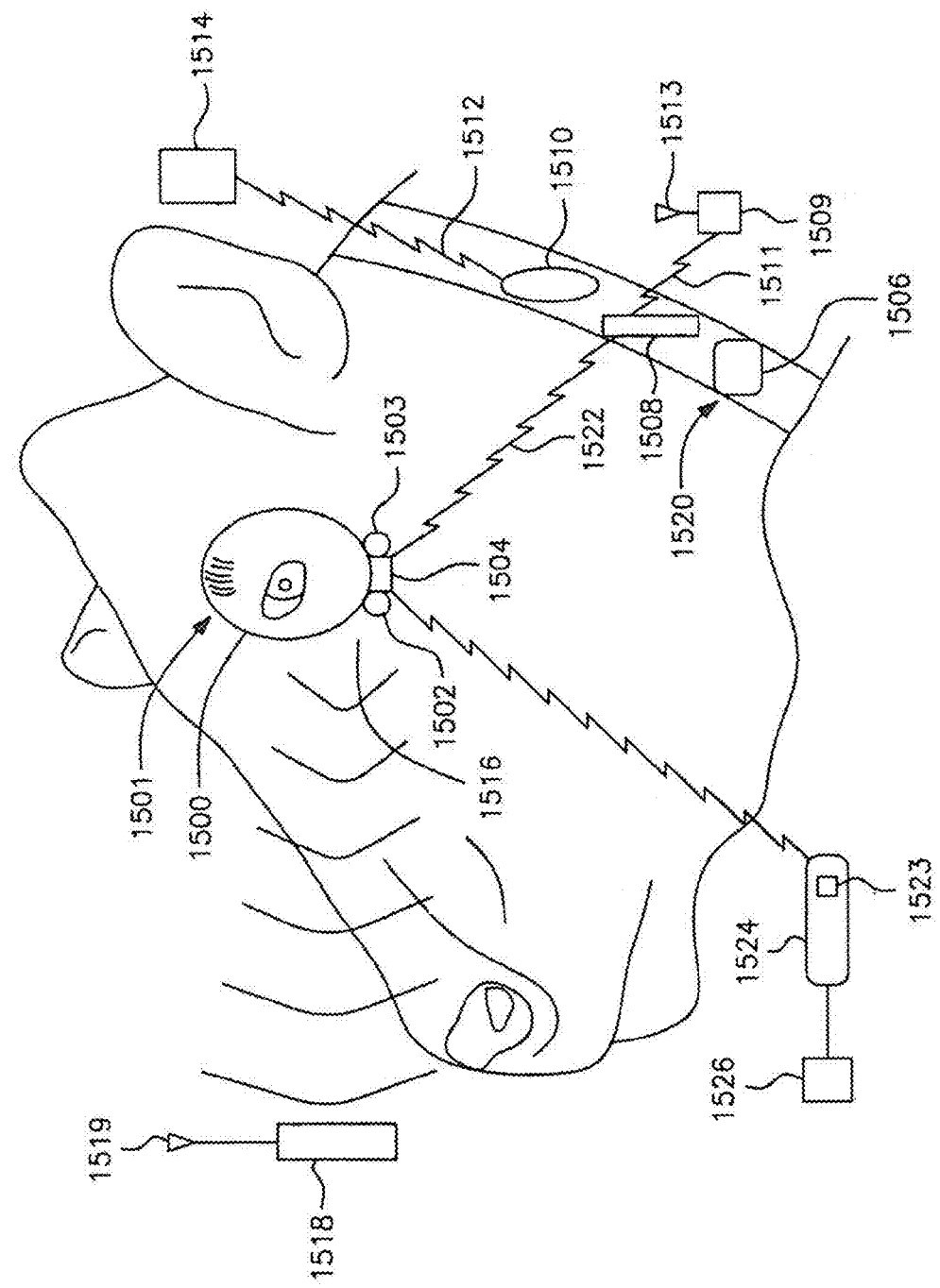
FIG. 74 is a perspective diagram showing preferred BTT measuring devices for animals.

In addition to measuring, storing, and transmitting biological parameters, the various apparatus of the present invention such as patches, eyewear, rings, contact lens, and the like include an identification and historical record acquisition and storage device for storing the user's identification and historical data preferably using a programmable rewritable electronic module in which data can be changed, added, or deleted from the module. The identification and historical data alone or in conjunction with the biological data (such as brain temperature and chemical measurements as glucose level and presence of antibodies) are transmitted preferably by wireless transmission to a monitoring station. Accordingly FIG. 74 shows a schematic view of the apparatus and system for biological monitoring, identification, and historical data used by an animal. It is understood that the system disclosed is applicable to humans as well as animals.

FIG. 74 is the schematic of a preferred embodiment for four legged creatures showing an exemplary comprehensive system that includes: an eye ring transmitter device 1501 with said eye loop or eye ring 1501 preferably including antenna 1500, sensor 1502, microprocessing, transmitting and memory module 1504, and power source 1503 with said ring placed on the eye preferably in the periphery of the eye in the eyelid pocket 1516; a collar 1520 with said collar 1520 preferably containing power source 1506, microprocessing, transmitting, and memory module 1508, and GPS transmission system 1510 coupled by wireless waves 1512 to orbiting satellites 1514 and module 1508 in bidirectional communication by wireless waves 1522 to module 1504 of ring 1501 to power ring 1501 and collect data from ring 1501 with said module 1508 in communication by radio waves 1511 to external radio receiving station 1509 and receiving antenna 1513; an externally placed receiver 1518 and antenna 1519 which receives the signal from module 1504 of ring 1501; and an external antenna 1524 located for instance in a feed lot connected to computer 1526 with said antenna 1524 in bidirectional communication with module 1504 of ring 1501.

Each eye ring 1501 has a unique serial number permanently or temporarily embedded to identify the animal remotely. A 24 hour temperature log is sent at each transmission, most preferably 6-12 times per day. A unique one-way statistical broadcast network architecture allows all members of the herd to share one frequency and one set of data receivers. The receiver is designed to receive temperature telemetry data from a network of livestock eye ring telemetry units and forward it to a collection computer for storage, display, and monitoring.

Although various communication and power systems are shown in FIG. 74, it is understood that the system can work with only one apparatus, for instance ring 1501 sending a signal to receiver 1518 and antenna 1519 for further processing and display, or preferably ring 1501 transmitting data to module 1508 of collar 1520 which working as a booster radio transmitter transmits the signal to antenna 1513 and remote station 1509 for processing, monitoring, and displaying the data.

It is understood that besides an active system with a battery working as the power source, a passive system in which the ring 1501 is powered by an external source such as electromagnetic induction provided by collar 1520 or antenna 1524 can be used. It is further understood that a hybrid system that includes both a power source comprised of battery 1503 and a passive system in module 1504 can be used in which module 1504 contains an antenna for receiving electromagnetic energy from module 1508 of collar 1520. In this embodiment the active part of the system using the memory in module 1504 powered by battery 1503 collects data from a sensor 1502 (e.g., thermistor) and stores the data in a memory chip in module 1504. The passive system containing antenna in module 1504 can be also activated when the four legged creature passes by a coupling antenna 1524, such as for instance an antenna placed in feed lots. After there is a coupling between the passive system 1504 in the ring 1501 and the external antenna 1524 in the feedlot, the data stored in the memory chip of module 1504 of the ring 1501 is received by the external antenna 1524 and transferred to a second memory chip 1523 that is part of the module external antenna 1524. The processor of module 1504 in the ring 1501 is adapted to transfer the stored data any time that there is a coupling with the external antenna 1524. A variety of inductive coupling schemes previously mentioned can be used for powering and collecting data from eye ring 1501 by antenna 1523 and 1509.

The data from a plurality of mammals (e.g., cattle) is transmitted to a receiving system. Preferably only one animal transmits at a specific time (equivalent to having only one animal in the system) to avoid data collisions in the form of interference that prevents successful wireless transmission of the biological parameters. Two exemplary schemes can be used, polling and broadcast. The polling approach requires each animal to be equipped with a receiver which receives an individual serial number request for data from a central location and triggers that animal's transmitter to send the data log. The other approach is a broadcast system, whereby each animal independently broadcasts its data log. The problem is to avoid collisions, that is, more than one animal transmitting at a time, which could prevent successful data transfer. Each animal transmitter will preferably transmit at a certain time and the receiver is adapted to receive the signal from each animal at a time.

The ring 1501 can yet include a solar battery arranged to capture sun light, digital transmission 16 bit ID# to identify the animal and track the animal throughout life. Preferred dimensions for outer diameter of ring 1501 for use in livestock are between 40 and 45 mm, preferably between 35 and 40 mm, and most preferably between 30 and 35 mm or less than 30 mm. For large animals such as an elephant, such as to detect moment of ovulation for artificial insemination and birth in captivity, the preferred outer diameter is between 90 and 100 mm, preferably between 75 and 90 mm, and most preferably between 50 and 75 mm or less than 50 mm. Preferred largest dimension of ring including circuit board and battery for livestock is between 15 and 20 mm, preferably between 10 and 15 mm, and most preferably less than 10 mm, and for large animals a factor of 10 to 15 mm is added to achieve optimal dimensions. The preferred height of the ring 1501 for livestock is between 9 and 12 mm, preferably 6 and 9 mm, and most preferably less than 5 mm, and for large animals a factor of 5 mm is added to achieve optimal dimensions. The preferred embodiment includes hardware disposed in one quadrant of the ring which contains the sensor and is located in the inferior eyelid pocket.

An alarm is activated when certain pre-set temperature limits are reached. The system of the invention can also be used with temperature being transmitted in real time for detecting the moment of heat in animals, which starts when the body temperature of the animal starts to rise. The method includes detection of heat, and then inseminating the animals preferably between 6 to 12 hours after initial detection of heat, and most preferably between 4 and 8 hours after heat detection.

Figure 75B:
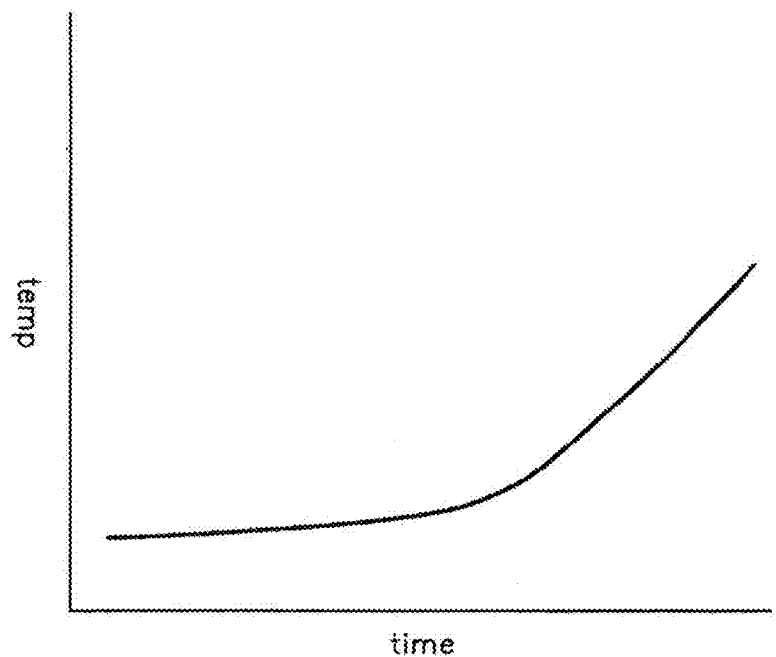
Figure 75C:
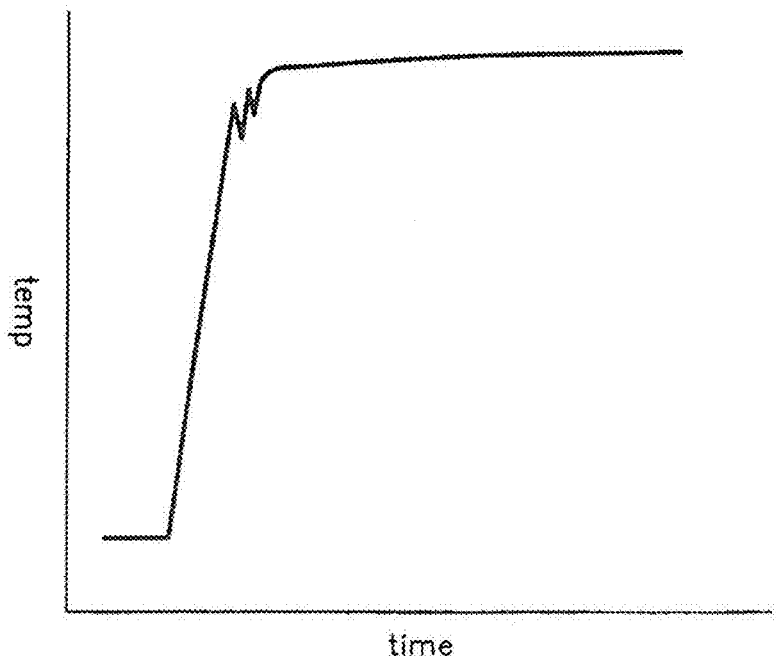
Figure 75D:
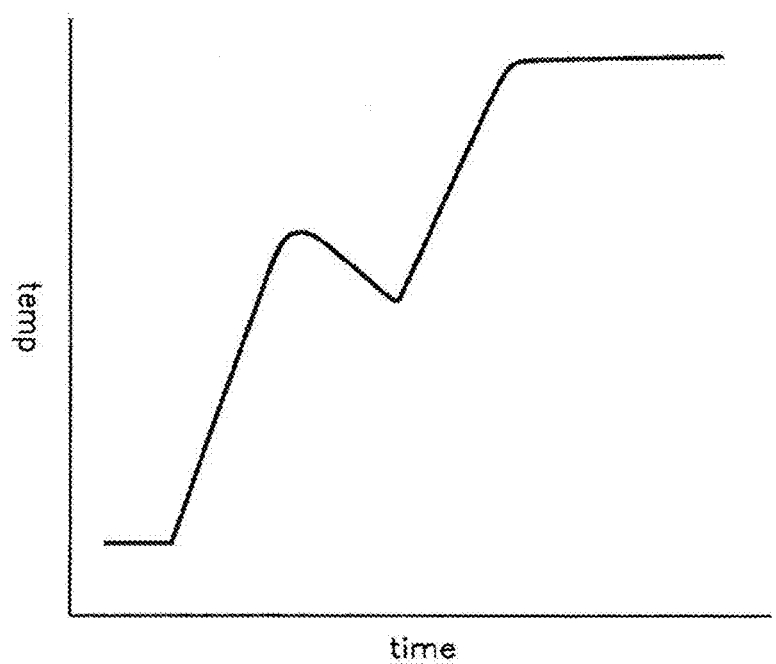
Figure 75E:
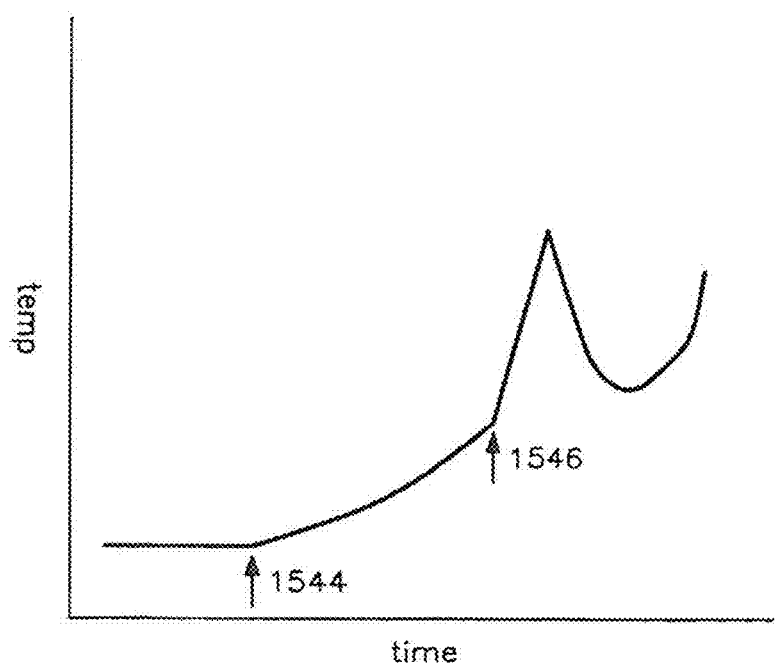

Preferably the temperature data stored over time (e.g., 24 hours) by module 1504 or 1508 is then downloaded to a computer system such as computer 1526 adapted to identify thermal signatures. Thermal signatures are representations of the temperature changes occurring over time and that reflect a particular biological condition. Exemplary thermal signatures are depicted in FIGS. 75A to 75E. FIG. 75A is a representation of a viral infection in which there is a relatively rapid increase in temperature, in this example there is a high temperature which corresponds to a pox virus infection such as foot and mouth disease. On the other hand a slow increase in temperature over 6 to 8 hours can indicate a thermal signature for hyperthermia due to hot weather, as shown in FIG. 75B. FIG. 75C shows a rapid increase in temperature reflecting bacterial infection, with spikes followed by sustained high temperature. FIG. 75D shows a thermal signature reflecting mastitis with a double hump in which there is an initial increase in temperature followed by a higher increase after the first episode. FIG. 75E shows a thermal signature indicating heat (arrow 1544) of animals, in which there is a gradual but progressive increase of the basal temperature. About 8 to 12 hours from beginning of heat there is a further increase in temperature indicating the moment of ovulation (arrow 1546), with a further sustained increase in temperature in the post-ovulation period. It is understood that a digital library of thermal signatures can be stored and used to identify the type of biological condition present based on the signal received from the ring or any other sensor measuring temperature at the BTT, for both humans and animals. The thermal signature acquired by the temperature measuring system is matched by a processing system to a thermal signature stored in the memory of a computer and associated software for matching and recognition of said thermal signatures. It is understood that the thermal signatures system of the present invention includes any temperature measuring system for both animals or humans in which a temperature disturbance is present, low or high temperature.

Figure 76A:
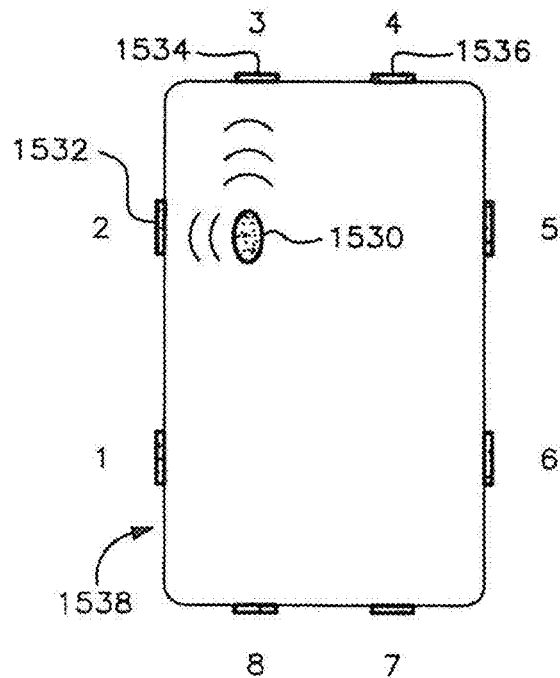
FIGS. 76A and 76B are schematic diagrams showing an antenna arrangement.
Figure 76B:
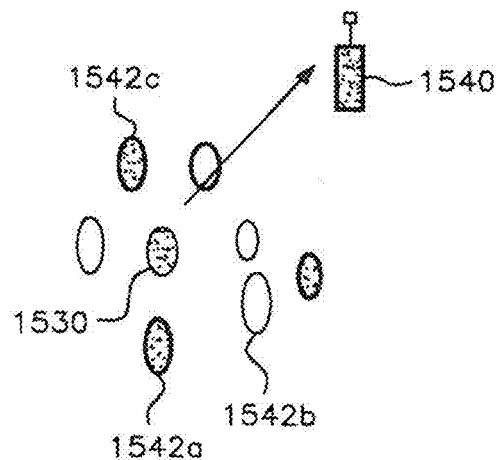

A plurality of antenna reception scheme can be used. FIG. 76A shows an exemplary antenna schemes arrangement 1538 including 8 antennas numbered 1 to 8 in a pen which can be used to cover a herd of 1000 to 2000 animals. At a particular time T1 animal 1530 transmits the data which is captured by the closest antenna, for instance antenna 1532. For animal use and to preserve power the data can be stored for 24 hours and when the animal goes by one of the antennas at time T1 the data is downloaded. When there is fever or a change in biological parameter the transmitting ring transmits the data continuously. Otherwise the ring only transmits data once a day. The antenna scheme also can be used as a locator of the animal. The pen and antenna scheme is plotted in a computer screen and depicted on the screen, and by identifying the antennas receiving the signal the animal can be located with the location highlighted in the computer screen. In FIG. 76A antennas 1534 and 1532 are receiving the signal whereas antenna 1536 is not receiving the signal since antenna 1536 is distant from the animal. Therefore animal 1530 is located in the area covered by antenna 1532 and 1534. FIG. 76B shows the precise location using a radio receiver direction finder, in which a radio receiver 1540 is carried by a farmer or located in the vicinity of the area covered by antennas 1532 and 1534 which contains animal with fever 1530 as well as healthy animals 1542a, 1542b, 1542c. Since animal 1530 is the only one emitting signal continuously, radio receiver 1540 can precisely identify sick animal 1530 among healthy animals. The ID of animal 1530 is transmitted in conjunction with the biological data for further identification of animal 1530. Alternatively, a farmer uses an electromagnetic hand held external power switch next to the animal to activate the circuit in the eye ring 1501 in order to manually initiate transmission of data to a receiver for further processing. Any lost animal could also be located with the present invention and an animal which ran from the pen could be identified as not emitting a signal within the pen.

Although a multiple antenna scheme is shown in FIG. 76A, the preferred embodiment includes an antenna 1513 or alternatively antenna 1519, and a weatherproof metal cased receiver unit with radio receiver module, computer interface, and power source such as receiver 1509 or alternatively receiver 1518.

When using a rewritable or programmable identification serial number, the eye ring 1501 can be reused and a new serial identification number programmed and written for said eye loop or eye ring 1501.

Although a ring in the eyelid pocket is shown, it is understood that another method and device includes a temperature signal coming from the BTT of cattle external to the eye which is located in the anterior corner of the eye (corner of the eye in animals is located in the most frontal part of the eye) with said signal being captured by contact or non contact temperature sensors as well as thermal imaging.

The signal from eye ring 1501 can preferably automatically activate another device. By way of illustration, a sprinkler system can be adapted to be activated by a radio signal from eye ring 1501 with said sprinkler system spraying cold water and cooling off the animal when a high body temperature signal is transmitted by eye ring 1501.

A variety of diseases can be monitored and detected by the apparatus of the invention. By way of illustration, a characteristic increase in brain temperature can detect foot-and-mouth disease, babesiosis, botulism, rabies, brucellosis, and any other disorder characterized by changes in temperature as well as detection of disorders by chemical and physical evaluation such as detection of prions in the eyelid or eye surface of an infected animal using antibodies against such prions and creating an identifiable label such as fluorescence or by generating a mechanical or electrical signal at the time of antigen-antibody interaction. Prions can cause bovine spongiform encephalopathy known also as "mad cow" disease and such prions can be present in the eye and can be detected by using an immobilized antibody contained in the eye ring against such prion or a product of such prion. By detecting mastitis (or an animal with fever) which is scheduled for milking, the present invention provides a method to prevent contaminating other animals being milked by generating a sequence for milking in which the animal with fever is milked last. This will avoid contaminating equipment with a sick animal and with said equipment being sequentially used in other healthy animals.

The present invention provides continuous monitoring of animals 24 hours a day from birth to slaughter with automatic analysis and detection of any disease that can cause a threat to human health or animal health, besides identification and location of the sick animal. Therefore with the present invention an animal with disease would not reach the consumer's table. The present invention therefore includes a method to increase food safety and to increase the value of the meat being consumed. The system of continuous disease monitoring is called DM24/7 (disease monitoring 24/7) and includes monitoring the biological variable 24 hours seven days a week from birth to slaughter, feeding the information into a computer system and recording that information. Any meat coming from an animal monitored with DM24/7 receives a seal called "Monitored Meat". This seal implies that the animal was monitored throughout life for the presence of infectious diseases. Any user buying "Monitored Meat" can log on the internet, and after entering the number (ID) of the meat which can be found in the package of the meat being purchased. Said user can have access to the thermal life and biological monitoring of the animal and for the presence of fever or disease of the animal which the meat was derived from. The method and device includes a video stream associated with the ID of the animal with said video or pictures showing the farm and information on the farm where the animal came from or the meat pack facility where the animal was processed, providing therefore a complete set of information about the animal and conditions in which such animal was raised. Besides viewing over the internet, at a private location such as at home, the system may also provide information at the point of sale. Accordingly, whenever the user purchases the product and a bar code for the product for instance is scanned, a video or photos of the farm or the company packing the meat appear on a screen at the point of sale. This method can be used when purchasing any other product and preferably allows the consumer to use idle time in the cashier's station to become more familiar with the product purchased.

Preferably the ring has a temperature sensor covered by insulating material (eg. polyurethane) in one end and with an exposed surface at the other end. The preferred measuring method uses the measuring surface facing the outer part of the anatomy of the eye pocket and the insulating part facing the inner part of the eyelid pocket.

The eye ring contains memory means for storing on a permanent or temporary basis a unique identification number that identifies the animal being monitored. The ID code in the processor of the ring is transmitted to a receiver as an individual number only for identification and tracking purposes or associated with a temperature value or other biological variable value. The memory chip in the ring can also contain the life history of the animal and historical data including weight, vaccines, birth date, birth location, gender, diseases, genetic make up, and the like.

Range of the entrance of BTT area is about 30 square cm and the general main entry point is 25 square cm and encompasses the medial corner of the eye and the area of the eyelid adjacent to the eyelid margin. The correlation coefficient between temperature at the BTT area and the core temperature reflecting the thermal status of the brain is 0.9.

Instead of using the whole face, the method for infrared or thermal imaging sensing as well as contact sensor includes a temperature signal which comes specifically from the BTT area, and the hottest spot in BTT area is then located and used as a source signal to activate another device or to deploy an action.

It is understood that an infrared thermal imaging camera can also be used and the point source emitting the highest amount of radiation from the entrance of the BTT is selected by the processor in the camera and the temperature level corresponding to the point source with highest thermal energy is displayed in the display. Exemplary infrared cameras include the BTT Thermoscan of the present invention.

The BTT Thermoscan of the present invention is adapted to view the entrance of the BTT around the medial corner of the eye, with the view of the sensor, by way of a lens, matching the entrance of the BTT area displayed in FIGS. 1A and 1B, and in FIGS. 3A to 9. Exemplary operational flow for measuring the temperature at the BTT with a thermal imaging system includes the first step of viewing the entrance of the BTT by radiation detector in the camera and a processor adapted to, after the first step, to search for the point source in the thermal image of the BTT with the highest emission of thermal radiation. In the following step the temperature of the point source in the thermal image of the BTT with the highest amount of radiation is calculated, with said calculated temperature value preferably displayed. In the next step, the calculated temperature value is transmitted by wire or wireless means to an article of manufacture that can remove heat or transfer heat to the body in a direct or indirect manner. In the following step, the temperature of the article of manufacture is adjusted in accordance with the signal received. Exemplary articles of manufacture that transfer or remove heat from the body in an indirect manner includes the air conditioner/heater systems of vehicles. Exemplary articles of manufacture that transfer or removes heat from the body in a direct manner includes vehicle seats. The measuring system in accordance with the present invention is adapted to seek for the hottest area around the corner of the eye and eyelid. Once the hottest spot around the medial corner of the eye and eyelid is found, a second step includes finding the hottest spot in the area identified in the first step, which means to find the hottest spot on the entrance of the BTT as shown in FIGS. 1A and 1B.

Figure 77A:
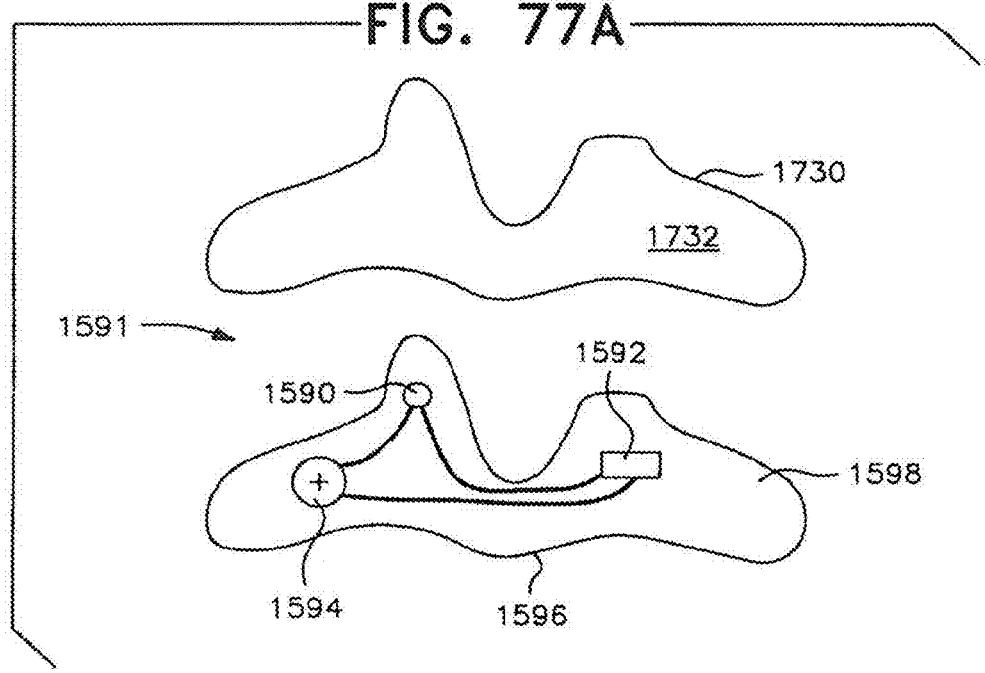
FIGS. 77A to 77C are schematic diagrams showing a support structure comprised of hook and loop fastener.
Figure 77B:
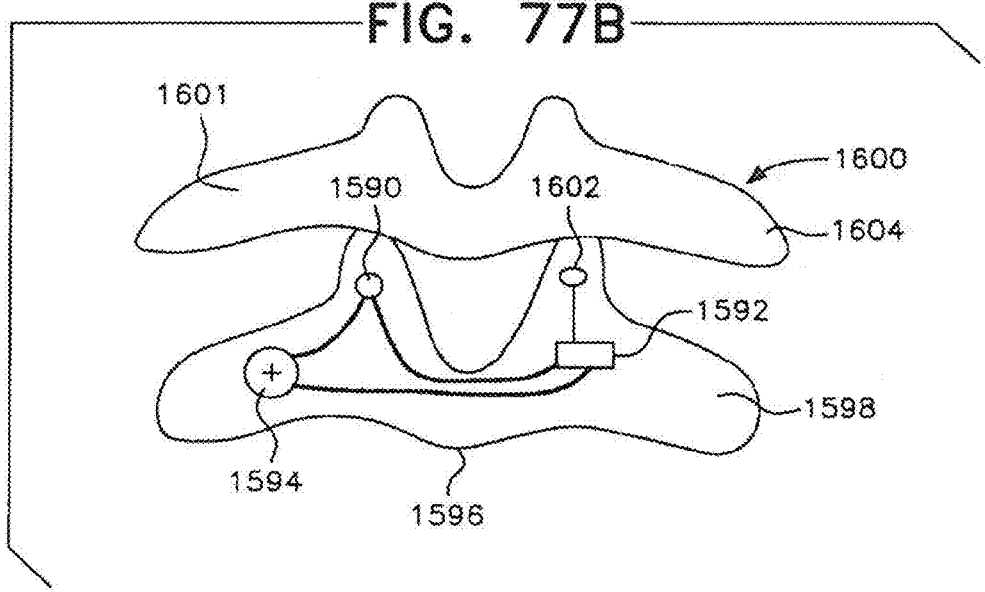
Figure 77C:
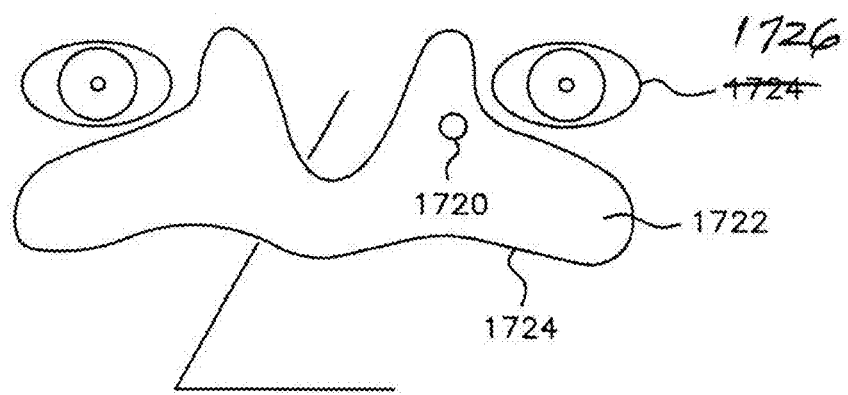

Now in accordance with another preferred embodiment of the present invention shown in FIG. 77A to 77C, an apparatus comprised of a patch for use in biological monitoring according to the invention comprises two parts: a durable part containing the sensor, electronics, and power source and a disposable part void of any hardware with said two parts durable and disposable being detachably coupled to each other preferably by a hook and loop fastener material (commercially available under the trade name VELCRO). Accordingly FIG. 77A is a schematic view showing a patch composed of two parts connected to each other by a hook and loop arrangement herein referred as VELCRO Patch with said VELCRO Patch 1591 including a disposable piece 1730 and durable piece 1596 with said durable piece 1596 housing and electrically connecting sensor 1590, power source 1594, and transmitter and processor module 1592 with VELCRO surface 1598 of durable piece 1596 detachably coupled to VELCRO surface of disposable piece 1730 and the external surface of said disposable piece 1730 covered by a liner 1732 which when peeled off exposes an adhesive surface which is applied to the skin. When in use the two parts 1730 and 1596 are connected and held in place by the hook and loop material, and liner 1732 is removed to expose the adhesive covering the external surface of disposable piece 1730 with said adhesive surface being applied to the skin in order to secure said VELCRO Patch 1591 to said skin with sensor 1590 resting adjacent to the entrance of the BTT to produce a signal representing by way of illustration the brain temperature. Although VELCRO hook and loop fastener was described as a preferred attachment between disposable and durable parts, it is understood that any other attachment device such as a disposable piece attached to a durable piece by means of glue, pins, and the like can be used or any other conventional fastening device.

FIG. 77B shows the two parts of a VELCRO Patch comprised of a disposable part 1600 which contains only VELCRO material and a durable part 1596 which contains sensor 1590, power source 1594, module 1592 which includes a transmitter, processor, piezoelectric piece, buzzer, and speaker, transmitter and processor module 1592, and LED 1602 electrically connected by wires contained in the VELCRO material with VELCRO surface 1598 of durable piece 1596 detachably coupled to VELCRO surface 1601 of disposable piece 1600 and the external surface of said disposable piece 1600 covered by a liner 1604 located on the opposite side of loop surface 1601 of disposable piece 1600 which when peeled off exposes an adhesive surface which is applied to the skin. Since the hardware housed in the durable part 1596 is relatively expensive said durable part 1596 with hardware is reusable while the disposable part 1600 can be made relatively inexpensively since it only comprises VELCRO loops and since said part is the part in contact with the skin said part 1600 may be disposed of after contacting the skin or when it is contaminated by body fluids. It is understood that the durable part can include a flexible plastic housing containing hardware and a disposable part comprised of a double coated adhesive tape. It is within the scope of the present invention to include a support structure such as a patch comprised of two parts in which a disposable part is in contact with the skin and a durable part housing hardware and electrical circuitry is not in contact with the skin. It is yet within the scope of the invention to include a support structure comprised of hook and loop material such as VELCRO comprised of two parts one disposable and durable part in which the disposable part is in contact with the skin and the durable part containing pieces in addition to the VELCRO material is durable and does not contact the skin. By way of illustration, but not by limitation, the durable part of the VELCRO can contain a spring load rod plate such as found in airway dilators (trade name BreatheRight for humans and Flair for animals) and the disposable part contains a release liner and adhesive surface which goes in contact with the skin of a human or animal. Another illustration includes a durable part housing a container with fluid or chemicals to be applied to the skin and disposable part which goes in contact with the skin by means of an adhesive surface or mechanical fasteners such as elastic bands. Yet another illustration includes a watch attached to a VELCRO material working as the durable part which contains, for instance, a sensing part for measuring glucose and a disposable part. Preferably the VELCRO part containing the hooks work as the durable part and houses pieces other than the VELCRO material while the Velcro part containing the loops work as the disposable part which preferably is in contact with the body part such as the skin.

When applied to the skin the VELCRO Patch works as one piece with durable and disposable parts connected by the hook and loop material and no hardware is visible on the surface of the durable part with the exception of a reporting device such as a LED to alert the user when the biological parameters are out of range. Accordingly FIG. 77C is a schematic view showing the VELCRO Patch of FIG. 77B, with said VELCRO Patch 1724 applied to the skin around the eyes 1726 and with an external surface of durable part 1722 containing LED 1720 which is activated by processor and driver module (not shown) housed in the durable part 1722 of VELCRO Patch 1724.

Figure 78:
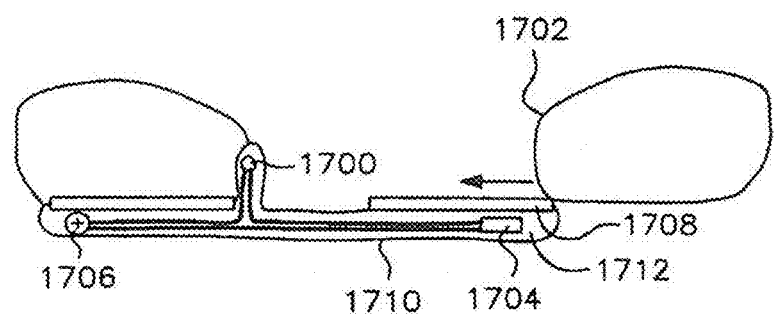
FIG. 78 is a schematic diagram showing a support structure comprised of hook and loop fastener with attached lenses.

VELCRO Patch of the present invention can further include attachment structure for attaching lenses to said VELCRO Patch, herein referred as VELCRO Eyewear. Accordingly FIG. 78 is a schematic view of VELCRO Eyewear 1710 comprised of the durable part 1712 which houses sensor 1700, power source 1706 and transmitter-processor module 1704 in addition to groove 1708 adapted to receive lens 1702 which can slide in and be secured at groove 1708. The groove mechanism of the invention allows for any type of lens to be used and replaced as needed. However it is understood that a permanent attachment of the lens 1702 to the VELCRO durable part 1712 can be used. It is also understood that the VELCRO material can be made in a way to conform to the anatomy of the face and that a variety of fastening devices previously described for attaching the lens can be used. The VELCRO Eyewear can yet have temples attached to its side for further securing to the face of the user. It is also understood that any sensor can be used including temperature, pressure, piezoelectric sensors for detecting pulse of a blood vessel, glucose sensor, and the like.

Figure 79A:
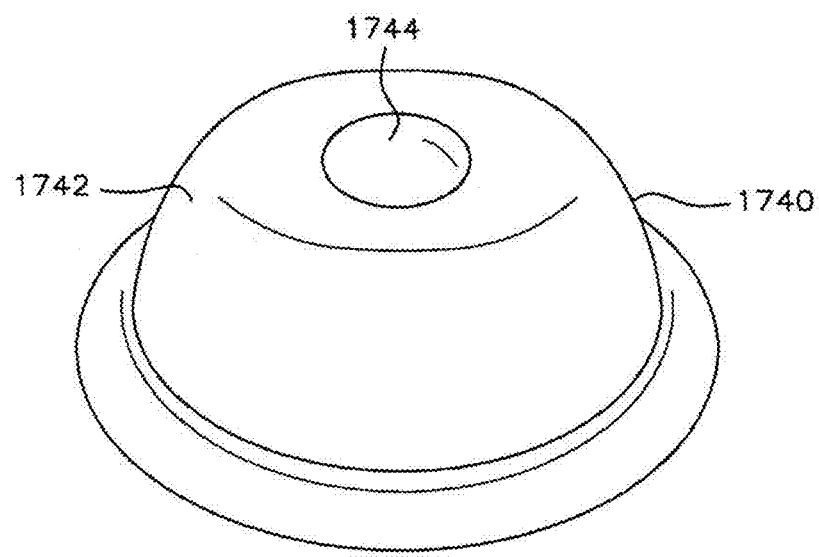
FIGS. 79A and 79B are perspective images of alternative support structures.
Figure 79B:
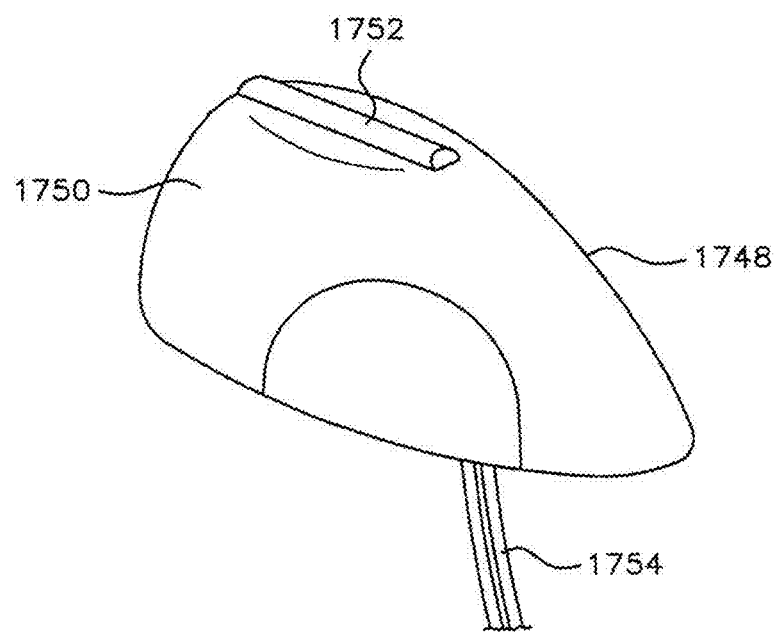

FIG. 79A is a perspective view showing another exemplary embodiment of a support structure 1740 comprised of a bowl-like structure with a substantially external convex surface 1742 to conform to the anatomy of the BTT entrance with said support structure 1740 housing sensor 1744 and electrical connection. FIG. 79B shows another embodiment of a support structure 1748 with a substantially convex outer surface 1750 to conform to the anatomy of the BTT with structure 1748 being also substantially elongated to match the geometry of the BTT entrance and further housing sensor 1752 and electrical connection 1754.

Figure 80:
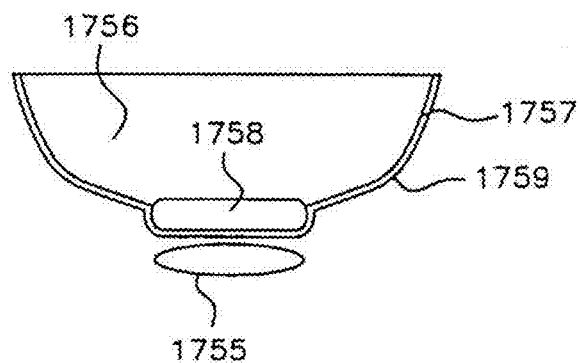
FIG. 80 is a schematic diagram showing a support structure of FIG. 79A.

FIG. 80 is a cross sectional diagram of a bowl shown in FIG. 79A including a holder 1756 in the shape of a bowl with an external convex surface 1757 and a sensor 1758 protruding through the surface of the bowl holder 1756 with said sensor being in close apposition to the skin 1759 at the BTT and its terminal blood vessel 1755.

Figure 81A:
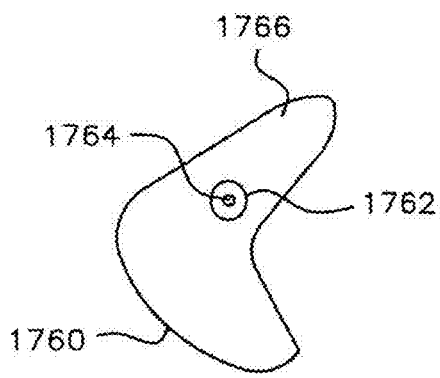
FIGS. 81A and 81D are schematic diagrams of a preferred support structure.
Figure 81B:
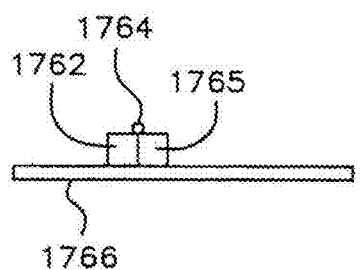
Figure 81C:
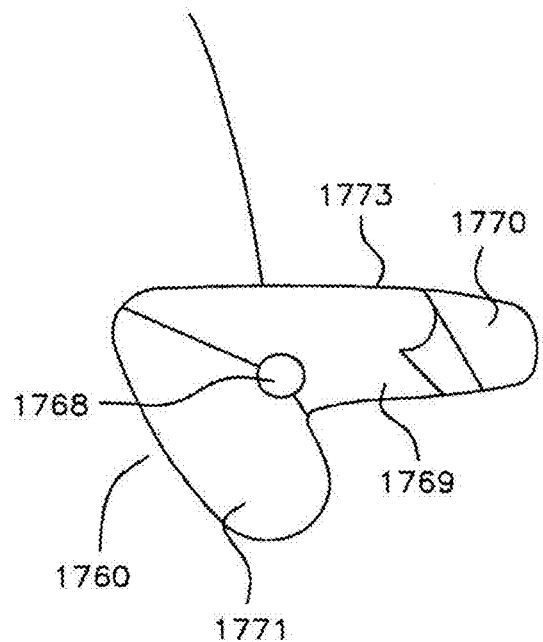
Figure 81D:
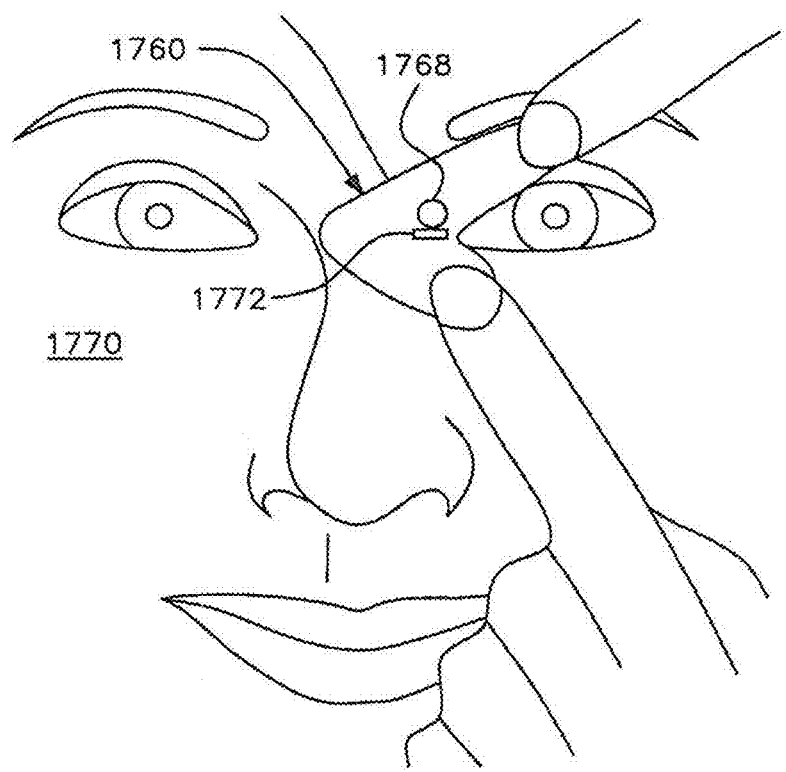

FIG. 81A is a schematic top view of another preferred embodiment for the support structure comprised of a boomerang or banana shape patch 1760 comprised of a thin insulating polyurethane layer 1766 housing a support structure 1762 which houses sensor 1764 with support structure 1762 having a different height than layer 1766 which makes sensor 1764 to protrude and be in higher position in relation to layer 1766. Surface of layer 1766 contains a pressure sensitive acrylic adhesive for securing said patch to the skin. FIG. 81B is a schematic side view of boomerang shape patch 1760 of FIG. 81A showing the different height between structure 1762, which houses sensor 1764 and wire 1765, and adhesive polyurethane layer 1766. The preferred height difference between the structures 1766 and 1762 is 5 mm, and preferably between 3 and 4 mm, and most preferably between 1 and 3 mm. FIG. 81C is a perspective view of patch 1760 with a release liner on the sensor area 1768 and a release liner 1773 comprised of two pieces, a superior piece 1769 and an inferior piece 1771. FIG. 81C shows the superior piece 1769 being peeled off to expose adhesive surface 1770. The release liner 1773 can comprise a single section or have a single or multiple slits to make a multiple section release liner. Suitable release liners for use with an adhesive layer are known in the art. According to this embodiment, when applying patch 1760 to the BTT area, sensor liner piece 1768 can be removed first and patch 1760 is then positioned with the sensor area aligned with the entrance of the BTT. Once the proper final position of the patch 1760 is determined, inferior piece liner 1771 is removed and patch 1760 applied to the nose area, and then superior piece liner 1769 can be removed and applied to the skin above the eyelid margin. FIG. 81D is a perspective view showing patch 1760 being applied to the skin of user 1770 with external markings on patch 1760 indicating sensor position 1768 and line 1772 for aligning with the corner of the eye. It is understood that the present invention includes a sensor arrangement within a support structure in which said sensor is located at a different height than the basic larger support structure comprising the patch.

Figure 82:
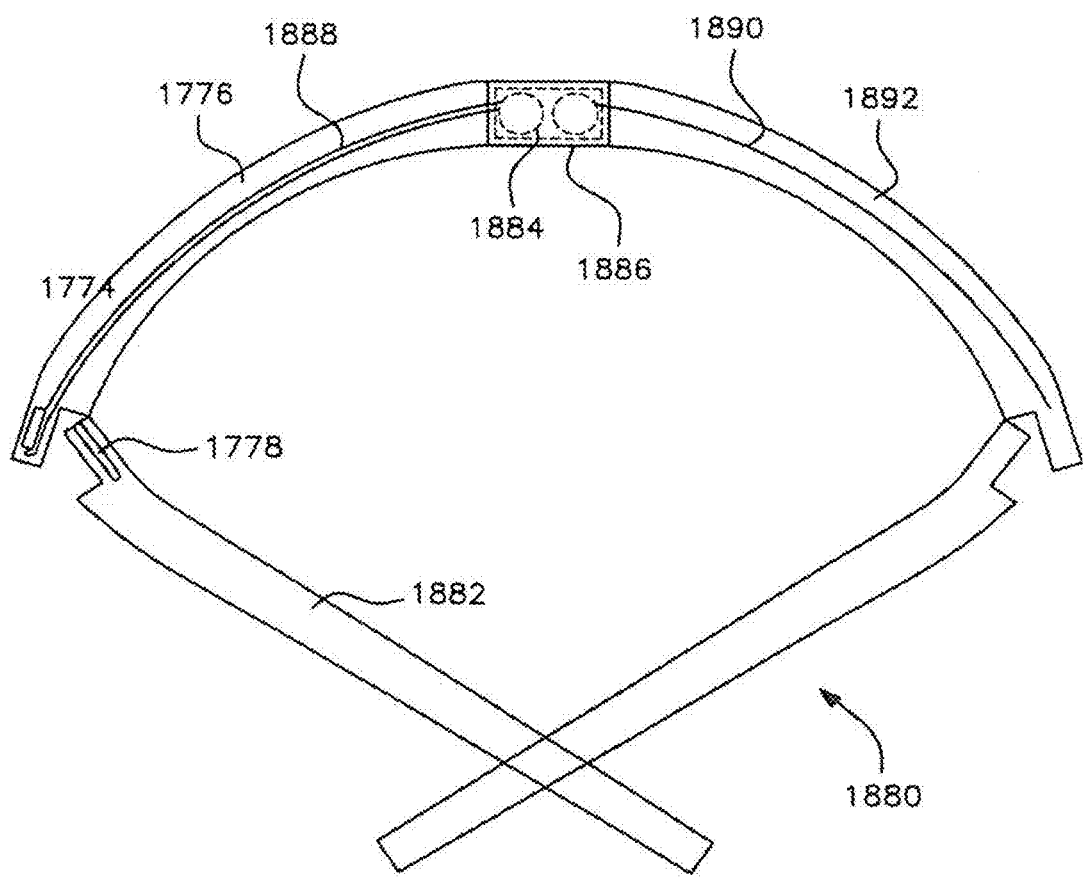
FIG. 82 is a schematic diagram showing electrical arrangement of a support structure comprised of eyewear.

FIG. 82 is a schematic top view of eyewear showing an exemplary electrical arrangement for support structure comprised of modified nose pads and frame of eyewear with said frame of eyewear 1880 including electromagnetic switch 1774 in left lens rim 1776 and magnetic rod 1778 in left temple 1882 for electrically turning the system on when in electrical contact, transmitter and power source module 1884 in nose bridge 1886 is electrically connected by wire 1888 in lens rim 1776 to switch 1774, and antenna 1890 in right lens rim 1892 connected to module 1884. When the temples are opened for using the eyewear an electrical connection is established between switch 1774 and magnetic rod 1778 which automatically activates the system. It is understood that a variety of spring mechanisms can be integrated into a shaft holding the sensors for better apposition of said sensors to the BTT area.

The present invention provides a method for optimizing fluid intake to achieve dehydration and avoid dehydration and overhydration. The present invention provides a continuous noninvasive core temperature monitoring, and when the temperature reaches certain pre-set levels such as increased temperature which reflects increased heat stored in the body, then by ingesting fluid the temperature can be lowered. Brain temperature reflects the hydration status and dehydration leads to an increase in the core (brain) temperature. The method in accordance with the present invention includes an algorithm for use in the situation of dehydrated, sedentary people exposed to heat (as illustrated by the excess mortality during heat waves), and people during physical activities. The invention showed that ingestion of 4 ounces of water every hour after body temperature reaches 100.4 degrees F. will lower the body temperature to 98.6 degrees F. and will keep the body temperature at lower than 99.5 degrees F. thus preventing the dangers of heat stroke. In case of athletes in athletic activities such as cycling, the invention showed that ingestion with fluid containing carbohydrates and minerals (e.g., trade name PowerAde of the Coca-Cola Company) can keep peak performance with ingestion of 6 to 8 ounces when the temperature at the BTT reaches 99.3 degrees Fahrenheit and performance is maintained with ingestion every 1 to 2 hours. A variety of algorithms for use in the situation of athletes at risk of overheating, can be created based on the principle of the invention. Special size containers for fluid or water can be used by an athlete who is aware of the fluid intake needed during a competition.

A method and algorithm to couple temperature (hypothermia) to nourishment (malnutrition) in elderly and in anorexia nervosa can be created, with the temperature level indicating malnutrition and further indicating what food to ingest to maintain adequate temperature. It is further understood that foods can be developed based on body temperature to achieve optimal nutritional value—fresh and frozen, or processed foods. It is yet understood that temperature changes indicating ovulation can be used as a method to create foods that increase fertility by identifying what food articles increase ovulation.

The present invention also provides methods and devices for evaluating diet such as caloric restriction in which the temperature indicates the metabolism and therefore a lower basal temperature indicates reduced metabolism and metabolic waste products including monitoring carbohydrate intake and metabolism. The present invention also provides methods for monitoring hypoglycemia in diabetes in which lowering of the temperature is a predictor of a hypoglycemic event. The invention also provides methods for detecting pulmonary infarction and cardiac events which are associated with a particular increase in temperature. Any condition which is associated with a change in temperature can be predicted and detected by the present invention from pregnancy disorders coupled to hypothermia to hyperthermia in head trauma.

The present invention provides a variety of other benefits. Other exemplary benefits include: 1. monitoring Multiple Sclerosis since increase in brain temperature can lead to worsening of the condition, and a corrective measure can be taken when the present invention identifies such increase in temperature, such as by drinking cold liquids at the appropriate time or cooling off the brain as previously described, 2. significant differences between left and right BTT can indicate a pathological central nervous system condition, 3. detecting increased brain temperature to reinforce diagnosis of meningitis or encephalitis and thus avoid excess use of lumbar tap in people without the infection, and 4. Young babies cannot regulate their body temperature in the same way that adults do and can easily become too hot. Sudden Infant Death Syndrome (SIDS) is more common in babies who have become overheated. By monitoring babies' temperature the present invention can alert parents in case the baby's temperature increases.

A receiver receiving signal from the sensor system of the present invention can be external or implantable. When implantable inside the body the receiver can be powered by magnetic induction externally or batteries recharged externally. The receiver receives the signal from a temperature sensor, glucose sensor, or the like and retransmits the signals for further display.

Any transmitter of the present invention can be integrated with Bluetooth, GRPS data transmission, and the like. The signal from the transmitter then can be captured by any Bluetooth enabled device such as cell phones, electronic organizers, computers, and the like. Software of the cell phone can be modified to receive the coded signal from a transmitter. Algorithm in the receiver will decrepit the signal and display the value. A cell phone can have an auto dial to call a doctor for example when fever is noted. It is understood that the signal from a cell phone or a signal directly from the transmitter of the support structure can be transmitted to a computer connected to the internet for further transmission over a distributed computer network.

The prior art used facial skin temperature as detecting means for monitoring body temperature. As seen in FIGS. 1A and 1B, temperature of the skin on the face varies significantly from area to area and is not representative of the core temperature. In addition facial skin temperature does not deliver thermal energy in a stable fashion. Any device or method that uses facial skin temperature to activate another device or monitor temperature of the body will not provide a precise nor accurate response. In addition facial skin temperature does not represent the thermal status of the body and has a poor correlation with core and brain temperature. The only skin surface of the body which is in direct and undisturbed communication with inside the body is the specialized area of special geometry located at the entrance of the BTT. Any temperature sensing device placed on or adjacent to the BTT entrance can measure core temperature in a precise and accurate manner. It is understood that any sensor including a colorimetric sticker such as with liquid crystal colorimetric thermometers can be used and placed on the skin at the entrance of the BTT area, and are within the scope of the invention.

Now referring to the previously described automated climate control system, an exemplary embodiment will be described in more detail. Although this exemplary preferred embodiment will be described for climate control in the cabin of a transportation vehicle (e.g., car) it is understood that the method, device and system can apply to any confined environment such as home, work place, a hotel room, and the like in which the temperature inside the confined environment is adjusted based on the temperature at the BTT for achieving thermal comfort for the subject inside the confined environment.

The temperature measurement at the BTT represents the thermal comfort of the body. Investigation by the present invention showed that the thermal comfort of the body is reduced as the temperature of the body increases or decreases reflected by a change in brain temperature at the BTT. Thermal comfort of a human being is reflected by the skin temperature at the BTT, with higher skin temperature at the BTT generating a hot body sensation while a lower skin temperature at the BTT generates a cold body sensation. In order to achieve thermal comfort for the occupants of a cabin the system of the invention manages cabin thermal comfort from the temperature signal generated at the BTT. The present invention preferably uses a particular specialized area in the face, and not the whole face to manage the cabin temperature and cabin thermal comfort. The present invention system preferably monitors temperature in less than the whole face which causes an optimal control of the heating and cooling of the cabin to achieve thermal comfort of the occupant of the cabin.

Figure 83:
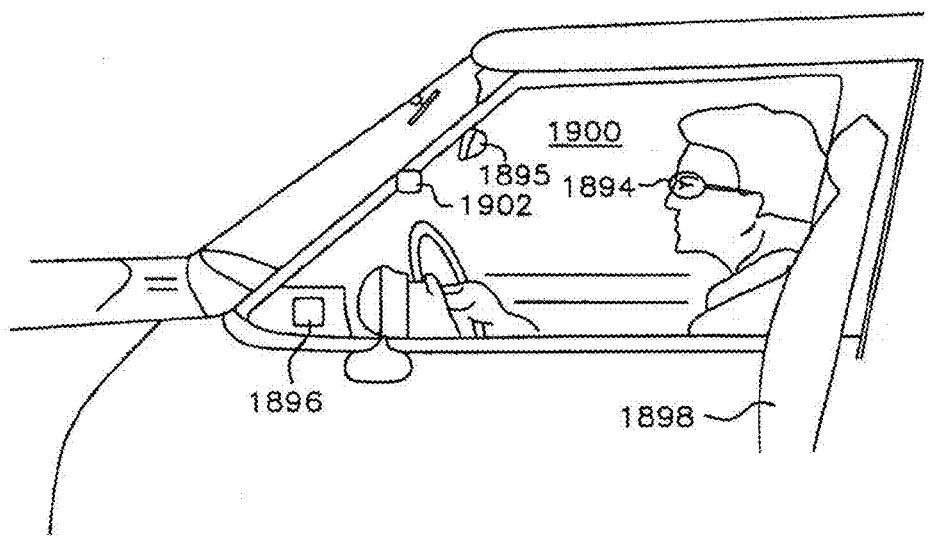
FIG. 83 is a perspective view showing an automated climate control system.

Since thermal comfort is reflected in the brain temperature adjusting the climate cabin based on the temperature of the BTT will provide a thermally comfortable environment for the occupant of the cabin. The BTT temperature is set for controlling the HVAC (heater-air conditioner) and other parts of the vehicle previously mentioned such as seats, carpets, and the like, which are adjusted to maintain the occupant's thermal sensation in a comfortable state. In particular, articles in contact or adjacent to the body are used to automatically remove or apply heat to the occupant's body based on the BTT signal. To further improve thermal comfort, the system includes a temperature sensor in the cabin for detecting cabin temperature. Accordingly, FIG. 83 shows an exemplary automated climate control system which includes BTT temperature sensing device 1894 for contact measurements (e.g., eyewear) and 1895 for non-contact measurements (e.g., infrared detector) for monitoring temperature at the BTT, control device 1896 adapted to automatically adjust articles 1898 in the cabin 1900 for removing or delivering heat based on the signal generated by BTT sensing device 1894, a cabin temperature sensor 1902 to detect the temperature in the cabin 1900, and an article 1898 inside the cabin adapted to remove heat when the signal from BTT sensor 1894 indicates high temperature or to deliver heat when the BTT sensor 1894 indicates low temperature. Although for illustration purposes a vehicle seat will be used as an article for removing/delivering heat, it is understood that other articles such as HVAC, carpet, steering wheel, and other articles previously mentioned can be used. As soon as the vehicle is started, the cabin sensor 1902 detects the cabin temperature and adjusts the article 1898 for removing or delivering heat based on the temperature signal from the cabin sensor 1902. Next or simultaneous with measurement of cabin temperature by sensor 1902, the output of BTT sensor 1894 is fed into control device 1896 which activates article 1898 to remove or deliver heat based on the signal from the BTT sensor 1894. If the BTT sensor 1894 indicates HIGH (>98.8° F.) then article 1898 will remove heat, and if LOW (<97.5° F.) is detected by BTT sensor 1894 then article 1898 will deliver heat, in order to achieve cabin thermal comfort. An exemplary embodiment for cooling includes control means 1896 connected to an air-conditioning control system for managing the amount of cool air being generated and blown in a proportional manner according to the temperature level output by BTT sensor 1894. For heating exemplarily the control device 1896 can be connected to a control system 1906 which gradually adjusts heat delivery by an electrically-based vehicle seat 1898 according to the output level by BTT sensor 1894. Control device 1896 is adapted to remain neutral and not to adjust article 1898 when temperature at the BTT is within 97.5° F. and 98.8° F. Since thermal comfort can vary from person to person, the system can be adapted for removing or delivering heat according to specific temperature thresholds in accordance with the occupant's individual needs, and not necessarily in accordance to defaults set at 97.5° F. and 98.8° F. It is understood that a combination of skin sensors placed in other parts of the body can be used in conjunction with BTT sensor 1894. It is yet understood that the rate of change in the skin temperature can be accounted for and fed into microcontroller which is adapted to adjust articles based on a large variation of skin temperature at the BTT site, with for instance a sudden cooling of the body of more than 0.6 degrees generating a corresponding decrease in the amount of cool air being generated or even shutting off an air conditioner system. It is also understood that BTT sensing devices include contact device (e.g., patches and eyewear of the present invention), non-contact devices (e.g., infrared devices of the present invention), thermal imaging (e.g., BTT Thermoscan of the present invention), and the like.

Figure 84:
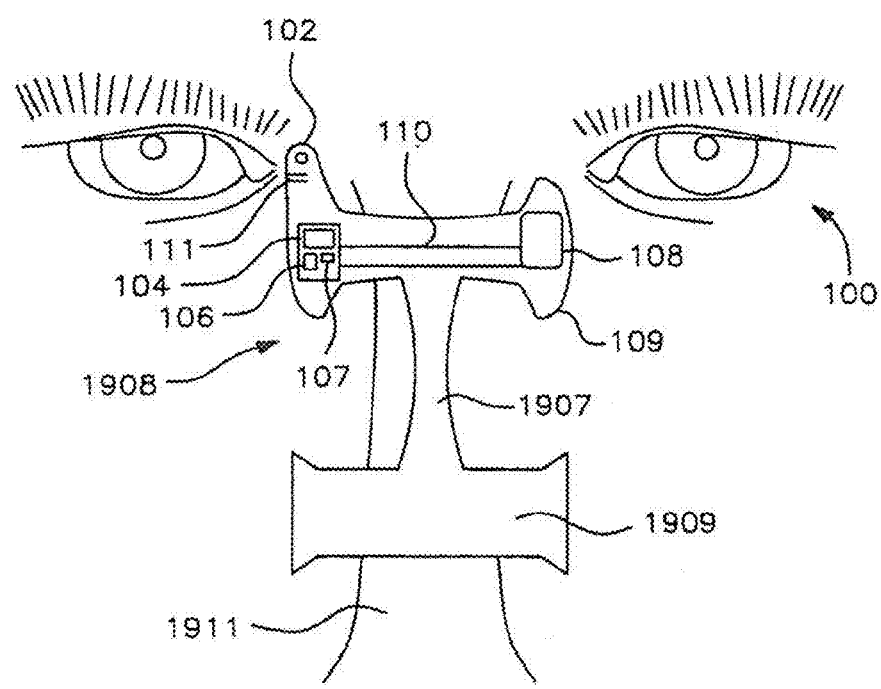
FIG. 84 is a perspective frontal view showing an nasal airway dilator as an extension of a patch of the present invention.

Yet another embodiment according to the present invention includes a support structure containing a sensor to measure biological parameters connected to a nasal strip for dilating airways of humans such as Breathe Right (commercially available under the trade name BreatheRight) and for dilating airway passages of animals (commercially available under the trade name Flair). Exemplary air dilator nasal strips were described in U.S. Pat. Nos. 5,533,503 and 5,913,873. The present invention incorporates airway dilators into patches for biological monitoring. The present invention can be an integral part of an airway dilator. The airway dilators can be an extension of the present invention. The coupling of a patch measuring biological parameters and an air dilator is convenient and beneficial since both are useful in the same activities. Nasal airway dilators are beneficial during sleeping, in athletic activities, or when suffering from a cold or respiratory infections and the patch of the present invention is used during sleeping, monitoring temperature changes in athletic activities, and monitoring fever during respiratory infections. Both nasal airway dilators and the patch of the present invention use an adhesive in its backing to secure to the skin and both are secured to the skin over the nasal bones, the patch of BTT located in the superior aspect of the nasal bone and the air dilator preferably in the inferior aspect of the nasal bone. The nasal airway dilator extension of the patch of the present invention is referred to herein as BioMonitor Dilator (BMD). Accordingly, FIG. 84 is a front perspective view of a preferred embodiment showing a person 100 wearing a BMD 1908 including a support structure comprised of a patch 109 connected by connecting arm 1907 to air dilator nasal strip 1909 with said BMD placed on the nose 1911 with patch 109 containing indicator lines 111 and containing an active sensor 102 positioned on the skin at the end of the tunnel on the upper part of the nose 1911 and air dilator nasal strip 1909 positioned on the skin of the lower part of the nose 1911 of user 100. The embodiment of the BMD 1908 shown in FIG. 84 provides transmitting device 104, processing device 106, AD converter 107 and sensing device 102 connected by flexible circuit 110 to power source 108 housed in patch 109. Although a connecting arm is shown it is understood that the BMD can be made as one piece in which the upper part houses the sensor and circuitry and the part on the lower aspect of the nose includes a spring loaded strip to act as nasal airway dilator. The present invention discloses a method of simultaneous monitoring biological parameters while dilating nasal airways.

Figure 85A:
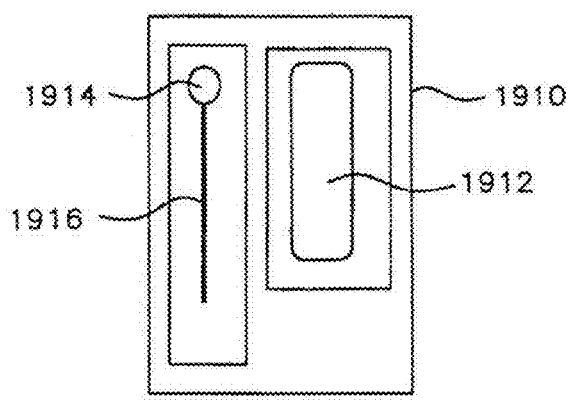
FIGS. 85A to 85C are schematic diagrams showing kits in accordance with the present invention.
Figure 85B:
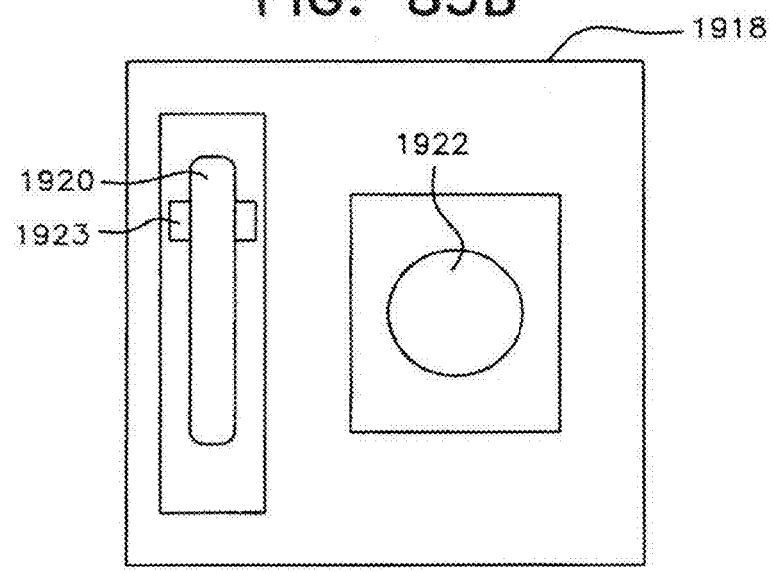
Figure 85C:
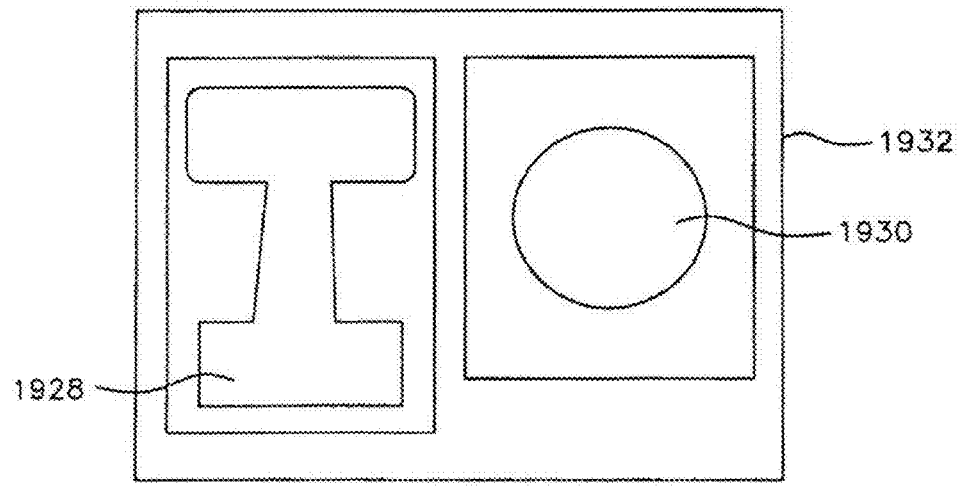

Another embodiment includes a plurality of kits shown in FIGS. 85A to 85D. Accordingly, FIG. 85A is a schematic view of a kit 1910 containing an adhesive tape 1912 and a free sensor 1914 attached to a wire 1916. The free sensor 1914 is unattached to a support structure and when in use said sensor is preferably placed in contact with the adhesive 1912 in order for the sensor 1914 to be secured to the skin by the adhesive surface of adhesive 1912. Another embodiment shown in FIG. 85B includes a kit 1918 containing a support structure 1920 such as a patch, clip, eyewear (e.g., eyeglasses, sunglasses, goggles, and safety glasses) and the like, and receiver 1922 illustrated as a watch, but also cell phone, electronic organizer, and the like can be used as a receiver and being part of the kit. Kit 1918 can also house a magnet 1923 in its structure which acts as a switch, as previously described. It is understood that kit 1918 can include only a patch with the magnet 1923 adjacent to said patch 1922. The watch 1922 preferably has a slanted surface for better viewing during athletic activities such as during cycling with the field of view of the watch 1926 directed at an angle toward the face of the cyclist, so just by looking down and without turning the head the user can see the temperature level displayed on the watch 1926. A further embodiment shown in FIG. 85C includes a kit 1932 containing specialized BMD patch 1928 and a receiver 1930 illustrated as a watch.

Another embodiment includes shoes with temperature sensor for detecting cold and with a radio transmitter to transmit the signal to a receiver (e.g., Watch). The signal from the shoe in conjunction with the signal from the TempAlert at the BTT provides a combination of preventive device against both frostbite and hypothermia.

It is understood that the support structure such as a patch may house vapors and when the outer surface of the patch is scratched mentholated vapors can be released to help soothe and relieve nasal congestion, which can be convenient when monitoring fevers with the patch.

It is also understood that steel or cooper can be placed on top of a sensor to increase thermal conductivity as well as any other conventional means to increase heat transfer to a sensor.

It is understood that any electrochemical sensor, thermoelectric sensor, acoustic sensor, piezoelectric sensor, optical sensor, and the like can be supported by the support structure for measuring biological parameters in accordance with the principles of the invention. It is understood that sensors using amperometric, potentiometric, conductometric, gravimetric, impedimetric, and fluorescent systems, and the like can be used in the apparatus of the invention for the measurement of biological parameters. It is also understood that other forms for biosensing can be used such as changes in ionic conductance, enthalpy, and mass as well as immunobiointeractions and the like. It is also understood that new materials and thermally conductive liquid crystal polymers that produce a response in accordance to temperature can be used in the invention and positioned at the BTT site.

The foregoing description should be considered as illustrative only of the principles of the invention. Since numerous modifications and changes will readily occur to those skilled in the art, it is not desired to limit the invention to the exact construction and operation shown and described, and, accordingly, all suitable modifications and equivalents may be resorted to, falling within the scope of the invention.

I claim:

1. A measuring system for placement on the skin at an end of a brain tunnel and for transmitting a signal to a remote receiver, said measuring system comprising
    a housing, a portion of said housing being sized and dimensioned for placement between an eyebrow and an eye of a subject on the skin at the end of the brain tunnel,
    a sensor positioned in the portion of the housing sized and dimensioned for placement between the eyebrow and the eye of the subject on the skin at the end of the brain tunnel, said sensor generating a signal based upon measurements of said skin at the end of the brain tunnel,
    said housing including a wireless transmitter for transmitting the signal from said sensor, and
    a receiver for said signal transmitted by said wireless transmitter, said reciever including at least one of a watch, a cellular phone, a computer, an internet appliance and a pager.

2. The measuring system as claimed in claim 1, wherein a distance from an outer edge of said housing to an outer edge of said sensor is equal to or less than 11 mm.

3. The measuring system as claimed in claim 2, wherein the distance is equal to or less than 6 mm.

4. The measuring system as claimed in claim 3, wherein the distance is equal to or less than 3 mm.

5. The measuring system as claimed in claim 1, wherein said housing includes at least one of a patch, a clip, a medial canthal pad of eyeglasses, a modified nose pad of eyeglasses and head mounted gear.

6. The measuring system as claimed in claim 5, wherein said patch measures less than 11 mm at its greatest dimension.

7. The measuring system as claimed in claim 1, wherein said housing includes a power source.

8. The measuring system as claimed in claim 1, wherein said housing includes a microprocessor.

9. The measuring system as claimed in claim 1, wherein said wireless transmitter transmits said signal by at least one of a radio frequency, light, sound and electromagnetic energy.

10. The measuring system as claimed in claim 1, wherein said wireless transmitter indicates by at least one of a visual, audio and tactile that the signal has been transmitted.

11. The measuring system as claimed in claim 1, further comprising a local reporting device in said housing for local reporting of the signal.

12. The measuring system as claimed in claim 1, wherein said sensor is an active sensor.

13. The measuring system as claimed in claim 1, wherein said sensor measures temperature.

14. The measuring system as claimed in claim 1, wherein said sensor measures glucose levels.

15. The measuring system as claimed in claim 1, wherein said sensor measures oxygen levels.

16. The measuring system as claimed in claim 1, wherein said sensor measures electrolyte levels.

17. The measuring system as claimed in claim 1, wherein said sensor measures pulse.

18. The measuring system as claimed in claim 1, wherein said sensor measures blood pressure.

19. The measuring system as claimed in claim 1, wherein said internet appliance receives said signal and controls at least one of a medical device, exercise equipment, a bicycle, clothing, footwear, a climate control system, an electric blanket, a vehicle seat, furniture, sports equipment and military gear.

20. The measuring system as claimed in claim 1, further comprising a wired transmitter connected by a wire from said housing to a display unit.

* * * * *